(12) United States Patent
An et al.

(10) Patent No.: US 10,113,203 B2
(45) Date of Patent: Oct. 30, 2018

(54) DIAGNOSIS KIT AND CHIP FOR BLADDER CANCER USING BLADDER CANCER SPECIFIC METHYLATION MARKER GENE

(71) Applicant: GENOMICTREE, INC., Daejeon (KR)

(72) Inventors: Sung Whan An, Daejeon (KR); Young Ho Moon, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

(21) Appl. No.: 15/709,348

(22) Filed: Sep. 19, 2017

(65) Prior Publication Data

US 2018/0016643 A1    Jan. 18, 2018

Related U.S. Application Data

(60) Continuation-in-part of application No. 15/585,716, filed on May 3, 2017, now Pat. No. 9,797,017, which is a continuation-in-part of application No. 15/016,366, filed on Feb. 5, 2016, now Pat. No. 9,670,551, which is a continuation-in-part of application No. 13/627,519, filed on Sep. 26, 2012, now Pat. No. 9,359,646, which is a division of application No. 12/744,491, filed as application No. PCT/KR2008/007081 on Dec. 1, 2008, now abandoned.

(30) Foreign Application Priority Data

Nov. 30, 2007    (KR) .......................... 10-2007-0124015

(51) Int. Cl.
C12Q 1/68        (2018.01)
C12Q 1/6886      (2018.01)
C12Q 1/686       (2018.01)

(52) U.S. Cl.
CPC ........... C12Q 1/6886 (2013.01); C12Q 1/686 (2013.01); *C12Q 2600/154* (2013.01); *C12Q 2600/156* (2013.01)

(58) Field of Classification Search
CPC . C12Q 1/686; C12Q 1/6886; C12Q 2600/154
USPC ................................................ 435/6.1, 6.14
See application file for complete search history.

(56) References Cited

U.S. PATENT DOCUMENTS

| | | | |
|---|---|---|---|
| 5,786,146 A | 7/1998 | Herman et al. | |
| 6,812,339 B1 | 11/2004 | Venter et al. | |
| 7,354,713 B2 | 4/2008 | Mertz et al. | |
| 7,972,772 B2 | 7/2011 | Nakamura et al. | |
| 8,062,892 B2 | 11/2011 | Schlegel et al. | |
| 8,173,602 B2 | 5/2012 | Albertson et al. | |
| 8,513,028 B2 | 8/2013 | Jang et al. | |
| 9,359,646 B2 | 6/2016 | An et al. | |
| 9,365,900 B2 | 6/2016 | An et al. | |
| 9,670,551 B2 | 6/2017 | An et al. | |
| 9,797,017 B2 * | 10/2017 | An ........................ | C12Q 1/6886 |
| 2002/0137086 A1 | 9/2002 | Olek et al. | |
| 2007/0298506 A1 | 12/2007 | Ordway et al. | |
| 2010/0304992 A1 | 12/2010 | An et al. | |
| 2013/0122495 A1 | 5/2013 | An et al. | |
| 2013/0123116 A1 | 5/2013 | An et al. | |
| 2016/0244843 A1 | 8/2016 | An et al. | |
| 2016/0244844 A1 | 8/2016 | An et al. | |
| 2017/0240976 A1 | 8/2017 | An et al. | |

FOREIGN PATENT DOCUMENTS

| | | |
|---|---|---|
| CA | 2288235 A1 | 12/1998 |
| DE | 20121960 U1 | 1/2004 |
| JP | 2002511749 A | 4/2002 |
| KR | 1020110049430 A | 5/2011 |
| KR | 1020120055917 A | 6/2012 |
| WO | 0119845 A1 | 3/2001 |
| WO | 2007143037 A2 | 12/2007 |

OTHER PUBLICATIONS

Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.

Bai, F., et al., "Establishment and characterization of a high metastatic potential in the peritoneum for human gastric cancer by orthotopic tumor cell implantation", "Dig Dis Sci.", Apr. 3, 2007, pp. 1571-1578, vol. 52, No. 6.

Chan, M., et al., "Hypermethlyation of Multiple Genes in Tumor Tissues and Voided Urine in Urinary Bladder Cancer Patients", "Clinical Cancer Research", Feb. 2002, pp. 464-470, vol. 8, No. 2.

Comb, M., et al., "CpG methylation inhibits proenkephalin gene expression and binding of the transcription factor AP-2", "Nucleic Acids Research", Jul. 11, 1990, pp. 3975-3982, vol. 18, No. 13.

Costello, J., et al., "Aberrant CpG-island methylation has non-random and tumour-type-specific patterns", "Nature Genetics", Feb. 2000, pp. 132-138, vol. 25.

(Continued)

*Primary Examiner* — Antonio Galisteo Gonzalez
(74) *Attorney, Agent, or Firm* — Hultquist, PLLC; Steven J. Hultquist

(57) ABSTRACT

The present invention relates to a kit and nucleic acid chip for diagnosing bladder cancer using a bladder cancer-specific marker gene. More particularly, the invention relates to a kit and nucleic acid chip for diagnosing bladder cancer, which can detect the promoter methylation of a bladder cancer-specific gene, the promoter or exon region of which is methylated specifically in transformed cells of bladder cancer. The use of the diagnostic kit or nucleic acid chip of the invention enables diagnosis of bladder cancer at an early stage of transformation, thus enabling early diagnosis of bladder cancer, and can diagnose bladder cancer in a more accurate and rapid manner compared to a conventional method.

21 Claims, 14 Drawing Sheets
(1 of 14 Drawing Sheet(s) Filed in Color)
Specification includes a Sequence Listing.

(56) References Cited

OTHER PUBLICATIONS

Das, P., et al., "DNA Methylation and Cancer", "Journal of Clinical Oncology", Nov. 15, 2004, pp. 4632-4641, vol. 22.
Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.
Fraga, M., et al., "The affinity of different MBD proteins for a specific methylated locus depends on their intrinsic binding properties", "Nucleic Acids Research", Mar. 15, 2003, pp. 1765-1774, vol. 31, No. 6.
Fukushima, N., et al., "Aberrant methylation of preproenkephalin and p16 genes in pancreatic intraepithelial neoplasia and pancreatic ductal adenocarcinoma", "American Journal of Pathology", May 2002, pp. 1573-1581, vol. 160.
Goo, Y., et al., "Stromal mesenchyme cell genes of the human prostate and bladder", "BMC Urology", Dec. 2005, pp. 1-11, vol. 5.
Ho, S., et al., "Techniques used in studies of epigenome dysregulation due to aberrant DNA methylation: An emphasis on fetal-based adult diseases", "Reproductive Toxicology", Apr.-May 2007, pp. 267-282, vol. 23.
Hoehn, B., et al., "Abstract 4517: Syndecan-2 methylation is an early detection biomarker for colorectal cancer with high sensitivity and specificity in small serum sample volumes", "Cancer Research", Apr. 15, 2012, p. 4517, vol. 72 (8 Supplement).
"Illumina DNA Methylation Analysis Data Sheet", "Data Sheet: Epigenetics", Apr. 6, 2012, pp. 1-7; (http://www.illumina.com/Documents/products/datasheets/datasheet_dna_methylation_analysis.pdf).
Jan, K., et al., "Abnormal DNA methylation according to the histologic types of early gastric adenocarcinoma", "Histopathology", Sep. 5, 2012, pp. 76-77, vol. 61 (Supplement 1).
Kawamoto, K., et al., "p16INK4a and p14ARF methylation as a potential biomarker for human bladder cancer", "Biochemical and Biophysical Research Communications", Jan. 20, 2006, pp. 790-796, vol. 339, No. 3.
Kristensen, E., et al., "A Novel 3-D Image-Based Morphological Method for Phenotypic Analysis", "IEEE Transaction on Biomedical Engineering", Dec. 2008, pp. 2826-2831, vol. 55, No. 12.
Liu, T., et al., "Regulation of Cdx2 expression by promoter methylation, and effects of Cdx2 transfection on morphology and gene expression of human esophageal epithelial cells", "Carcinogenesis", Sep. 21, 2006, pp. 488-496, vol. 28, No. 2.
Marsit, C., et al., "Examination of a CpG Island Methylator Phenotype and Implications of Methylation Profiles in Solid Tumors", "Cancer Research", Nov. 1, 2006, pp. 10621-10629, vol. 66, No. 21.
Matsusaka, K., et al., "Classification of Epstein-Barr Virus-Positive Gastric Cancers by Definition of DNA Methylation Epigenotypes", "Cancer Research", Dec. 1, 2011, pp. 7187-7197, vol. 71, No. 23.
Old, R., et al., "Candidate epigenetic biomarkers for non-invasive prenatal diagnosis of Down syndrome", "Reproductive Biomedicine Online", Aug. 2007, pp. 227-235, vol. 15, No. 2.
"Promega's Protocols & Applications Guide Chapter 1: Nucleic Acid Amplification", "Promega's Protocols & Applications Guide", Mar. 2011, pp. 1-26.
Sambrook, J., et al., "Molecular Cloning: A Laboratory Manual: Second Edition", 1989, pp. v-xxxii (Table of Contents only), Publisher: Cold Spring Harbor Laboratory Press, Published in: US.
Sanchez-Cespedes, M., et al., "Gene Promoter Hypermethylation in Tumors and Serum of Head and Neck Cancer Patients", "Cancer Research", Feb. 15, 2000, pp. 892-895, vol. 60.
Sato, F., et al., "CpG Island Hypermethylation in Progression of Esophageal and Gastric Cancer", "Cancer", Dec. 16, 2005, pp. 483-493, vol. 106, No. 3.
Schulz, W., "DNA methylation in urological malignancies (review)", "International Journal of Oncology", Jul. 1998, pp. 151-167, vol. 13.
Strachan, T., et al., "Human Molecular Genetics. 2nd edition Chapter 5: Nucleic acid hybridization assays", 1999, pp. 95-118, Publisher: John Wiley & Sons, Inc. (by arragement with BIOS Scientific Publishers Ltd), Published in: New York, NY USA.
Suh, N., et al., "Value of CDX2, villin, and alpha-methylacyl coenzyme A racemase immunostains in the distinction between primary adenocarcinoma of the bladder and secondary colorectal adenocarcinoma", "Modern Pathology", Sep. 2005, pp. 1217-1222, vol. 18, No. 9.
Tanay, A., et al., "Hyperconserved CpG domains underlie Polycomb-binding sites", "PNAS", Mar. 27, 2007, pp. 5521-5526, vol. 104.
Ueki, T., et al., "Identification and characterization of differential! menthylated CpG islands in pancreatic carcinoma", "Cancer Research", Dec. 2001, pp. 8540-8546, vol. 61.
Utikal, J., et al., "The expression of metastasis suppressor MIM/MTSS1 is regulated by DNA methylation", "International Journal of Cancer", Nov. 16, 2006, pp. 2287-2293, vol. 119, No. 10.
Wiksten, J., et al., "Epithelial and stromal syndecan-1 expression as predictor of outcome in patients with gastric cancer", "Int. J. Cancer (Pred. Oncol.)", Jan. 20, 2001, pp. 1-6, vol. 95.
Yamaki, A., et al., "Molecular mechanisms of human single minded2 (SIM2) gene expression: identification of a promrter site in the SIM2 genomic sequence", "Gene", May 2001, pp. 265-275, vol. 270.
Yates, D., et al., "Promoter Hypermethylation Identifies Progression Risk in Bladder Cancer", "Clinical Cancer Research", Apr. 1, 2007, pp. 2046-2053, vol. 13, No. 7.
Zouridis, H., et al., "Methylation Subtypes and Large-Scale Epigenetic Alterations in Gastric Cancer", "Science Translational Medicine", Oct. 17, 2012, pp. 1-12, vol. 4, No. 156.

* cited by examiner

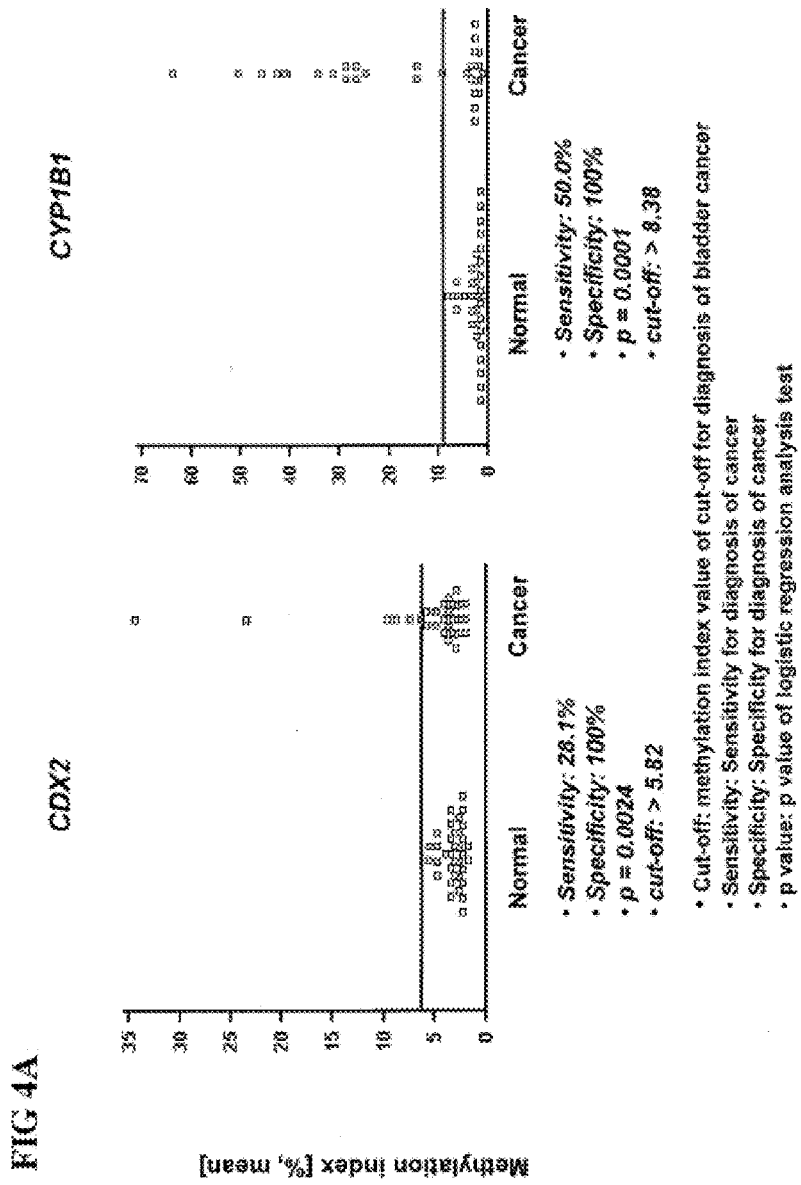

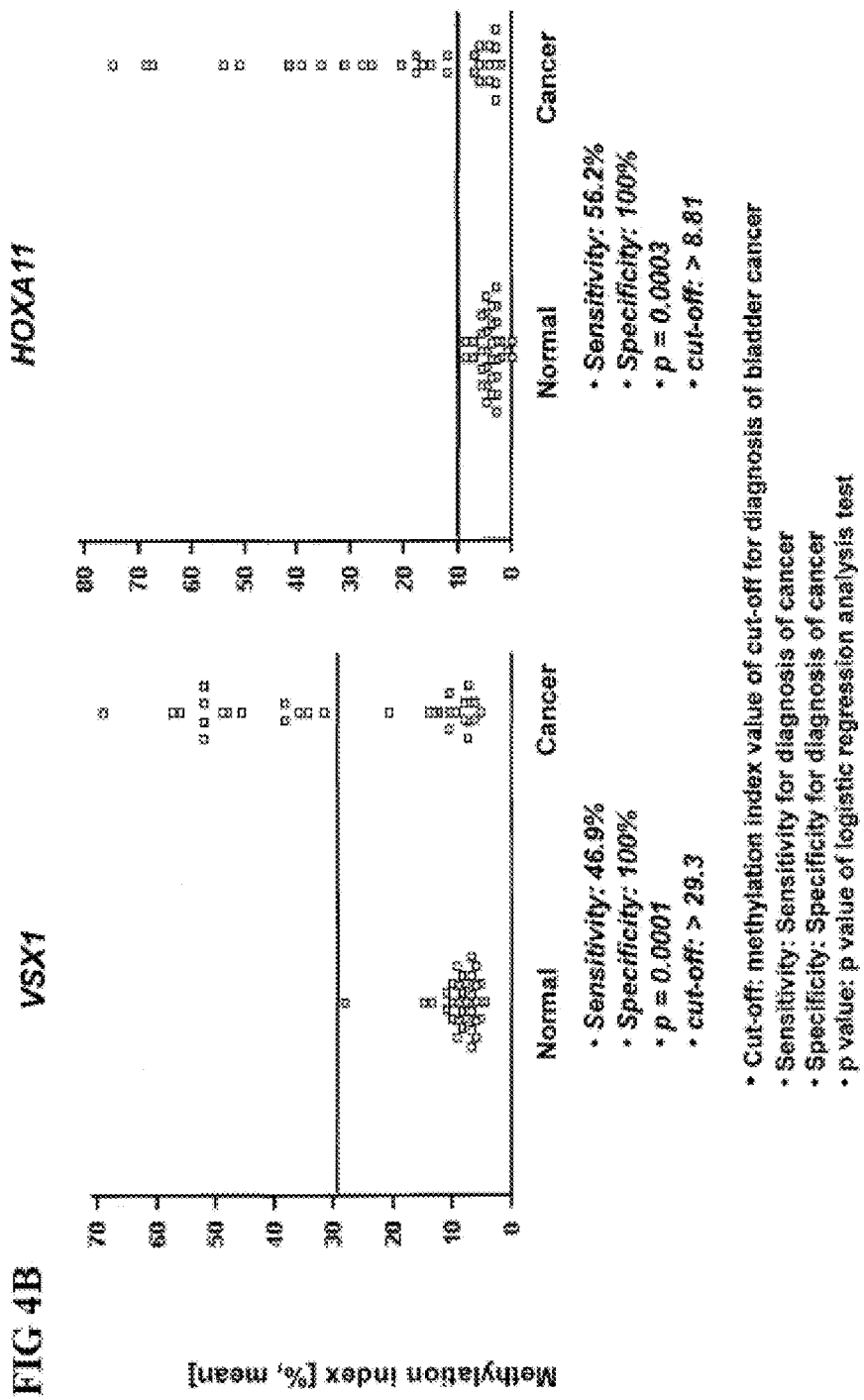

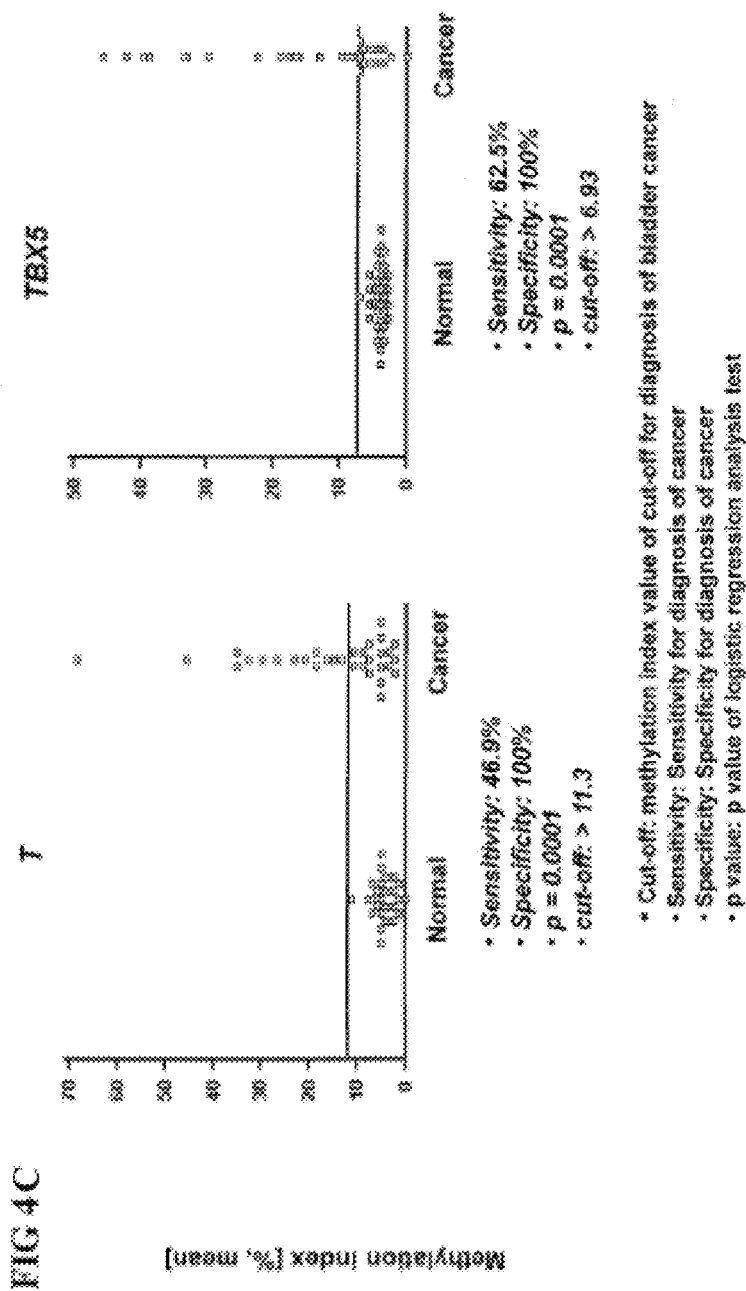

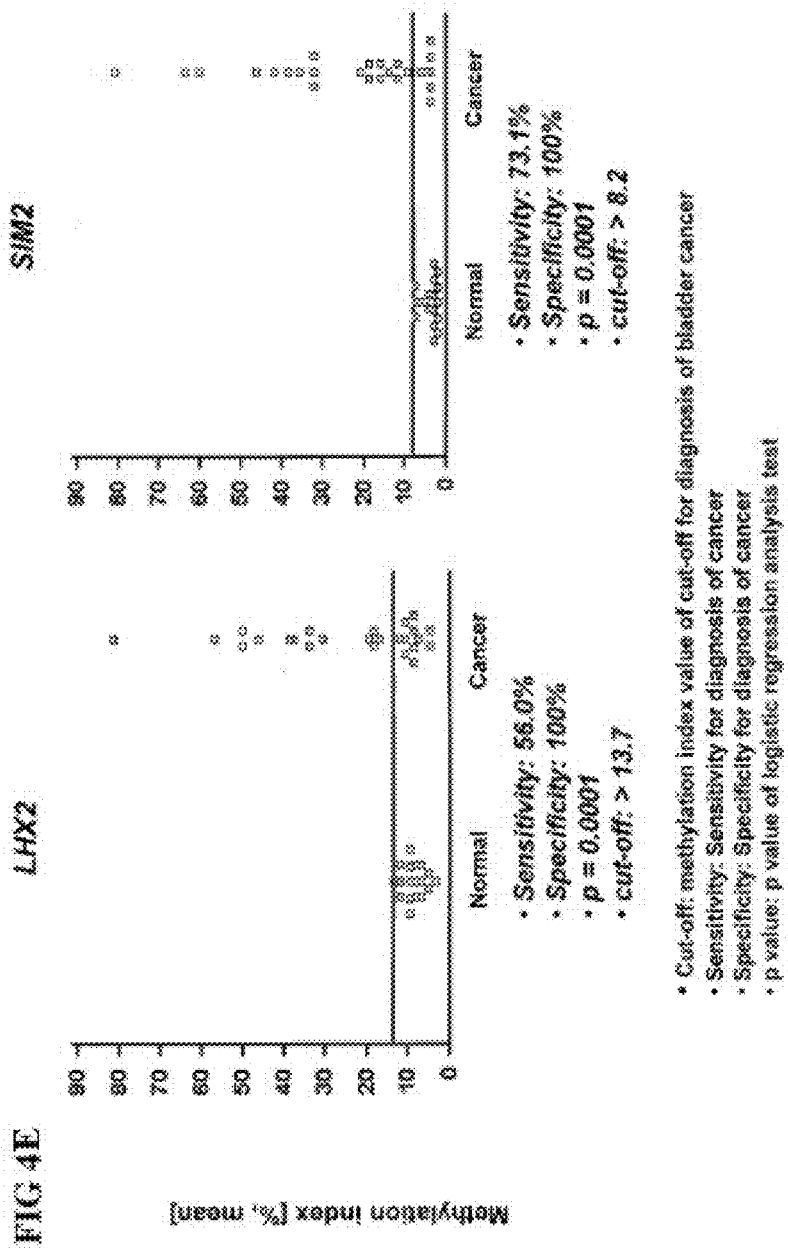

SEQUENCE LISTING

<160> NUMBER OF SEQ ID NOS: 1221

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tggtgtttgt gttattatta atag                                              24

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
cacctccttc ccactaaact a                                                 21

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
gtaagggtat gggaattga                                                    19

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
cccttaaaaa cctaacaaaa tc                                                22

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggagtgggat tgaggagatt t                                                 21

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
aaacccaacc aaccctcat                                                    19

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
agtaagttta tgggaggggg att                                         23

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
cccccataca acatacttat actca                                       25

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct

<400> SEQUENCE: 9
ggaggaatgt tattgtttaa agagat                                      26

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
caaccccttc taaaaaatat cc                                          22

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gggtttggag ttaggttatg                                             20

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
aaatctaaac ttaccccaa ct                                           22

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
atattttatt gtatgggttt tttaatag                                    28

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
acaacctcaa caaaaaatc                                               19

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
agatagggga taattttat                                               19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
cctcccaaac taaaattt                                                18

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
gtagaaggga aataaggttg aaa                                          23

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
actaaaaccc caatactccc a                                            21

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
gtggatttag attaggattt tgt                                          23

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20 cacccteccc aaattctt                                                      18

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
attaatagag ttttgtaaat at                                                 22

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct

<400> SEQUENCE: 22
aagggtatgg gaattg                                                        16

<210> SEQ ID NO 23
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
tttgggattg ggaag                                                         15

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
tagtttaggg tatttttat ttat                                                24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
gtgaaagtaa tgatatagta gaaa                                               24

<210> SEQ ID NO 26
<211> LENGTH: 15
<212> TYPE: DNA
<213> ORGANISM: Artificial Sequence
<220> FEATURE:
<223> OTHER INFORMATION: Synthetic Construct

<400> SEQUENCE: 26
tttgggggtt gggga                                                         15

<210> SEQ ID NO 27

```
<211> LENGTH: 17
<212> TYPE: DNA
<213> ORGANISM: Artificial Sequence
<220> FEATURE:
<223> OTHER INFORMATION: Synthetic Construct

<400> SEQUENCE: 27
gggtgtttta ggtagtt                                                  17

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
cctcccaaac taaaatttc                                                19

<210> SEQ ID NO 29
<211> LENGTH: 15
<212> TYPE: DNA
<213> ORGANISM: Artificial Sequence
<220> FEATURE:
<223> OTHER INFORMATION: Synthetic Construct

<400> SEQUENCE: 29
tgggggtaga ggaga                                                    15

<210> SEQ ID NO 30
<211> LENGTH: 16
<212> TYPE: DNA
<213> ORGANISM: Artificial Sequence
<220> FEATURE:
<223> OTHER INFORMATION: Synthetic Construct

<400> SEQUENCE: 30
cctccccaaa ttcttc                                                   16

<210> SEQ ID NO 31
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 31
actgcccttc tctcaatgat tcggattttg taacggggtt tgcaatttgc ttccggttgt    60
atttctcagg aagtccgatg acactcggct gtccaggcca ggcgctggaa gtccccagg   120 aggaccagct cggtctccca cctcttgagt gcacagctcc ttggcccctg agtaccccac   180
cacccccatt tccagccttc ttccttacaa acacgaaggg tgggaggaac cagaaaacag   240
gggatcccgc agccctaggc tagttctgat cgctttcagg tgtctgcaga ggcaagttgc   300
tggttgtcac ctgtaaaatg gggaggataa aaacacctcc cagattttgt tctagatcct   360
agggggatgt gaggctcaag ggagataaag gacactggag agcaccctag aaatgacagg   420
atgaaggcga tggtgacaaa tatccgagcg aaacgcttga caatgagaac agacaagtgc   480
aggtctccag gagtgccgcg agcgcccgcg ggttctgaga gcgctcaaag ccgccgagtc   540
aggctgccca gcccgccggg cctgccgcca gtgatcctca ttcccgaatc tggcagcgct   600
gtcaaaggct tgtattagga ggtgaacggc ggccgcaggc ccactccacg cggttgctga   660
aaccgagctg ggcgcgcgcg ggggccgaat ctcgccgcct ccgcgctcct gtcggggcag   720
```

```
ctcccgatcc cgggctgcgc ggcttcggtc cccaagacgg ccacttccag ccctaggccc      780
cttggccgca gcgcttccca aaccaagaga gatcctttct caactcagag cttttcatta      840
gcagtcgtta ataatggccc tgagttgcct tatcatctcc tggaaatgag aaataaattt      900
cttcggagaa cgtttcccTT tgtaaaggac agagagtttt aaagatacag gtatgatgta      960
agacacataa atacctaggt aagcattagc agaaattctc ttttccttat atttaagtat     1020
aataaacata caagtgtagc tcaatgaatt ttcacaaact gacattctgt gtaaccagca     1080
gcctaagaaa ctgctttacc aacgatcccc tagctcgcct ccagttatgc acgccaataa     1140
ccactagcct aacttctacc acatgcccat tacttctgta gtttaaaact tctgattctt     1200
gaatgtaaac gtttaacaat aaatcgcttg aatttaactc aaatttcaaa tgtaagatga     1260
agtcagagat gcagcctgaa tctaggatca taatttgtct tgtgcggagg gcgagtaatt     1320
tccttgggca agaaaataac tggaggtgac agttgtttgg ggctgcagtc gtccgggcca     1380
ggagcacagg gcgggaagga atggcccatc tcttagggct ctctgcttgt cacctaccag     1440
gttggtcaga aacgttctca tcaaagcaat ggttctcttt tcttttctct tgggacaga      1500 aggagtttct tgaccgccct cttccctgca aatgcataaa caaccactgc tcctgtctcc     1560
aagctcagat tcctaccaag atagccttTT ctcttcccct ctcttttgta agtctcttga     1620
tttcattctt tgaacctgtg attggaggtt aaagtgcacc aggttggaag gaggaagctc     1680
ttaacaataa aggtttgaat atttagctgt gtcaggtcgc tgccctctca cgagcctccc     1740
tcccctttat cttttaaaat gcaaattatg tttcgagggg ttgtgcgtag agtgcgcgct     1800
gcgcctcgac gtctccaacc attggtgtct gtgtcattac taatagagtc ttgtaaacac     1860
tcgttaatca cggaaggccg ccggcctggg gctccgcacg ccagcctgtg gcgggtcttc     1920
cccgcctctg cagcctagtg ggaaggaggt gggaggaaag aaggaagaaa gggagggagg     1980
gaggaggcag gccagaggga                                                 2000
```

<210> SEQ ID NO 32
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 32

```
aggcgcgact gtgcgtgcgc agccgagggt ggtggcggcc ggcaccccac gccaagggtg       60
gtggtggccg gcaccccacc ctcggccgcc gcctccgcgt gtcaggtgcc gtgagaagcg      120
cgggaggagc ggccgcaggc agcgcccagg gatatgactg gagccgactt ccagaagcg      180 gcgcacgcaa agcccagctc cgcacgcaaa ggggaggcga cagcagaaac ttcaacccga     240
taaagttcgc cggagcgcgg agattcgcct cctcctgcca ctctccgccc cgctcgggtc     300
ccgccccgct agctccccca ggccccccca gtcgccccag cttggctccc cgccctgcgc     360
caacggcttc catcgcagcc tgggcggccc cgcgcccacc agcgggcggc gccacctgga     420
gtggcctcta cgcgggaaat ctcagggcca gctgcgcccc aggagccttt gtgtgcccaa     480
gcactgtcgg ggccccgggg cggggagcg gctactttta gggattcctg atctcgccgc     540
aagaactgga aaaaatttag catgccaaag agcctccact gaggtggcaa tttgtttgcg     600
agaacctaag ataaaattta aacaaccaac caggggcgct gtgaggcaaa ccgctgccac     660
tacactggct ttccgggaag caagctcaag tcgcggagag ggaagggagg tcgtgcgctc     720
```

```
ggggcggggc gcgctcccaa gtcgagcgca gcggccgggg caggttgtac cgagcgtggt    780
tctggggaca ccgtgcggcc tcgattggag gtggctgtga tgaagcgcgg ttaccgcaca    840
atggaaacgt gggcacctcc gctcccatga aagcctgctg gtagagctcc gaggccggcc    900
ggtgcgcctg gacgggagtc cgggtcaaag cggcctggtg tgcggcgcgc ccgcccccc     960 gcaggccccg ccctgccagg tcgcgctgcc ctccttctac ccagtcctta aaacccggag    1020
gagcgggatg gcgcgctttg actctggagt gggagtggga gcgagcgctt ctgcgactcc    1080
agttgtgaga gccgcaaggg catgggaatt gacgccactc accgaccccc agtctcaatc    1140
tcaacgctgt gaggaaacct cgactttgcc aggtccccaa gggcagcggg gctcggcgag    1200
cgaggcaccc ttctccgtcc ccatcccaat ccaagcgctc ctggcactga cgacgccaag    1260
agactcgagt gggagttaaa gcttccagtg agggcagcag gtgtccaggc cgggctgcgg    1320
gttcctgttg acgtcttgcc ctaggcaaag gtcccagttc cttctcggag ccggctgtcc    1380
cgcgccactg gaaaccgcac ctccccgcag gtcagtctgt ctgccgaggc gctgcccggc    1440
gacctcttca gatggattat tacaggtagc gggtggcgtg gtaggtactt taaaggaaat    1500
caagcgccac cgcctcgatg cccgcagcgt tgtccccaga ttgcaggaac cgttacgcgc    1560
cttgcgggga ggggaagggt ttggcgctgg gttacgcga ggtggaaaca cgccccttct     1620
cttctccaag ggagagtggg ttggggatgg aagggggcgt cttcggccat ttctccagag    1680
agtcagctcc gacctctcca cccaacggca ctcagtcccc agaggctggg gtaggggcgt    1740
ggggcgcccg ctcctgtctc tgcaccccctg agtgtcacgc cttctcctct ctgtccccag    1800
catgggcacc agcctcagcc cgaacgaccc ttggccgcta aacccgctgt ccatccagca    1860
gaccacgctc ctgctactcc tgtcggtgct ggccactgtg catgtgggcc agcggctgct    1920
gaggcaacgg aggcggcagc tccggtccgc gcccccgggc ccgtttgcgt ggccactgat    1980
cggaaacgcg gcggcggtgg                                                 2000
```

<210> SEQ ID NO 33
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 33

```
caaaatgagt ttaagacgat ccttcccgag gcgccgcggt cactatagag agtgtctgag     60
gctgggctcc taccgcctgg ccttttggtg tctttggatc actggctatc tactcggggt    120
ctgtcactcc cgtgatcgcc taccttccag ggagacctag ggagggaga ccccaagacc     180 tgtcccaggt gaggccactt ggtcggcacc cggggctgca gcacggcgc ccgcgtccgc     240 cctcgcccct taggctttcc attcgcgggc gaccccggtc gggccacctt agaatcgact    300
accctgcctg cctgactggt ctcgggctac aaactgtgtg gaagcgtagg tatctcactt    360
aactgctacc ccaaattcgg atttacaaac gactacgcag tcccgaatgc ccaacgcctt    420
ccctaaaccc agagataaat ctgggggaaa attcctcgcg gagcggaaaa caacgccagc    480
gtctaaagcg ttctgccccg agctggagtg gttcaaaaga caatgatctc aaaagaaagt    540
gattgttttg gtaatcccgg gaacagcttg caaggggag atttgggtct tcctttagta     600
acggaaagtc aatgcgcagc ctcctgtaat tatccttatc ggaagcccct tgtttaatct    660
gcatgtttag cggaggcccc actcgaacgc gcagcgagtg ggagacccac tttgcagggc    720
ccaggctcgg gctccggtcc ctgcgtgcgc gcaggcagcc gcgccgggtt cccgcggagc    780
```

```
tcaggcgttt gctcctccct cgctgcggga cctcggactg taggaccctc agggagtggg    840
actgaggaga tctgcttccg gggttctggg attgggaagc gggggacgca gggctccgag    900
cgatgagggc tggttgggtt caaagcgcga accagtagtt acttacccac gtgcttgggg    960
ccaactttag cgaatatcag agtttcactg attattcaaa gaatcaggct ttctttgaat   1020
aatcgtgaaa ttggacaata aattgtaagc cccgatgaaa aggtgtgctt tccagtagac   1080
agactctatt ttatttcaat ttacctccct ccactcctcc ccaatttagg gttgctggat   1140
aaaatactga tacatactcc tacaaaaaaa aaagccctc ctttttatc tgaaatcaca    1200 tttcactgag ccgacagtgt tttgttggtt aaacctggta ccctgcccgt ctcagccccg   1260
ggcagtccac tcctctctct gcttctctcc cttccccag ctcttgtgag tctgccaccc    1320
cctacagttc agcccgtgga gtgttgggga tggacctggg ggtggatttg gatgaggta    1380 gaatgaccat ggattaaagg gatggaggta ggatgaccat ggattaaata cacggttttc   1440 attccttttcc ccttggggat tttcagagaa ggccttctta caggaaggcc ttcgtggcac   1500
cggcggcgga ggtggagggc tggctgggga catatatggg gtagccatcg gggtgtggtt   1560
gggaatgggg tcctaggtct taataggcag ttgggtcgca tcaaagaagc ttcagggcag   1620
ctgggagtgg ggcctccacc cagagagtct ggaaggaagg agaaggccac gccaggatgt   1680
agaacttgcg acttttcgag ggacaggcag acagcggagt cactgtccct taccttcttt   1740
cctcccctcc ctcctagaat gggggtgggg tgggtgggg tgggctggac agaagagagg    1800
aggagaagga ggtgactgag gggactgcag ctgggtgggc ggtaaccgag gggagggaa    1860 ctggtggcgt ccccatctcg cggggtccgg aacggcgacg cgcccgcgcc cagctgattg   1920
gagcccttca ggcctcccgc gcccgaccgg cagcccaatc ctataaagct tcctctaagc   1980
tgggccctcc gcaaacggga                                              2000

<210> SEQ ID NO 34
<211> LENGTH: 4000
<212> TYPE: DNA
<213> ORGANISM: Artificial Sequence
<220> FEATURE:
<223> OTHER INFORMATION: Synthetic Construct

<400> SEQUENCE: 34
ttgtgataag caatccttgt aaaggtggtg gtggggggag gtggagagcc acataaacat      60
taatgctaat aaattagttt actcgactac agagtaatta cttcatatta ttgatattta    120
cagcaggtat tcaaatgcaa tggtaggcca ttatttggag aaaatacata ataagaatat    180
ttcttttcca gtgcaataca cgattagatt tgttattgag tcagttacag tcagctcagc    240
aataaataaa taaatcgatg ttgacactta aataccaaag atcttagagt ttatactcta    300
aatctcccca agatatgtaa ataactttgg ctatttcctg gagagggaaa aacaaaaggt    360
tatcttttta catatttttt tattttcctt cagcaacatc ccagatcctt ccaagaagag    420
agttgttggg aggcctcagg tctgggccct tctcagctcc tggctctgcc tggctgctct    480
gtgctctgtg tcctctcctt tctttcgctt cctccaaaca ttgctccttc aatcctgcag    540 gatgggagc atattttgcc ttcttaattt attttttttc ctcttctcaa gaaagctaga    600
ctcagagtat tgctatggcc tctctctatc cttagcacaa acctagcttt ttaaagacat    660
ccctgtttcc ccaggtgcag ggagttcggg aagcacctct ccttctctg gtattgtatt    720 cctcctgtgg aatgagcagt aggaaaggca cagagctctc tgagtttttg ccctgcacat    780
```

```
cccttgcttt cactctcaca cattgcaagg aaggagagta ggagagtagg tgggttaccc      840 cttttctcagc cacctctcct tggccctcag cccgtcctttt ccacctccat tctccccaca    900
cccctggagc tctgtaagca gcctgatggg ccccccacga agatgcagca tacccaggag      960
aagtctcctc ggatgtcagc gcctctaaag cagcccaagg cttgcctcaa ttgcatggtt     1020
tcccgagtcc tcagctccag aagaccaggc agatgggtgg accggtgagc agcagggcag    1080
cccctgtgcc tctgtctctg ccgagtcact ccgaagcccg gcaggcagcg aggaggaggg    1140
agtttctcca aggacagaag gtgggatgaa gaggtaggca gggaagatga ggggagaggt    1200
ggatcccggg taagacgaag gcccttccgg gccctgcgga tcagtgacaa accgcgggga    1260
gaagccgttc tggctgttgg cggtttaggg acggaaggca ctaaagcgct cggaagtga     1320 ccatgaatga gagagtgtaa tcaagtcacc gtgcaaatcg acaagccac caggcaggca    1380 catccacggc ttcaaactct ggccccgaag gggttccggc tagggtcgga ggcagaggcg    1440
cttcccagag caagtctatg ggaggggac tgcgaagaag gggtgcaaa tgcgagactc    1500 caggagaaca gactccgaga ccacaggcca cacagcgacg gactcccacc tggctatccc    1560
cagtccaggg catccctcac ccacccgggg agctgcgggt gggaggtggg gacgagagtt    1620
gagctctcac cgccctctgc acactcgaga acgaggaccc tgcaattgag cacaagcatg    1680
ctgcatgggg gcgcacccca gcctctccgc gcgcgccggg aggccccccca gccaacatga   1740 gttacaccgg cgattacgtg cttttcggtga gaacaccgag tgacgatctg ttgcttcccc    1800
tgaggtggct acaaagaaag gaagccggga gggaggggag aggaggaaaa aaaaaaaagg    1860
aaaggggggg ggaaaaggcc cggactagct agcagcttgt caatttcaac atcgggtcac    1920
atgaccagca cctccctgct aaggatgggg atagatttcc acgtcagctt acgtctccaa    1980 atttctacttt cacggatccg ttgtgataag caatccttgt aaaggtggtg gtgggggggag  2040 gtggagagcc acataaacat taatgctaat aaattagttt actcgactac agagtaatta    2100
cttcatatta ttgatattta cagcaggtat tcaaatgcaa tggtaggcca ttatttggag     2160
aaaatacata ataagaatat ttcttttcca gtgcaataca cgattagatt tgttattgag    2220
tcagttacag tcagctcagc aataaataaa taaatcgatg ttgacactta aataccaaag    2280
atcttagagt ttatactcta aatctccccca agatatgtaa ataactttgg ctatttcctg    2340
gagagggaaa aacaaaaggt tatcttttta catattttttt tatttcctt cagcaacatc     2400 ccagatcctt ccaagaagag agttgttggg aggcctcagg tctgggccct tctcagctcc    2460
tggctctgcc tggctgctct gtgctctgtg tcctctcctt tctttcgctt cctccaaaca    2520
ttgctccttc aatcctgcag gatggggagc atattttgcc ttcttaattt attttttttc    2580
ctcttctcaa gaaagctaga ctcagagtat tgctatggcc tctctctatc cttagcacaa    2640
acctagcttt ttaaagacat ccctgtttcc ccaggtgcag ggagttcggg aagcacctct    2700
cctttctctg gtattgtatt cctcctgtgg aatgagcagt aggaaaggca cagagctctc    2760
tgagtttttg ccctgcacat cccttgcttt cactctcaca cattgcaagg aaggagagta    2820
ggagagtagg tgggttaccc cttttctcagc cacctctcct tggccctcag cccgtcctttt  2880 ccacctccat tctccccaca cccctggagc tctgtaagca gcctgatggg ccccccacga    2940
agatgcagca tacccaggag aagtctcctc ggatgtcagc gcctctaaag cagcccaagg    3000
cttgcctcaa ttgcatggtt tcccgagtcc tcagctccag aagaccaggc agatgggtgg    3060
accggtgagc agcagggcag cccctgtgcc tctgtctctg ccgagtcact ccgaagcccg    3120
gcaggcagcg aggaggaggg agtttctcca aggacagaag gtgggatgaa gaggtaggca    3180
```

| | | |
|---|---|---|
| gggaagatga ggggagaggt ggatcccggg taagacgaag gcccttccgg gccctgcgga | 3240 | |
| tcagtgacaa accgcgggga gaagccgttc tggctgttgg cggtttaggg acggaaggca | 3300 | |
| ctaaagcgct tcggaagtga ccatgaatga gagagtgtaa tcaagtcacc gtgcaaatcg | 3360 | |
| gacaagccac caggcaggca catccacggc ttcaaactct ggccccgaag gggttccggc | 3420 | |
| tagggtcgga ggcagaggcg cttcccagag caagtctatg ggaggggac tgcgaagaag | 3480 | |
| ggggtgcaaa tgcgagactc caggagaaca gactccgaga ccacaggcca cacagcgacg | 3540 | |
| gactcccacc tggctatccc cagtccaggg catccctcac ccacccgggg agctgcgggt | 3600 | |
| gggaggtggg gacgagagtt gagctctcac cgccctctgc acactcgaga acgaggaccc | 3660 | |
| tgcaattgag cacaagcatg ctgcatgggg gcgcacccca gcctctccgc gcgcgccggg | 3720 | |
| aggccccca gccaacatga gttacaccgg cgattacgtg ctttcggtga aacaccgag | 3780 | |
| tgacgatctg ttgcttcccc tgaggtggct acaaagaaag gaagccggga gggaggggag | 3840 | |
| aggaggaaaa aaaaaaagg aaggggggg ggaaaaggcc cggactagct agcagcttgt | 3900 | |
| caatttcaac atcgggtcac atgaccagca cctccctgct aaggatgggg atagatttcc | 3960 | |
| acgtcagctt acgtctccaa atttctactt cacggatccg | 4000 | |

<210> SEQ ID NO 35
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 35

| | | |
|---|---|---|
| agcttcattg ttgcctgctt ctaaagataa atggctttgc ttttcagaa gggattgggc | 60 | |
| ccaggaaaac tgcctctctg ggagtcgagt ggggtgtgtg tgtgtgtttt cttataaaat | 120 | |
| gtttcaagca tgttttcggt gggacagttg catcctgagg cccagccata aggctttgtc | 180 | |
| ttgtttttct ctgaatggct gggcttgcca aggagagata gaccctggga gcgaaacagc | 240 | |
| tggcggtgcc tcagcccctc tttcctccca aggaagcgca ttgttattaa ctgggaattc | 300 | |
| tttatagccg ggctggagga agttttggct gtaaactgtc atgcactgca gccttcgctg | 360 | |
| aaaaggcgga gggagtgggc ctggtcctgg gaaccgagga acaaagatca gaaaatcagc | 420 | |
| cacagaaagg ggaggaaaaa taacgttag aaagtgaaga caggtgacac tacacaagtg | 480 | |
| ctggccaaag tcggtgactt ccaacctcta cctcctccga cttgggtggt tcaattcctg | 540 | |
| ggtcgtactc ttcaatgctt cagacattct ctctggagag tagaaatttt attacgcgtg | 600 | |
| ttagaaacgg aatattcttt cctgctgaag ttgtattctt atttggccgt gccctcctg | 660 | |
| ttcgaacag ttttagagcg atctgttaaa ccctccagtc ttctttggcg cttcccgact | 720 | |
| gtgggaaaag cggccgcgac gccgtccgag cgcaggggag ggatccagcc ttcgggactc | 780 | |
| cttttgccctg aagccgcagg agaggtttcg ctcccgtgcc tagggttccg aggccctcaa | 840 | |
| ttgcctggga cccaccctcg ttcctccttc acctccctc cacttttccc ttttatctta | 900 | |
| tcctcgggag gccttgggcc aaagcgatga cctcttagac attttaatac ccggagtaag | 960 | |
| gagagtaaca cgcaccacgc tctccccaa agccaggac ccgatgagcc agtgaaggcg | 1020 | |
| tgtcaggagg gtccggcgtc aggagcaaat gaggtccttt tggtgcctct ttctagaagg | 1080 | |
| aaacttcccc acctcgggtc agcccctgg gaatatccat gcatcccaga catcaaaaga | 1140 | |
| cactgagaaa tgcggacagg gactagacgc tccggcttcc tgactcgtcg gtgtaagttg | 1200 | |

```
gagaagggag agaaggagcc ctgtccccca cgggcggcag gcacccttcc ccgggactgg    1260
ctcctggcag ccctccgcat accgcgaggc gggtcgatcc ctcgagtccc gggcggggat    1320
ccctccttcg gcttccccag caattcccga ccccggagcg agcccggctg ggcgaggggc    1380
gaggggcagg gggcagggg cagggagac ttagcgcggg gcgcagatac catgtccgcg    1440
ggaaagcccc cttgctaggg cgcaagactc ctctgaactc gctgcccac ccgatgcgca    1500 ggctttctct agaggggttg gggctggggt gcccgctcag gagaccggga aacagaggct    1560
gctacccgag gcaggccctc gtccagcgaa tgggcgaggt gtgcagaagc gcaaagccag    1620
gccttggaag ggggagcttc tgcctccttc ccccttcctg ggctcccgtt ttaggaggaa    1680
tgttactgtt taaagagacc ccactgaact atttcctgct cattgtcacc tctccttcgc    1740
tctcctcgcg taagttctca ccgaaaggta ataaaacaac cgctgccgac accgcttggc    1800
gctgggccgg gcggggaaag cgccccgagt cccactagtc cggaccaccc cgccagcccc    1860
gaccttctcc caccttccgt gaaagcaatg acacagcaga aaccacgcac acgcctggca    1920
cactcgatgc gcgcgctgac ctcggcaaca agtcctgttt ttataagaga gcgaggagga    1980
cacttctcag aagggggttgt                                               2000

<210> SEQ ID NO 36
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 36
ataataacag ccagtattct tcccacatac ttccggtcaa agtggggaa accagaaacc     60 gaataaaaca ttgggaagag acatactgtg ttcctggaaa aaatataaca gagccagatt   120
taactcggtg agagggaaag tgacccccctt gagaaaccag ggaatgtctc accctcagac   180 caacccttc ttttgcaaat tgaattggtc aaagtttagt tttgtcatca tttctattgt    240
tataattctt attcatttc ccagccccgt ccacacttct attttttcact accccccacgc   300 cccacaagtt gccaccgggt caggtgggga catatccgga gagaaataga aagggatgca   360
ttttaaagcg agttctcttt tgagaggaaa acaatgggta gttttggaag tgtctttctt   420
aaaaacggaa ggagaaggtg aagaaaaaaa ttatcaacag caatgggccc ctttggtttg   480
ggttttgact ttttaaagag gaacctctgc tgtcctgttg cagtattaaa atcagggcag   540
gaattttgca aaatgagaaa aataaacttc gggagaaaac ccagctggga gcagcttcgg   600
gaaagcgaca gttctccgaa aggaggaagg gaggatgcgc gctgtagccg gctccggagt   660
ttactgcccg aacgattggg gaaaagaacg aggattctca aatctagttg cgatctctcg   720
tctctccttt attctgttcg tggtgcgggc ttcggagcgt ctgggaaagc cagtctgtga   780
agctggactt gcagaatcct ttgaatgccg gtccaggtgg ctgcagggcc cgcagtccgg   840
gatgccggag aaaggaacca caaggaaaag acgctacgct cggagtttcc ccttttcctt   900
gcagccccgg cggggcctag gcctcggttt ccggcccacc tcggctcaga ggtcaagtag   960
gaactcatct cgtcgaccta gggtttggga gaaggatttc gggttgcgtt cttggcatct  1020
gggagcaaac acgagcctcg gatttgggga catatcgtta ttaacagctt gggaaacgaa  1080
agcgaagctc ggggcagcca ctgcagcctg gctgagagaa aggacgcggg ttgtgctctc  1140
tggaagcaaa ggggtctgcg gcccagctgg cctgggagct tgtggccggc gctgaaagct  1200
gcccgctctc cccgcgggcc tgaccttggc tcccgccgca gctctgccgg ccgactgcct  1260
```

```
ccctgcacat tttgctgccg ttccagtcct tacaggaccg ggcctggagc caggccatgc    1320
ttcggaaagc cctggggagtt ggggacgcgc aaaacccaga atcgaacccc gaagctgggg    1380
gcaagtccag attcagacgt ccagctccct cgggacccct tggcggagaa cttacccttc    1440
cggaaggccc gacgctctcc ggctctgtgc tgggcaggcc tagctcttct ctcggcgcca    1500
ccaggggcgt ctacgcggta cgttttgcaa ctcaacctag tgggtttcca gcggtgcgca    1560
aaagtttgcg agcatccacc actgcgctgc ttagaaattg tgcccattga tcagactaaa    1620
aataatagtc gtcgtgatta caaaacaaaa tagagtgcct cgtgcctcgg cgggccctgg    1680
tacaataatt attctctaca gaaccacct ctctccactc ccaccctac tccaccaccc    1740 actcgcaccc cgcccctgcc gggccactct gggacgaatt gcattcttgg acctttctct    1800
ccgcaaggca cattacggag aactccctct gtctcgtgtc cctccacga caacccagta    1860 attatttcta tgcaagtctg caagagggca ctgagttatc gcatcccaag cctaaccagc    1920
tagagcggcg cctcggtatt catttgccca gagctcctcc gcggggatt taaaaataat    1980 aataataata ataaggatcc                                                2000

<210> SEQ ID NO 37
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 37
agcgactgta gaaatcagcc ctttgcagag ggcgcagagg gcctggaaac ctctgggacc      60
ttttcccagg aactgtttat ggtttccccc taggtctagg agacatagat gcataggtgg     120
attggataca tcgatggtag ctataaggta agcagacaat ggtcacagat ggaaaggtgg     180
acggacggat gacggatggt tagaagatgt tttgagggct tgctatagtg ccaggcacaa     240
ggctaagaga tttcgtccac tatttcattt gattctctcc agaaccttat gaatggcata     300
ttacctctgt tcctattttt caaatagga aactgaggcc tcaggcaatg taagcagctt     360
gccgcttagc aatcttttgc agagccagga agcgggaaag cgtgtcttaa tggacagtac     420
cagcctccac agtgtgccct cggccccctc ccggtggaga agaggttcca gccccggcg     480 tcccgggtag ggtgtccctc atccctcct ccccaccaca ctcctggcgc gctgacatta     540 caccccgcccc ggcacccccc tctcactgat ccaacacccc cggacaccct ggacagcgct     600
ctcaaggcag taggtcttcg acttgggagc cccggggagc tggttaaaca cggatcctct     660
cccacagtgg ctgaaaagcg cgcagtcccg gaacctgagg gtttacctgc ttctacgctt     720
ggccaagggt ctctaactgg aaaggtgaaa attctgtcct gagattttaa gattcccaga     780
aactttcaat cgttcagttc ctgtaaccat taattgagcg cctaaactgc gcaccttgac     840
gctgttagat gctgcagtaa ggaactcgga gtcaagtgtg ggggacaggt tggtcaataa     900
atgacgacat tccggacggc tgtgcttggt gcccacgggg acccgcgagg gggcccaggg     960
aggaggcggg aaaggggcag gttcaccggc ccgctgggtc tccagcacat tccagaagtc    1020
taagccagtc catctatcct tccaaacgcc cccacctcgc ttccctccct ggagcccgca    1080
tcccacggtg caatttcagt gactttatgc ggagaaactt gatcctatct cactctcccc    1140
aaacttccta actgccttgg gtttgtcacc tggccgtgtg gggagccacc gagcgccccc    1200
tgtggccccc acccgagctc ggcgggggga gcggcgcgcg ggtgctgggg gaccgacccc    1260
```

```
tcccgcgaag gcgtcggcgc ggggctggcg tagggcctgc gtcagctgca gcccgccggc   1320
gattggggcg cgcgcgcctc cttcggtttg gggctaatta taaagtggct ccagcagccg   1380
ttaagccccg ggacggcgag gcaggcgctc agagcccgc agcctggccc gtgaccccgc    1440
agagacgctg aggaccgcga cggtgaggcc ctacgtccgc cagcacaccc gggcccgctt   1500
ctccccgacg cccgccctcc tcacacttgc cttcttctct tccctctaga gtcgtgtctg   1560
aacccggctt ttccaattgg cctgctccat ccgaacagcg tcaacgtgag tgaatttgcc   1620
cgaagcttgt ctttgctgag cgggtttggg gacgtctgcc cgccctcttt cccttcacat   1680
ttcattgcat gggttcccca acagcgttcc ctggttcttc tttgtgaccc cagtcaatgt   1740
cctgcctccc ccggctcccg ctctctcgcc cctggtctgc ggcgttctct ccggaatctt   1800
gccctgggcc gcggacgccc aggaaaagag ccgggtgccc caggcagcct cgcgttgggg   1860
gcgaccgcgc catcccggga accgcgaggc gatctgagtc gcctccacgt ctacctaaaa   1920
gctgtcggcc gggagggcgg ggccccagaa aggagcattc ctgcgggctt ttgctcgacg   1980
atcccctgct gaggctgtcg                                               2000

<210> SEQ ID NO 38
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 38
gtatacttca gagagaagac tgaaacttct agagactgtt tctagcatcc ttaagtaact     60
gcagacactt ataatactga atgatatcct agttataaat aattcttatc cataacttaa    120
atccatcttg aggctctact aagtaaatct tccttaacct acttagagga tgtgcagtag    180
cgatgaaagt agcctttctt ttcttttttt tttttttttt ttttgagacg gagtctcgct    240
ctgtcgccag gctggagtac agtggcgcga tctcggctca ctgtaacctc ctccgcctcc    300
tgggttccag cgattctcct gcctcagcct cccgagtagc tgggactaca ggcgtgcgcc    360
accactccca cataattttt tgtattttta gtagagacgg ggtttcaccg tgttggccag    420
gatggtctca atctcttga cctcgtgatc tgtgtgctgg gagtacaggc gtgagccacc     480
gcgcccggcc ttaagcccct ttctttaagg ctcaagggca tattttcaca ctgcagtgca    540
tcacaaccgt tttcattctt ccagtgttcc tttcttctgg tctccagcca cctgccaggt    600
acttctgatt aattacatat aagatttatc caagccaccc cctccgtttc taccaactgg    660
acttcattct cttcagttcc tgctagaatg cacctcctac ctgaagtctt ccctcatcaa    720
tgccctccat gatcagcctt tgactctgga atcccttaat atattcctca gatcattaga    780
ggttttctga gtcatcatct gagattttc attaaattgt ggagtttgag cagccagtcc     840
tgagctgtcg gactcagttc caaatagaag tcctagttaa agacacaaaa acaagaagat    900
gggttagctg cggctcgaag agctggtgag cgcgaccaca gggcagcttg cggacggttc    960
tttcggacag gacaagggcg agggaaacgg cagaatggtg acgcacctga gtgcgcccac   1020
tagacgaaag aagaccaact aagccttcgt gtagtgcgta gacaggccga cacacacaca   1080
cacacacaca cacacacact aacacacacg caaagacagt gagggagcga gaggcgcatc   1140
cccaggtagc tgacaatgac acggcccga tccggacgcg ggcttaaagc ccccgactt      1200 ccggagtgcc cccctccccg gcgacctccg gagattaccg ctggcgcatc tctccgccct   1260
gcccggctcc ggcgccctcc cctcccccg cagccgcagc tccccgcccc ccgcgaacgc     1320
```

```
ggctccccag tgtcctccag aacgcccgcg tggctgtcgg gtttcgaacc ccagggccga   1380
ctctagtact cggcgcgcgc gccgccgcgt cgccgaccag cctgcggccc ccgcatcaat   1440
cattaacggg gcggcccggg ctgcggcggc ccgaggaggg ggatggtacg gaactcgaga   1500
caggggacaa ctctatcccc cgaagcggcc gcgaaaccct agcctgggag ccccccgccc   1560
ttcctcggtg cgcccgtccc tccctccgcg cctcggctcg cacatcccca cctcccgctc   1620 cggggcggc ggcggcggag gcacccgcac cgcgcgatgc ccagtcaccg ctgccgcgct   1680
gccgccgcag tcagccgcgc cgccgccgct gccgcagcgc gggcggccgc gcgccggtag   1740
caggggcttg gcgaggaagc cgctgagcct cgcgcgctcc gcgctcctgg cggtcgcagc   1800
gctgcctatt aattgattct cttattgatt tatttaattt ttaggagcgg ctgctcggag   1860
gcacgggtct tctcctaaac ctgcagcgac gcccccggcg tgggcacaaa ggctccgacg   1920
gcggccggcg ggggctgccc agcgcccggg agccggcgcc agaggtcgcc tgcgcgcgcc   1980
ctagccgagc cccgggcacc                                               2000
```

<210> SEQ ID NO 39  
<211> LENGTH: 1000  
<212> TYPE: DNA  
<213> ORGANISM: Artificial Sequence  
<220> FEATURE:  
<223> OTHER INFORMATION: Synthetic Construct

<400> SEQUENCE: 39

```
ttcatcttaa agaatctgag ttgaatagag agggaaatga ggggcgggtg ttcgctccaa     60
cgaaatcgct tggaggatca tggggcgtgt gtccctgtgt gcggaactgg gaggaaaacg    120
cagcccccag tttggtaaat ggtgaagcag cggtaggccg gtcggtggcg cggatttaag    180
atttgctgaa ggcactacca cagatgtagc tctctggaac ttccatccct cctctcctac    240
caccccccaa aaaagacaa aaccgagttc agaccggctc ccccaacacc aagccgcttc    300
tatttatcaa gtgggtcaac ttccactcgg aagcacctcg cggggctcgg ctccagggca    360
cctggtggct ggggagctgt attgttttcc tgggcacgga ggttcggcgc cggttttagg    420
attgtgcaaa aagagagtag aaggtacaga gatttatttc tgcttttttgc tgttcagccg    480 ccgtttgccc cagcgaggtg ggctggaggc tgaatttcaa gccttgttta acctctacaa    540
gagacaccct ccattcagcc atctcacttt ctctctggcc tccctctctc tttttttcct    600
ttccgttctc tccgtccttt ctctctatct ctgtctctgt gtgtgtcgtg tttgttcccg    660
tgccctcctc tccgaccttg gccggggctc ctagtcctga gagaaacggc gttcggtgcg    720
ccggcggtgg ctatgcggct ggctcttttcg gggctcccgg gactaggttg gggaaagagg    780
gcatctcccc ggcctctcgg ggcccagccc agtcttccta gatctggcgt ccgcccttcc    840
ctcccctccc gcactggcag gagagaaatg gccgcagtgt gggccgcggg gcagctagga    900
ctggaaagcg gggaccctgg agggtgcgat cgcggacggg gtgtgcgggc gcgggtcgtg    960
tgcgtgtgcg tgcagggttc cgaccacggg gacacgagct                          1000
```

<210> SEQ ID NO 40  
<211> LENGTH: 1000  
<212> TYPE: DNA  
<213> ORGANISM: Artificial Sequence  
<220> FEATURE:  
<223> OTHER INFORMATION: Synthetic Construct

<400> SEQUENCE: 40

```
gtggagggcg ttggaccttc ttccgcaatc gggaccactc caggtctccc cggagaaggc    60
tgagtctcca gcgcgtggat tcagatcagg actctgtcta agtaggcgag agctggggat   120
accgctgggg gctttggcga agctaagaaa gcactggctt cttattctca ccagacatct   180
caacacccac gtgcgctggg tcccgcagtc tctcgcccgc ccacgcgggt cccagccct    240 ggtccttact ccccgcgcgg gaagaatctg gggagggtgg gggcggagag gcggctgatc   300
ggagagtggg agggaggatg ggagatgggc agaggctgcc cgcatcaggg ccaggacaga   360
cgtccgcgcg gccccaggca ctcacttgag tgtcacgcaa gtcacccaa caccgcacaa    420 gacagtggcg gggtgcgcac cgaggcccct acctgggggg tgtgcgcgca ctgaacgacc   480
ccttctccag gtgcgcgagc cgctccggcg gccgtgcaca ctgcgccccc ttccgcccac   540
ctgcctggcc tgcgtttcta accacgcggg cggtcccgag acttcgcgca aaaggcagga   600
ccgcgactcc caataatgat atcttcgaaa taccccctg ctgagccggc gcccagggcc    660
gggggtagag tcccgagtcc cttttgcgga attaaggaga cctctggcga ccggggagcc   720 tgccccctgtg accgctccag cagccctgc cgcgtgcgtg cccgagtgtg gcccgcagct   780
cccaaagccc aggtgtgtgt ggcctagggc ggggagagtt ggcgacccgg gccatcacc    840 gccccagtgc caccgcccca gtgcctgacc agatggggtg cggtccctac gcccggcgtg   900
gccccgccgc cgctcagatc tgaagtccgg cttcgctcg ccctgcgcgg cggaacctct   960
gacccggagc agctctaggc cgtgggcttc gtctcctcct                        1000
```

```
<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
ttcttattct caccagacat ctcaacaccc                                      30

<210> SEQ ID NO 42
<211> LENGTH: 25
<212> TYPE: DNA
<213> ORGANISM: Artificial Sequence
<220> FEATURE:
<223> OTHER INFORMATION: Synthetic Construct

<400> SEQUENCE: 42
atctcccatc ctccctccca ctctc                                           25

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
ttgtaattat taat                                                       14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
```
ctcgcgaatc cccg                                                    14

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gttaataaat gacgatattt cggac                                        25

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
tgtaattatt aatt                                                    14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
ctcgcgaatc cccg                                                    14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
gtaattatta attg                                                    14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
ctcgcgaatc cccg                                                    14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
taattattaa ttga                                                    14

<210> SEQ ID NO 51
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 51
ctcgcgaatc cccg                                                        14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
aattattaat tgag                                                        14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
ctcgcgaatc cccg                                                        14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
attattaatt gagc                                                        14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
ctcgcgaatc cccg                                                        14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
ttattaattg agcg                                                        14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
ctcgcgaatc cccg                                                        14
```

```
<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
tattaattga gcgt                                                        14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
ctcgcgaatc cccg                                                        14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
attaattgag cgtt                                                        14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
ctcgcgaatc cccg                                                        14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
ttaattgagc gttt                                                        14

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
ctcgcgaatc cccg                                                        14

<210> SEQ ID NO 64
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 64
taattgagcg ttta                                                        14

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
ctcgcgaatc cccg                                                        14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
aattgagcgt ttaa                                                        14

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
ctcgcgaatc cccg                                                        14

<210> SEQ ID NO 68
<211> LENGTH: 14
<212> TYPE: DNA
<213> ORGANISM: Artificial Sequence
<220> FEATURE:
<223> OTHER INFORMATION: Synthetic Construct

<400> SEQUENCE: 68
attgagcgtt taaa                                                        14

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
ctcgcgaatc cccg                                                        14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
ttgagcgttt aaat                                                        14
```

```
<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
ctcgcgaatc cccg                                                        14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
tgagcgttta aatt                                                        14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
ctcgcgaatc cccg                                                        14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
gagcgtttaa attg                                                        14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
ctcgcgaatc cccg                                                        14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76 agcgttttaaa ttgc                                                       14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 77
ctcgcgaatc cccg                                                    14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
gcgtttaaat tgcg                                                    14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
ctcgcgaatc cccg                                                    14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
cgtttaaatt gcgt                                                    14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
ctcgcgaatc cccg                                                    14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
gtttaaattg cgta                                                    14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
ctcgcgaatc cccg                                                    14

<210> SEQ ID NO 84
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 84
tttaaattgc gtat                                                         14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
ctcgcgaatc cccg                                                         14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
ttaaattgcg tatt                                                         14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
ctcgcgaatc cccg                                                         14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
taaattgcgt attt                                                         14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
ctcgcgaatc cccg                                                         14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
```

-continued

```
aaattgcgta tttt                                                14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
ctcgcgaatc cccg                                                14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
aattgcgtat tttg                                                14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
ctcgcgaatc cccg                                                14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
attgcgtatt ttga                                                14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
ctcgcgaatc cccg                                                14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
ttgcgtattt tgac                                                14

<210> SEQ ID NO 97
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 97
ctcgcgaatc cccg                                                              14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
tgcgtatttt gacg                                                              14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
ctcgcgaatc cccg                                                              14

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
gcgtattttg acgt                                                              14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101
ctcgcgaatc cccg                                                              14

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102
cgtattttga cgtt                                                              14

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
ctcgcgaatc cccg                                                              14
```

```
<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
gtattttgac gttg                                                       14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
ctcgcgaatc cccg                                                       14

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
tattttgacg ttgt                                                       14

<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
ctcgcgaatc cccg                                                       14

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
attttgacgt tgtt                                                       14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
ctcgcgaatc cccg                                                       14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 110
ttttgacgtt gtta                                              14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
ctcgcgaatc cccg                                              14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
tttgacgttg ttag                                              14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
ctcgcgaatc cccg                                              14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114
ttgacgttgt taga                                              14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
ctcgcgaatc cccg                                              14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
tgacgttgtt agat                                              14

<210> SEQ ID NO 117
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
ctcgcgaatc cccg                                                       14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
gacgttgtta gatg                                                       14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
ctcgcgaatc cccg                                                       14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
acgttgttag atgt                                                       14

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
ctcgcgaatc cccg                                                       14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
cgttgttaga tgtt                                                       14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123
```
ctcgcgaatc cccg                                                         14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124
gttgttagat gttg                                                         14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
ctcgcgaatc cccg                                                         14

<210> SEQ ID NO 126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 126
ttgttagatg ttgt                                                         14

<210> SEQ ID NO 127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 127
ctcgcgaatc cccg                                                         14

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
tgttagatgt tgta                                                         14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
ctcgcgaatc cccg                                                         14

<210> SEQ ID NO 130
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 130
gttagatgtt gtag                                                        14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
ctcgcgaatc cccg                                                        14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
ttagatgttg tagt                                                        14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
ctcgcgaatc cccg                                                        14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
tagatgttgt agta                                                        14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
ctcgcgaatc cccg                                                        14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
agatgttgta gtaa                                                        14
```

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
ctcgcgaatc cccg                                                        14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
gatgttgtag taag                                                        14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
ctcgcgaatc cccg                                                        14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 140
atgttgtagt aagg                                                        14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
ctcgcgaatc cccg                                                        14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
tgttgtagta agga                                                        14

<210> SEQ ID NO 143
<211> LENGTH: 14
<212> TYPE: DNA
<213> ORGANISM: Artificial Sequence
<220> FEATURE:

<223> OTHER INFORMATION: Synthetic Construct

<400> SEQUENCE: 143
ctcgcgaatc cccg                                                          14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
gttgtagtaa ggaa                                                          14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
ctcgcgaatc cccg                                                          14

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
ttgtagtaag gaat                                                          14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
ctcgcgaatc cccg                                                          14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
tgtagtaagg aatt                                                          14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
ctcgcgaatc cccg                                                          14

```
<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150
gtagtaagga attc                                                        14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
ctcgcgaatc cccg                                                        14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152
tagtaaggaa ttcg                                                        14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
ctcgcgaatc cccg                                                        14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 154
agtaaggaat tcgg                                                        14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
ctcgcgaatc cccg                                                        14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 156
gtaaggaatt cgga                                                         14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
ctcgcgaatc cccg                                                         14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
taaggaattc ggag                                                         14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
ctcgcgaatc cccg                                                         14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
aaggaattcg gagt                                                         14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
ctcgcgaatc cccg                                                         14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
aggaattcgg agtt                                                         14

<210> SEQ ID NO 163
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 163
ctcgcgaatc cccg                                                         14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
ggaattcgga gtta                                                         14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
ctcgcgaatc cccg                                                         14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166
gaattcggag ttaa                                                         14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
ctcgcgaatc cccg                                                         14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
aattcggagt taag                                                         14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
```

```
ctcgcgaatc cccg                                                      14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
attcggagtt aagt                                                      14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
ctcgcgaatc cccg                                                      14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
ttcggagtta agtg                                                      14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
ctcgcgaatc cccg                                                      14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
tcggagttaa gtgt                                                      14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
ctcgcgaatc cccg                                                      14

<210> SEQ ID NO 176
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 176
cggagttaag tgtg                                                        14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
ctcgcgaatc cccg                                                        14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
ggagttaagt gtgg                                                        14

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
ctcgcgaatc cccg                                                        14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
gagttaagtg tggg                                                        14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
ctcgcgaatc cccg                                                        14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
agttaagtgt gggg                                                        14
```

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183
ctcgcgaatc cccg                                                      14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
gttaagtgtg gggg                                                      14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185
ctaaaaaccc aacg                                                      14

<210> SEQ ID NO 186
<211> LENGTH: 25
<212> TYPE: DNA
<213> ORGANISM: Artificial Sequence
<220> FEATURE:
<223> OTHER INFORMATION: Synthetic Construct

<400> SEQUENCE: 186
attcgcgagg gggtttaggg aggag                                          25

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187
ttaagtgtgg ggga                                                      14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188
ctaaaaaccc aacg                                                      14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 189
taagtgtggg ggat                                                    14

<210> SEQ ID NO 190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 190
ctaaaaaccc aacg                                                    14

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
aagtgtgggg gata                                                    14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
ctaaaaaccc aacg                                                    14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
agtgtggggg atag                                                    14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
ctaaaaaccc aacg                                                    14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
gtgtggggga tagg                                                    14

<210> SEQ ID NO 196
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
ctaaaaaccc aacg                                                         14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
tgtgggggat aggt                                                         14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
ctaaaaaccc aacg                                                         14

<210> SEQ ID NO 199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199
gtgggggata ggtt                                                         14

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
ctaaaaaccc aacg                                                         14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201
tgggggatag gttg                                                         14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
```

```
ctaaaaaccc aacg                                                      14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
gggggatagg ttgg                                                      14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
ctaaaaaccc aacg                                                      14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
ggggataggt tggt                                                      14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
ctaaaaaccc aacg                                                      14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
gggataggtt ggtt                                                      14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
ctaaaaaccc aacg                                                      14

<210> SEQ ID NO 209
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 209
ggataggttg gtta                                                         14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210 ctaaaaccc aacg                                                          14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
gataggttgg ttaa                                                         14

<210> SEQ ID NO 212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 212 ctaaaaccc aacg                                                          14

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
ataggttggt taat                                                         14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214 ctaaaaccc aacg                                                          14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
taggttggtt aata                                                         14
```

```
<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
ctaaaaaccc aacg                                                       14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
aggttggtta ataa                                                       14

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
ctaaaaaccc aacg                                                       14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
ggttggttaa taaa                                                       14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220
ctaaaaaccc aacg                                                       14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
gttggttaat aaat                                                       14

<210> SEQ ID NO 222
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 222
ctaaaaaccc aacg                                                          14

<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223
ttggttaata aatg                                                          14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
ctaaaaaccc aacg                                                          14

<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
tggttaataa atga                                                          14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
ctaaaaaccc aacg                                                          14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
ggttaataaa tgac                                                          14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
ctaaaaaccc aacg                                                          14

```
<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
gttaataaat gacg                                                        14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
ctaaaaaccc aacg                                                        14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
ttaataaatg acga                                                        14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
ctaaaaaccc aacg                                                        14

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 233
taataaatga cgat                                                        14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
ctaaaaaccc aacg                                                        14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 235
aataaatgac gata                                                14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
ctaaaaaccc aacg                                                14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
ataaatgacg atat                                                14

<210> SEQ ID NO 238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 238
ctaaaaaccc aacg                                                14

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
taaatgacga tatt                                                14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
ctaaaaaccc aacg                                                14

<210> SEQ ID NO 241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
aaatgacgat attt                                                14

<210> SEQ ID NO 242
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 242
ctaaaaaccc aacg                                                       14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
aatgacgata tttc                                                       14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
ctaaaaaccc aacg                                                       14

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245
atgacgatat ttcg                                                       14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
ctaaaaaccc aacg                                                       14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247
tgacgatatt tcgg                                                       14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
```

```
ctaaaaaccc aacg                                                          14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249
gacgatattt cgga                                                          14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
ctaaaaaccc aacg                                                          14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251
acgatatttc ggac                                                          14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
ctaaaaaccc aacg                                                          14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
cgatatttcg gacg                                                          14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
ctaaaaaccc aacg                                                          14

<210> SEQ ID NO 255
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 255
gatatttcgg acgg                                                         14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
ctaaaaaccc aacg                                                         14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
atatttcgga cggt                                                         14

<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
ctaaaaaccc aacg                                                         14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
tatttcggac ggtt                                                         14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
ctaaaaaccc aacg                                                         14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
atttcggacg gttg                                                         14
```

```
<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
ctaaaaaccc aacg                                                      14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
tttcggacgg ttgt                                                      14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264
ctaaaaaccc aacg                                                      14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
ttcggacggt tgtg                                                      14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
ctaaaaaccc aacg                                                      14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267
tcggacggtt gtgt                                                      14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 268
ctaaaaaccc aacg                                                    14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
cggacggttg tgtt                                                    14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
ctaaaaaccc aacg                                                    14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
ggacggttgt gttt                                                    14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
ctaaaaaccc aacg                                                    14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
gacggttgtg tttg                                                    14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
ctaaaaaccc aacg                                                    14

<210> SEQ ID NO 275

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
acggttgtgt ttgg                                                      14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
ctaaaaaccc aacg                                                      14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277
cggttgtgtt tggt                                                      14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
ctaaaaaccc aacg                                                      14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279
ggttgtgttt ggtg                                                      14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280 ctaaaaccc aacg                                                       14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
```

```
gttgtgtttg gtgt                                                        14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
ctaaaaaccc aacg                                                        14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
ttgtgtttgg tgtt                                                        14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
ctaaaaaccc aacg                                                        14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
tgtgtttggt gttt                                                        14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
ctaaaaaccc aacg                                                        14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
gtgtttggtg ttta                                                        14

<210> SEQ ID NO 288
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 288
ctaaaaaccc aacg                                                    14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
tgtttggtgt ttac                                                    14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
ctaaaaaccc aacg                                                    14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
gtttggtgtt tacg                                                    14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
ctaaaaaccc aacg                                                    14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
tttggtgttt acgg                                                    14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
ctaaaaaccc aacg                                                    14
```

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
ttggtgttta cggg                                                      14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
ctaaaaaccc aacg                                                      14

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
tggtgtttac gggg                                                      14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
acgaaataaa aacg                                                      14

<210> SEQ ID NO 299
<211> LENGTH: 25
<212> TYPE: DNA
<213> ORGANISM: Artificial Sequence
<220> FEATURE:
<223> OTHER INFORMATION: Synthetic Construct

<400> SEQUENCE: 299
gggaaagggg taggtttatc ggttc                                          25

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300
ggtgtttacg ggga                                                      14

<210> SEQ ID NO 301
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 301
acgaaataaa aacg                                                    14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
gtgtttacgg ggat                                                    14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
acgaaataaa aacg                                                    14

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
tgtttacggg gatt                                                    14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
acgaaataaa aacg                                                    14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
gtttacgggg attc                                                    14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
acgaaataaa aacg                                                    14
```

```
<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
tttacgggga ttcg                                                        14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
acgaaataaa aacg                                                        14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
ttacggggat tcgc                                                        14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
acgaaataaa aacg                                                        14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
tacggggatt cgcg                                                        14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
acgaaataaa aacg                                                        14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 314
acggggattc gcga                                              14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
acgaaataaa aacg                                              14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
cggggattcg cgag                                              14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
acgaaataaa aacg                                              14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
ggggattcgc gagg                                              14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
acgaaataaa aacg                                              14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
gggattcgcg aggg                                              14

<210> SEQ ID NO 321
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 321
acgaaataaa aacg                                                         14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
ggattcgcga gggg                                                         14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
acgaaataaa aacg                                                         14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
gattcgcgag gggg                                                         14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325
acgaaataaa aacg                                                         14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
attcgcgagg gggt                                                         14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
```
acgaaataaa aacg                                                      14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
ttcgcgaggg ggtt                                                      14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
acgaaataaa aacg                                                      14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
tcgcgagggg gttt                                                      14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
acgaaataaa aacg                                                      14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
cgcgaggggg ttta                                                      14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
acgaaataaa aacg                                                      14

<210> SEQ ID NO 334
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 334
gcgagggggt ttag                                                         14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
acgaaataaa aacg                                                         14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336 cgaggggtt tagg                                                          14

<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
acgaaataaa aacg                                                         14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338 gaggggttt aggg                                                          14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
acgaaataaa aacg                                                         14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
gtttgttatt tggt                                                         14
```

```
<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341
acgcaaaccc tacg                                                        14

<210> SEQ ID NO 342
<211> LENGTH: 25
<212> TYPE: DNA
<213> ORGANISM: Artificial Sequence
<220> FEATURE:
<223> OTHER INFORMATION: Synthetic Construct

<400> SEQUENCE: 342
atttttttcg cgaaggcgtc ggcgc                                            25

<210> SEQ ID NO 343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 343
tttgttattt ggtc                                                        14

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
acgcaaaccc tacg                                                        14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345
ttgttatttg gtcg                                                        14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
acgcaaaccc tacg                                                        14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 347
tgttatttgg tcgt                                              14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
acgcaaaccc tacg                                              14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
gttatttggt cgtg                                              14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
acgcaaaccc tacg                                              14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351
ttatttggtc gtgt                                              14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
acgcaaaccc tacg                                              14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
tatttggtcg tgtg                                              14

<210> SEQ ID NO 354

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
acgcaaaccc tacg                                                        14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
atttggtcgt gtgg                                                        14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
acgcaaaccc tacg                                                        14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
tttggtcgtg tggg                                                        14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
acgcaaaccc tacg                                                        14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
ttggtcgtgt gggg                                                        14

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
```
acgcaaaccc tacg                                                        14

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361
tggtcgtgtg ggga                                                        14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
acgcaaaccc tacg                                                        14

<210> SEQ ID NO 363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 363
ggtcgtgtgg ggag                                                        14

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364
acgcaaaccc tacg                                                        14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
gtcgtgtggg gagt                                                        14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366
acgcaaaccc tacg                                                        14

<210> SEQ ID NO 367
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 367
tcgtgtgggg agtt                                                         14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
acgcaaaccc tacg                                                         14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
cgtgtgggga gtta                                                         14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
acgcaaaccc tacg                                                         14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
gtgtggggag ttat                                                         14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
acgcaaaccc tacg                                                         14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
tgtggggagt tatc                                                         14
```

```
<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374
acgcaaaccc tacg                                                        14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
gtggggagtt atcg                                                        14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
acgcaaaccc tacg                                                        14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
tggggagtta tcga                                                        14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
acgcaaaccc tacg                                                        14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
ggggagttat cgag                                                        14

<210> SEQ ID NO 380
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 380
acgcaaaccc tacg                    14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
gggagttatc gagc                    14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
acgcaaaccc tacg                    14

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
ggagttatcg agcg                    14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
acgcaaaccc tacg                    14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
gagttatcga gcgt                    14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
acgcaaaccc tacg                    14

```
<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
agttatcgag cgtt                                                        14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
acgcaaaccc tacg                                                        14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
gttatcgagc gttt                                                        14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
acgcaaaccc tacg                                                        14

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391
ttatcgagcg tttt                                                        14

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392
acgcaaaccc tacg                                                        14

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 393
tatcgagcgt tttt                                                    14

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
acgcaaaccc tacg                                                    14

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395
atcgagcgtt tttt                                                    14

<210> SEQ ID NO 396
<211> LENGTH: 14
<212> TYPE: DNA
<213> ORGANISM: Artificial Sequence
<220> FEATURE:
<223> OTHER INFORMATION: Synthetic Construct

<400> SEQUENCE: 396
acgcaaaccc tacg                                                    14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
tcgagcgttt tttg                                                    14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
acgcaaaccc tacg                                                    14

<210> SEQ ID NO 399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
cgagcgtttt ttgt                                                    14

<210> SEQ ID NO 400
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 400
acgcaaaccc tacg                                                       14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
gagcgttttt tgtg                                                       14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
acgcaaaccc tacg                                                       14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
agcgtttttt gtgg                                                       14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
acgcaaaccc tacg                                                       14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
gcgttttttg tggt                                                       14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
```
acgcaaaccc tacg                                          14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407 cgtttttttgt ggtt                                          14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
acgcaaaccc tacg                                          14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409 gtttttttgtg gttt                                          14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
acgcaaaccc tacg                                          14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411 tttttttgtgg tttt                                          14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
acgcaaaccc tacg                                          14

<210> SEQ ID NO 413
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 413
tttttgtggt tttt                                                              14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
acgcaaaccc tacg                                                              14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
ttttgtggtt ttta                                                              14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
acgcaaaccc tacg                                                              14

<210> SEQ ID NO 417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
tttgtggttt ttat                                                              14

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418
acgcaaaccc tacg                                                              14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
ttgtggtttt tatt                                                              14
```

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420
acgcaaaccc tacg                                                        14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
tgtggttttt attc                                                        14

<210> SEQ ID NO 422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 422
acgcaaaccc tacg                                                        14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
gtggttttta ttcg                                                        14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
acgcaaaccc tacg                                                        14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
tggtttttat tcga                                                        14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 426
acgcaaaccc tacg                                                         14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
ggtttttatt cgag                                                         14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
acgcaaaccc tacg                                                         14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
gtttttattc gagt                                                         14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
acgcaaaccc tacg                                                         14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
tttttattcg agtt                                                         14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
acgcaaaccc tacg                                                         14

<210> SEQ ID NO 433
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 433
ttttattcga gttc                                                      14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434
acgcaaaccc tacg                                                      14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct

<400> SEQUENCE: 435
tttattcgag ttcg                                                      14

<210> SEQ ID NO 436
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
acgcaaaccc tacg                                                      14

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
ttattcgagt tcgg                                                      14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
acgcaaaccc tacg                                                      14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
```
tattcgagtt cggc                                                    14

<210> SEQ ID NO 440
<211> LENGTH: 14
<212> TYPE: DNA
<213> ORGANISM: Artificial Sequence
<220> FEATURE:
<223> OTHER INFORMATION: Synthetic Construct

<400> SEQUENCE: 440
acgcaaaccc tacg                                                    14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
attcgagttc ggcg                                                    14

<210> SEQ ID NO 442
<211> LENGTH: 14
<212> TYPE: DNA
<213> ORGANISM: Artificial Sequence
<220> FEATURE:
<223> OTHER INFORMATION: Synthetic Construct

<400> SEQUENCE: 442
acgcaaaccc tacg                                                    14

<210> SEQ ID NO 443
<211> LENGTH: 14
<212> TYPE: DNA
<213> ORGANISM: Artificial Sequence
<220> FEATURE:
<223> OTHER INFORMATION: Synthetic Construct

<400> SEQUENCE: 443
ttcgagttcg gcgg                                                    14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444
acgcaaaccc tacg                                                    14

<210> SEQ ID NO 445
<211> LENGTH: 14
<212> TYPE: DNA
<213> ORGANISM: Artificial Sequence
<220> FEATURE:
<223> OTHER INFORMATION: Synthetic Construct

<400> SEQUENCE: 445
tcgagttcgg cggg                                                    14

<210> SEQ ID NO 446
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 446
acgcaaaccc tacg                                                       14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447
cgagttcggc gggg                                                       14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
acgcaaaccc tacg                                                       14

<210> SEQ ID NO 449
<211> LENGTH: 14
<212> TYPE: DNA
<213> ORGANISM: Artificial Sequence
<220> FEATURE:
<223> OTHER INFORMATION: Synthetic Construct

<400> SEQUENCE: 449
gagttcggcg gggg                                                       14

<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450
acgcaaaccc tacg                                                       14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451
agttcggcgg gggg                                                       14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
acgcaaaccc tacg                                                       14
```

<210> SEQ ID NO 453
<211> LENGTH: 14
<212> TYPE: DNA
<213> ORGANISM: Artificial Sequence
<220> FEATURE:
<223> OTHER INFORMATION: Synthetic Construct

<400> SEQUENCE: 453
gttcggcggg ggga                                                      14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
acgcaaaccc tacg                                                      14

<210> SEQ ID NO 455
<211> LENGTH: 14
<212> TYPE: DNA
<213> ORGANISM: Artificial Sequence
<220> FEATURE:
<223> OTHER INFORMATION: Synthetic Construct

<400> SEQUENCE: 455
ttcggcgggg ggag                                                      14

<210> SEQ ID NO 456
<211> LENGTH: 14
<212> TYPE: DNA
<213> ORGANISM: Artificial Sequence
<220> FEATURE:
<223> OTHER INFORMATION: Synthetic Construct

<400> SEQUENCE: 456
acgcaaaccc tacg                                                      14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457
tcggcggggg gagc                                                      14

<210> SEQ ID NO 458
<211> LENGTH: 14
<212> TYPE: DNA
<213> ORGANISM: Artificial Sequence
<220> FEATURE:
<223> OTHER INFORMATION: Synthetic Construct

<400> SEQUENCE: 458
acgcaaaccc tacg                                                      14

<210> SEQ ID NO 459
<211> LENGTH: 14
<212> TYPE: DNA
<213> ORGANISM: Artificial Sequence
<220> FEATURE:

<223> OTHER INFORMATION: Synthetic Construct

<400> SEQUENCE: 459
cggcgggggg agcg                                                     14

<210> SEQ ID NO 460
<211> LENGTH: 14
<212> TYPE: DNA
<213> ORGANISM: Artificial Sequence
<220> FEATURE:
<223> OTHER INFORMATION: Synthetic Construct

<400> SEQUENCE: 460
acgcaaaccc tacg                                                     14

<210> SEQ ID NO 461
<211> LENGTH: 14
<212> TYPE: DNA
<213> ORGANISM: Artificial Sequence
<220> FEATURE:
<223> OTHER INFORMATION: Synthetic Construct

<400> SEQUENCE: 461
ggcgggggga gcgg                                                     14

<210> SEQ ID NO 462
<211> LENGTH: 14
<212> TYPE: DNA
<213> ORGANISM: Artificial Sequence
<220> FEATURE:
<223> OTHER INFORMATION: Synthetic Construct

<400> SEQUENCE: 462
acgcaaaccc tacg                                                     14

<210> SEQ ID NO 463
<211> LENGTH: 14
<212> TYPE: DNA
<213> ORGANISM: Artificial Sequence
<220> FEATURE:
<223> OTHER INFORMATION: Synthetic Construct

<400> SEQUENCE: 463
gcggggggag cggc                                                     14

<210> SEQ ID NO 464
<211> LENGTH: 14
<212> TYPE: DNA
<213> ORGANISM: Artificial Sequence
<220> FEATURE:
<223> OTHER INFORMATION: Synthetic Construct

<400> SEQUENCE: 464
acgcaaaccc tacg                                                     14

<210> SEQ ID NO 465
<211> LENGTH: 14
<212> TYPE: DNA
<213> ORGANISM: Artificial Sequence
<220> FEATURE:
<223> OTHER INFORMATION: Synthetic Construct

<400> SEQUENCE: 465 cgggggagc ggcg                                                      14

```
<210> SEQ ID NO 466
<211> LENGTH: 14
<212> TYPE: DNA
<213> ORGANISM: Artificial Sequence
<220> FEATURE:
<223> OTHER INFORMATION: Synthetic Construct

<400> SEQUENCE: 466
acgcaaaccc tacg                                                        14

<210> SEQ ID NO 467
<211> LENGTH: 14
<212> TYPE: DNA
<213> ORGANISM: Artificial Sequence
<220> FEATURE:
<223> OTHER INFORMATION: Synthetic Construct

<400> SEQUENCE: 467 gggggagcg gcgc                                                         14

<210> SEQ ID NO 468
<211> LENGTH: 14
<212> TYPE: DNA
<213> ORGANISM: Artificial Sequence
<220> FEATURE:
<223> OTHER INFORMATION: Synthetic Construct

<400> SEQUENCE: 468
ttaaccccaa accg                                                        14

<210> SEQ ID NO 469
<211> LENGTH: 26
<212> TYPE: DNA
<213> ORGANISM: Artificial Sequence
<220> FEATURE:
<223> OTHER INFORMATION: Synthetic Construct

<400> SEQUENCE: 469
agttcgtcgg cgattggggc gcgcgc                                           26

<210> SEQ ID NO 470
<211> LENGTH: 14
<212> TYPE: DNA
<213> ORGANISM: Artificial Sequence
<220> FEATURE:
<223> OTHER INFORMATION: Synthetic Construct

<400> SEQUENCE: 470
gggggagcgg cgcg                                                        14

<210> SEQ ID NO 471
<211> LENGTH: 14
<212> TYPE: DNA
<213> ORGANISM: Artificial Sequence
<220> FEATURE:
<223> OTHER INFORMATION: Synthetic Construct

<400> SEQUENCE: 471
ttaaccccaa accg                                                        14

<210> SEQ ID NO 472
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 472
ggggagcggc gcgc                                                         14

<210> SEQ ID NO 473
<211> LENGTH: 14
<212> TYPE: DNA
<213> ORGANISM: Artificial Sequence
<220> FEATURE:
<223> OTHER INFORMATION: Synthetic Construct

<400> SEQUENCE: 473
ttaaccccaa accg                                                         14

<210> SEQ ID NO 474
<211> LENGTH: 14
<212> TYPE: DNA
<213> ORGANISM: Artificial Sequence
<220> FEATURE:
<223> OTHER INFORMATION: Synthetic Construct

<400> SEQUENCE: 474
gggagcggcg cgcg                                                         14

<210> SEQ ID NO 475
<211> LENGTH: 14
<212> TYPE: DNA
<213> ORGANISM: Artificial Sequence
<220> FEATURE:
<223> OTHER INFORMATION: Synthetic Construct

<400> SEQUENCE: 475
ttaaccccaa accg                                                         14

<210> SEQ ID NO 476
<211> LENGTH: 14
<212> TYPE: DNA
<213> ORGANISM: Artificial Sequence
<220> FEATURE:
<223> OTHER INFORMATION: Synthetic Construct

<400> SEQUENCE: 476
ggagcggcgc gcgg                                                         14

<210> SEQ ID NO 477
<211> LENGTH: 14
<212> TYPE: DNA
<213> ORGANISM: Artificial Sequence
<220> FEATURE:
<223> OTHER INFORMATION: Synthetic Construct

<400> SEQUENCE: 477
ttaaccccaa accg                                                         14

<210> SEQ ID NO 478
<211> LENGTH: 14
<212> TYPE: DNA
<213> ORGANISM: Artificial Sequence
<220> FEATURE:
<223> OTHER INFORMATION: Synthetic Construct

<400> SEQUENCE: 478
gagcggcgcg cggg                                                         14

<210> SEQ ID NO 479
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 479
ttaaccccaa accg                                                        14

<210> SEQ ID NO 480
<211> LENGTH: 14
<212> TYPE: DNA
<213> ORGANISM: Artificial Sequence
<220> FEATURE:
<223> OTHER INFORMATION: Synthetic Construct

<400> SEQUENCE: 480
agcggcgcgc gggt                                                        14

<210> SEQ ID NO 481
<211> LENGTH: 14
<212> TYPE: DNA
<213> ORGANISM: Artificial Sequence
<220> FEATURE:
<223> OTHER INFORMATION: Synthetic Construct

<400> SEQUENCE: 481
ttaaccccaa accg                                                        14

<210> SEQ ID NO 482
<211> LENGTH: 14
<212> TYPE: DNA
<213> ORGANISM: Artificial Sequence
<220> FEATURE:
<223> OTHER INFORMATION: Synthetic Construct

<400> SEQUENCE: 482
gcggcgcgcg ggtg                                                        14

<210> SEQ ID NO 483
<211> LENGTH: 14
<212> TYPE: DNA
<213> ORGANISM: Artificial Sequence
<220> FEATURE:
<223> OTHER INFORMATION: Synthetic Construct

<400> SEQUENCE: 483
ttaaccccaa accg                                                        14

<210> SEQ ID NO 484
<211> LENGTH: 14
<212> TYPE: DNA
<213> ORGANISM: Artificial Sequence
<220> FEATURE:
<223> OTHER INFORMATION: Synthetic Construct

<400> SEQUENCE: 484
cggcgcgcgg gtgt                                                        14

<210> SEQ ID NO 485
<211> LENGTH: 14
<212> TYPE: DNA
<213> ORGANISM: Artificial Sequence
<220> FEATURE:
<223> OTHER INFORMATION: Synthetic Construct

<400> SEQUENCE: 485
``` ttaacccccaa accg                                        14

<210> SEQ ID NO 486
<211> LENGTH: 14
<212> TYPE: DNA
<213> ORGANISM: Artificial Sequence
<220> FEATURE:
<223> OTHER INFORMATION: Synthetic Construct

<400> SEQUENCE: 486
ggcgcgcggg tgtt                                         14

<210> SEQ ID NO 487
<211> LENGTH: 14
<212> TYPE: DNA
<213> ORGANISM: Artificial Sequence
<220> FEATURE:
<223> OTHER INFORMATION: Synthetic Construct

<400> SEQUENCE: 487 ttaacccccaa accg                                        14

<210> SEQ ID NO 488
<211> LENGTH: 14
<212> TYPE: DNA
<213> ORGANISM: Artificial Sequence
<220> FEATURE:
<223> OTHER INFORMATION: Synthetic Construct

<400> SEQUENCE: 488
gcgcgcgggt gttg                                         14

<210> SEQ ID NO 489
<211> LENGTH: 14
<212> TYPE: DNA
<213> ORGANISM: Artificial Sequence
<220> FEATURE:
<223> OTHER INFORMATION: Synthetic Construct

<400> SEQUENCE: 489 ttaacccccaa accg                                        14

<210> SEQ ID NO 490
<211> LENGTH: 14
<212> TYPE: DNA
<213> ORGANISM: Artificial Sequence
<220> FEATURE:
<223> OTHER INFORMATION: Synthetic Construct

<400> SEQUENCE: 490
cgcgcgggtg ttgg                                         14

<210> SEQ ID NO 491
<211> LENGTH: 14
<212> TYPE: DNA
<213> ORGANISM: Artificial Sequence
<220> FEATURE:
<223> OTHER INFORMATION: Synthetic Construct

<400> SEQUENCE: 491 ttaacccccaa accg                                        14

<210> SEQ ID NO 492
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 492
gcgcgggtgt tggg                                                        14

<210> SEQ ID NO 493
<211> LENGTH: 14
<212> TYPE: DNA
<213> ORGANISM: Artificial Sequence
<220> FEATURE:
<223> OTHER INFORMATION: Synthetic Construct

<400> SEQUENCE: 493
ttaaccccaa accg                                                        14

<210> SEQ ID NO 494
<211> LENGTH: 14
<212> TYPE: DNA
<213> ORGANISM: Artificial Sequence
<220> FEATURE:
<223> OTHER INFORMATION: Synthetic Construct

<400> SEQUENCE: 494
cgcgggtgtt gggg                                                        14

<210> SEQ ID NO 495
<211> LENGTH: 14
<212> TYPE: DNA
<213> ORGANISM: Artificial Sequence
<220> FEATURE:
<223> OTHER INFORMATION: Synthetic Construct

<400> SEQUENCE: 495
ttaaccccaa accg                                                        14

<210> SEQ ID NO 496
<211> LENGTH: 14
<212> TYPE: DNA
<213> ORGANISM: Artificial Sequence
<220> FEATURE:
<223> OTHER INFORMATION: Synthetic Construct

<400> SEQUENCE: 496
gcgggtgttg gggg                                                        14

<210> SEQ ID NO 497
<211> LENGTH: 14
<212> TYPE: DNA
<213> ORGANISM: Artificial Sequence
<220> FEATURE:
<223> OTHER INFORMATION: Synthetic Construct

<400> SEQUENCE: 497
ttaaccccaa accg                                                        14

<210> SEQ ID NO 498
<211> LENGTH: 14
<212> TYPE: DNA
<213> ORGANISM: Artificial Sequence
<220> FEATURE:
<223> OTHER INFORMATION: Synthetic Construct

<400> SEQUENCE: 498
cgggtgttgg ggga                                                        14
```

```
<210> SEQ ID NO 499
<211> LENGTH: 14
<212> TYPE: DNA
<213> ORGANISM: Artificial Sequence
<220> FEATURE:
<223> OTHER INFORMATION: Synthetic Construct

<400> SEQUENCE: 499
ttaaccccaa accg                                                          14

<210> SEQ ID NO 500
<211> LENGTH: 14
<212> TYPE: DNA
<213> ORGANISM: Artificial Sequence
<220> FEATURE:
<223> OTHER INFORMATION: Synthetic Construct

<400> SEQUENCE: 500
gggtgttggg ggat                                                          14

<210> SEQ ID NO 501
<211> LENGTH: 14
<212> TYPE: DNA
<213> ORGANISM: Artificial Sequence
<220> FEATURE:
<223> OTHER INFORMATION: Synthetic Construct

<400> SEQUENCE: 501
ttaaccccaa accg                                                          14

<210> SEQ ID NO 502
<211> LENGTH: 14
<212> TYPE: DNA
<213> ORGANISM: Artificial Sequence
<220> FEATURE:
<223> OTHER INFORMATION: Synthetic Construct

<400> SEQUENCE: 502
ggtgttgggg gatc                                                          14

<210> SEQ ID NO 503
<211> LENGTH: 14
<212> TYPE: DNA
<213> ORGANISM: Artificial Sequence
<220> FEATURE:
<223> OTHER INFORMATION: Synthetic Construct

<400> SEQUENCE: 503
ttaaccccaa accg                                                          14

<210> SEQ ID NO 504
<211> LENGTH: 14
<212> TYPE: DNA
<213> ORGANISM: Artificial Sequence
<220> FEATURE:
<223> OTHER INFORMATION: Synthetic Construct

<400> SEQUENCE: 504
gtgttggggg atcg                                                          14

<210> SEQ ID NO 505
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 505
ttaaccccaa accg                                                        14

<210> SEQ ID NO 506
<211> LENGTH: 14
<212> TYPE: DNA
<213> ORGANISM: Artificial Sequence
<220> FEATURE:
<223> OTHER INFORMATION: Synthetic Construct

<400> SEQUENCE: 506
tgttggggga tcga                                                        14

<210> SEQ ID NO 507
<211> LENGTH: 14
<212> TYPE: DNA
<213> ORGANISM: Artificial Sequence
<220> FEATURE:
<223> OTHER INFORMATION: Synthetic Construct

<400> SEQUENCE: 507
ttaaccccaa accg                                                        14

<210> SEQ ID NO 508
<211> LENGTH: 14
<212> TYPE: DNA
<213> ORGANISM: Artificial Sequence
<220> FEATURE:
<223> OTHER INFORMATION: Synthetic Construct

<400> SEQUENCE: 508
gttgggggat cgat                                                        14

<210> SEQ ID NO 509
<211> LENGTH: 14
<212> TYPE: DNA
<213> ORGANISM: Artificial Sequence
<220> FEATURE:
<223> OTHER INFORMATION: Synthetic Construct

<400> SEQUENCE: 509
ttaaccccaa accg                                                        14

<210> SEQ ID NO 510
<211> LENGTH: 14
<212> TYPE: DNA
<213> ORGANISM: Artificial Sequence
<220> FEATURE:
<223> OTHER INFORMATION: Synthetic Construct

<400> SEQUENCE: 510
ttgggggatc gatt                                                        14

<210> SEQ ID NO 511
<211> LENGTH: 14
<212> TYPE: DNA
<213> ORGANISM: Artificial Sequence
<220> FEATURE:
<223> OTHER INFORMATION: Synthetic Construct

<400> SEQUENCE: 511
ttaaccccaa accg                                                        14

<210> SEQ ID NO 512
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 512
tgggggatcg attt                                                         14

<210> SEQ ID NO 513
<211> LENGTH: 14
<212> TYPE: DNA
<213> ORGANISM: Artificial Sequence
<220> FEATURE:
<223> OTHER INFORMATION: Synthetic Construct

<400> SEQUENCE: 513
ttaaccccaa accg                                                         14

<210> SEQ ID NO 514
<211> LENGTH: 14
<212> TYPE: DNA
<213> ORGANISM: Artificial Sequence
<220> FEATURE:
<223> OTHER INFORMATION: Synthetic Construct

<400> SEQUENCE: 514
gggggatcga tttt                                                         14

<210> SEQ ID NO 515
<211> LENGTH: 14
<212> TYPE: DNA
<213> ORGANISM: Artificial Sequence
<220> FEATURE:
<223> OTHER INFORMATION: Synthetic Construct

<400> SEQUENCE: 515
ttaaccccaa accg                                                         14

<210> SEQ ID NO 516
<211> LENGTH: 14
<212> TYPE: DNA
<213> ORGANISM: Artificial Sequence
<220> FEATURE:
<223> OTHER INFORMATION: Synthetic Construct

<400> SEQUENCE: 516
ggggatcgat tttt                                                         14

<210> SEQ ID NO 517
<211> LENGTH: 14
<212> TYPE: DNA
<213> ORGANISM: Artificial Sequence
<220> FEATURE:
<223> OTHER INFORMATION: Synthetic Construct

<400> SEQUENCE: 517
ttaaccccaa accg                                                         14

<210> SEQ ID NO 518
<211> LENGTH: 14
<212> TYPE: DNA
<213> ORGANISM: Artificial Sequence
<220> FEATURE:
<223> OTHER INFORMATION: Synthetic Construct

<400> SEQUENCE: 518
```
gggatcgatt tttt                                                         14

<210> SEQ ID NO 519
<211> LENGTH: 14
<212> TYPE: DNA
<213> ORGANISM: Artificial Sequence
<220> FEATURE:
<223> OTHER INFORMATION: Synthetic Construct

<400> SEQUENCE: 519
ttaaccccaa accg                                                         14

<210> SEQ ID NO 520
<211> LENGTH: 14
<212> TYPE: DNA
<213> ORGANISM: Artificial Sequence
<220> FEATURE:
<223> OTHER INFORMATION: Synthetic Construct

<400> SEQUENCE: 520
ggatcgattt tttt                                                         14

<210> SEQ ID NO 521
<211> LENGTH: 14
<212> TYPE: DNA
<213> ORGANISM: Artificial Sequence
<220> FEATURE:
<223> OTHER INFORMATION: Synthetic Construct

<400> SEQUENCE: 521
ttaaccccaa accg                                                         14

<210> SEQ ID NO 522
<211> LENGTH: 14
<212> TYPE: DNA
<213> ORGANISM: Artificial Sequence
<220> FEATURE:
<223> OTHER INFORMATION: Synthetic Construct

<400> SEQUENCE: 522
gatcgatttt tttc                                                         14

<210> SEQ ID NO 523
<211> LENGTH: 14
<212> TYPE: DNA
<213> ORGANISM: Artificial Sequence
<220> FEATURE:
<223> OTHER INFORMATION: Synthetic Construct

<400> SEQUENCE: 523
ttaaccccaa accg                                                         14

<210> SEQ ID NO 524
<211> LENGTH: 14
<212> TYPE: DNA
<213> ORGANISM: Artificial Sequence
<220> FEATURE:
<223> OTHER INFORMATION: Synthetic Construct

<400> SEQUENCE: 524
atcgattttt ttcg                                                         14

<210> SEQ ID NO 525
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 525 ttaacccaa accg                                                        14

<210> SEQ ID NO 526
<211> LENGTH: 14
<212> TYPE: DNA
<213> ORGANISM: Artificial Sequence
<220> FEATURE:
<223> OTHER INFORMATION: Synthetic Construct

<400> SEQUENCE: 526 tcgattttt tcgc                                                        14

<210> SEQ ID NO 527
<211> LENGTH: 14
<212> TYPE: DNA
<213> ORGANISM: Artificial Sequence
<220> FEATURE:
<223> OTHER INFORMATION: Synthetic Construct

<400> SEQUENCE: 527 ttaacccaa accg                                                        14

<210> SEQ ID NO 528
<211> LENGTH: 14
<212> TYPE: DNA
<213> ORGANISM: Artificial Sequence
<220> FEATURE:
<223> OTHER INFORMATION: Synthetic Construct

<400> SEQUENCE: 528 cgatttttt cgcg                                                        14

<210> SEQ ID NO 529
<211> LENGTH: 14
<212> TYPE: DNA
<213> ORGANISM: Artificial Sequence
<220> FEATURE:
<223> OTHER INFORMATION: Synthetic Construct

<400> SEQUENCE: 529 ttaacccaa accg                                                        14

<210> SEQ ID NO 530
<211> LENGTH: 14
<212> TYPE: DNA
<213> ORGANISM: Artificial Sequence
<220> FEATURE:
<223> OTHER INFORMATION: Synthetic Construct

<400> SEQUENCE: 530 gattttttc gcga                                                        14

<210> SEQ ID NO 531
<211> LENGTH: 14
<212> TYPE: DNA
<213> ORGANISM: Artificial Sequence
<220> FEATURE:
<223> OTHER INFORMATION: Synthetic Construct

<400> SEQUENCE: 531 ttaacccaa accg                                                        14
```

<210> SEQ ID NO 532
<211> LENGTH: 14
<212> TYPE: DNA
<213> ORGANISM: Artificial Sequence
<220> FEATURE:
<223> OTHER INFORMATION: Synthetic Construct

<400> SEQUENCE: 532 attttttcg cgaa                                                        14

<210> SEQ ID NO 533
<211> LENGTH: 14
<212> TYPE: DNA
<213> ORGANISM: Artificial Sequence
<220> FEATURE:
<223> OTHER INFORMATION: Synthetic Construct

<400> SEQUENCE: 533
ttaaccccaa accg                                                       14

<210> SEQ ID NO 534
<211> LENGTH: 14
<212> TYPE: DNA
<213> ORGANISM: Artificial Sequence
<220> FEATURE:
<223> OTHER INFORMATION: Synthetic Construct

<400> SEQUENCE: 534
tttttttcgc gaag                                                       14

<210> SEQ ID NO 535
<211> LENGTH: 14
<212> TYPE: DNA
<213> ORGANISM: Artificial Sequence
<220> FEATURE:
<223> OTHER INFORMATION: Synthetic Construct

<400> SEQUENCE: 535
ttaaccccaa accg                                                       14

<210> SEQ ID NO 536
<211> LENGTH: 14
<212> TYPE: DNA
<213> ORGANISM: Artificial Sequence
<220> FEATURE:
<223> OTHER INFORMATION: Synthetic Construct

<400> SEQUENCE: 536 tttttcgcg aagg                                                        14

<210> SEQ ID NO 537
<211> LENGTH: 14
<212> TYPE: DNA
<213> ORGANISM: Artificial Sequence
<220> FEATURE:
<223> OTHER INFORMATION: Synthetic Construct

<400> SEQUENCE: 537
ttaaccccaa accg                                                       14

<210> SEQ ID NO 538
<211> LENGTH: 14
<212> TYPE: DNA
<213> ORGANISM: Artificial Sequence
<220> FEATURE:

<223> OTHER INFORMATION: Synthetic Construct

<400> SEQUENCE: 538
tttttcgcga aggc                                                       14

<210> SEQ ID NO 539
<211> LENGTH: 14
<212> TYPE: DNA
<213> ORGANISM: Artificial Sequence
<220> FEATURE:
<223> OTHER INFORMATION: Synthetic Construct

<400> SEQUENCE: 539
ttaaccccaa accg                                                       14

<210> SEQ ID NO 540
<211> LENGTH: 14
<212> TYPE: DNA
<213> ORGANISM: Artificial Sequence
<220> FEATURE:
<223> OTHER INFORMATION: Synthetic Construct

<400> SEQUENCE: 540
ttttcgcgaa ggcg                                                       14

<210> SEQ ID NO 541
<211> LENGTH: 14
<212> TYPE: DNA
<213> ORGANISM: Artificial Sequence
<220> FEATURE:
<223> OTHER INFORMATION: Synthetic Construct

<400> SEQUENCE: 541
ttaaccccaa accg                                                       14

<210> SEQ ID NO 542
<211> LENGTH: 14
<212> TYPE: DNA
<213> ORGANISM: Artificial Sequence
<220> FEATURE:
<223> OTHER INFORMATION: Synthetic Construct

<400> SEQUENCE: 542
tttcgcgaag gcgt                                                       14

<210> SEQ ID NO 543
<211> LENGTH: 14
<212> TYPE: DNA
<213> ORGANISM: Artificial Sequence
<220> FEATURE:
<223> OTHER INFORMATION: Synthetic Construct

<400> SEQUENCE: 543
ttaaccccaa accg                                                       14

<210> SEQ ID NO 544
<211> LENGTH: 14
<212> TYPE: DNA
<213> ORGANISM: Artificial Sequence
<220> FEATURE:
<223> OTHER INFORMATION: Synthetic Construct

<400> SEQUENCE: 544
ttcgcgaagg cgtc                                                       14

```
<210> SEQ ID NO 545
<211> LENGTH: 14
<212> TYPE: DNA
<213> ORGANISM: Artificial Sequence
<220> FEATURE:
<223> OTHER INFORMATION: Synthetic Construct

<400> SEQUENCE: 545
ttaaccccaa accg                                                         14

<210> SEQ ID NO 546
<211> LENGTH: 14
<212> TYPE: DNA
<213> ORGANISM: Artificial Sequence
<220> FEATURE:
<223> OTHER INFORMATION: Synthetic Construct

<400> SEQUENCE: 546
tcgcgaaggc gtcg                                                         14

<210> SEQ ID NO 547
<211> LENGTH: 14
<212> TYPE: DNA
<213> ORGANISM: Artificial Sequence
<220> FEATURE:
<223> OTHER INFORMATION: Synthetic Construct

<400> SEQUENCE: 547
ttaaccccaa accg                                                         14

<210> SEQ ID NO 548
<211> LENGTH: 14
<212> TYPE: DNA
<213> ORGANISM: Artificial Sequence
<220> FEATURE:
<223> OTHER INFORMATION: Synthetic Construct

<400> SEQUENCE: 548
cgcgaaggcg tcgg                                                         14

<210> SEQ ID NO 549
<211> LENGTH: 14
<212> TYPE: DNA
<213> ORGANISM: Artificial Sequence
<220> FEATURE:
<223> OTHER INFORMATION: Synthetic Construct

<400> SEQUENCE: 549
ttaaccccaa accg                                                         14

<210> SEQ ID NO 550
<211> LENGTH: 14
<212> TYPE: DNA
<213> ORGANISM: Artificial Sequence
<220> FEATURE:
<223> OTHER INFORMATION: Synthetic Construct

<400> SEQUENCE: 550
gcgaaggcgt cggc                                                         14

<210> SEQ ID NO 551
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 551
ttaaccccaa accg                                                      14

<210> SEQ ID NO 552
<211> LENGTH: 14
<212> TYPE: DNA
<213> ORGANISM: Artificial Sequence
<220> FEATURE:
<223> OTHER INFORMATION: Synthetic Construct

<400> SEQUENCE: 552
cgaaggcgtc ggcg                                                      14

<210> SEQ ID NO 553
<211> LENGTH: 14
<212> TYPE: DNA
<213> ORGANISM: Artificial Sequence
<220> FEATURE:
<223> OTHER INFORMATION: Synthetic Construct

<400> SEQUENCE: 553
ttaaccccaa accg                                                      14

<210> SEQ ID NO 554
<211> LENGTH: 14
<212> TYPE: DNA
<213> ORGANISM: Artificial Sequence
<220> FEATURE:
<223> OTHER INFORMATION: Synthetic Construct

<400> SEQUENCE: 554
gaaggcgtcg gcgc                                                      14

<210> SEQ ID NO 555
<211> LENGTH: 14
<212> TYPE: DNA
<213> ORGANISM: Artificial Sequence
<220> FEATURE:
<223> OTHER INFORMATION: Synthetic Construct

<400> SEQUENCE: 555
ttaaccccaa accg                                                      14

<210> SEQ ID NO 556
<211> LENGTH: 14
<212> TYPE: DNA
<213> ORGANISM: Artificial Sequence
<220> FEATURE:
<223> OTHER INFORMATION: Synthetic Construct

<400> SEQUENCE: 556
aaggcgtcgg cgcg                                                      14

<210> SEQ ID NO 557
<211> LENGTH: 14
<212> TYPE: DNA
<213> ORGANISM: Artificial Sequence
<220> FEATURE:
<223> OTHER INFORMATION: Synthetic Construct

<400> SEQUENCE: 557
ttaaccccaa accg                                                      14

<210> SEQ ID NO 558
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 558
aggcgtcggc gcgg                                                            14

<210> SEQ ID NO 559
<211> LENGTH: 14
<212> TYPE: DNA
<213> ORGANISM: Artificial Sequence
<220> FEATURE:
<223> OTHER INFORMATION: Synthetic Construct

<400> SEQUENCE: 559
ttaaccccaa accg                                                            14

<210> SEQ ID NO 560
<211> LENGTH: 14
<212> TYPE: DNA
<213> ORGANISM: Artificial Sequence
<220> FEATURE:
<223> OTHER INFORMATION: Synthetic Construct

<400> SEQUENCE: 560
ggcgtcggcg cggg                                                            14

<210> SEQ ID NO 561
<211> LENGTH: 14
<212> TYPE: DNA
<213> ORGANISM: Artificial Sequence
<220> FEATURE:
<223> OTHER INFORMATION: Synthetic Construct

<400> SEQUENCE: 561
ttaaccccaa accg                                                            14

<210> SEQ ID NO 562
<211> LENGTH: 14
<212> TYPE: DNA
<213> ORGANISM: Artificial Sequence
<220> FEATURE:
<223> OTHER INFORMATION: Synthetic Construct

<400> SEQUENCE: 562
gcgtcggcgc gggg                                                            14

<210> SEQ ID NO 563
<211> LENGTH: 14
<212> TYPE: DNA
<213> ORGANISM: Artificial Sequence
<220> FEATURE:
<223> OTHER INFORMATION: Synthetic Construct

<400> SEQUENCE: 563
ttaaccccaa accg                                                            14

<210> SEQ ID NO 564
<211> LENGTH: 14
<212> TYPE: DNA
<213> ORGANISM: Artificial Sequence
<220> FEATURE:
<223> OTHER INFORMATION: Synthetic Construct

<400> SEQUENCE: 564
```
cgtcggcgcg gggt                                        14

<210> SEQ ID NO 565
<211> LENGTH: 14
<212> TYPE: DNA
<213> ORGANISM: Artificial Sequence
<220> FEATURE:
<223> OTHER INFORMATION: Synthetic Construct

<400> SEQUENCE: 565 ttaacccccaa accg                                       14

<210> SEQ ID NO 566
<211> LENGTH: 14
<212> TYPE: DNA
<213> ORGANISM: Artificial Sequence
<220> FEATURE:
<223> OTHER INFORMATION: Synthetic Construct

<400> SEQUENCE: 566
gtcggcgcgg ggtt                                        14

<210> SEQ ID NO 567
<211> LENGTH: 14
<212> TYPE: DNA
<213> ORGANISM: Artificial Sequence
<220> FEATURE:
<223> OTHER INFORMATION: Synthetic Construct

<400> SEQUENCE: 567 ttaacccccaa accg                                       14

<210> SEQ ID NO 568
<211> LENGTH: 14
<212> TYPE: DNA
<213> ORGANISM: Artificial Sequence
<220> FEATURE:
<223> OTHER INFORMATION: Synthetic Construct

<400> SEQUENCE: 568
tcggcgcggg gttg                                        14

<210> SEQ ID NO 569
<211> LENGTH: 14
<212> TYPE: DNA
<213> ORGANISM: Artificial Sequence
<220> FEATURE:
<223> OTHER INFORMATION: Synthetic Construct

<400> SEQUENCE: 569 ttaacccccaa accg                                       14

<210> SEQ ID NO 570
<211> LENGTH: 14
<212> TYPE: DNA
<213> ORGANISM: Artificial Sequence
<220> FEATURE:
<223> OTHER INFORMATION: Synthetic Construct

<400> SEQUENCE: 570
cggcgcgggg ttgg                                        14

<210> SEQ ID NO 571
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 571 ttaacccaa accg                                                          14

<210> SEQ ID NO 572
<211> LENGTH: 14
<212> TYPE: DNA
<213> ORGANISM: Artificial Sequence
<220> FEATURE:
<223> OTHER INFORMATION: Synthetic Construct

<400> SEQUENCE: 572
ggcgcggggt tggc                                                         14

<210> SEQ ID NO 573
<211> LENGTH: 14
<212> TYPE: DNA
<213> ORGANISM: Artificial Sequence
<220> FEATURE:
<223> OTHER INFORMATION: Synthetic Construct

<400> SEQUENCE: 573 ttaacccaa accg                                                          14

<210> SEQ ID NO 574
<211> LENGTH: 14
<212> TYPE: DNA
<213> ORGANISM: Artificial Sequence
<220> FEATURE:
<223> OTHER INFORMATION: Synthetic Construct

<400> SEQUENCE: 574
gcgcggggtt ggcg                                                         14

<210> SEQ ID NO 575
<211> LENGTH: 14
<212> TYPE: DNA
<213> ORGANISM: Artificial Sequence
<220> FEATURE:
<223> OTHER INFORMATION: Synthetic Construct

<400> SEQUENCE: 575
ttaaccccaa accg                                                         14

<210> SEQ ID NO 576
<211> LENGTH: 14
<212> TYPE: DNA
<213> ORGANISM: Artificial Sequence
<220> FEATURE:
<223> OTHER INFORMATION: Synthetic Construct

<400> SEQUENCE: 576
cgcggggttg gcgt                                                         14

<210> SEQ ID NO 577
<211> LENGTH: 14
<212> TYPE: DNA
<213> ORGANISM: Artificial Sequence
<220> FEATURE:
<223> OTHER INFORMATION: Synthetic Construct

<400> SEQUENCE: 577
ttaaccccaa accg                                                         14
```

```
<210> SEQ ID NO 578
<211> LENGTH: 14
<212> TYPE: DNA
<213> ORGANISM: Artificial Sequence
<220> FEATURE:
<223> OTHER INFORMATION: Synthetic Construct

<400> SEQUENCE: 578
gcggggttgg cgta                                                        14

<210> SEQ ID NO 579
<211> LENGTH: 14
<212> TYPE: DNA
<213> ORGANISM: Artificial Sequence
<220> FEATURE:
<223> OTHER INFORMATION: Synthetic Construct

<400> SEQUENCE: 579
cgaaactcta aacg                                                        14

<210> SEQ ID NO 580
<211> LENGTH: 25
<212> TYPE: DNA
<213> ORGANISM: Artificial Sequence
<220> FEATURE:
<223> OTHER INFORMATION: Synthetic Construct

<400> SEQUENCE: 580
agtagtcgtt aagtttcggg acggc                                            25

<210> SEQ ID NO 581
<211> LENGTH: 14
<212> TYPE: DNA
<213> ORGANISM: Artificial Sequence
<220> FEATURE:
<223> OTHER INFORMATION: Synthetic Construct

<400> SEQUENCE: 581
cggggttggc gtag                                                        14

<210> SEQ ID NO 582
<211> LENGTH: 14
<212> TYPE: DNA
<213> ORGANISM: Artificial Sequence
<220> FEATURE:
<223> OTHER INFORMATION: Synthetic Construct

<400> SEQUENCE: 582
cgaaactcta aacg                                                        14

<210> SEQ ID NO 583
<211> LENGTH: 14
<212> TYPE: DNA
<213> ORGANISM: Artificial Sequence
<220> FEATURE:
<223> OTHER INFORMATION: Synthetic Construct

<400> SEQUENCE: 583
ggggttggcg tagg                                                        14

<210> SEQ ID NO 584
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 584
cgaaactcta aacg                                                      14

<210> SEQ ID NO 585
<211> LENGTH: 14
<212> TYPE: DNA
<213> ORGANISM: Artificial Sequence
<220> FEATURE:
<223> OTHER INFORMATION: Synthetic Construct

<400> SEQUENCE: 585
gggttggcgt aggg                                                      14

<210> SEQ ID NO 586
<211> LENGTH: 14
<212> TYPE: DNA
<213> ORGANISM: Artificial Sequence
<220> FEATURE:
<223> OTHER INFORMATION: Synthetic Construct

<400> SEQUENCE: 586
cgaaactcta aacg                                                      14

<210> SEQ ID NO 587
<211> LENGTH: 14
<212> TYPE: DNA
<213> ORGANISM: Artificial Sequence
<220> FEATURE:
<223> OTHER INFORMATION: Synthetic Construct

<400> SEQUENCE: 587
ggttggcgta gggt                                                      14

<210> SEQ ID NO 588
<211> LENGTH: 14
<212> TYPE: DNA
<213> ORGANISM: Artificial Sequence
<220> FEATURE:
<223> OTHER INFORMATION: Synthetic Construct

<400> SEQUENCE: 588
cgaaactcta aacg                                                      14

<210> SEQ ID NO 589
<211> LENGTH: 14
<212> TYPE: DNA
<213> ORGANISM: Artificial Sequence
<220> FEATURE:
<223> OTHER INFORMATION: Synthetic Construct

<400> SEQUENCE: 589
gttggcgtag ggtt                                                      14

<210> SEQ ID NO 590
<211> LENGTH: 14
<212> TYPE: DNA
<213> ORGANISM: Artificial Sequence
<220> FEATURE:
<223> OTHER INFORMATION: Synthetic Construct

<400> SEQUENCE: 590
cgaaactcta aacg                                                      14

<210> SEQ ID NO 591
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 591
ttggcgtagg gttt                                                    14

<210> SEQ ID NO 592
<211> LENGTH: 14
<212> TYPE: DNA
<213> ORGANISM: Artificial Sequence
<220> FEATURE:
<223> OTHER INFORMATION: Synthetic Construct

<400> SEQUENCE: 592
cgaaactcta aacg                                                    14

<210> SEQ ID NO 593
<211> LENGTH: 14
<212> TYPE: DNA
<213> ORGANISM: Artificial Sequence
<220> FEATURE:
<223> OTHER INFORMATION: Synthetic Construct

<400> SEQUENCE: 593
tggcgtaggg tttg                                                    14

<210> SEQ ID NO 594
<211> LENGTH: 14
<212> TYPE: DNA
<213> ORGANISM: Artificial Sequence
<220> FEATURE:
<223> OTHER INFORMATION: Synthetic Construct

<400> SEQUENCE: 594
cgaaactcta aacg                                                    14

<210> SEQ ID NO 595
<211> LENGTH: 14
<212> TYPE: DNA
<213> ORGANISM: Artificial Sequence
<220> FEATURE:
<223> OTHER INFORMATION: Synthetic Construct

<400> SEQUENCE: 595
ggcgtagggt ttgc                                                    14

<210> SEQ ID NO 596
<211> LENGTH: 14
<212> TYPE: DNA
<213> ORGANISM: Artificial Sequence
<220> FEATURE:
<223> OTHER INFORMATION: Synthetic Construct

<400> SEQUENCE: 596
cgaaactcta aacg                                                    14

<210> SEQ ID NO 597
<211> LENGTH: 14
<212> TYPE: DNA
<213> ORGANISM: Artificial Sequence
<220> FEATURE:
<223> OTHER INFORMATION: Synthetic Construct

<400> SEQUENCE: 597
```
gcgtagggtt tgcg                                                    14

<210> SEQ ID NO 598
<211> LENGTH: 14
<212> TYPE: DNA
<213> ORGANISM: Artificial Sequence
<220> FEATURE:
<223> OTHER INFORMATION: Synthetic Construct

<400> SEQUENCE: 598
cgaaactcta aacg                                                    14

<210> SEQ ID NO 599
<211> LENGTH: 14
<212> TYPE: DNA
<213> ORGANISM: Artificial Sequence
<220> FEATURE:
<223> OTHER INFORMATION: Synthetic Construct

<400> SEQUENCE: 599
cgtagggttt gcgt                                                    14

<210> SEQ ID NO 600
<211> LENGTH: 14
<212> TYPE: DNA
<213> ORGANISM: Artificial Sequence
<220> FEATURE:
<223> OTHER INFORMATION: Synthetic Construct

<400> SEQUENCE: 600
cgaaactcta aacg                                                    14

<210> SEQ ID NO 601
<211> LENGTH: 14
<212> TYPE: DNA
<213> ORGANISM: Artificial Sequence
<220> FEATURE:
<223> OTHER INFORMATION: Synthetic Construct

<400> SEQUENCE: 601
gtagggtttg cgtt                                                    14

<210> SEQ ID NO 602
<211> LENGTH: 14
<212> TYPE: DNA
<213> ORGANISM: Artificial Sequence
<220> FEATURE:
<223> OTHER INFORMATION: Synthetic Construct

<400> SEQUENCE: 602
cgaaactcta aacg                                                    14

<210> SEQ ID NO 603
<211> LENGTH: 14
<212> TYPE: DNA
<213> ORGANISM: Artificial Sequence
<220> FEATURE:
<223> OTHER INFORMATION: Synthetic Construct

<400> SEQUENCE: 603
tagggtttgc gtta                                                    14

<210> SEQ ID NO 604
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 604
cgaaactcta aacg                                                      14

<210> SEQ ID NO 605
<211> LENGTH: 14
<212> TYPE: DNA
<213> ORGANISM: Artificial Sequence
<220> FEATURE:
<223> OTHER INFORMATION: Synthetic Construct

<400> SEQUENCE: 605
agggtttgcg ttag                                                      14

<210> SEQ ID NO 606
<211> LENGTH: 14
<212> TYPE: DNA
<213> ORGANISM: Artificial Sequence
<220> FEATURE:
<223> OTHER INFORMATION: Synthetic Construct

<400> SEQUENCE: 606
cgaaactcta aacg                                                      14

<210> SEQ ID NO 607
<211> LENGTH: 14
<212> TYPE: DNA
<213> ORGANISM: Artificial Sequence
<220> FEATURE:
<223> OTHER INFORMATION: Synthetic Construct

<400> SEQUENCE: 607
gggtttgcgt tagt                                                      14

<210> SEQ ID NO 608
<211> LENGTH: 14
<212> TYPE: DNA
<213> ORGANISM: Artificial Sequence
<220> FEATURE:
<223> OTHER INFORMATION: Synthetic Construct

<400> SEQUENCE: 608
cgaaactcta aacg                                                      14

<210> SEQ ID NO 609
<211> LENGTH: 14
<212> TYPE: DNA
<213> ORGANISM: Artificial Sequence
<220> FEATURE:
<223> OTHER INFORMATION: Synthetic Construct

<400> SEQUENCE: 609
ggtttgcgtt agtt                                                      14

<210> SEQ ID NO 610
<211> LENGTH: 14
<212> TYPE: DNA
<213> ORGANISM: Artificial Sequence
<220> FEATURE:
<223> OTHER INFORMATION: Synthetic Construct

<400> SEQUENCE: 610
cgaaactcta aacg                                                      14
```

<210> SEQ ID NO 611
<211> LENGTH: 14
<212> TYPE: DNA
<213> ORGANISM: Artificial Sequence
<220> FEATURE:
<223> OTHER INFORMATION: Synthetic Construct

<400> SEQUENCE: 611
gtttgcgtta gttg                                                     14

<210> SEQ ID NO 612
<211> LENGTH: 14
<212> TYPE: DNA
<213> ORGANISM: Artificial Sequence
<220> FEATURE:
<223> OTHER INFORMATION: Synthetic Construct

<400> SEQUENCE: 612
cgaaactcta aacg                                                     14

<210> SEQ ID NO 613
<211> LENGTH: 14
<212> TYPE: DNA
<213> ORGANISM: Artificial Sequence
<220> FEATURE:
<223> OTHER INFORMATION: Synthetic Construct

<400> SEQUENCE: 613
tttgcgttag ttgt                                                     14

<210> SEQ ID NO 614
<211> LENGTH: 14
<212> TYPE: DNA
<213> ORGANISM: Artificial Sequence
<220> FEATURE:
<223> OTHER INFORMATION: Synthetic Construct

<400> SEQUENCE: 614
cgaaactcta aacg                                                     14

<210> SEQ ID NO 615
<211> LENGTH: 14
<212> TYPE: DNA
<213> ORGANISM: Artificial Sequence
<220> FEATURE:
<223> OTHER INFORMATION: Synthetic Construct

<400> SEQUENCE: 615
ttgcgttagt tgta                                                     14

<210> SEQ ID NO 616
<211> LENGTH: 14
<212> TYPE: DNA
<213> ORGANISM: Artificial Sequence
<220> FEATURE:
<223> OTHER INFORMATION: Synthetic Construct

<400> SEQUENCE: 616
cgaaactcta aacg                                                     14

<210> SEQ ID NO 617
<211> LENGTH: 14
<212> TYPE: DNA
<213> ORGANISM: Artificial Sequence
<220> FEATURE:

<223> OTHER INFORMATION: Synthetic Construct

<400> SEQUENCE: 617
tgcgttagtt gtag                                                        14

<210> SEQ ID NO 618
<211> LENGTH: 14
<212> TYPE: DNA
<213> ORGANISM: Artificial Sequence
<220> FEATURE:
<223> OTHER INFORMATION: Synthetic Construct

<400> SEQUENCE: 618
cgaaactcta aacg                                                        14

<210> SEQ ID NO 619
<211> LENGTH: 14
<212> TYPE: DNA
<213> ORGANISM: Artificial Sequence
<220> FEATURE:
<223> OTHER INFORMATION: Synthetic Construct

<400> SEQUENCE: 619
gcgttagttg tagt                                                        14

<210> SEQ ID NO 620
<211> LENGTH: 14
<212> TYPE: DNA
<213> ORGANISM: Artificial Sequence
<220> FEATURE:
<223> OTHER INFORMATION: Synthetic Construct

<400> SEQUENCE: 620
cgaaactcta aacg                                                        14

<210> SEQ ID NO 621
<211> LENGTH: 14
<212> TYPE: DNA
<213> ORGANISM: Artificial Sequence
<220> FEATURE:
<223> OTHER INFORMATION: Synthetic Construct

<400> SEQUENCE: 621
cgttagttgt agtt                                                        14

<210> SEQ ID NO 622
<211> LENGTH: 14
<212> TYPE: DNA
<213> ORGANISM: Artificial Sequence
<220> FEATURE:
<223> OTHER INFORMATION: Synthetic Construct

<400> SEQUENCE: 622
cgaaactcta aacg                                                        14

<210> SEQ ID NO 623
<211> LENGTH: 14
<212> TYPE: DNA
<213> ORGANISM: Artificial Sequence
<220> FEATURE:
<223> OTHER INFORMATION: Synthetic Construct

<400> SEQUENCE: 623
gttagttgta gttc                                                        14

```
<210> SEQ ID NO 624
<211> LENGTH: 14
<212> TYPE: DNA
<213> ORGANISM: Artificial Sequence
<220> FEATURE:
<223> OTHER INFORMATION: Synthetic Construct

<400> SEQUENCE: 624
cgaaactcta aacg                                                          14

<210> SEQ ID NO 625
<211> LENGTH: 14
<212> TYPE: DNA
<213> ORGANISM: Artificial Sequence
<220> FEATURE:
<223> OTHER INFORMATION: Synthetic Construct

<400> SEQUENCE: 625
ttagttgtag ttcg                                                          14

<210> SEQ ID NO 626
<211> LENGTH: 14
<212> TYPE: DNA
<213> ORGANISM: Artificial Sequence
<220> FEATURE:
<223> OTHER INFORMATION: Synthetic Construct

<400> SEQUENCE: 626
cgaaactcta aacg                                                          14

<210> SEQ ID NO 627
<211> LENGTH: 14
<212> TYPE: DNA
<213> ORGANISM: Artificial Sequence
<220> FEATURE:
<223> OTHER INFORMATION: Synthetic Construct

<400> SEQUENCE: 627
tagttgtagt tcgt                                                          14

<210> SEQ ID NO 628
<211> LENGTH: 14
<212> TYPE: DNA
<213> ORGANISM: Artificial Sequence
<220> FEATURE:
<223> OTHER INFORMATION: Synthetic Construct

<400> SEQUENCE: 628
cgaaactcta aacg                                                          14

<210> SEQ ID NO 629
<211> LENGTH: 14
<212> TYPE: DNA
<213> ORGANISM: Artificial Sequence
<220> FEATURE:
<223> OTHER INFORMATION: Synthetic Construct

<400> SEQUENCE: 629
agttgtagtt cgtc                                                          14

<210> SEQ ID NO 630
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 630
cgaaactcta aacg                                                    14

<210> SEQ ID NO 631
<211> LENGTH: 14
<212> TYPE: DNA
<213> ORGANISM: Artificial Sequence
<220> FEATURE:
<223> OTHER INFORMATION: Synthetic Construct

<400> SEQUENCE: 631
gttgtagttc gtcg                                                    14

<210> SEQ ID NO 632
<211> LENGTH: 14
<212> TYPE: DNA
<213> ORGANISM: Artificial Sequence
<220> FEATURE:
<223> OTHER INFORMATION: Synthetic Construct

<400> SEQUENCE: 632
cgaaactcta aacg                                                    14

<210> SEQ ID NO 633
<211> LENGTH: 14
<212> TYPE: DNA
<213> ORGANISM: Artificial Sequence
<220> FEATURE:
<223> OTHER INFORMATION: Synthetic Construct

<400> SEQUENCE: 633
ttgtagttcg tcgg                                                    14

<210> SEQ ID NO 634
<211> LENGTH: 14
<212> TYPE: DNA
<213> ORGANISM: Artificial Sequence
<220> FEATURE:
<223> OTHER INFORMATION: Synthetic Construct

<400> SEQUENCE: 634
cgaaactcta aacg                                                    14

<210> SEQ ID NO 635
<211> LENGTH: 14
<212> TYPE: DNA
<213> ORGANISM: Artificial Sequence
<220> FEATURE:
<223> OTHER INFORMATION: Synthetic Construct

<400> SEQUENCE: 635
tgtagttcgt cggc                                                    14

<210> SEQ ID NO 636
<211> LENGTH: 14
<212> TYPE: DNA
<213> ORGANISM: Artificial Sequence
<220> FEATURE:
<223> OTHER INFORMATION: Synthetic Construct

<400> SEQUENCE: 636
cgaaactcta aacg                                                    14

<210> SEQ ID NO 637
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 637
gtagttcgtc ggcg                                                    14

<210> SEQ ID NO 638
<211> LENGTH: 14
<212> TYPE: DNA
<213> ORGANISM: Artificial Sequence
<220> FEATURE:
<223> OTHER INFORMATION: Synthetic Construct

<400> SEQUENCE: 638
cgaaactcta aacg                                                    14

<210> SEQ ID NO 639
<211> LENGTH: 14
<212> TYPE: DNA
<213> ORGANISM: Artificial Sequence
<220> FEATURE:
<223> OTHER INFORMATION: Synthetic Construct

<400> SEQUENCE: 639
tagttcgtcg gcga                                                    14

<210> SEQ ID NO 640
<211> LENGTH: 14
<212> TYPE: DNA
<213> ORGANISM: Artificial Sequence
<220> FEATURE:
<223> OTHER INFORMATION: Synthetic Construct

<400> SEQUENCE: 640
cgaaactcta aacg                                                    14

<210> SEQ ID NO 641
<211> LENGTH: 14
<212> TYPE: DNA
<213> ORGANISM: Artificial Sequence
<220> FEATURE:
<223> OTHER INFORMATION: Synthetic Construct

<400> SEQUENCE: 641
agttcgtcgg cgat                                                    14

<210> SEQ ID NO 642
<211> LENGTH: 14
<212> TYPE: DNA
<213> ORGANISM: Artificial Sequence
<220> FEATURE:
<223> OTHER INFORMATION: Synthetic Construct

<400> SEQUENCE: 642
cgaaactcta aacg                                                    14

<210> SEQ ID NO 643
<211> LENGTH: 14
<212> TYPE: DNA
<213> ORGANISM: Artificial Sequence
<220> FEATURE:
<223> OTHER INFORMATION: Synthetic Construct

<400> SEQUENCE: 643
```
gttcgtcggc gatt                                                         14

<210> SEQ ID NO 644
<211> LENGTH: 14
<212> TYPE: DNA
<213> ORGANISM: Artificial Sequence
<220> FEATURE:
<223> OTHER INFORMATION: Synthetic Construct

<400> SEQUENCE: 644
cgaaactcta aacg                                                         14

<210> SEQ ID NO 645
<211> LENGTH: 14
<212> TYPE: DNA
<213> ORGANISM: Artificial Sequence
<220> FEATURE:
<223> OTHER INFORMATION: Synthetic Construct

<400> SEQUENCE: 645
ttcgtcggcg attg                                                         14

<210> SEQ ID NO 646
<211> LENGTH: 14
<212> TYPE: DNA
<213> ORGANISM: Artificial Sequence
<220> FEATURE:
<223> OTHER INFORMATION: Synthetic Construct

<400> SEQUENCE: 646
cgaaactcta aacg                                                         14

<210> SEQ ID NO 647
<211> LENGTH: 14
<212> TYPE: DNA
<213> ORGANISM: Artificial Sequence
<220> FEATURE:
<223> OTHER INFORMATION: Synthetic Construct

<400> SEQUENCE: 647
tcgtcggcga ttgg                                                         14

<210> SEQ ID NO 648
<211> LENGTH: 14
<212> TYPE: DNA
<213> ORGANISM: Artificial Sequence
<220> FEATURE:
<223> OTHER INFORMATION: Synthetic Construct

<400> SEQUENCE: 648
cgaaactcta aacg                                                         14

<210> SEQ ID NO 649
<211> LENGTH: 14
<212> TYPE: DNA
<213> ORGANISM: Artificial Sequence
<220> FEATURE:
<223> OTHER INFORMATION: Synthetic Construct

<400> SEQUENCE: 649
cgtcggcgat tggg                                                         14

<210> SEQ ID NO 650
<211> LENGTH: 14
<212> TYPE: DNA
<213> ORGANISM: Artificial Sequence
<220> FEATURE:
<223> OTHER INFORMATION: Synthetic Construct

<400> SEQUENCE: 650
cgaaactcta aacg                                                            14

<210> SEQ ID NO 651
<211> LENGTH: 14
<212> TYPE: DNA
<213> ORGANISM: Artificial Sequence
<220> FEATURE:
<223> OTHER INFORMATION: Synthetic Construct

<400> SEQUENCE: 651
gtcggcgatt gggg                                                            14

<210> SEQ ID NO 652
<211> LENGTH: 14
<212> TYPE: DNA
<213> ORGANISM: Artificial Sequence
<220> FEATURE:
<223> OTHER INFORMATION: Synthetic Construct

<400> SEQUENCE: 652
cgaaactcta aacg                                                            14

<210> SEQ ID NO 653
<211> LENGTH: 14
<212> TYPE: DNA
<213> ORGANISM: Artificial Sequence
<220> FEATURE:
<223> OTHER INFORMATION: Synthetic Construct

<400> SEQUENCE: 653
tcggcgattg gggc                                                            14

<210> SEQ ID NO 654
<211> LENGTH: 14
<212> TYPE: DNA
<213> ORGANISM: Artificial Sequence
<220> FEATURE:
<223> OTHER INFORMATION: Synthetic Construct

<400> SEQUENCE: 654
cgaaactcta aacg                                                            14

<210> SEQ ID NO 655
<211> LENGTH: 14
<212> TYPE: DNA
<213> ORGANISM: Artificial Sequence
<220> FEATURE:
<223> OTHER INFORMATION: Synthetic Construct

<400> SEQUENCE: 655
cggcgattgg ggcg                                                            14

<210> SEQ ID NO 656
<211> LENGTH: 14
<212> TYPE: DNA
<213> ORGANISM: Artificial Sequence
<220> FEATURE:
<223> OTHER INFORMATION: Synthetic Construct

<400> SEQUENCE: 656
cgaaactcta aacg                                                            14

```
<210> SEQ ID NO 657
<211> LENGTH: 14
<212> TYPE: DNA
<213> ORGANISM: Artificial Sequence
<220> FEATURE:
<223> OTHER INFORMATION: Synthetic Construct

<400> SEQUENCE: 657
ggcgattggg gcgc                                                          14

<210> SEQ ID NO 658
<211> LENGTH: 14
<212> TYPE: DNA
<213> ORGANISM: Artificial Sequence
<220> FEATURE:
<223> OTHER INFORMATION: Synthetic Construct

<400> SEQUENCE: 658
cgaaactcta aacg                                                          14

<210> SEQ ID NO 659
<211> LENGTH: 14
<212> TYPE: DNA
<213> ORGANISM: Artificial Sequence
<220> FEATURE:
<223> OTHER INFORMATION: Synthetic Construct

<400> SEQUENCE: 659
gcgattgggg cgcg                                                          14

<210> SEQ ID NO 660
<211> LENGTH: 14
<212> TYPE: DNA
<213> ORGANISM: Artificial Sequence
<220> FEATURE:
<223> OTHER INFORMATION: Synthetic Construct

<400> SEQUENCE: 660
cgaaactcta aacg                                                          14

<210> SEQ ID NO 661
<211> LENGTH: 14
<212> TYPE: DNA
<213> ORGANISM: Artificial Sequence
<220> FEATURE:
<223> OTHER INFORMATION: Synthetic Construct

<400> SEQUENCE: 661
cgattggggc gcgc                                                          14

<210> SEQ ID NO 662
<211> LENGTH: 14
<212> TYPE: DNA
<213> ORGANISM: Artificial Sequence
<220> FEATURE:
<223> OTHER INFORMATION: Synthetic Construct

<400> SEQUENCE: 662
cgaaactcta aacg                                                          14

<210> SEQ ID NO 663
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 663
gattggggcg cgcg                                                        14

<210> SEQ ID NO 664
<211> LENGTH: 14
<212> TYPE: DNA
<213> ORGANISM: Artificial Sequence
<220> FEATURE:
<223> OTHER INFORMATION: Synthetic Construct

<400> SEQUENCE: 664
cgaaactcta aacg                                                        14

<210> SEQ ID NO 665
<211> LENGTH: 14
<212> TYPE: DNA
<213> ORGANISM: Artificial Sequence
<220> FEATURE:
<223> OTHER INFORMATION: Synthetic Construct

<400> SEQUENCE: 665
attggggcgc gcgc                                                        14

<210> SEQ ID NO 666
<211> LENGTH: 14
<212> TYPE: DNA
<213> ORGANISM: Artificial Sequence
<220> FEATURE:
<223> OTHER INFORMATION: Synthetic Construct

<400> SEQUENCE: 666
cgaaactcta aacg                                                        14

<210> SEQ ID NO 667
<211> LENGTH: 14
<212> TYPE: DNA
<213> ORGANISM: Artificial Sequence
<220> FEATURE:
<223> OTHER INFORMATION: Synthetic Construct

<400> SEQUENCE: 667
ttggggcgcg cgcg                                                        14

<210> SEQ ID NO 668
<211> LENGTH: 14
<212> TYPE: DNA
<213> ORGANISM: Artificial Sequence
<220> FEATURE:
<223> OTHER INFORMATION: Synthetic Construct

<400> SEQUENCE: 668
cgaaactcta aacg                                                        14

<210> SEQ ID NO 669
<211> LENGTH: 14
<212> TYPE: DNA
<213> ORGANISM: Artificial Sequence
<220> FEATURE:
<223> OTHER INFORMATION: Synthetic Construct

<400> SEQUENCE: 669
tggggcgcgc gcgt                                                        14

<210> SEQ ID NO 670
```

-continued

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 670
cgaaactcta aacg                                                        14

<210> SEQ ID NO 671
<211> LENGTH: 14
<212> TYPE: DNA
<213> ORGANISM: Artificial Sequence
<220> FEATURE:
<223> OTHER INFORMATION: Synthetic Construct

<400> SEQUENCE: 671
ggggcgcgcg cgtt                                                        14

<210> SEQ ID NO 672
<211> LENGTH: 14
<212> TYPE: DNA
<213> ORGANISM: Artificial Sequence
<220> FEATURE:
<223> OTHER INFORMATION: Synthetic Construct

<400> SEQUENCE: 672
cgaaactcta aacg                                                        14

<210> SEQ ID NO 673
<211> LENGTH: 14
<212> TYPE: DNA
<213> ORGANISM: Artificial Sequence
<220> FEATURE:
<223> OTHER INFORMATION: Synthetic Construct

<400> SEQUENCE: 673
gggcgcgcgc gttt                                                        14

<210> SEQ ID NO 674
<211> LENGTH: 14
<212> TYPE: DNA
<213> ORGANISM: Artificial Sequence
<220> FEATURE:
<223> OTHER INFORMATION: Synthetic Construct

<400> SEQUENCE: 674
cgaaactcta aacg                                                        14

<210> SEQ ID NO 675
<211> LENGTH: 14
<212> TYPE: DNA
<213> ORGANISM: Artificial Sequence
<220> FEATURE:
<223> OTHER INFORMATION: Synthetic Construct

<400> SEQUENCE: 675
ggcgcgcgcg tttt                                                        14

<210> SEQ ID NO 676
<211> LENGTH: 14
<212> TYPE: DNA
<213> ORGANISM: Artificial Sequence
<220> FEATURE:
<223> OTHER INFORMATION: Synthetic Construct

<400> SEQUENCE: 676
```
cgaaactcta aacg					14

<210> SEQ ID NO 677
<211> LENGTH: 14
<212> TYPE: DNA
<213> ORGANISM: Artificial Sequence
<220> FEATURE:
<223> OTHER INFORMATION: Synthetic Construct

<400> SEQUENCE: 677
gcgcgcgcgt tttt					14

<210> SEQ ID NO 678
<211> LENGTH: 14
<212> TYPE: DNA
<213> ORGANISM: Artificial Sequence
<220> FEATURE:
<223> OTHER INFORMATION: Synthetic Construct

<400> SEQUENCE: 678
cgaaactcta aacg					14

<210> SEQ ID NO 679
<211> LENGTH: 14
<212> TYPE: DNA
<213> ORGANISM: Artificial Sequence
<220> FEATURE:
<223> OTHER INFORMATION: Synthetic Construct

<400> SEQUENCE: 679
cgcgcgcgtt tttt					14

<210> SEQ ID NO 680
<211> LENGTH: 14
<212> TYPE: DNA
<213> ORGANISM: Artificial Sequence
<220> FEATURE:
<223> OTHER INFORMATION: Synthetic Construct

<400> SEQUENCE: 680
cgaaactcta aacg					14

<210> SEQ ID NO 681
<211> LENGTH: 14
<212> TYPE: DNA
<213> ORGANISM: Artificial Sequence
<220> FEATURE:
<223> OTHER INFORMATION: Synthetic Construct

<400> SEQUENCE: 681
gcgcgcgttt tttt					14

<210> SEQ ID NO 682
<211> LENGTH: 14
<212> TYPE: DNA
<213> ORGANISM: Artificial Sequence
<220> FEATURE:
<223> OTHER INFORMATION: Synthetic Construct

<400> SEQUENCE: 682
cgaaactcta aacg					14

<210> SEQ ID NO 683
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 683
cgcgcgtttt tttc                                                        14

<210> SEQ ID NO 684
<211> LENGTH: 14
<212> TYPE: DNA
<213> ORGANISM: Artificial Sequence
<220> FEATURE:
<223> OTHER INFORMATION: Synthetic Construct

<400> SEQUENCE: 684
cgaaactcta aacg                                                        14

<210> SEQ ID NO 685
<211> LENGTH: 14
<212> TYPE: DNA
<213> ORGANISM: Artificial Sequence
<220> FEATURE:
<223> OTHER INFORMATION: Synthetic Construct

<400> SEQUENCE: 685
gcgcgttttt ttcg                                                        14

<210> SEQ ID NO 686
<211> LENGTH: 14
<212> TYPE: DNA
<213> ORGANISM: Artificial Sequence
<220> FEATURE:
<223> OTHER INFORMATION: Synthetic Construct

<400> SEQUENCE: 686
cgaaactcta aacg                                                        14

<210> SEQ ID NO 687
<211> LENGTH: 14
<212> TYPE: DNA
<213> ORGANISM: Artificial Sequence
<220> FEATURE:
<223> OTHER INFORMATION: Synthetic Construct

<400> SEQUENCE: 687 cgcgttttt tcgg                                                         14

<210> SEQ ID NO 688
<211> LENGTH: 14
<212> TYPE: DNA
<213> ORGANISM: Artificial Sequence
<220> FEATURE:
<223> OTHER INFORMATION: Synthetic Construct

<400> SEQUENCE: 688
cgaaactcta aacg                                                        14

<210> SEQ ID NO 689
<211> LENGTH: 14
<212> TYPE: DNA
<213> ORGANISM: Artificial Sequence
<220> FEATURE:
<223> OTHER INFORMATION: Synthetic Construct

<400> SEQUENCE: 689
gcgttttttt cggt                                                        14
```

```
<210> SEQ ID NO 690
<211> LENGTH: 14
<212> TYPE: DNA
<213> ORGANISM: Artificial Sequence
<220> FEATURE:
<223> OTHER INFORMATION: Synthetic Construct

<400> SEQUENCE: 690
cgaaactcta aacg                                                       14

<210> SEQ ID NO 691
<211> LENGTH: 14
<212> TYPE: DNA
<213> ORGANISM: Artificial Sequence
<220> FEATURE:
<223> OTHER INFORMATION: Synthetic Construct

<400> SEQUENCE: 691 cgttttttc ggtt                                                        14

<210> SEQ ID NO 692
<211> LENGTH: 14
<212> TYPE: DNA
<213> ORGANISM: Artificial Sequence
<220> FEATURE:
<223> OTHER INFORMATION: Synthetic Construct

<400> SEQUENCE: 692
cgaaactcta aacg                                                       14

<210> SEQ ID NO 693
<211> LENGTH: 14
<212> TYPE: DNA
<213> ORGANISM: Artificial Sequence
<220> FEATURE:
<223> OTHER INFORMATION: Synthetic Construct

<400> SEQUENCE: 693
gtttttttcg gttt                                                       14

<210> SEQ ID NO 694
<211> LENGTH: 14
<212> TYPE: DNA
<213> ORGANISM: Artificial Sequence
<220> FEATURE:
<223> OTHER INFORMATION: Synthetic Construct

<400> SEQUENCE: 694
cgaaactcta aacg                                                       14

<210> SEQ ID NO 695
<211> LENGTH: 14
<212> TYPE: DNA
<213> ORGANISM: Artificial Sequence
<220> FEATURE:
<223> OTHER INFORMATION: Synthetic Construct

<400> SEQUENCE: 695
tttttttcgg tttg                                                       14

<210> SEQ ID NO 696
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 696
cgaaactcta aacg                                                         14

<210> SEQ ID NO 697
<211> LENGTH: 14
<212> TYPE: DNA
<213> ORGANISM: Artificial Sequence
<220> FEATURE:
<223> OTHER INFORMATION: Synthetic Construct

<400> SEQUENCE: 697 tttttcggt ttgg                                                          14

<210> SEQ ID NO 698
<211> LENGTH: 14
<212> TYPE: DNA
<213> ORGANISM: Artificial Sequence
<220> FEATURE:
<223> OTHER INFORMATION: Synthetic Construct

<400> SEQUENCE: 698
cgaaactcta aacg                                                         14

<210> SEQ ID NO 699
<211> LENGTH: 14
<212> TYPE: DNA
<213> ORGANISM: Artificial Sequence
<220> FEATURE:
<223> OTHER INFORMATION: Synthetic Construct

<400> SEQUENCE: 699
tttttcggtt tggg                                                         14

<210> SEQ ID NO 700
<211> LENGTH: 14
<212> TYPE: DNA
<213> ORGANISM: Artificial Sequence
<220> FEATURE:
<223> OTHER INFORMATION: Synthetic Construct

<400> SEQUENCE: 700
cgaaactcta aacg                                                         14

<210> SEQ ID NO 701
<211> LENGTH: 14
<212> TYPE: DNA
<213> ORGANISM: Artificial Sequence
<220> FEATURE:
<223> OTHER INFORMATION: Synthetic Construct

<400> SEQUENCE: 701
ttttcggttt gggg                                                         14

<210> SEQ ID NO 702
<211> LENGTH: 14
<212> TYPE: DNA
<213> ORGANISM: Artificial Sequence
<220> FEATURE:
<223> OTHER INFORMATION: Synthetic Construct

<400> SEQUENCE: 702
cgaaactcta aacg                                                         14

```
<210> SEQ ID NO 703
<211> LENGTH: 14
<212> TYPE: DNA
<213> ORGANISM: Artificial Sequence
<220> FEATURE:
<223> OTHER INFORMATION: Synthetic Construct

<400> SEQUENCE: 703
tttcggtttg gggt                                                      14

<210> SEQ ID NO 704
<211> LENGTH: 14
<212> TYPE: DNA
<213> ORGANISM: Artificial Sequence
<220> FEATURE:
<223> OTHER INFORMATION: Synthetic Construct

<400> SEQUENCE: 704
tatactaacg aacg                                                      14

<210> SEQ ID NO 705
<211> LENGTH: 25
<212> TYPE: DNA
<213> ORGANISM: Artificial Sequence
<220> FEATURE:
<223> OTHER INFORMATION: Synthetic Construct

<400> SEQUENCE: 705
tcgtagagac gttgaggatc gcgac                                          25

<210> SEQ ID NO 706
<211> LENGTH: 14
<212> TYPE: DNA
<213> ORGANISM: Artificial Sequence
<220> FEATURE:
<223> OTHER INFORMATION: Synthetic Construct

<400> SEQUENCE: 706
ttcggtttgg ggtt                                                      14

<210> SEQ ID NO 707
<211> LENGTH: 14
<212> TYPE: DNA
<213> ORGANISM: Artificial Sequence
<220> FEATURE:
<223> OTHER INFORMATION: Synthetic Construct

<400> SEQUENCE: 707
tatactaacg aacg                                                      14

<210> SEQ ID NO 708
<211> LENGTH: 14
<212> TYPE: DNA
<213> ORGANISM: Artificial Sequence
<220> FEATURE:
<223> OTHER INFORMATION: Synthetic Construct

<400> SEQUENCE: 708
tcggtttggg gtta                                                      14

<210> SEQ ID NO 709
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 709
tatactaacg aacg                                                    14

<210> SEQ ID NO 710
<211> LENGTH: 14
<212> TYPE: DNA
<213> ORGANISM: Artificial Sequence
<220> FEATURE:
<223> OTHER INFORMATION: Synthetic Construct

<400> SEQUENCE: 710
cggtttgggg ttaa                                                    14

<210> SEQ ID NO 711
<211> LENGTH: 14
<212> TYPE: DNA
<213> ORGANISM: Artificial Sequence
<220> FEATURE:
<223> OTHER INFORMATION: Synthetic Construct

<400> SEQUENCE: 711
tatactaacg aacg                                                    14

<210> SEQ ID NO 712
<211> LENGTH: 14
<212> TYPE: DNA
<213> ORGANISM: Artificial Sequence
<220> FEATURE:
<223> OTHER INFORMATION: Synthetic Construct

<400> SEQUENCE: 712
ggtttggggt taat                                                    14

<210> SEQ ID NO 713
<211> LENGTH: 14
<212> TYPE: DNA
<213> ORGANISM: Artificial Sequence
<220> FEATURE:
<223> OTHER INFORMATION: Synthetic Construct

<400> SEQUENCE: 713
tatactaacg aacg                                                    14

<210> SEQ ID NO 714
<211> LENGTH: 14
<212> TYPE: DNA
<213> ORGANISM: Artificial Sequence
<220> FEATURE:
<223> OTHER INFORMATION: Synthetic Construct

<400> SEQUENCE: 714
gtttggggtt aatt                                                    14

<210> SEQ ID NO 715
<211> LENGTH: 14
<212> TYPE: DNA
<213> ORGANISM: Artificial Sequence
<220> FEATURE:
<223> OTHER INFORMATION: Synthetic Construct

<400> SEQUENCE: 715
tatactaacg aacg                                                    14

<210> SEQ ID NO 716
<211> LENGTH: 14
```

<212> TYPE: DNA
<213> ORGANISM: Artificial Sequence
<220> FEATURE:
<223> OTHER INFORMATION: Synthetic Construct

<400> SEQUENCE: 716
tttggggtta atta                                                         14

<210> SEQ ID NO 717
<211> LENGTH: 14
<212> TYPE: DNA
<213> ORGANISM: Artificial Sequence
<220> FEATURE:
<223> OTHER INFORMATION: Synthetic Construct

<400> SEQUENCE: 717
tatactaacg aacg                                                         14

<210> SEQ ID NO 718
<211> LENGTH: 14
<212> TYPE: DNA
<213> ORGANISM: Artificial Sequence
<220> FEATURE:
<223> OTHER INFORMATION: Synthetic Construct

<400> SEQUENCE: 718
ttggggttaa ttat                                                         14

<210> SEQ ID NO 719
<211> LENGTH: 14
<212> TYPE: DNA
<213> ORGANISM: Artificial Sequence
<220> FEATURE:
<223> OTHER INFORMATION: Synthetic Construct

<400> SEQUENCE: 719
tatactaacg aacg                                                         14

<210> SEQ ID NO 720
<211> LENGTH: 14
<212> TYPE: DNA
<213> ORGANISM: Artificial Sequence
<220> FEATURE:
<223> OTHER INFORMATION: Synthetic Construct

<400> SEQUENCE: 720
tggggttaat tata                                                         14

<210> SEQ ID NO 721
<211> LENGTH: 14
<212> TYPE: DNA
<213> ORGANISM: Artificial Sequence
<220> FEATURE:
<223> OTHER INFORMATION: Synthetic Construct

<400> SEQUENCE: 721
tatactaacg aacg                                                         14

<210> SEQ ID NO 722
<211> LENGTH: 14
<212> TYPE: DNA
<213> ORGANISM: Artificial Sequence
<220> FEATURE:
<223> OTHER INFORMATION: Synthetic Construct

<400> SEQUENCE: 722
ggggttaatt ataa                                                              14

<210> SEQ ID NO 723
<211> LENGTH: 14
<212> TYPE: DNA
<213> ORGANISM: Artificial Sequence
<220> FEATURE:
<223> OTHER INFORMATION: Synthetic Construct

<400> SEQUENCE: 723
tatactaacg aacg                                                              14

<210> SEQ ID NO 724
<211> LENGTH: 14
<212> TYPE: DNA
<213> ORGANISM: Artificial Sequence
<220> FEATURE:
<223> OTHER INFORMATION: Synthetic Construct

<400> SEQUENCE: 724
gggttaatta taaa                                                              14

<210> SEQ ID NO 725
<211> LENGTH: 14
<212> TYPE: DNA
<213> ORGANISM: Artificial Sequence
<220> FEATURE:
<223> OTHER INFORMATION: Synthetic Construct

<400> SEQUENCE: 725
tatactaacg aacg                                                              14

<210> SEQ ID NO 726
<211> LENGTH: 14
<212> TYPE: DNA
<213> ORGANISM: Artificial Sequence
<220> FEATURE:
<223> OTHER INFORMATION: Synthetic Construct

<400> SEQUENCE: 726
ggttaattat aaag                                                              14

<210> SEQ ID NO 727
<211> LENGTH: 14
<212> TYPE: DNA
<213> ORGANISM: Artificial Sequence
<220> FEATURE:
<223> OTHER INFORMATION: Synthetic Construct

<400> SEQUENCE: 727
tatactaacg aacg                                                              14

<210> SEQ ID NO 728
<211> LENGTH: 14
<212> TYPE: DNA
<213> ORGANISM: Artificial Sequence
<220> FEATURE:
<223> OTHER INFORMATION: Synthetic Construct

<400> SEQUENCE: 728
gttaattata aagt                                                              14

<210> SEQ ID NO 729
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 729
tatactaacg aacg                                                        14

<210> SEQ ID NO 730
<211> LENGTH: 14
<212> TYPE: DNA
<213> ORGANISM: Artificial Sequence
<220> FEATURE:
<223> OTHER INFORMATION: Synthetic Construct

<400> SEQUENCE: 730
ttaattataa agtg                                                        14

<210> SEQ ID NO 731
<211> LENGTH: 14
<212> TYPE: DNA
<213> ORGANISM: Artificial Sequence
<220> FEATURE:
<223> OTHER INFORMATION: Synthetic Construct

<400> SEQUENCE: 731
tatactaacg aacg                                                        14

<210> SEQ ID NO 732
<211> LENGTH: 14
<212> TYPE: DNA
<213> ORGANISM: Artificial Sequence
<220> FEATURE:
<223> OTHER INFORMATION: Synthetic Construct

<400> SEQUENCE: 732
taattataaa gtgg                                                        14

<210> SEQ ID NO 733
<211> LENGTH: 14
<212> TYPE: DNA
<213> ORGANISM: Artificial Sequence
<220> FEATURE:
<223> OTHER INFORMATION: Synthetic Construct

<400> SEQUENCE: 733
tatactaacg aacg                                                        14

<210> SEQ ID NO 734
<211> LENGTH: 14
<212> TYPE: DNA
<213> ORGANISM: Artificial Sequence
<220> FEATURE:
<223> OTHER INFORMATION: Synthetic Construct

<400> SEQUENCE: 734
aattataaag tggt                                                        14

<210> SEQ ID NO 735
<211> LENGTH: 14
<212> TYPE: DNA
<213> ORGANISM: Artificial Sequence
<220> FEATURE:
<223> OTHER INFORMATION: Synthetic Construct

<400> SEQUENCE: 735
tatactaacg aacg                                                        14
```

```
<210> SEQ ID NO 736
<211> LENGTH: 14
<212> TYPE: DNA
<213> ORGANISM: Artificial Sequence
<220> FEATURE:
<223> OTHER INFORMATION: Synthetic Construct

<400> SEQUENCE: 736
attataaagt ggtt                                                         14

<210> SEQ ID NO 737
<211> LENGTH: 14
<212> TYPE: DNA
<213> ORGANISM: Artificial Sequence
<220> FEATURE:
<223> OTHER INFORMATION: Synthetic Construct

<400> SEQUENCE: 737
tatactaacg aacg                                                         14

<210> SEQ ID NO 738
<211> LENGTH: 14
<212> TYPE: DNA
<213> ORGANISM: Artificial Sequence
<220> FEATURE:
<223> OTHER INFORMATION: Synthetic Construct

<400> SEQUENCE: 738
ttataaagtg gttt                                                         14

<210> SEQ ID NO 739
<211> LENGTH: 14
<212> TYPE: DNA
<213> ORGANISM: Artificial Sequence
<220> FEATURE:
<223> OTHER INFORMATION: Synthetic Construct

<400> SEQUENCE: 739
tatactaacg aacg                                                         14

<210> SEQ ID NO 740
<211> LENGTH: 14
<212> TYPE: DNA
<213> ORGANISM: Artificial Sequence
<220> FEATURE:
<223> OTHER INFORMATION: Synthetic Construct

<400> SEQUENCE: 740
tataaagtgg tttt                                                         14

<210> SEQ ID NO 741
<211> LENGTH: 14
<212> TYPE: DNA
<213> ORGANISM: Artificial Sequence
<220> FEATURE:
<223> OTHER INFORMATION: Synthetic Construct

<400> SEQUENCE: 741
tatactaacg aacg                                                         14

<210> SEQ ID NO 742
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 742
ataaagtggt ttta                                                          14

<210> SEQ ID NO 743
<211> LENGTH: 14
<212> TYPE: DNA
<213> ORGANISM: Artificial Sequence
<220> FEATURE:
<223> OTHER INFORMATION: Synthetic Construct

<400> SEQUENCE: 743
tatactaacg aacg                                                          14

<210> SEQ ID NO 744
<211> LENGTH: 14
<212> TYPE: DNA
<213> ORGANISM: Artificial Sequence
<220> FEATURE:
<223> OTHER INFORMATION: Synthetic Construct

<400> SEQUENCE: 744
taaagtggtt ttag                                                          14

<210> SEQ ID NO 745
<211> LENGTH: 14
<212> TYPE: DNA
<213> ORGANISM: Artificial Sequence
<220> FEATURE:
<223> OTHER INFORMATION: Synthetic Construct

<400> SEQUENCE: 745
tatactaacg aacg                                                          14

<210> SEQ ID NO 746
<211> LENGTH: 14
<212> TYPE: DNA
<213> ORGANISM: Artificial Sequence
<220> FEATURE:
<223> OTHER INFORMATION: Synthetic Construct

<400> SEQUENCE: 746
aaagtggttt tagt                                                          14

<210> SEQ ID NO 747
<211> LENGTH: 14
<212> TYPE: DNA
<213> ORGANISM: Artificial Sequence
<220> FEATURE:
<223> OTHER INFORMATION: Synthetic Construct

<400> SEQUENCE: 747
tatactaacg aacg                                                          14

<210> SEQ ID NO 748
<211> LENGTH: 14
<212> TYPE: DNA
<213> ORGANISM: Artificial Sequence
<220> FEATURE:
<223> OTHER INFORMATION: Synthetic Construct

<400> SEQUENCE: 748
aagtggtttt agta                                                          14

<210> SEQ ID NO 749
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 749
tatactaacg aacg                                                       14

<210> SEQ ID NO 750
<211> LENGTH: 14
<212> TYPE: DNA
<213> ORGANISM: Artificial Sequence
<220> FEATURE:
<223> OTHER INFORMATION: Synthetic Construct

<400> SEQUENCE: 750
agtggtttta gtag                                                       14

<210> SEQ ID NO 751
<211> LENGTH: 14
<212> TYPE: DNA
<213> ORGANISM: Artificial Sequence
<220> FEATURE:
<223> OTHER INFORMATION: Synthetic Construct

<400> SEQUENCE: 751
tatactaacg aacg                                                       14

<210> SEQ ID NO 752
<211> LENGTH: 14
<212> TYPE: DNA
<213> ORGANISM: Artificial Sequence
<220> FEATURE:
<223> OTHER INFORMATION: Synthetic Construct

<400> SEQUENCE: 752
gtggttttag tagt                                                       14

<210> SEQ ID NO 753
<211> LENGTH: 14
<212> TYPE: DNA
<213> ORGANISM: Artificial Sequence
<220> FEATURE:
<223> OTHER INFORMATION: Synthetic Construct

<400> SEQUENCE: 753
tatactaacg aacg                                                       14

<210> SEQ ID NO 754
<211> LENGTH: 14
<212> TYPE: DNA
<213> ORGANISM: Artificial Sequence
<220> FEATURE:
<223> OTHER INFORMATION: Synthetic Construct

<400> SEQUENCE: 754
tggttttagt agtc                                                       14

<210> SEQ ID NO 755
<211> LENGTH: 14
<212> TYPE: DNA
<213> ORGANISM: Artificial Sequence
<220> FEATURE:
<223> OTHER INFORMATION: Synthetic Construct

<400> SEQUENCE: 755
```
tatactaacg aacg                                                          14

<210> SEQ ID NO 756
<211> LENGTH: 14
<212> TYPE: DNA
<213> ORGANISM: Artificial Sequence
<220> FEATURE:
<223> OTHER INFORMATION: Synthetic Construct

<400> SEQUENCE: 756
ggttttagta gtcg                                                          14

<210> SEQ ID NO 757
<211> LENGTH: 14
<212> TYPE: DNA
<213> ORGANISM: Artificial Sequence
<220> FEATURE:
<223> OTHER INFORMATION: Synthetic Construct

<400> SEQUENCE: 757
tatactaacg aacg                                                          14

<210> SEQ ID NO 758
<211> LENGTH: 14
<212> TYPE: DNA
<213> ORGANISM: Artificial Sequence
<220> FEATURE:
<223> OTHER INFORMATION: Synthetic Construct

<400> SEQUENCE: 758
gttttagtag tcgt                                                          14

<210> SEQ ID NO 759
<211> LENGTH: 14
<212> TYPE: DNA
<213> ORGANISM: Artificial Sequence
<220> FEATURE:
<223> OTHER INFORMATION: Synthetic Construct

<400> SEQUENCE: 759
tatactaacg aacg                                                          14

<210> SEQ ID NO 760
<211> LENGTH: 14
<212> TYPE: DNA
<213> ORGANISM: Artificial Sequence
<220> FEATURE:
<223> OTHER INFORMATION: Synthetic Construct

<400> SEQUENCE: 760
ttttagtagt cgtt                                                          14

<210> SEQ ID NO 761
<211> LENGTH: 14
<212> TYPE: DNA
<213> ORGANISM: Artificial Sequence
<220> FEATURE:
<223> OTHER INFORMATION: Synthetic Construct

<400> SEQUENCE: 761
tatactaacg aacg                                                          14

<210> SEQ ID NO 762
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 762
tttagtagtc gtta                                                          14

<210> SEQ ID NO 763
<211> LENGTH: 14
<212> TYPE: DNA
<213> ORGANISM: Artificial Sequence
<220> FEATURE:
<223> OTHER INFORMATION: Synthetic Construct

<400> SEQUENCE: 763
tatactaacg aacg                                                          14

<210> SEQ ID NO 764
<211> LENGTH: 14
<212> TYPE: DNA
<213> ORGANISM: Artificial Sequence
<220> FEATURE:
<223> OTHER INFORMATION: Synthetic Construct

<400> SEQUENCE: 764
ttagtagtcg ttaa                                                          14

<210> SEQ ID NO 765
<211> LENGTH: 14
<212> TYPE: DNA
<213> ORGANISM: Artificial Sequence
<220> FEATURE:
<223> OTHER INFORMATION: Synthetic Construct

<400> SEQUENCE: 765
tatactaacg aacg                                                          14

<210> SEQ ID NO 766
<211> LENGTH: 14
<212> TYPE: DNA
<213> ORGANISM: Artificial Sequence
<220> FEATURE:
<223> OTHER INFORMATION: Synthetic Construct

<400> SEQUENCE: 766
tagtagtcgt taag                                                          14

<210> SEQ ID NO 767
<211> LENGTH: 14
<212> TYPE: DNA
<213> ORGANISM: Artificial Sequence
<220> FEATURE:
<223> OTHER INFORMATION: Synthetic Construct

<400> SEQUENCE: 767
tatactaacg aacg                                                          14

<210> SEQ ID NO 768
<211> LENGTH: 14
<212> TYPE: DNA
<213> ORGANISM: Artificial Sequence
<220> FEATURE:
<223> OTHER INFORMATION: Synthetic Construct

<400> SEQUENCE: 768
agtagtcgtt aagt                                                          14
```

<210> SEQ ID NO 769
<211> LENGTH: 14
<212> TYPE: DNA
<213> ORGANISM: Artificial Sequence
<220> FEATURE:
<223> OTHER INFORMATION: Synthetic Construct

<400> SEQUENCE: 769
tatactaacg aacg                                                        14

<210> SEQ ID NO 770
<211> LENGTH: 14
<212> TYPE: DNA
<213> ORGANISM: Artificial Sequence
<220> FEATURE:
<223> OTHER INFORMATION: Synthetic Construct

<400> SEQUENCE: 770
gtagtcgtta agtt                                                        14

<210> SEQ ID NO 771
<211> LENGTH: 14
<212> TYPE: DNA
<213> ORGANISM: Artificial Sequence
<220> FEATURE:
<223> OTHER INFORMATION: Synthetic Construct

<400> SEQUENCE: 771
tatactaacg aacg                                                        14

<210> SEQ ID NO 772
<211> LENGTH: 14
<212> TYPE: DNA
<213> ORGANISM: Artificial Sequence
<220> FEATURE:
<223> OTHER INFORMATION: Synthetic Construct

<400> SEQUENCE: 772
tagtcgttaa gttt                                                        14

<210> SEQ ID NO 773
<211> LENGTH: 14
<212> TYPE: DNA
<213> ORGANISM: Artificial Sequence
<220> FEATURE:
<223> OTHER INFORMATION: Synthetic Construct

<400> SEQUENCE: 773
tatactaacg aacg                                                        14

<210> SEQ ID NO 774
<211> LENGTH: 14
<212> TYPE: DNA
<213> ORGANISM: Artificial Sequence
<220> FEATURE:
<223> OTHER INFORMATION: Synthetic Construct

<400> SEQUENCE: 774
agtcgttaag tttc                                                        14

<210> SEQ ID NO 775
<211> LENGTH: 14
<212> TYPE: DNA
<213> ORGANISM: Artificial Sequence
<220> FEATURE:

<223> OTHER INFORMATION: Synthetic Construct

<400> SEQUENCE: 775
tatactaacg aacg                                                         14

<210> SEQ ID NO 776
<211> LENGTH: 14
<212> TYPE: DNA
<213> ORGANISM: Artificial Sequence
<220> FEATURE:
<223> OTHER INFORMATION: Synthetic Construct

<400> SEQUENCE: 776
gtcgttaagt ttcg                                                         14

<210> SEQ ID NO 777
<211> LENGTH: 14
<212> TYPE: DNA
<213> ORGANISM: Artificial Sequence
<220> FEATURE:
<223> OTHER INFORMATION: Synthetic Construct

<400> SEQUENCE: 777
tatactaacg aacg                                                         14

<210> SEQ ID NO 778
<211> LENGTH: 14
<212> TYPE: DNA
<213> ORGANISM: Artificial Sequence
<220> FEATURE:
<223> OTHER INFORMATION: Synthetic Construct

<400> SEQUENCE: 778
tcgttaagtt tcgg                                                         14

<210> SEQ ID NO 779
<211> LENGTH: 14
<212> TYPE: DNA
<213> ORGANISM: Artificial Sequence
<220> FEATURE:
<223> OTHER INFORMATION: Synthetic Construct

<400> SEQUENCE: 779
tatactaacg aacg                                                         14

<210> SEQ ID NO 780
<211> LENGTH: 14
<212> TYPE: DNA
<213> ORGANISM: Artificial Sequence
<220> FEATURE:
<223> OTHER INFORMATION: Synthetic Construct

<400> SEQUENCE: 780
cgttaagttt cggg                                                         14

<210> SEQ ID NO 781
<211> LENGTH: 14
<212> TYPE: DNA
<213> ORGANISM: Artificial Sequence
<220> FEATURE:
<223> OTHER INFORMATION: Synthetic Construct

<400> SEQUENCE: 781
tatactaacg aacg                                                         14

```
<210> SEQ ID NO 782
<211> LENGTH: 14
<212> TYPE: DNA
<213> ORGANISM: Artificial Sequence
<220> FEATURE:
<223> OTHER INFORMATION: Synthetic Construct

<400> SEQUENCE: 782
gttaagtttc ggga                                                        14

<210> SEQ ID NO 783
<211> LENGTH: 14
<212> TYPE: DNA
<213> ORGANISM: Artificial Sequence
<220> FEATURE:
<223> OTHER INFORMATION: Synthetic Construct

<400> SEQUENCE: 783
tatactaacg aacg                                                        14

<210> SEQ ID NO 784
<211> LENGTH: 14
<212> TYPE: DNA
<213> ORGANISM: Artificial Sequence
<220> FEATURE:
<223> OTHER INFORMATION: Synthetic Construct

<400> SEQUENCE: 784
ttaagtttcg gac                                                         14

<210> SEQ ID NO 785
<211> LENGTH: 14
<212> TYPE: DNA
<213> ORGANISM: Artificial Sequence
<220> FEATURE:
<223> OTHER INFORMATION: Synthetic Construct

<400> SEQUENCE: 785
tatactaacg aacg                                                        14

<210> SEQ ID NO 786
<211> LENGTH: 14
<212> TYPE: DNA
<213> ORGANISM: Artificial Sequence
<220> FEATURE:
<223> OTHER INFORMATION: Synthetic Construct

<400> SEQUENCE: 786
taagtttcgg gacg                                                        14

<210> SEQ ID NO 787
<211> LENGTH: 14
<212> TYPE: DNA
<213> ORGANISM: Artificial Sequence
<220> FEATURE:
<223> OTHER INFORMATION: Synthetic Construct

<400> SEQUENCE: 787
tatactaacg aacg                                                        14

<210> SEQ ID NO 788
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 788
aagtttcggg acgg                                                    14

<210> SEQ ID NO 789
<211> LENGTH: 14
<212> TYPE: DNA
<213> ORGANISM: Artificial Sequence
<220> FEATURE:
<223> OTHER INFORMATION: Synthetic Construct

<400> SEQUENCE: 789
tatactaacg aacg                                                    14

<210> SEQ ID NO 790
<211> LENGTH: 14
<212> TYPE: DNA
<213> ORGANISM: Artificial Sequence
<220> FEATURE:
<223> OTHER INFORMATION: Synthetic Construct

<400> SEQUENCE: 790
agtttcggga cggc                                                    14

<210> SEQ ID NO 791
<211> LENGTH: 14
<212> TYPE: DNA
<213> ORGANISM: Artificial Sequence
<220> FEATURE:
<223> OTHER INFORMATION: Synthetic Construct

<400> SEQUENCE: 791
tatactaacg aacg                                                    14

<210> SEQ ID NO 792
<211> LENGTH: 14
<212> TYPE: DNA
<213> ORGANISM: Artificial Sequence
<220> FEATURE:
<223> OTHER INFORMATION: Synthetic Construct

<400> SEQUENCE: 792
gtttcgggac ggcg                                                    14

<210> SEQ ID NO 793
<211> LENGTH: 14
<212> TYPE: DNA
<213> ORGANISM: Artificial Sequence
<220> FEATURE:
<223> OTHER INFORMATION: Synthetic Construct

<400> SEQUENCE: 793
tatactaacg aacg                                                    14

<210> SEQ ID NO 794
<211> LENGTH: 14
<212> TYPE: DNA
<213> ORGANISM: Artificial Sequence
<220> FEATURE:
<223> OTHER INFORMATION: Synthetic Construct

<400> SEQUENCE: 794
tttcgggacg gcga                                                    14

<210> SEQ ID NO 795
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 795
tatactaacg aacg                                                     14

<210> SEQ ID NO 796
<211> LENGTH: 14
<212> TYPE: DNA
<213> ORGANISM: Artificial Sequence
<220> FEATURE:
<223> OTHER INFORMATION: Synthetic Construct

<400> SEQUENCE: 796
ttcgggacgg cgag                                                     14

<210> SEQ ID NO 797
<211> LENGTH: 14
<212> TYPE: DNA
<213> ORGANISM: Artificial Sequence
<220> FEATURE:
<223> OTHER INFORMATION: Synthetic Construct

<400> SEQUENCE: 797
tatactaacg aacg                                                     14

<210> SEQ ID NO 798
<211> LENGTH: 14
<212> TYPE: DNA
<213> ORGANISM: Artificial Sequence
<220> FEATURE:
<223> OTHER INFORMATION: Synthetic Construct

<400> SEQUENCE: 798
tcgggacggc gagg                                                     14

<210> SEQ ID NO 799
<211> LENGTH: 14
<212> TYPE: DNA
<213> ORGANISM: Artificial Sequence
<220> FEATURE:
<223> OTHER INFORMATION: Synthetic Construct

<400> SEQUENCE: 799
tatactaacg aacg                                                     14

<210> SEQ ID NO 800
<211> LENGTH: 14
<212> TYPE: DNA
<213> ORGANISM: Artificial Sequence
<220> FEATURE:
<223> OTHER INFORMATION: Synthetic Construct

<400> SEQUENCE: 800
cgggacggcg aggt                                                     14

<210> SEQ ID NO 801
<211> LENGTH: 14
<212> TYPE: DNA
<213> ORGANISM: Artificial Sequence
<220> FEATURE:
<223> OTHER INFORMATION: Synthetic Construct

<400> SEQUENCE: 801
```
tatactaacg aacg                                                    14

<210> SEQ ID NO 802
<211> LENGTH: 14
<212> TYPE: DNA
<213> ORGANISM: Artificial Sequence
<220> FEATURE:
<223> OTHER INFORMATION: Synthetic Construct

<400> SEQUENCE: 802
gggacggcga ggta                                                    14

<210> SEQ ID NO 803
<211> LENGTH: 14
<212> TYPE: DNA
<213> ORGANISM: Artificial Sequence
<220> FEATURE:
<223> OTHER INFORMATION: Synthetic Construct

<400> SEQUENCE: 803
tatactaacg aacg                                                    14

<210> SEQ ID NO 804
<211> LENGTH: 14
<212> TYPE: DNA
<213> ORGANISM: Artificial Sequence
<220> FEATURE:
<223> OTHER INFORMATION: Synthetic Construct

<400> SEQUENCE: 804
ggacggcgag gtag                                                    14

<210> SEQ ID NO 805
<211> LENGTH: 14
<212> TYPE: DNA
<213> ORGANISM: Artificial Sequence
<220> FEATURE:
<223> OTHER INFORMATION: Synthetic Construct

<400> SEQUENCE: 805
tatactaacg aacg                                                    14

<210> SEQ ID NO 806
<211> LENGTH: 14
<212> TYPE: DNA
<213> ORGANISM: Artificial Sequence
<220> FEATURE:
<223> OTHER INFORMATION: Synthetic Construct

<400> SEQUENCE: 806
gacggcgagg tagg                                                    14

<210> SEQ ID NO 807
<211> LENGTH: 14
<212> TYPE: DNA
<213> ORGANISM: Artificial Sequence
<220> FEATURE:
<223> OTHER INFORMATION: Synthetic Construct

<400> SEQUENCE: 807
tatactaacg aacg                                                    14

<210> SEQ ID NO 808
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 808
acggcgaggt aggc                                                         14

<210> SEQ ID NO 809
<211> LENGTH: 14
<212> TYPE: DNA
<213> ORGANISM: Artificial Sequence
<220> FEATURE:
<223> OTHER INFORMATION: Synthetic Construct

<400> SEQUENCE: 809
tatactaacg aacg                                                         14

<210> SEQ ID NO 810
<211> LENGTH: 14
<212> TYPE: DNA
<213> ORGANISM: Artificial Sequence
<220> FEATURE:
<223> OTHER INFORMATION: Synthetic Construct

<400> SEQUENCE: 810
cggcgaggta ggcg                                                         14

<210> SEQ ID NO 811
<211> LENGTH: 14
<212> TYPE: DNA
<213> ORGANISM: Artificial Sequence
<220> FEATURE:
<223> OTHER INFORMATION: Synthetic Construct

<400> SEQUENCE: 811
tatactaacg aacg                                                         14

<210> SEQ ID NO 812
<211> LENGTH: 14
<212> TYPE: DNA
<213> ORGANISM: Artificial Sequence
<220> FEATURE:
<223> OTHER INFORMATION: Synthetic Construct

<400> SEQUENCE: 812
ggcgaggtag gcgt                                                         14

<210> SEQ ID NO 813
<211> LENGTH: 14
<212> TYPE: DNA
<213> ORGANISM: Artificial Sequence
<220> FEATURE:
<223> OTHER INFORMATION: Synthetic Construct

<400> SEQUENCE: 813
tatactaacg aacg                                                         14

<210> SEQ ID NO 814
<211> LENGTH: 14
<212> TYPE: DNA
<213> ORGANISM: Artificial Sequence
<220> FEATURE:
<223> OTHER INFORMATION: Synthetic Construct

<400> SEQUENCE: 814
gcgaggtagg cgtt                                                         14
```

<210> SEQ ID NO 815
<211> LENGTH: 14
<212> TYPE: DNA
<213> ORGANISM: Artificial Sequence
<220> FEATURE:
<223> OTHER INFORMATION: Synthetic Construct

<400> SEQUENCE: 815
tatactaacg aacg                                                      14

<210> SEQ ID NO 816
<211> LENGTH: 14
<212> TYPE: DNA
<213> ORGANISM: Artificial Sequence
<220> FEATURE:
<223> OTHER INFORMATION: Synthetic Construct

<400> SEQUENCE: 816
cgaggtaggc gttt                                                      14

<210> SEQ ID NO 817
<211> LENGTH: 14
<212> TYPE: DNA
<213> ORGANISM: Artificial Sequence
<220> FEATURE:
<223> OTHER INFORMATION: Synthetic Construct

<400> SEQUENCE: 817
tatactaacg aacg                                                      14

<210> SEQ ID NO 818
<211> LENGTH: 14
<212> TYPE: DNA
<213> ORGANISM: Artificial Sequence
<220> FEATURE:
<223> OTHER INFORMATION: Synthetic Construct

<400> SEQUENCE: 818
gaggtaggcg ttta                                                      14

<210> SEQ ID NO 819
<211> LENGTH: 14
<212> TYPE: DNA
<213> ORGANISM: Artificial Sequence
<220> FEATURE:
<223> OTHER INFORMATION: Synthetic Construct

<400> SEQUENCE: 819
tatactaacg aacg                                                      14

<210> SEQ ID NO 820
<211> LENGTH: 14
<212> TYPE: DNA
<213> ORGANISM: Artificial Sequence
<220> FEATURE:
<223> OTHER INFORMATION: Synthetic Construct

<400> SEQUENCE: 820
aggtaggcgt ttag                                                      14

<210> SEQ ID NO 821
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 821
tatactaacg aacg                                                        14

<210> SEQ ID NO 822
<211> LENGTH: 14
<212> TYPE: DNA
<213> ORGANISM: Artificial Sequence
<220> FEATURE:
<223> OTHER INFORMATION: Synthetic Construct

<400> SEQUENCE: 822
ggtaggcgtt taga                                                        14

<210> SEQ ID NO 823
<211> LENGTH: 14
<212> TYPE: DNA
<213> ORGANISM: Artificial Sequence
<220> FEATURE:
<223> OTHER INFORMATION: Synthetic Construct

<400> SEQUENCE: 823
tatactaacg aacg                                                        14

<210> SEQ ID NO 824
<211> LENGTH: 14
<212> TYPE: DNA
<213> ORGANISM: Artificial Sequence
<220> FEATURE:
<223> OTHER INFORMATION: Synthetic Construct

<400> SEQUENCE: 824
gtaggcgttt agag                                                        14

<210> SEQ ID NO 825
<211> LENGTH: 14
<212> TYPE: DNA
<213> ORGANISM: Artificial Sequence
<220> FEATURE:
<223> OTHER INFORMATION: Synthetic Construct

<400> SEQUENCE: 825
tatactaacg aacg                                                        14

<210> SEQ ID NO 826
<211> LENGTH: 14
<212> TYPE: DNA
<213> ORGANISM: Artificial Sequence
<220> FEATURE:
<223> OTHER INFORMATION: Synthetic Construct

<400> SEQUENCE: 826
taggcgttta gagt                                                        14

<210> SEQ ID NO 827
<211> LENGTH: 14
<212> TYPE: DNA
<213> ORGANISM: Artificial Sequence
<220> FEATURE:
<223> OTHER INFORMATION: Synthetic Construct

<400> SEQUENCE: 827
tatactaacg aacg                                                        14

<210> SEQ ID NO 828
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 828
aggcgtttag agtt                                                         14

<210> SEQ ID NO 829
<211> LENGTH: 14
<212> TYPE: DNA
<213> ORGANISM: Artificial Sequence
<220> FEATURE:
<223> OTHER INFORMATION: Synthetic Construct

<400> SEQUENCE: 829
tatactaacg aacg                                                         14

<210> SEQ ID NO 830
<211> LENGTH: 14
<212> TYPE: DNA
<213> ORGANISM: Artificial Sequence
<220> FEATURE:
<223> OTHER INFORMATION: Synthetic Construct

<400> SEQUENCE: 830
ggcgtttaga gttt                                                         14

<210> SEQ ID NO 831
<211> LENGTH: 14
<212> TYPE: DNA
<213> ORGANISM: Artificial Sequence
<220> FEATURE:
<223> OTHER INFORMATION: Synthetic Construct

<400> SEQUENCE: 831
tatactaacg aacg                                                         14

<210> SEQ ID NO 832
<211> LENGTH: 14
<212> TYPE: DNA
<213> ORGANISM: Artificial Sequence
<220> FEATURE:
<223> OTHER INFORMATION: Synthetic Construct

<400> SEQUENCE: 832
gcgtttagag tttc                                                         14

<210> SEQ ID NO 833
<211> LENGTH: 14
<212> TYPE: DNA
<213> ORGANISM: Artificial Sequence
<220> FEATURE:
<223> OTHER INFORMATION: Synthetic Construct

<400> SEQUENCE: 833
tatactaacg aacg                                                         14

<210> SEQ ID NO 834
<211> LENGTH: 14
<212> TYPE: DNA
<213> ORGANISM: Artificial Sequence
<220> FEATURE:
<223> OTHER INFORMATION: Synthetic Construct

<400> SEQUENCE: 834
```
cgtttagagt ttcg                                                14

<210> SEQ ID NO 835
<211> LENGTH: 14
<212> TYPE: DNA
<213> ORGANISM: Artificial Sequence
<220> FEATURE:
<223> OTHER INFORMATION: Synthetic Construct

<400> SEQUENCE: 835
tatactaacg aacg                                                14

<210> SEQ ID NO 836
<211> LENGTH: 14
<212> TYPE: DNA
<213> ORGANISM: Artificial Sequence
<220> FEATURE:
<223> OTHER INFORMATION: Synthetic Construct

<400> SEQUENCE: 836
gtttagagtt tcgt                                                14

<210> SEQ ID NO 837
<211> LENGTH: 14
<212> TYPE: DNA
<213> ORGANISM: Artificial Sequence
<220> FEATURE:
<223> OTHER INFORMATION: Synthetic Construct

<400> SEQUENCE: 837
tatactaacg aacg                                                14

<210> SEQ ID NO 838
<211> LENGTH: 14
<212> TYPE: DNA
<213> ORGANISM: Artificial Sequence
<220> FEATURE:
<223> OTHER INFORMATION: Synthetic Construct

<400> SEQUENCE: 838
tttagagttt cgta                                                14

<210> SEQ ID NO 839
<211> LENGTH: 14
<212> TYPE: DNA
<213> ORGANISM: Artificial Sequence
<220> FEATURE:
<223> OTHER INFORMATION: Synthetic Construct

<400> SEQUENCE: 839
tatactaacg aacg                                                14

<210> SEQ ID NO 840
<211> LENGTH: 14
<212> TYPE: DNA
<213> ORGANISM: Artificial Sequence
<220> FEATURE:
<223> OTHER INFORMATION: Synthetic Construct

<400> SEQUENCE: 840
ttagagtttc gtag                                                14

<210> SEQ ID NO 841
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 841
cgactctaaa aaaa                                                         14

<210> SEQ ID NO 842
<211> LENGTH: 25
<212> TYPE: DNA
<213> ORGANISM: Artificial Sequence
<220> FEATURE:
<223> OTHER INFORMATION: Synthetic Construct

<400> SEQUENCE: 842
tcgggttcgt tttttttcga cgttc                                             25

<210> SEQ ID NO 843
<211> LENGTH: 14
<212> TYPE: DNA
<213> ORGANISM: Artificial Sequence
<220> FEATURE:
<223> OTHER INFORMATION: Synthetic Construct

<400> SEQUENCE: 843
tagagtttcg tagt                                                         14

<210> SEQ ID NO 844
<211> LENGTH: 14
<212> TYPE: DNA
<213> ORGANISM: Artificial Sequence
<220> FEATURE:
<223> OTHER INFORMATION: Synthetic Construct

<400> SEQUENCE: 844
cgactctaaa aaaa                                                         14

<210> SEQ ID NO 845
<211> LENGTH: 14
<212> TYPE: DNA
<213> ORGANISM: Artificial Sequence
<220> FEATURE:
<223> OTHER INFORMATION: Synthetic Construct

<400> SEQUENCE: 845
agagtttcgt agtt                                                         14

<210> SEQ ID NO 846
<211> LENGTH: 14
<212> TYPE: DNA
<213> ORGANISM: Artificial Sequence
<220> FEATURE:
<223> OTHER INFORMATION: Synthetic Construct

<400> SEQUENCE: 846
cgactctaaa aaaa                                                         14

<210> SEQ ID NO 847
<211> LENGTH: 14
<212> TYPE: DNA
<213> ORGANISM: Artificial Sequence
<220> FEATURE:
<223> OTHER INFORMATION: Synthetic Construct

<400> SEQUENCE: 847
gagtttcgta gttt                                                         14
```

<210> SEQ ID NO 848
<211> LENGTH: 14
<212> TYPE: DNA
<213> ORGANISM: Artificial Sequence
<220> FEATURE:
<223> OTHER INFORMATION: Synthetic Construct

<400> SEQUENCE: 848
cgactctaaa aaaa                                                        14

<210> SEQ ID NO 849
<211> LENGTH: 14
<212> TYPE: DNA
<213> ORGANISM: Artificial Sequence
<220> FEATURE:
<223> OTHER INFORMATION: Synthetic Construct

<400> SEQUENCE: 849
agtttcgtag tttg                                                        14

<210> SEQ ID NO 850
<211> LENGTH: 14
<212> TYPE: DNA
<213> ORGANISM: Artificial Sequence
<220> FEATURE:
<223> OTHER INFORMATION: Synthetic Construct

<400> SEQUENCE: 850
cgactctaaa aaaa                                                        14

<210> SEQ ID NO 851
<211> LENGTH: 14
<212> TYPE: DNA
<213> ORGANISM: Artificial Sequence
<220> FEATURE:
<223> OTHER INFORMATION: Synthetic Construct

<400> SEQUENCE: 851
gtttcgtagt ttgg                                                        14

<210> SEQ ID NO 852
<211> LENGTH: 14
<212> TYPE: DNA
<213> ORGANISM: Artificial Sequence
<220> FEATURE:
<223> OTHER INFORMATION: Synthetic Construct

<400> SEQUENCE: 852
cgactctaaa aaaa                                                        14

<210> SEQ ID NO 853
<211> LENGTH: 14
<212> TYPE: DNA
<213> ORGANISM: Artificial Sequence
<220> FEATURE:
<223> OTHER INFORMATION: Synthetic Construct

<400> SEQUENCE: 853
tttcgtagtt tggt                                                        14

<210> SEQ ID NO 854
<211> LENGTH: 14
<212> TYPE: DNA
<213> ORGANISM: Artificial Sequence
<220> FEATURE:

<223> OTHER INFORMATION: Synthetic Construct

<400> SEQUENCE: 854
cgactctaaa aaaa                                                14

<210> SEQ ID NO 855
<211> LENGTH: 14
<212> TYPE: DNA
<213> ORGANISM: Artificial Sequence
<220> FEATURE:
<223> OTHER INFORMATION: Synthetic Construct

<400> SEQUENCE: 855
ttcgtagttt ggtt                                                14

<210> SEQ ID NO 856
<211> LENGTH: 14
<212> TYPE: DNA
<213> ORGANISM: Artificial Sequence
<220> FEATURE:
<223> OTHER INFORMATION: Synthetic Construct

<400> SEQUENCE: 856
cgactctaaa aaaa                                                14

<210> SEQ ID NO 857
<211> LENGTH: 14
<212> TYPE: DNA
<213> ORGANISM: Artificial Sequence
<220> FEATURE:
<223> OTHER INFORMATION: Synthetic Construct

<400> SEQUENCE: 857
tcgtagtttg gttc                                                14

<210> SEQ ID NO 858
<211> LENGTH: 14
<212> TYPE: DNA
<213> ORGANISM: Artificial Sequence
<220> FEATURE:
<223> OTHER INFORMATION: Synthetic Construct

<400> SEQUENCE: 858
cgactctaaa aaaa                                                14

<210> SEQ ID NO 859
<211> LENGTH: 14
<212> TYPE: DNA
<213> ORGANISM: Artificial Sequence
<220> FEATURE:
<223> OTHER INFORMATION: Synthetic Construct

<400> SEQUENCE: 859
cgtagtttgg ttcg                                                14

<210> SEQ ID NO 860
<211> LENGTH: 14
<212> TYPE: DNA
<213> ORGANISM: Artificial Sequence
<220> FEATURE:
<223> OTHER INFORMATION: Synthetic Construct

<400> SEQUENCE: 860
cgactctaaa aaaa                                                14

<210> SEQ ID NO 861
<211> LENGTH: 14
<212> TYPE: DNA
<213> ORGANISM: Artificial Sequence
<220> FEATURE:
<223> OTHER INFORMATION: Synthetic Construct

<400> SEQUENCE: 861
gtagtttggt tcgt                                                   14

<210> SEQ ID NO 862
<211> LENGTH: 14
<212> TYPE: DNA
<213> ORGANISM: Artificial Sequence
<220> FEATURE:
<223> OTHER INFORMATION: Synthetic Construct

<400> SEQUENCE: 862
cgactctaaa aaaa                                                   14

<210> SEQ ID NO 863
<211> LENGTH: 14
<212> TYPE: DNA
<213> ORGANISM: Artificial Sequence
<220> FEATURE:
<223> OTHER INFORMATION: Synthetic Construct

<400> SEQUENCE: 863
tagtttggtt cgtg                                                   14

<210> SEQ ID NO 864
<211> LENGTH: 14
<212> TYPE: DNA
<213> ORGANISM: Artificial Sequence
<220> FEATURE:
<223> OTHER INFORMATION: Synthetic Construct

<400> SEQUENCE: 864
cgactctaaa aaaa                                                   14

<210> SEQ ID NO 865
<211> LENGTH: 14
<212> TYPE: DNA
<213> ORGANISM: Artificial Sequence
<220> FEATURE:
<223> OTHER INFORMATION: Synthetic Construct

<400> SEQUENCE: 865
agtttggttc gtga                                                   14

<210> SEQ ID NO 866
<211> LENGTH: 14
<212> TYPE: DNA
<213> ORGANISM: Artificial Sequence
<220> FEATURE:
<223> OTHER INFORMATION: Synthetic Construct

<400> SEQUENCE: 866
cgactctaaa aaaa                                                   14

<210> SEQ ID NO 867
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 867
gtttggttcg tgat                                                     14

<210> SEQ ID NO 868
<211> LENGTH: 14
<212> TYPE: DNA
<213> ORGANISM: Artificial Sequence
<220> FEATURE:
<223> OTHER INFORMATION: Synthetic Construct

<400> SEQUENCE: 868
cgactctaaa aaaa                                                     14

<210> SEQ ID NO 869
<211> LENGTH: 14
<212> TYPE: DNA
<213> ORGANISM: Artificial Sequence
<220> FEATURE:
<223> OTHER INFORMATION: Synthetic Construct

<400> SEQUENCE: 869
tttggttcgt gatt                                                     14

<210> SEQ ID NO 870
<211> LENGTH: 14
<212> TYPE: DNA
<213> ORGANISM: Artificial Sequence
<220> FEATURE:
<223> OTHER INFORMATION: Synthetic Construct

<400> SEQUENCE: 870
cgactctaaa aaaa                                                     14

<210> SEQ ID NO 871
<211> LENGTH: 14
<212> TYPE: DNA
<213> ORGANISM: Artificial Sequence
<220> FEATURE:
<223> OTHER INFORMATION: Synthetic Construct

<400> SEQUENCE: 871
ttggttcgtg attt                                                     14

<210> SEQ ID NO 872
<211> LENGTH: 14
<212> TYPE: DNA
<213> ORGANISM: Artificial Sequence
<220> FEATURE:
<223> OTHER INFORMATION: Synthetic Construct

<400> SEQUENCE: 872
cgactctaaa aaaa                                                     14

<210> SEQ ID NO 873
<211> LENGTH: 14
<212> TYPE: DNA
<213> ORGANISM: Artificial Sequence
<220> FEATURE:
<223> OTHER INFORMATION: Synthetic Construct

<400> SEQUENCE: 873
tggttcgtga tttc                                                     14

<210> SEQ ID NO 874
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 874
cgactctaaa aaaa                                                      14

<210> SEQ ID NO 875
<211> LENGTH: 14
<212> TYPE: DNA
<213> ORGANISM: Artificial Sequence
<220> FEATURE:
<223> OTHER INFORMATION: Synthetic Construct

<400> SEQUENCE: 875
ggttcgtgat ttcg                                                      14

<210> SEQ ID NO 876
<211> LENGTH: 14
<212> TYPE: DNA
<213> ORGANISM: Artificial Sequence
<220> FEATURE:
<223> OTHER INFORMATION: Synthetic Construct

<400> SEQUENCE: 876
cgactctaaa aaaa                                                      14

<210> SEQ ID NO 877
<211> LENGTH: 14
<212> TYPE: DNA
<213> ORGANISM: Artificial Sequence
<220> FEATURE:
<223> OTHER INFORMATION: Synthetic Construct

<400> SEQUENCE: 877
gttcgtgatt tcgt                                                      14

<210> SEQ ID NO 878
<211> LENGTH: 14
<212> TYPE: DNA
<213> ORGANISM: Artificial Sequence
<220> FEATURE:
<223> OTHER INFORMATION: Synthetic Construct

<400> SEQUENCE: 878
cgactctaaa aaaa                                                      14

<210> SEQ ID NO 879
<211> LENGTH: 14
<212> TYPE: DNA
<213> ORGANISM: Artificial Sequence
<220> FEATURE:
<223> OTHER INFORMATION: Synthetic Construct

<400> SEQUENCE: 879
ttcgtgattt cgta                                                      14

<210> SEQ ID NO 880
<211> LENGTH: 14
<212> TYPE: DNA
<213> ORGANISM: Artificial Sequence
<220> FEATURE:
<223> OTHER INFORMATION: Synthetic Construct

<400> SEQUENCE: 880
```
cgactctaaa aaaa                                                     14

<210> SEQ ID NO 881
<211> LENGTH: 14
<212> TYPE: DNA
<213> ORGANISM: Artificial Sequence
<220> FEATURE:
<223> OTHER INFORMATION: Synthetic Construct

<400> SEQUENCE: 881
tcgtgatttc gtag                                                     14

<210> SEQ ID NO 882
<211> LENGTH: 14
<212> TYPE: DNA
<213> ORGANISM: Artificial Sequence
<220> FEATURE:
<223> OTHER INFORMATION: Synthetic Construct

<400> SEQUENCE: 882
cgactctaaa aaaa                                                     14

<210> SEQ ID NO 883
<211> LENGTH: 14
<212> TYPE: DNA
<213> ORGANISM: Artificial Sequence
<220> FEATURE:
<223> OTHER INFORMATION: Synthetic Construct

<400> SEQUENCE: 883
cgtgatttcg taga                                                     14

<210> SEQ ID NO 884
<211> LENGTH: 14
<212> TYPE: DNA
<213> ORGANISM: Artificial Sequence
<220> FEATURE:
<223> OTHER INFORMATION: Synthetic Construct

<400> SEQUENCE: 884
cgactctaaa aaaa                                                     14

<210> SEQ ID NO 885
<211> LENGTH: 14
<212> TYPE: DNA
<213> ORGANISM: Artificial Sequence
<220> FEATURE:
<223> OTHER INFORMATION: Synthetic Construct

<400> SEQUENCE: 885
gtgatttcgt agag                                                     14

<210> SEQ ID NO 886
<211> LENGTH: 14
<212> TYPE: DNA
<213> ORGANISM: Artificial Sequence
<220> FEATURE:
<223> OTHER INFORMATION: Synthetic Construct

<400> SEQUENCE: 886
cgactctaaa aaaa                                                     14

<210> SEQ ID NO 887
<211> LENGTH: 14
<212> TYPE: DNA
<213> ORGANISM: Artificial Sequence -continued

```
<220> FEATURE:
<223> OTHER INFORMATION: Synthetic Construct

<400> SEQUENCE: 887
tgatttcgta gaga                                                         14

<210> SEQ ID NO 888
<211> LENGTH: 14
<212> TYPE: DNA
<213> ORGANISM: Artificial Sequence
<220> FEATURE:
<223> OTHER INFORMATION: Synthetic Construct

<400> SEQUENCE: 888
cgactctaaa aaaa                                                         14

<210> SEQ ID NO 889
<211> LENGTH: 14
<212> TYPE: DNA
<213> ORGANISM: Artificial Sequence
<220> FEATURE:
<223> OTHER INFORMATION: Synthetic Construct

<400> SEQUENCE: 889
gatttcgtag agac                                                         14

<210> SEQ ID NO 890
<211> LENGTH: 14
<212> TYPE: DNA
<213> ORGANISM: Artificial Sequence
<220> FEATURE:
<223> OTHER INFORMATION: Synthetic Construct

<400> SEQUENCE: 890
cgactctaaa aaaa                                                         14

<210> SEQ ID NO 891
<211> LENGTH: 14
<212> TYPE: DNA
<213> ORGANISM: Artificial Sequence
<220> FEATURE:
<223> OTHER INFORMATION: Synthetic Construct

<400> SEQUENCE: 891
atttcgtaga gacg                                                         14

<210> SEQ ID NO 892
<211> LENGTH: 14
<212> TYPE: DNA
<213> ORGANISM: Artificial Sequence
<220> FEATURE:
<223> OTHER INFORMATION: Synthetic Construct

<400> SEQUENCE: 892
cgactctaaa aaaa                                                         14

<210> SEQ ID NO 893
<211> LENGTH: 14
<212> TYPE: DNA
<213> ORGANISM: Artificial Sequence
<220> FEATURE:
<223> OTHER INFORMATION: Synthetic Construct

<400> SEQUENCE: 893
tttcgtagag acgt                                                         14
```

```
<210> SEQ ID NO 894
<211> LENGTH: 14
<212> TYPE: DNA
<213> ORGANISM: Artificial Sequence
<220> FEATURE:
<223> OTHER INFORMATION: Synthetic Construct

<400> SEQUENCE: 894
cgactctaaa aaaa                                                      14

<210> SEQ ID NO 895
<211> LENGTH: 14
<212> TYPE: DNA
<213> ORGANISM: Artificial Sequence
<220> FEATURE:
<223> OTHER INFORMATION: Synthetic Construct

<400> SEQUENCE: 895
ttcgtagaga cgtt                                                      14

<210> SEQ ID NO 896
<211> LENGTH: 14
<212> TYPE: DNA
<213> ORGANISM: Artificial Sequence
<220> FEATURE:
<223> OTHER INFORMATION: Synthetic Construct

<400> SEQUENCE: 896
cgactctaaa aaaa                                                      14

<210> SEQ ID NO 897
<211> LENGTH: 14
<212> TYPE: DNA
<213> ORGANISM: Artificial Sequence
<220> FEATURE:
<223> OTHER INFORMATION: Synthetic Construct

<400> SEQUENCE: 897
tcgtagagac gttg                                                      14

<210> SEQ ID NO 898
<211> LENGTH: 14
<212> TYPE: DNA
<213> ORGANISM: Artificial Sequence
<220> FEATURE:
<223> OTHER INFORMATION: Synthetic Construct

<400> SEQUENCE: 898
cgactctaaa aaaa                                                      14

<210> SEQ ID NO 899
<211> LENGTH: 14
<212> TYPE: DNA
<213> ORGANISM: Artificial Sequence
<220> FEATURE:
<223> OTHER INFORMATION: Synthetic Construct

<400> SEQUENCE: 899
cgtagagacg ttga                                                      14

<210> SEQ ID NO 900
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 900
cgactctaaa aaaa                                                      14

<210> SEQ ID NO 901
<211> LENGTH: 14
<212> TYPE: DNA
<213> ORGANISM: Artificial Sequence
<220> FEATURE:
<223> OTHER INFORMATION: Synthetic Construct

<400> SEQUENCE: 901
gtagagacgt tgag                                                      14

<210> SEQ ID NO 902
<211> LENGTH: 14
<212> TYPE: DNA
<213> ORGANISM: Artificial Sequence
<220> FEATURE:
<223> OTHER INFORMATION: Synthetic Construct

<400> SEQUENCE: 902
cgactctaaa aaaa                                                      14

<210> SEQ ID NO 903
<211> LENGTH: 14
<212> TYPE: DNA
<213> ORGANISM: Artificial Sequence
<220> FEATURE:
<223> OTHER INFORMATION: Synthetic Construct

<400> SEQUENCE: 903
tagagacgtt gagg                                                      14

<210> SEQ ID NO 904
<211> LENGTH: 14
<212> TYPE: DNA
<213> ORGANISM: Artificial Sequence
<220> FEATURE:
<223> OTHER INFORMATION: Synthetic Construct

<400> SEQUENCE: 904
cgactctaaa aaaa                                                      14

<210> SEQ ID NO 905
<211> LENGTH: 14
<212> TYPE: DNA
<213> ORGANISM: Artificial Sequence
<220> FEATURE:
<223> OTHER INFORMATION: Synthetic Construct

<400> SEQUENCE: 905
agagacgttg agga                                                      14

<210> SEQ ID NO 906
<211> LENGTH: 14
<212> TYPE: DNA
<213> ORGANISM: Artificial Sequence
<220> FEATURE:
<223> OTHER INFORMATION: Synthetic Construct

<400> SEQUENCE: 906
cgactctaaa aaaa                                                      14

<210> SEQ ID NO 907
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 907
gagacgttga ggat                                                   14

<210> SEQ ID NO 908
<211> LENGTH: 14
<212> TYPE: DNA
<213> ORGANISM: Artificial Sequence
<220> FEATURE:
<223> OTHER INFORMATION: Synthetic Construct

<400> SEQUENCE: 908
cgactctaaa aaaa                                                   14

<210> SEQ ID NO 909
<211> LENGTH: 14
<212> TYPE: DNA
<213> ORGANISM: Artificial Sequence
<220> FEATURE:
<223> OTHER INFORMATION: Synthetic Construct

<400> SEQUENCE: 909
agacgttgag gatc                                                   14

<210> SEQ ID NO 910
<211> LENGTH: 14
<212> TYPE: DNA
<213> ORGANISM: Artificial Sequence
<220> FEATURE:
<223> OTHER INFORMATION: Synthetic Construct

<400> SEQUENCE: 910
cgactctaaa aaaa                                                   14

<210> SEQ ID NO 911
<211> LENGTH: 14
<212> TYPE: DNA
<213> ORGANISM: Artificial Sequence
<220> FEATURE:
<223> OTHER INFORMATION: Synthetic Construct

<400> SEQUENCE: 911
gacgttgagg atcg                                                   14

<210> SEQ ID NO 912
<211> LENGTH: 14
<212> TYPE: DNA
<213> ORGANISM: Artificial Sequence
<220> FEATURE:
<223> OTHER INFORMATION: Synthetic Construct

<400> SEQUENCE: 912
cgactctaaa aaaa                                                   14

<210> SEQ ID NO 913
<211> LENGTH: 14
<212> TYPE: DNA
<213> ORGANISM: Artificial Sequence
<220> FEATURE:
<223> OTHER INFORMATION: Synthetic Construct

<400> SEQUENCE: 913
```
acgttgagga tcgc					14

<210> SEQ ID NO 914
<211> LENGTH: 14
<212> TYPE: DNA
<213> ORGANISM: Artificial Sequence
<220> FEATURE:
<223> OTHER INFORMATION: Synthetic Construct

<400> SEQUENCE: 914
cgactctaaa aaaa					14

<210> SEQ ID NO 915
<211> LENGTH: 14
<212> TYPE: DNA
<213> ORGANISM: Artificial Sequence
<220> FEATURE:
<223> OTHER INFORMATION: Synthetic Construct

<400> SEQUENCE: 915
cgttgaggat cgcg					14

<210> SEQ ID NO 916
<211> LENGTH: 14
<212> TYPE: DNA
<213> ORGANISM: Artificial Sequence
<220> FEATURE:
<223> OTHER INFORMATION: Synthetic Construct

<400> SEQUENCE: 916
cgactctaaa aaaa					14

<210> SEQ ID NO 917
<211> LENGTH: 14
<212> TYPE: DNA
<213> ORGANISM: Artificial Sequence
<220> FEATURE:
<223> OTHER INFORMATION: Synthetic Construct

<400> SEQUENCE: 917
gttgaggatc gcga					14

<210> SEQ ID NO 918
<211> LENGTH: 14
<212> TYPE: DNA
<213> ORGANISM: Artificial Sequence
<220> FEATURE:
<223> OTHER INFORMATION: Synthetic Construct

<400> SEQUENCE: 918
cgactctaaa aaaa					14

<210> SEQ ID NO 919
<211> LENGTH: 14
<212> TYPE: DNA
<213> ORGANISM: Artificial Sequence
<220> FEATURE:
<223> OTHER INFORMATION: Synthetic Construct

<400> SEQUENCE: 919
ttgaggatcg cgac					14

<210> SEQ ID NO 920
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 920
cgactctaaa aaaa                                                          14

<210> SEQ ID NO 921
<211> LENGTH: 14
<212> TYPE: DNA
<213> ORGANISM: Artificial Sequence
<220> FEATURE:
<223> OTHER INFORMATION: Synthetic Construct

<400> SEQUENCE: 921
tgaggatcgc gacg                                                          14

<210> SEQ ID NO 922
<211> LENGTH: 14
<212> TYPE: DNA
<213> ORGANISM: Artificial Sequence
<220> FEATURE:
<223> OTHER INFORMATION: Synthetic Construct

<400> SEQUENCE: 922
cgactctaaa aaaa                                                          14

<210> SEQ ID NO 923
<211> LENGTH: 14
<212> TYPE: DNA
<213> ORGANISM: Artificial Sequence
<220> FEATURE:
<223> OTHER INFORMATION: Synthetic Construct

<400> SEQUENCE: 923
gaggatcgcg acgg                                                          14

<210> SEQ ID NO 924
<211> LENGTH: 14
<212> TYPE: DNA
<213> ORGANISM: Artificial Sequence
<220> FEATURE:
<223> OTHER INFORMATION: Synthetic Construct

<400> SEQUENCE: 924
cgactctaaa aaaa                                                          14

<210> SEQ ID NO 925
<211> LENGTH: 14
<212> TYPE: DNA
<213> ORGANISM: Artificial Sequence
<220> FEATURE:
<223> OTHER INFORMATION: Synthetic Construct

<400> SEQUENCE: 925
aggatcgcga cggt                                                          14

<210> SEQ ID NO 926
<211> LENGTH: 14
<212> TYPE: DNA
<213> ORGANISM: Artificial Sequence
<220> FEATURE:
<223> OTHER INFORMATION: Synthetic Construct

<400> SEQUENCE: 926
cgactctaaa aaaa                                                          14
```

<210> SEQ ID NO 927
<211> LENGTH: 14
<212> TYPE: DNA
<213> ORGANISM: Artificial Sequence
<220> FEATURE:
<223> OTHER INFORMATION: Synthetic Construct

<400> SEQUENCE: 927
ggatcgcgac ggtg                                                     14

<210> SEQ ID NO 928
<211> LENGTH: 14
<212> TYPE: DNA
<213> ORGANISM: Artificial Sequence
<220> FEATURE:
<223> OTHER INFORMATION: Synthetic Construct

<400> SEQUENCE: 928
cgactctaaa aaaa                                                     14

<210> SEQ ID NO 929
<211> LENGTH: 14
<212> TYPE: DNA
<213> ORGANISM: Artificial Sequence
<220> FEATURE:
<223> OTHER INFORMATION: Synthetic Construct

<400> SEQUENCE: 929
gatcgcgacg gtga                                                     14

<210> SEQ ID NO 930
<211> LENGTH: 14
<212> TYPE: DNA
<213> ORGANISM: Artificial Sequence
<220> FEATURE:
<223> OTHER INFORMATION: Synthetic Construct

<400> SEQUENCE: 930
cgactctaaa aaaa                                                     14

<210> SEQ ID NO 931
<211> LENGTH: 14
<212> TYPE: DNA
<213> ORGANISM: Artificial Sequence
<220> FEATURE:
<223> OTHER INFORMATION: Synthetic Construct

<400> SEQUENCE: 931
atcgcgacgg tgag                                                     14

<210> SEQ ID NO 932
<211> LENGTH: 14
<212> TYPE: DNA
<213> ORGANISM: Artificial Sequence
<220> FEATURE:
<223> OTHER INFORMATION: Synthetic Construct

<400> SEQUENCE: 932
cgactctaaa aaaa                                                     14

<210> SEQ ID NO 933
<211> LENGTH: 14
<212> TYPE: DNA
<213> ORGANISM: Artificial Sequence
<220> FEATURE:

<223> OTHER INFORMATION: Synthetic Construct

<400> SEQUENCE: 933
tcgcgacggt gagg                                                       14

<210> SEQ ID NO 934
<211> LENGTH: 14
<212> TYPE: DNA
<213> ORGANISM: Artificial Sequence
<220> FEATURE:
<223> OTHER INFORMATION: Synthetic Construct

<400> SEQUENCE: 934
cgactctaaa aaaa                                                       14

<210> SEQ ID NO 935
<211> LENGTH: 14
<212> TYPE: DNA
<213> ORGANISM: Artificial Sequence
<220> FEATURE:
<223> OTHER INFORMATION: Synthetic Construct

<400> SEQUENCE: 935
cgcgacggtg aggt                                                       14

<210> SEQ ID NO 936
<211> LENGTH: 14
<212> TYPE: DNA
<213> ORGANISM: Artificial Sequence
<220> FEATURE:
<223> OTHER INFORMATION: Synthetic Construct

<400> SEQUENCE: 936
cgactctaaa aaaa                                                       14

<210> SEQ ID NO 937
<211> LENGTH: 14
<212> TYPE: DNA
<213> ORGANISM: Artificial Sequence
<220> FEATURE:
<223> OTHER INFORMATION: Synthetic Construct

<400> SEQUENCE: 937
gcgacggtga ggtt                                                       14

<210> SEQ ID NO 938
<211> LENGTH: 14
<212> TYPE: DNA
<213> ORGANISM: Artificial Sequence
<220> FEATURE:
<223> OTHER INFORMATION: Synthetic Construct

<400> SEQUENCE: 938
cgactctaaa aaaa                                                       14

<210> SEQ ID NO 939
<211> LENGTH: 14
<212> TYPE: DNA
<213> ORGANISM: Artificial Sequence
<220> FEATURE:
<223> OTHER INFORMATION: Synthetic Construct

<400> SEQUENCE: 939
cgacggtgag gttt                                                       14

```
<210> SEQ ID NO 940
<211> LENGTH: 14
<212> TYPE: DNA
<213> ORGANISM: Artificial Sequence
<220> FEATURE:
<223> OTHER INFORMATION: Synthetic Construct

<400> SEQUENCE: 940
cgactctaaa aaaa                                                         14

<210> SEQ ID NO 941
<211> LENGTH: 14
<212> TYPE: DNA
<213> ORGANISM: Artificial Sequence
<220> FEATURE:
<223> OTHER INFORMATION: Synthetic Construct

<400> SEQUENCE: 941
gacggtgagg tttt                                                         14

<210> SEQ ID NO 942
<211> LENGTH: 14
<212> TYPE: DNA
<213> ORGANISM: Artificial Sequence
<220> FEATURE:
<223> OTHER INFORMATION: Synthetic Construct

<400> SEQUENCE: 942
cgactctaaa aaaa                                                         14

<210> SEQ ID NO 943
<211> LENGTH: 14
<212> TYPE: DNA
<213> ORGANISM: Artificial Sequence
<220> FEATURE:
<223> OTHER INFORMATION: Synthetic Construct

<400> SEQUENCE: 943
acggtgaggt ttta                                                         14

<210> SEQ ID NO 944
<211> LENGTH: 14
<212> TYPE: DNA
<213> ORGANISM: Artificial Sequence
<220> FEATURE:
<223> OTHER INFORMATION: Synthetic Construct

<400> SEQUENCE: 944
cgactctaaa aaaa                                                         14

<210> SEQ ID NO 945
<211> LENGTH: 14
<212> TYPE: DNA
<213> ORGANISM: Artificial Sequence
<220> FEATURE:
<223> OTHER INFORMATION: Synthetic Construct

<400> SEQUENCE: 945
cggtgaggtt ttac                                                         14

<210> SEQ ID NO 946
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 946
cgactctaaa aaaa                                                      14

<210> SEQ ID NO 947
<211> LENGTH: 14
<212> TYPE: DNA
<213> ORGANISM: Artificial Sequence
<220> FEATURE:
<223> OTHER INFORMATION: Synthetic Construct

<400> SEQUENCE: 947
ggtgaggttt tacg                                                      14

<210> SEQ ID NO 948
<211> LENGTH: 14
<212> TYPE: DNA
<213> ORGANISM: Artificial Sequence
<220> FEATURE:
<223> OTHER INFORMATION: Synthetic Construct

<400> SEQUENCE: 948
cgactctaaa aaaa                                                      14

<210> SEQ ID NO 949
<211> LENGTH: 14
<212> TYPE: DNA
<213> ORGANISM: Artificial Sequence
<220> FEATURE:
<223> OTHER INFORMATION: Synthetic Construct

<400> SEQUENCE: 949
gtgaggtttt acgt                                                      14

<210> SEQ ID NO 950
<211> LENGTH: 14
<212> TYPE: DNA
<213> ORGANISM: Artificial Sequence
<220> FEATURE:
<223> OTHER INFORMATION: Synthetic Construct

<400> SEQUENCE: 950
cgactctaaa aaaa                                                      14

<210> SEQ ID NO 951
<211> LENGTH: 14
<212> TYPE: DNA
<213> ORGANISM: Artificial Sequence
<220> FEATURE:
<223> OTHER INFORMATION: Synthetic Construct

<400> SEQUENCE: 951
tgaggtttta cgtt                                                      14

<210> SEQ ID NO 952
<211> LENGTH: 14
<212> TYPE: DNA
<213> ORGANISM: Artificial Sequence
<220> FEATURE:
<223> OTHER INFORMATION: Synthetic Construct

<400> SEQUENCE: 952
cgactctaaa aaaa                                                      14

<210> SEQ ID NO 953
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 953
gaggttttac gttc                                                           14

<210> SEQ ID NO 954
<211> LENGTH: 14
<212> TYPE: DNA
<213> ORGANISM: Artificial Sequence
<220> FEATURE:
<223> OTHER INFORMATION: Synthetic Construct

<400> SEQUENCE: 954
cgactctaaa aaaa                                                           14

<210> SEQ ID NO 955
<211> LENGTH: 14
<212> TYPE: DNA
<213> ORGANISM: Artificial Sequence
<220> FEATURE:
<223> OTHER INFORMATION: Synthetic Construct

<400> SEQUENCE: 955
aggttttacg ttcg                                                           14

<210> SEQ ID NO 956
<211> LENGTH: 14
<212> TYPE: DNA
<213> ORGANISM: Artificial Sequence
<220> FEATURE:
<223> OTHER INFORMATION: Synthetic Construct

<400> SEQUENCE: 956
cgactctaaa aaaa                                                           14

<210> SEQ ID NO 957
<211> LENGTH: 14
<212> TYPE: DNA
<213> ORGANISM: Artificial Sequence
<220> FEATURE:
<223> OTHER INFORMATION: Synthetic Construct

<400> SEQUENCE: 957
ggttttacgt tcgt                                                           14

<210> SEQ ID NO 958
<211> LENGTH: 14
<212> TYPE: DNA
<213> ORGANISM: Artificial Sequence
<220> FEATURE:
<223> OTHER INFORMATION: Synthetic Construct

<400> SEQUENCE: 958
cgactctaaa aaaa                                                           14

<210> SEQ ID NO 959
<211> LENGTH: 14
<212> TYPE: DNA
<213> ORGANISM: Artificial Sequence
<220> FEATURE:
<223> OTHER INFORMATION: Synthetic Construct

<400> SEQUENCE: 959
```
gttttacgtt cgtt                                                                  14

<210> SEQ ID NO 960
<211> LENGTH: 14
<212> TYPE: DNA
<213> ORGANISM: Artificial Sequence
<220> FEATURE:
<223> OTHER INFORMATION: Synthetic Construct

<400> SEQUENCE: 960
cgactctaaa aaaa                                                                  14

<210> SEQ ID NO 961
<211> LENGTH: 14
<212> TYPE: DNA
<213> ORGANISM: Artificial Sequence
<220> FEATURE:
<223> OTHER INFORMATION: Synthetic Construct

<400> SEQUENCE: 961
ttttacgttc gtta                                                                  14

<210> SEQ ID NO 962
<211> LENGTH: 14
<212> TYPE: DNA
<213> ORGANISM: Artificial Sequence
<220> FEATURE:
<223> OTHER INFORMATION: Synthetic Construct

<400> SEQUENCE: 962
cgactctaaa aaaa                                                                  14

<210> SEQ ID NO 963
<211> LENGTH: 14
<212> TYPE: DNA
<213> ORGANISM: Artificial Sequence
<220> FEATURE:
<223> OTHER INFORMATION: Synthetic Construct

<400> SEQUENCE: 963
tttacgttcg ttag                                                                  14

<210> SEQ ID NO 964
<211> LENGTH: 14
<212> TYPE: DNA
<213> ORGANISM: Artificial Sequence
<220> FEATURE:
<223> OTHER INFORMATION: Synthetic Construct

<400> SEQUENCE: 964
cgactctaaa aaaa                                                                  14

<210> SEQ ID NO 965
<211> LENGTH: 14
<212> TYPE: DNA
<213> ORGANISM: Artificial Sequence
<220> FEATURE:
<223> OTHER INFORMATION: Synthetic Construct

<400> SEQUENCE: 965
ttacgttcgt tagt                                                                  14

<210> SEQ ID NO 966
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 966
cgactctaaa aaaa                                                              14

<210> SEQ ID NO 967
<211> LENGTH: 14
<212> TYPE: DNA
<213> ORGANISM: Artificial Sequence
<220> FEATURE:
<223> OTHER INFORMATION: Synthetic Construct

<400> SEQUENCE: 967
tacgttcgtt agta                                                              14

<210> SEQ ID NO 968
<211> LENGTH: 14
<212> TYPE: DNA
<213> ORGANISM: Artificial Sequence
<220> FEATURE:
<223> OTHER INFORMATION: Synthetic Construct

<400> SEQUENCE: 968
cgactctaaa aaaa                                                              14

<210> SEQ ID NO 969
<211> LENGTH: 14
<212> TYPE: DNA
<213> ORGANISM: Artificial Sequence
<220> FEATURE:
<223> OTHER INFORMATION: Synthetic Construct

<400> SEQUENCE: 969
acgttcgtta gtat                                                              14

<210> SEQ ID NO 970
<211> LENGTH: 14
<212> TYPE: DNA
<213> ORGANISM: Artificial Sequence
<220> FEATURE:
<223> OTHER INFORMATION: Synthetic Construct

<400> SEQUENCE: 970
cgactctaaa aaaa                                                              14

<210> SEQ ID NO 971
<211> LENGTH: 14
<212> TYPE: DNA
<213> ORGANISM: Artificial Sequence
<220> FEATURE:
<223> OTHER INFORMATION: Synthetic Construct

<400> SEQUENCE: 971
cgttcgttag tata                                                              14

<210> SEQ ID NO 972
<211> LENGTH: 14
<212> TYPE: DNA
<213> ORGANISM: Artificial Sequence
<220> FEATURE:
<223> OTHER INFORMATION: Synthetic Construct

<400> SEQUENCE: 972
cgactctaaa aaaa                                                              14
```

```
<210> SEQ ID NO 973
<211> LENGTH: 14
<212> TYPE: DNA
<213> ORGANISM: Artificial Sequence
<220> FEATURE:
<223> OTHER INFORMATION: Synthetic Construct

<400> SEQUENCE: 973
gttcgttagt atat                                                       14

<210> SEQ ID NO 974
<211> LENGTH: 14
<212> TYPE: DNA
<213> ORGANISM: Artificial Sequence
<220> FEATURE:
<223> OTHER INFORMATION: Synthetic Construct

<400> SEQUENCE: 974
cgactctaaa aaaa                                                       14

<210> SEQ ID NO 975
<211> LENGTH: 14
<212> TYPE: DNA
<213> ORGANISM: Artificial Sequence
<220> FEATURE:
<223> OTHER INFORMATION: Synthetic Construct

<400> SEQUENCE: 975
ttcgttagta tatt                                                       14

<210> SEQ ID NO 976
<211> LENGTH: 14
<212> TYPE: DNA
<213> ORGANISM: Artificial Sequence
<220> FEATURE:
<223> OTHER INFORMATION: Synthetic Construct

<400> SEQUENCE: 976
caaattcact cacg                                                       14

<210> SEQ ID NO 977
<211> LENGTH: 25
<212> TYPE: DNA
<213> ORGANISM: Artificial Sequence
<220> FEATURE:
<223> OTHER INFORMATION: Synthetic Construct

<400> SEQUENCE: 977
aattggtttg ttttattcga atagc                                           25

<210> SEQ ID NO 978
<211> LENGTH: 14
<212> TYPE: DNA
<213> ORGANISM: Artificial Sequence
<220> FEATURE:
<223> OTHER INFORMATION: Synthetic Construct

<400> SEQUENCE: 978
tcgttagtat attc                                                       14

<210> SEQ ID NO 979
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 979
caaattcact cacg                                                          14

<210> SEQ ID NO 980
<211> LENGTH: 14
<212> TYPE: DNA
<213> ORGANISM: Artificial Sequence
<220> FEATURE:
<223> OTHER INFORMATION: Synthetic Construct

<400> SEQUENCE: 980
cgttagtata ttcg                                                          14

<210> SEQ ID NO 981
<211> LENGTH: 14
<212> TYPE: DNA
<213> ORGANISM: Artificial Sequence
<220> FEATURE:
<223> OTHER INFORMATION: Synthetic Construct

<400> SEQUENCE: 981
caaattcact cacg                                                          14

<210> SEQ ID NO 982
<211> LENGTH: 14
<212> TYPE: DNA
<213> ORGANISM: Artificial Sequence
<220> FEATURE:
<223> OTHER INFORMATION: Synthetic Construct

<400> SEQUENCE: 982
gttagtatat tcgg                                                          14

<210> SEQ ID NO 983
<211> LENGTH: 14
<212> TYPE: DNA
<213> ORGANISM: Artificial Sequence
<220> FEATURE:
<223> OTHER INFORMATION: Synthetic Construct

<400> SEQUENCE: 983
caaattcact cacg                                                          14

<210> SEQ ID NO 984
<211> LENGTH: 14
<212> TYPE: DNA
<213> ORGANISM: Artificial Sequence
<220> FEATURE:
<223> OTHER INFORMATION: Synthetic Construct

<400> SEQUENCE: 984
ttagtatatt cggg                                                          14

<210> SEQ ID NO 985
<211> LENGTH: 14
<212> TYPE: DNA
<213> ORGANISM: Artificial Sequence
<220> FEATURE:
<223> OTHER INFORMATION: Synthetic Construct

<400> SEQUENCE: 985
caaattcact cacg                                                          14

<210> SEQ ID NO 986

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 986
tagtatattc gggt                                                     14

<210> SEQ ID NO 987
<211> LENGTH: 14
<212> TYPE: DNA
<213> ORGANISM: Artificial Sequence
<220> FEATURE:
<223> OTHER INFORMATION: Synthetic Construct

<400> SEQUENCE: 987
caaattcact cacg                                                     14

<210> SEQ ID NO 988
<211> LENGTH: 14
<212> TYPE: DNA
<213> ORGANISM: Artificial Sequence
<220> FEATURE:
<223> OTHER INFORMATION: Synthetic Construct

<400> SEQUENCE: 988
agtatattcg ggtt                                                     14

<210> SEQ ID NO 989
<211> LENGTH: 14
<212> TYPE: DNA
<213> ORGANISM: Artificial Sequence
<220> FEATURE:
<223> OTHER INFORMATION: Synthetic Construct

<400> SEQUENCE: 989
caaattcact cacg                                                     14

<210> SEQ ID NO 990
<211> LENGTH: 14
<212> TYPE: DNA
<213> ORGANISM: Artificial Sequence
<220> FEATURE:
<223> OTHER INFORMATION: Synthetic Construct

<400> SEQUENCE: 990
gtatattcgg gttc                                                     14

<210> SEQ ID NO 991
<211> LENGTH: 14
<212> TYPE: DNA
<213> ORGANISM: Artificial Sequence
<220> FEATURE:
<223> OTHER INFORMATION: Synthetic Construct

<400> SEQUENCE: 991
caaattcact cacg                                                     14

<210> SEQ ID NO 992
<211> LENGTH: 14
<212> TYPE: DNA
<213> ORGANISM: Artificial Sequence
<220> FEATURE:
<223> OTHER INFORMATION: Synthetic Construct

<400> SEQUENCE: 992
```
tatattcggg ttcg                                                14

<210> SEQ ID NO 993
<211> LENGTH: 14
<212> TYPE: DNA
<213> ORGANISM: Artificial Sequence
<220> FEATURE:
<223> OTHER INFORMATION: Synthetic Construct

<400> SEQUENCE: 993
caaattcact cacg                                                14

<210> SEQ ID NO 994
<211> LENGTH: 14
<212> TYPE: DNA
<213> ORGANISM: Artificial Sequence
<220> FEATURE:
<223> OTHER INFORMATION: Synthetic Construct

<400> SEQUENCE: 994
atattcgggt tcgt                                                14

<210> SEQ ID NO 995
<211> LENGTH: 14
<212> TYPE: DNA
<213> ORGANISM: Artificial Sequence
<220> FEATURE:
<223> OTHER INFORMATION: Synthetic Construct

<400> SEQUENCE: 995
caaattcact cacg                                                14

<210> SEQ ID NO 996
<211> LENGTH: 14
<212> TYPE: DNA
<213> ORGANISM: Artificial Sequence
<220> FEATURE:
<223> OTHER INFORMATION: Synthetic Construct

<400> SEQUENCE: 996
tattcgggtt cgtt                                                14

<210> SEQ ID NO 997
<211> LENGTH: 14
<212> TYPE: DNA
<213> ORGANISM: Artificial Sequence
<220> FEATURE:
<223> OTHER INFORMATION: Synthetic Construct

<400> SEQUENCE: 997
caaattcact cacg                                                14

<210> SEQ ID NO 998
<211> LENGTH: 14
<212> TYPE: DNA
<213> ORGANISM: Artificial Sequence
<220> FEATURE:
<223> OTHER INFORMATION: Synthetic Construct

<400> SEQUENCE: 998
attcgggttc gttt                                                14

<210> SEQ ID NO 999
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 999
caaattcact cacg                                                        14

<210> SEQ ID NO 1000
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1000
ttcgggttcg tttt                                                        14

<210> SEQ ID NO 1001
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1001
caaattcact cacg                                                        14

<210> SEQ ID NO 1002
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1002
tcgggttcgt tttt                                                        14

<210> SEQ ID NO 1003
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1003
caaattcact cacg                                                        14

<210> SEQ ID NO 1004
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1004
cgggttcgtt tttt                                                        14

<210> SEQ ID NO 1005
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1005
caaattcact cacg                                                        14
```

```
<210> SEQ ID NO 1006
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1006
gggttcgttt tttt                                                     14

<210> SEQ ID NO 1007
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1007
caaattcact cacg                                                     14

<210> SEQ ID NO 1008
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1008
ggttcgtttt tttt                                                     14

<210> SEQ ID NO 1009
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1009
caaattcact cacg                                                     14

<210> SEQ ID NO 1010
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1010
gttcgttttt tttc                                                     14

<210> SEQ ID NO 1011
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1011
caaattcact cacg                                                     14

<210> SEQ ID NO 1012
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 1012
ttcgtttttt ttcg                                                14

<210> SEQ ID NO 1013
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1013
caaattcact cacg                                                14

<210> SEQ ID NO 1014
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1014
tcgttttttt tcga                                                14

<210> SEQ ID NO 1015
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1015
caaattcact cacg                                                14

<210> SEQ ID NO 1016
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1016
cgtttttttt cgac                                                14

<210> SEQ ID NO 1017
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1017
caaattcact cacg                                                14

<210> SEQ ID NO 1018
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1018
gttttttttc gacg                                                14

```
<210> SEQ ID NO 1019
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1019
caaattcact cacg                                                         14

<210> SEQ ID NO 1020
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1020 tttttttcg acgt                                                          14

<210> SEQ ID NO 1021
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1021
caaattcact cacg                                                         14

<210> SEQ ID NO 1022
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1022
tttttttcga cgtt                                                         14

<210> SEQ ID NO 1023
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1023
caaattcact cacg                                                         14

<210> SEQ ID NO 1024
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1024 tttttttcgac gttc                                                        14

<210> SEQ ID NO 1025
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1025
caaattcact cacg                                                        14

<210> SEQ ID NO 1026
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1026
tttttcgacg ttcg                                                        14

<210> SEQ ID NO 1027
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1027
caaattcact cacg                                                        14

<210> SEQ ID NO 1028
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1028
ttttcgacgt tcgt                                                        14

<210> SEQ ID NO 1029
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1029
caaattcact cacg                                                        14

<210> SEQ ID NO 1030
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1030
tttcgacgtt cgtt                                                        14

<210> SEQ ID NO 1031
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1031
caaattcact cacg                                                        14

<210> SEQ ID NO 1032
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1032
ttcgacgttc gttt                                                       14

<210> SEQ ID NO 1033
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1033
caaattcact cacg                                                       14

<210> SEQ ID NO 1034
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1034
tcgacgttcg tttt                                                       14

<210> SEQ ID NO 1035
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1035
caaattcact cacg                                                       14

<210> SEQ ID NO 1036
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1036
cgacgttcgt tttt                                                       14

<210> SEQ ID NO 1037
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1037
caaattcact cacg                                                       14

<210> SEQ ID NO 1038
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1038
```

```
gacgttcgtt tttt                                                14
```

<210> SEQ ID NO 1039
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1039

```
caaattcact cacg                                                14
```

<210> SEQ ID NO 1040
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1040

```
acgttcgttt tttt                                                14
```

<210> SEQ ID NO 1041
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1041

```
caaattcact cacg                                                14
```

<210> SEQ ID NO 1042
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1042

```
cgttcgtttt tttt                                                14
```

<210> SEQ ID NO 1043
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1043

```
caaattcact cacg                                                14
```

<210> SEQ ID NO 1044
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1044

```
gttcgttttt ttta                                                14
```

<210> SEQ ID NO 1045
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1045
caaattcact cacg                                                            14

<210> SEQ ID NO 1046
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1046
ttcgtttttt ttat                                                            14

<210> SEQ ID NO 1047
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1047
caaattcact cacg                                                            14

<210> SEQ ID NO 1048
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1048
tcgttttttt tata                                                            14

<210> SEQ ID NO 1049
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1049
caaattcact cacg                                                            14

<210> SEQ ID NO 1050
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1050 cgttttttttt atat                                                           14

<210> SEQ ID NO 1051
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1051
caaattcact cacg                                                            14
```

```
<210> SEQ ID NO 1052
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1052
gtttttttta tatt                                                       14

<210> SEQ ID NO 1053
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1053
caaattcact cacg                                                       14

<210> SEQ ID NO 1054
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1054 tttttttat attt                                                        14

<210> SEQ ID NO 1055
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1055
caaattcact cacg                                                       14

<210> SEQ ID NO 1056
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1056 ttttttata tttg                                                        14

<210> SEQ ID NO 1057
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1057
caaattcact cacg                                                       14

<210> SEQ ID NO 1058
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1058 tttttatat ttgt                                                        14

<210> SEQ ID NO 1059
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1059
caaattcact cacg                                                       14

<210> SEQ ID NO 1060
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1060
tttttatatt tgtt                                                       14

<210> SEQ ID NO 1061
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1061
caaattcact cacg                                                       14

<210> SEQ ID NO 1062
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1062 tttatattt gttt                                                        14

<210> SEQ ID NO 1063
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1063
caaattcact cacg                                                       14

<210> SEQ ID NO 1064
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1064
tttatatttg tttt                                                       14

<210> SEQ ID NO 1065

<211> LENGTH: 14
<212> TYPE: DNA
<213> ORGANISM: Artificial Sequence
<220> FEATURE:
<223> OTHER INFORMATION: Synthetic Construct

<400> SEQUENCE: 1065
caaattcact cacg                                                       14

<210> SEQ ID NO 1066
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1066
ttatatttgt tttt                                                       14

<210> SEQ ID NO 1067
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1067
caaattcact cacg                                                       14

<210> SEQ ID NO 1068
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1068
tatatttgtt tttt                                                       14

<210> SEQ ID NO 1069
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1069
caaattcact cacg                                                       14

<210> SEQ ID NO 1070
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1070
atatttgttt tttt                                                       14

<210> SEQ ID NO 1071
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1071
caaattcact cacg                                                        14

<210> SEQ ID NO 1072
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1072
tatttgtttt tttt                                                        14

<210> SEQ ID NO 1073
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1073
caaattcact cacg                                                        14

<210> SEQ ID NO 1074
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1074
atttgttttt tttt                                                        14

<210> SEQ ID NO 1075
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1075
caaattcact cacg                                                        14

<210> SEQ ID NO 1076
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1076 tttgttttttt tttt                                                       14

<210> SEQ ID NO 1077
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1077
caaattcact cacg                                                        14

<210> SEQ ID NO 1078
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1078
ttgttttttt tttt                                                        14

<210> SEQ ID NO 1079
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1079
caaattcact cacg                                                        14

<210> SEQ ID NO 1080
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1080 tgttttttt tttt                                                         14

<210> SEQ ID NO 1081
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1081
caaattcact cacg                                                        14

<210> SEQ ID NO 1082
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1082
gttttttttt tttt                                                        14

<210> SEQ ID NO 1083
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1083
caaattcact cacg                                                        14

<210> SEQ ID NO 1084
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1084
tttttttttt tttt                                                        14
```

<210> SEQ ID NO 1085
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1085
caaattcact cacg                                                        14

<210> SEQ ID NO 1086
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1086
tttttttttt ttta                                                        14

<210> SEQ ID NO 1087
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1087
caaattcact cacg                                                        14

<210> SEQ ID NO 1088
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1088
tttttttttt ttag                                                        14

<210> SEQ ID NO 1089
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1089
caaattcact cacg                                                        14

<210> SEQ ID NO 1090
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1090
tttttttttt taga                                                        14

<210> SEQ ID NO 1091
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 1091
caaattcact cacg                                                        14

<210> SEQ ID NO 1092
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1092
tttttttttt agag                                                        14

<210> SEQ ID NO 1093
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1093
caaattcact cacg                                                        14

<210> SEQ ID NO 1094
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1094
ttttttttta gagt                                                        14

<210> SEQ ID NO 1095
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1095
caaattcact cacg                                                        14

<210> SEQ ID NO 1096
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1096 tttttttag agtc                                                         14

<210> SEQ ID NO 1097
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1097
aaaaaaaaaa aacg                                                        14
```

```
<210> SEQ ID NO 1098
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1098
tgttcgaagt ttgttttgt tgagc                                          25

<210> SEQ ID NO 1099
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1099
tttttttaga gtcg                                                      14

<210> SEQ ID NO 1100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1100
aaaaaaaaaa aacg                                                      14

<210> SEQ ID NO 1101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1101 tttttagag tcgt                                                       14

<210> SEQ ID NO 1102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1102
aaaaaaaaaa aacg                                                      14

<210> SEQ ID NO 1103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1103
tttttagagt cgtg                                                      14

<210> SEQ ID NO 1104
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1104
aaaaaaaaaa aacg                                                14

<210> SEQ ID NO 1105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1105
ttttagagtc gtgt                                                14

<210> SEQ ID NO 1106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1106
aaaaaaaaaa aacg                                                14

<210> SEQ ID NO 1107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1107
tttagagtcg tgtt                                                14

<210> SEQ ID NO 1108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1108
aaaaaaaaaa aacg                                                14

<210> SEQ ID NO 1109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1109
ttagagtcgt gttt                                                14

<210> SEQ ID NO 1110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1110
aaaaaaaaaa aacg                                                14

<210> SEQ ID NO 1111
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1111
tagagtcgtg tttg                                              14

<210> SEQ ID NO 1112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1112
aaaaaaaaaa aacg                                              14

<210> SEQ ID NO 1113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1113
agagtcgtgt ttga                                              14

<210> SEQ ID NO 1114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1114
aaaaaaaaaa aacg                                              14

<210> SEQ ID NO 1115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1115
gagtcgtgtt tgaa                                              14

<210> SEQ ID NO 1116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1116
aaaaaaaaaa aacg                                              14

<210> SEQ ID NO 1117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1117
```
agtcgtgttt gaat                                                      14

<210> SEQ ID NO 1118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1118
aaaaaaaaaa aacg                                                      14

<210> SEQ ID NO 1119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1119
gtcgtgtttg aatt                                                      14

<210> SEQ ID NO 1120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1120
aaaaaaaaaa aacg                                                      14

<210> SEQ ID NO 1121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1121
tcgtgtttga attc                                                      14

<210> SEQ ID NO 1122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1122
aaaaaaaaaa aacg                                                      14

<210> SEQ ID NO 1123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1123
cgtgtttgaa ttcg                                                      14

<210> SEQ ID NO 1124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1124
aaaaaaaaaa aacg                                                    14

<210> SEQ ID NO 1125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1125
gtgtttgaat tcgg                                                    14

<210> SEQ ID NO 1126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1126
aaaaaaaaaa aacg                                                    14

<210> SEQ ID NO 1127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1127
tgtttgaatt cggt                                                    14

<210> SEQ ID NO 1128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1128
aaaaaaaaaa aacg                                                    14

<210> SEQ ID NO 1129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1129
gtttgaattc ggtt                                                    14

<210> SEQ ID NO 1130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1130
aaaaaaaaaa aacg                                                    14

```
<210> SEQ ID NO 1131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1131
tttgaattcg gttt                                                       14

<210> SEQ ID NO 1132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1132
aaaaaaaaaa aacg                                                       14

<210> SEQ ID NO 1133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1133
ttgaattcgg tttt                                                       14

<210> SEQ ID NO 1134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1134
aaaaaaaaaa aacg                                                       14

<210> SEQ ID NO 1135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1135
tgaattcggt tttt                                                       14

<210> SEQ ID NO 1136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1136
aaaaaaaaaa aacg                                                       14

<210> SEQ ID NO 1137
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1137
gaattcggtt tttt                                                    14

<210> SEQ ID NO 1138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1138
aaaaaaaaaa aacg                                                    14

<210> SEQ ID NO 1139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1139
aattcggttt tttt                                                    14

<210> SEQ ID NO 1140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1140
aaaaaaaaaa aacg                                                    14

<210> SEQ ID NO 1141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1141
attcggtttt ttta                                                    14

<210> SEQ ID NO 1142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1142
aaaaaaaaaa aacg                                                    14

<210> SEQ ID NO 1143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1143
ttcggttttt ttaa                                                    14

<210> SEQ ID NO 1144
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1144
aaaaaaaaaa aacg                                                     14

<210> SEQ ID NO 1145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1145 tcggttttttt taat                                                    14

<210> SEQ ID NO 1146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1146
aaaaaaaaaa aacg                                                     14

<210> SEQ ID NO 1147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1147
cggttttttt aatt                                                     14

<210> SEQ ID NO 1148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1148
aaaaaaaaaa aacg                                                     14

<210> SEQ ID NO 1149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1149
ggttttttta attg                                                     14

<210> SEQ ID NO 1150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1150
```
aaaaaaaaaa aacg                                                    14

<210> SEQ ID NO 1151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1151
gtttttttaa ttgg                                                    14

<210> SEQ ID NO 1152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1152
aaaaaaaaaa aacg                                                    14

<210> SEQ ID NO 1153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1153 ttttttaat tggt                                                     14

<210> SEQ ID NO 1154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1154
aaaaaaaaaa aacg                                                    14

<210> SEQ ID NO 1155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1155 tttttttaatt ggtt                                                   14

<210> SEQ ID NO 1156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1156
aaaaaaaaaa aacg                                                    14

<210> SEQ ID NO 1157
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1157
tttttaattg gttt                                                    14

<210> SEQ ID NO 1158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1158
aaaaaaaaaa aacg                                                    14

<210> SEQ ID NO 1159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1159
ttttaattgg tttg                                                    14

<210> SEQ ID NO 1160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1160
aaaaaaaaaa aacg                                                    14

<210> SEQ ID NO 1161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1161
tttaattggt ttgt                                                    14

<210> SEQ ID NO 1162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1162
aaaaaaaaaa aacg                                                    14

<210> SEQ ID NO 1163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1163
ttaattggtt tgtt                                                    14
```

```
<210> SEQ ID NO 1164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1164
aaaaaaaaaa aacg                                                       14

<210> SEQ ID NO 1165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1165
taattggttt gttt                                                       14

<210> SEQ ID NO 1166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1166
aaaaaaaaaa aacg                                                       14

<210> SEQ ID NO 1167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1167
aattggtttg tttt                                                       14

<210> SEQ ID NO 1168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1168
aaaaaaaaaa aacg                                                       14

<210> SEQ ID NO 1169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1169
attggtttgt ttta                                                       14

<210> SEQ ID NO 1170
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 1170
aaaaaaaaaa aacg                                                         14

<210> SEQ ID NO 1171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1171
ttggtttgtt ttat                                                         14

<210> SEQ ID NO 1172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1172
aaaaaaaaaa aacg                                                         14

<210> SEQ ID NO 1173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1173
tggtttgttt tatt                                                         14

<210> SEQ ID NO 1174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1174
aaaaaaaaaa aacg                                                         14

<210> SEQ ID NO 1175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1175
ggtttgtttt attc                                                         14

<210> SEQ ID NO 1176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1176
aaaaaaaaaa aacg                                                         14

```
<210> SEQ ID NO 1177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1177
gtttgtttta ttcg                                                        14

<210> SEQ ID NO 1178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1178
aaaaaaaaaa aacg                                                        14

<210> SEQ ID NO 1179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1179
tttgttttat tcga                                                        14

<210> SEQ ID NO 1180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1180
aaaaaaaaaa aacg                                                        14

<210> SEQ ID NO 1181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1181
ttgttttatt cgaa                                                        14

<210> SEQ ID NO 1182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1182
aaaaaaaaaa aacg                                                        14

<210> SEQ ID NO 1183
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1183
tgttttattc gaat                                                     14

<210> SEQ ID NO 1184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1184
aaaaaaaaaa aacg                                                     14

<210> SEQ ID NO 1185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1185
gttttattcg aata                                                     14

<210> SEQ ID NO 1186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1186
aaaaaaaaaa aacg                                                     14

<210> SEQ ID NO 1187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1187
ttttattcga atag                                                     14

<210> SEQ ID NO 1188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1188
aaaaaaaaaa aacg                                                     14

<210> SEQ ID NO 1189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1189
tttattcgaa tagc                                                     14

<210> SEQ ID NO 1190
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1190
aaaaaaaaaa aacg                                                          14

<210> SEQ ID NO 1191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1191
ttattcgaat agcg                                                          14

<210> SEQ ID NO 1192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1192
aaaaaaaaaa aacg                                                          14

<210> SEQ ID NO 1193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1193
tattcgaata gcgt                                                          14

<210> SEQ ID NO 1194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1194
aaaaaaaaaa aacg                                                          14

<210> SEQ ID NO 1195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1195
attcgaatag cgtt                                                          14

<210> SEQ ID NO 1196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1196
```
aaaaaaaaaa aacg                                                                14

<210> SEQ ID NO 1197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1197
ttcgaatagc gtta                                                                14

<210> SEQ ID NO 1198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1198
aaaaaaaaaa aacg                                                                14

<210> SEQ ID NO 1199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1199
tcgaatagcg ttaa                                                                14

<210> SEQ ID NO 1200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1200
aaaaaaaaaa aacg                                                                14

<210> SEQ ID NO 1201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1201
cgaatagcgt taac                                                                14

<210> SEQ ID NO 1202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1202
aaaaaaaaaa aacg                                                                14

<210> SEQ ID NO 1203
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1203
gaatagcgtt aacg                                                    14

<210> SEQ ID NO 1204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1204
aaaaaaaaaa aacg                                                    14

<210> SEQ ID NO 1205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1205
aatagcgtta acgt                                                    14

<210> SEQ ID NO 1206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1206
aaaaaaaaaa aacg                                                    14

<210> SEQ ID NO 1207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1207
atagcgttaa cgtg                                                    14

<210> SEQ ID NO 1208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1208
aaaaaaaaaa aacg                                                    14

<210> SEQ ID NO 1209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1209
tagcgttaac gtga                                                    14
```

```
<210> SEQ ID NO 1210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1210
aaaaccaaaa aacg                                                          14

<210> SEQ ID NO 1211
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1211
cgtttgttcg ttttttttt tttta                                               25

<210> SEQ ID NO 1212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1212
agcgttaacg tgag                                                          14

<210> SEQ ID NO 1213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1213
aaaaccaaaa aacg                                                          14

<210> SEQ ID NO 1214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1214
gcgttaacgt gagt                                                          14

<210> SEQ ID NO 1215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1215
aaaaccaaaa aacg                                                          14

<210> SEQ ID NO 1216
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1216
cgttaacgtg agtg                                                        14

<210> SEQ ID NO 1217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1217
aaaaccaaaa aacg                                                        14

<210> SEQ ID NO 1218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1218
gttaacgtga gtga                                                        14

<210> SEQ ID NO 1219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1219
aaaaccaaaa aacg                                                        14

<210> SEQ ID NO 1220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1220
ttaacgtgag tgaa                                                        14

<210> SEQ ID NO 1221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1221
aaaaccaaaa aacg                                                        14
```

DIAGNOSIS KIT AND CHIP FOR BLADDER CANCER USING BLADDER CANCER SPECIFIC METHYLATION MARKER GENE

CROSS-REFERENCE TO RELATED APPLICATIONS

This is a continuation-in-part application under 35 U.S.C. § 120 of U.S. patent application Ser. No. 15/585,716 filed on May 3, 2017, published as U.S. Patent Application Publication No. 2017/0240976, which in turn is a continuation-in-part application of U.S. patent application Ser. No. 15/016,366 filed on Feb. 5, 2016, now U.S. Pat. No. 9,670,551, which in turn is a continuation-in-part application of U.S. patent application Ser. No. 13/627,519, now U.S. Pat. No. 9,359,646, filed on Sep. 26, 2012, which in turn is a divisional application of U.S. patent application Ser. No. 12/744,491 filed on Jun. 24, 2010 entitled "DIAGNOSIS KIT AND CHIP FOR BLADDER CANCER USING BLADDER CANCER SPECIFIC METHYLATION MARKER GENE" in the name of Sung Wan A N, et al, which is a U.S. national stage application under the provisions of 35 U.S.C. § 371 of International Patent Application No. PCT/KR2008/007081 filed on Dec. 1, 2008, which claims priority of Korean Patent Application No. 10-2007-0124015 filed on Nov. 30, 2007, all of which are hereby incorporated by reference herein in their respective entireties.

TECHNICAL FIELD

The present invention relates to a kit and nucleic acid chip for diagnosing bladder cancer using a bladder cancer-specific marker gene, and more particularly to a kit and nucleic acid chip for diagnosing bladder cancer, which can detect the promoter methylation of a bladder cancer-specific gene, the promoter region of which is methylated specifically in transformed cells of bladder cancer.

BACKGROUND ART

Bladder cancer is the most frequent cancer of the urinary system and was found to be caused by many factors. It is known that bladder cancer is mainly caused by smoking or various chemical substances (paints for leather, air pollutants, artificial sweetening agents, nitrates and the like) which irritate the bladder wall while they are excreted as urine after being absorbed in vivo.

As conventional methods for diagnosing bladder cancer, a method of finding abnormal cells in urine is used, but has low accuracy. Also, cystoscopy comprising inserting a catheter into the bladder and collecting suspected tissue from the bladder is an invasive method having relatively high accuracy.

Generally, when bladder cancer is diagnosed at an early stage, the survival rate of bladder cancer patients is increased, but it is not easy to diagnose bladder cancer at an early stage. As a method for diagnosing bladder cancer, a method of incising part of the body is currently being used, but it has difficulty in diagnosing bladder cancer at an early stage.

Bladder cancers are classified, according to invasion into the muscular layer of the bladder, into superficial cancer and invasive cancer. Generally, about 30% of patients upon diagnosis of bladder cancer are invasive bladder cancer patients. Thus, in order to increase the survival period of patients, it is the best method to diagnose bladder cancer at early stage when the bladder cancer lesions are small. Accordingly, there is an urgent need to development a diagnostic method more efficient than various prior diagnostic methods for bladder cancer, that is, a bladder cancer-specific biomarker which allows early diagnosis of bladder cancer, can treat a large amount of samples and has high sensitivity and specificity.

Recently, methods of diagnosing cancer through the measurement of DNA methylation have been suggested. DNA methylation occurs mainly on the cytosine of CpG islands in the promoter region of a specific gene to interfere with the binding of transcription factors, thus silencing the expression of the gene. Thus, detecting the methylation of CpG islands in the promoter of tumor inhibitory genes greatly assists in cancer research. Recently, an attempt has been actively made to determine promoter methylation, by methods such as methylation-specific PCR (hereinafter referred to as MSP) or automatic DNA sequencing, for the diagnosis and screening of cancer.

Although there are disputes on whether the methylation of promoter CpG islands directly induces cancer development or causes a secondary change after cancer development, it has been found that tumor suppressor genes, DNA repair genes, cell cycle regulatory genes and the line in several cancers are hypermethylated, and thus the expression of these genes are silenced. Particularly, it is known that the hypermethylation of the promoter region of a specific gene occurs at an early stage of cancer development.

Thus, the methylation of the promoter methylation of tumor-associated genes is an important indication of cancer and can be used in many applications, including the diagnosis and early diagnosis of cancer, the prediction of cancer development, the prediction of prognosis of cancer, follow-up examination after treatment, and the prediction of responses to anticancer therapy. Recently, an actual attempt to examine the promoter methylation of tumor-associated genes in blood, sputum, saliva, feces and to use the examined results for diagnosis and treatment of various cancers has been actively made (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119: 1219, 2000).

Accordingly, the present inventors have made many efforts to develop a diagnostic kit capable of effectively diagnosing bladder cancer and, as a result, have found that bladder cancer can be diagnosed by measuring the methylation degree using as a biomarker the promoter of methylation-associated genes which are expressed specifically in bladder cancer cells, thereby completing the present invention.

SUMMARY OF INVENTION

It is, therefore, an object of the present invention to provide a kit for diagnosing bladder cancer, which comprises the methylated promoter or exon region of a bladder cancer marker gene.

Another object of the present invention is to provide a nucleic acid chip for diagnosing bladder cancer, which comprises a probe capable of hybridizing with a fragment containing the CpG island of the bladder cancer-specific marker gene.

Still another object of the present invention is to provide a method for measuring the methylation of the promoter or exon region of a gene originated from a clinical sample.

To achieve the above objects, the present invention provides a kit for diagnosing bladder cancer, which comprises the methylated promoter or exon region of a bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (*Drosophila*).

The present invention also provides a nucleic acid chip for diagnosing bladder cancer, which comprises a probe capable of hybridizing with a fragment containing the CpG island of the promoter or exon region of the bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (*Drosophila*).

The present invention also provides a method for detecting the methylation of the promoter or exon region of a clinical sample-originated gene selected from the group consisting of CDX2, CYP1B1, VSX1, HOXA11, T, TBX5, PENK, PAQR9, LHX2 and SIM2.

Other features and embodiments of the present invention will be more apparent from the following detailed description and the appended claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3A shows measurement results for the methylation degrees of the CDX2, the CYP1B1 and the T biomarker genes in the urinary cells of normal persons, Cystitis patients, hematuria patients and bladder cancer patients.

FIG. 3B shows measurement results for the methylation degrees of the TBX5, the LHX2 and the SIM2 biomarker genes in the urinary cells of normal persons, Cystitis patients, hematuria patients and bladder cancer patients.

FIG. 3C shows measurement results for the methylation degrees of the VSX1, the HOXA11 and the PENK biomarker genes in the urinary cells of normal persons, Cystitis patients, hematuria patients and bladder cancer patients.

FIG. 3D shows measurement results for the methylation degrees of the PAQR9 biomarker genes in the urinary cells of normal persons, Cystitis patients, hematuria patients and bladder cancer patients.

FIG. 4A shows the results of receiver operating characteristic (ROC) curve analysis conducted to measure the sensitivity and specificity of the CDX2 and the CYP1B1 methylation biomarkers for diagnosis of bladder cancer.

FIG. 4B shows the results of receiver operation characteristic (ROC) curve analysis conducted to measure the sensitivity and specificity of the VSX1 and the HOXA11 methylation biomarkers for diagnosis of bladder cancer.

FIG. 4C shows the results of receiver operating characteristic (ROC) curve analysis conducted to measure the sensitivity and specificity of the T and the TBX5 methylation biomarkers for diagnosis of bladder cancer.

FIG. 4E shows the results of receiver operating characteristic (ROC) curve analysis conducted to measure the sensitivity and specificity of the LHX2 and the SIM2 methylation biomarkers for diagnosis of bladder cancer.

DETAILED DESCRIPTION OF THE INVENTION, AND PREFERRED EMBODIMENTS

Figure 1:
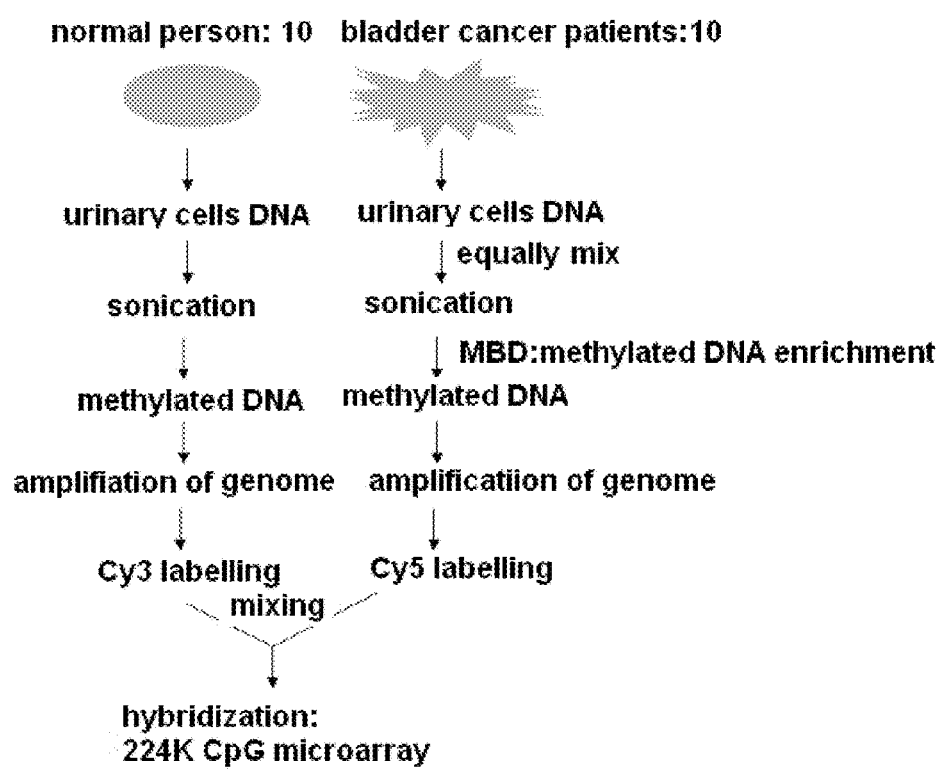
FIG. 1 is a schematic diagram showing a process of discovering a methylated biomarker for diagnosis of bladder cancer from the urinary cells of normal persons and bladder cancer patients through CpG microarray analysis.

In one aspect, the present invention relates to a kit for diagnosing bladder cancer, which comprises the methylated promoter or exon region of a bladder cancer marker gene.

In another aspect, the present invention relates to a nucleic acid chip for diagnosing bladder cancer, which comprises a probe capable of hybridizing with a fragment containing the CpG island of the promoter or exon region of a bladder cancer marker gene.

In the present invention, the promoter or exon region may contain at least one methylated CpG dinucleotide. Also, the promoter or exon region is any one of DNA sequences represented in SEQ ID NO: 31 to SEQ ID NO: 40.

In the present invention, the probe preferably has a size ranging from 10 bp to 1 kb, and has a homology with a base sequence containing the CpG island of the promoter or exon region of a bladder cancer marker gene, such that it can hybridize with the base sequence. More preferably, the probe has a size of 10-100 bp, and has a homology with a base sequence containing the CpG island of the promoter or exon region of a bladder cancer marker gene, such that it can hybridize with the base sequence in strict conditions. If the size of the probe is less than 10 bp, non-specific hybridization will occur, and if it is more than 1 kb, the binding between the probes will occur, thus making it difficult to read hybridization results.

A method for screening a methylation marker gene according to the present invention comprises the steps of: (a) isolating genomic DNAs from transformed cells and non-transformed cells; (b) reacting the isolated genomic DNAs to with a protein binding to methylated DNA and isolating methylated DNAs from the genomic DNAs; and (c) amplifying the isolated methylated DNAs, hybridizing the amplified DNAs to CpG microarrays, and selecting a methylation marker gene showing the greatest difference in methylation degree between normal cells and cancer cells among from the hybridized genes.

By the method for screening the methylation biomarker gene, it is possible to screen various genes, which are methylated not only in bladder cancer, but also in various dysplasic stages which progress to bladder cancer. The screened genes are also useful for blood cancer screening, risk assessment, prognosis, disease identification, disease staging, and selection of therapeutic targets.

The identification of the methylated gene in bladder cancer and abnormalities at various stages enables early diagnosis of bladder cancer in an accurate and effective manner, and allows establishment of methylation data using multiple genes and identification of new therapeutic targets. Additionally, methylation data according to the present invention enables establishment of a more accurate system for diagnosing bladder cancer, when it is used together with a method for detecting other non-methylation-associated biomarkers.

The inventive method enables diagnosis of bladder cancer progression at various stages by determining the methylation stage of at least one nucleic acid biomarker obtained from a sample. When the methylation stage of nucleic acid isolated from a sample at each stage of bladder cancer is compared with the methylation stage of at least one nucleic acid obtained from a sample having no abnormality in the cell proliferation of bladder tissue, a certain stage of bladder cancer in the sample can be determined. The methylation stage may be hypermethylation.

In one embodiment of the present invention, nucleic acid can be methylated in the regulatory region of a gene. In another embodiment, since methylation begins from the outer boundary of the regulatory region of a gene and then spreads inward, detection of methylation at the outer boundary of the regulatory region enables early diagnosis of genes which are involved in cell transformation.

In still another embodiment of the present invention, the cell growth abnormality (dysplasia) of bladder tissue can be diagnosed by detecting the methylation of at least one nucleic acid of the following nucleic acids using a kit or a nucleic acid chip: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (*Drosophila*) gene and combination thereof.

The use of the diagnostic kit or nucleic acid chip of the present invention can determine the cell growth abnormality of bladder tissue in a sample. The method for determining the cell growth abnormality of bladder tissue comprises determining the methylation of at least one nucleic acid isolated from a sample. In the method, the methylation stage of at least one nucleic acid is compared with the methylation stage of a nucleic acid isolated from a sample having no cell growth abnormality (dysplasia).

The examples of said nucleic acid are follows: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (*Drosophila*) gene and combination thereof.

In still another embodiment of the present invention, cells capable of forming bladder cancer can be diagnosed at an early stage using the methylation gene marker. When genes confirmed to be methylated in cancer cells are methylated in cells which seem to be normal clinically or morphologically, the cells that seem to be normal are cells, the carcinogenesis of which is in progress. Thus, bladder cancer can be diagnosed at an early stage by detecting the methylation of bladder cancer-specific genes in the cells that seem to be normal.

The use of the methylation marker gene of the present invention enables detection of the cell growth abnormality (dysplasia progression) of bladder tissue in a sample. The method for detecting the cell growth abnormality (dysplasia progression) of bladder tissue comprises bringing at least one nucleic acid isolated from a sample into contact with an agent capable of determining the methylation status of the nucleic acid. The method comprises determining the methylation status of at least one region in at least one nucleic acid, and the methylation status of the nucleic acid differs from the methylation status of the same region in a nucleic acid isolated from a sample having no cell growth abnormality (dysplasia progression) of bladder tissue.

In still another embodiment of the present invention, transformed bladder cancer cells can be detected by examining the methylation of a marker gene using the above-described kit or nucleic acid chip.

In still another embodiment of the present invention, bladder cancer can be diagnosed by examining the methylation of a marker gene using the above-described kit or nucleic acid chip.

In still another embodiment of the present invention, the likelihood of progression to bladder cancer can be diagnosed by examining the methylation of a marker gene with the above-described kit or nucleic acid chip in a sample showing a normal phenotype. The sample may be solid or liquid tissue, cell, urine, serum or plasma.

In still another aspect, the present invention relates to a method for detecting the promoter methylation of a clinical sample-originated gene.

In the present invention, the method for measuring the promoter methylation of a clinical sample-originated gene may be selected from the group consisting of PCR, methylation specific PCR, real-time methylation specific PCR, PCR using a methylated DNA-specific binding protein, quantitative PCR, pyrosequencing and bisulfite sequencing, and the clinical sample is preferably a tissue, cell, blood or urine originated from patients suspected of cancer or subjects to be diagnosed.

In the present invention, the method for detecting the promoter methylation of the gene comprises the steps of: (a) isolating a sample DNA from a clinical sample; (b) amplifying the isolated DNA with primers capable of amplifying a fragment containing the promoter CpG island of a gene selected from the group consisting of CDX2, CYP1B1, VSX1, HOXA11, T, TBX5, PENK, PAQR9, LHX2 and SIM2; and (c) determining the promoter methylation of the DNA on the basis of whether the DNA has been amplified or not in step (b).

In an embodiment of the present disclosure, primer(s) that could amplify a methylated CpG of PENK might be used, and such primer(s) comprises at least one or more CpG dinucleotide in a region which hybridizes to the methylated CpG of PENK Specifically, the primer(s) for amplifying a methylated CpG of PENK comprise sequence(s) having a homology of 50% or more with sequence(s) selected from the group consisting of SEQ ID NOs: 43-44, 46-185, 187-298, 300-341, 343-468, 470-579, 581-704, 706-841, 843-976, 978-1097, 1099-1210, 1212-1221. Preferably, the primer(s) for amplifying a methylated CpG of PENK comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 43-44, 46-185, 187-298, 300-341, 343-468, 470-579, 581-704, 706-841, 843-976, 978-1097, 1099-1210, 1212-1221.

If required, probe(s) capable of hybridizing with a methylated CpG of PENK might be used. The probe(s) capable of hybridizing with a methylated CpG of PENK comprise at least one or more CpG dinucleotide in a region which hybridizes to the methylated CpG of PENK. Specifically, probe(s) might comprise sequence(s) having a homology of 50% or more with sequence(s) selected from the group consisting of SEQ ID NOs: 45, 186, 299, 342, 469, 580, 705, 842, 977, 1098 and 1211. Preferably, the probe(s) capable of hybridizing with a methylated CpG of PENK comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 45, 186, 299, 342, 469, 580, 705, 842, 977, 1098 and 1211.

In another embodiment of the present invention, the likelihood of development of tissue to bladder cancer can be evaluated by examining the methylation frequency of a gene which is methylated specifically in bladder cancer and determining the methylation frequency of tissue having the likelihood of progression to bladder cancer.

As used herein, "cell conversion" refers to the change in characteristics of a cell from one form to another such as from normal to abnormal, non-tumorous to tumorous, undifferentiated to differentiated, stem cell to non-stem cell. Further, the conversion may be recognized by morphology of the cell, phenotype of the cell, biochemical characteristics and so on.

As used herein, the term "early diagnosis" of cancer refers to discovering the likelihood of cancer before metastasis. Preferably, it refers to discovering the likelihood of cancer before a morphological change in a sample tissue or cell is observed. Additionally, the term "early diagnosis" of transformation the high probability of a cell to undergo transformation in its early stages before the cell is morphologically designated as being transformed.

As used herein, the term "hypermethylation" refers to the methylation of CpG islands.

As used herein, the term "sample" or "biological sample" is referred to in its broadest sense, and includes any biological sample obtained from an individual, body fluid, cell line, tissue culture or other sources, according to the type of analysis that is to be performed. Methods of obtaining body fluid and tissue biopsy from mammals are generally widely known. A preferred source is bladder biopsy.

Screening for Methylation Regulated Biomarkers

The present invention is directed to a method of determining biomarker genes that are methylated when the cell or tissue is converted or changed from one type of cell to another. As used herein, "converted" cell refers to the change in characteristics of a cell or tissue from one form to another such as from normal to abnormal, non-tumorous to tumorous, undifferentiated to differentiated and so on.

In one Example of the present invention, urinary cells were isolated from the urine of normal persons and bladder cancer patients, and then genomic DNAs were isolated from the urinary cells. In order to obtain only methylated DNAs from the genomic DNAs, the genomic DNAs were allowed to react with McrBt binding to methylated DNA, and then methylated DNAs binding to the McrBt protein were isolated. The isolated methylated DNAs binding to the McrBt protein were amplified, and then the DNAs originated from the normal persons were labeled with Cy3, and the DNAs originated from the bladder cancer patients were labeled with Cy5. Then, the DNAs were hybridized to human CpG-island microarrays, and 10 genes showing the greatest difference in methylation degree between the normal persons and the bladder cancer patients were selected as biomarkers.

In the present invention, in order to further confirm whether the 10 biomarkers have been methylated, pyrosequencing was performed.

Specifically, total genomic DNA was isolated from the bladder cell lines RT-4, J82, HT1197 and HT1376 and treated with bisulfite. The genomic DNA converted with bisulfite was amplified. Then, the amplified PCR product was subjected to pyrosequencing in order to measure the methylation degree of the genes. As a result, it could be seen that the 10 biomarkers were all methylated.

Biomarker for Bladder Cancer

The present invention provides a biomarker for diagnosing bladder cancer.

Biomarkers for Bladder Cancer—Using Cancer Cells for Comparison with Normal Cells In one embodiment of the present invention, it is understood that "normal" cells are those that do not show any abnormal morphological or cytological changes. "Tumor" cells mean cancer cells. "Non-tumor" cells are those cells that were part of the diseased tissue but were not considered to be the tumor portion.

In one aspect, the present invention is based on the relationship between bladder cancer and the hypermethylation of the promoter or exon region of the following 10 genes: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (*Drosophila*); gene.

With other applications of the diagnostic kit or nucleic acid chip of the present invention, the invention can diagnose a cellular proliferative disorder of bladder tissue in a subject by determining the state of methylation of one or more nucleic acids isolated from the subject, wherein the state of methylation of one or more nucleic acids as compared with the state of methylation of one or more nucleic acids from a subject not having the cellular proliferative disorder of bladder tissue is indicative of a cellular proliferative disorder of bladder tissue in the subject. A preferred nucleic acid is a CpG-containing nucleic acid, such as a CpG island.

With other applications of the diagnostic kit or nucleic acid chip of the present invention, the cell growth abnormality of bladder tissue in a subject can be diagnosed comprising determining the methylation of one or more nucleic acids isolated from the subject. Said nucleic acid is preferably encoding the followings: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (*Drosophila*); gene and combinations thereof. The state of methylation of one or more nucleic acids as compared with the state of methylation of said nucleic acid from a subject not having a predisposition to the cellular proliferative disorder of bladder tissue is indicative of a cell proliferative disorder of bladder tissue in the subject.

As used herein, "predisposition" refers to an increased likelihood that an individual will have a disorder. Although a subject with a predisposition does not yet have the disorder, there exists an increased propensity to the disease.

Another embodiment of the invention provides a method for diagnosing a cellular proliferative disorder of bladder tissue in a subject comprising contacting a nucleic acid-containing specimen from the subject with an agent that provides a determination of the methylation state of nucleic acids in the specimen, and identifying the methylation state of at least one region of at least one nucleic acid, wherein the methylation state of at least one region of at least one nucleic acid that is different from the methylation state of the same region of the same nucleic acid in a subject not having the cellular proliferative disorder is indicative of a cellular proliferative disorder of bladder tissue in the subject.

The inventive method includes determining the state of methylation of one or more regions of one or more nucleic acids isolated from the subject. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded, to DNA or RNA of genomic or synthetic origin which may represent a sense or antisense strand, peptide nucleic acid (PNA), or to any DNA-like or RNA-like material of natural or synthetic origin. As will be understood by those of skill in the art, when the nucleic acid is RNA, the deoxynucleotides A, G, C, and T are replaced by ribonucleotides A, G, C, and U, respectively.

The nucleic acid of interest can be any nucleic acid where it is desirable to detect the presence of a differentially methylated CpG island. The CpG island is a CpG rich region of a nucleic acid sequence.

Methylation

Any nucleic acid sample, in purified or nonpurified form, can be utilized in accordance with the present invention, provided it contains or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten fold relative to the rest of the genome. CpG islands have an average G*C content of about 60%, and general DNA have an average G*C contents of about 40%. The islands take the form of stretches of DNA typically about one to two kilobases long. There are about 45,000 such islands in the human genome.

In many genes, the CpG islands begin just upstream of a promoter and extend downstream into the transcribed region. Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), in downstream of coding regions, for example, enhancer regions, and in introns.

In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample.

A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the nucleic acid sequence is present initially in a pure form, the nucleic acid may be a minor fraction of a complex mixture, such as contained in whole human DNA. The nucleic acid-containing sample used for determination of the state of methylation of nucleic acids contained in the sample or detection of methylated CpG islands may be extracted by a variety of techniques such as that described by Sambrook, et al. (Molecular Cloning: A Laboratory Manual, Cold Spring Harbor, N.Y., 1989; incorporated in its entirety herein by reference).

A nucleic acid can contain a regulatory region which is a region of DNA that encodes information or controls transcription of the nucleic acid. Regulatory regions include at least one promoter. A "promoter" is a minimal sequence sufficient to direct transcription, to render promoter-dependent gene expression controllable for cell-type specific, tissue-specific, or inducible by external signals or agents. Promoters may be located in the 5' or 3' regions of the gene. Promoter regions, in whole or in part, of a number of nucleic acids can be examined for sites of CpG-island methylation. Moreover, it is generally recognized that methylation of the target gene promoter proceeds naturally from the outer boundary inward. Therefore, early stage of cell conversion can be detected by assaying for methylation in these outer areas of the promoter region.

Nucleic acids isolated from a subject are obtained in a biological specimen from the subject. If it is desired to detect bladder cancer or stages of bladder cancer progression, the nucleic acid may be isolated from bladder tissue by scraping or taking a biopsy. These specimens may be obtained by various medical procedures known to those of skill in the art.

In one aspect of the invention, the state of methylation in nucleic acids of the sample obtained from a subject is hypermethylation compared with the same regions of the nucleic acid in a subject not having the cellular proliferative disorder of bladder tissue. Hypermethylation, as used herein, is the presence of methylated alleles in one or more nucleic acids. Nucleic acids from a subject not having a cellular proliferative disorder of bladder tissues contain no detectable methylated alleles when the same nucleic acids are examined.

Sample

The present invention describes early diagnosis of bladder cancer and utilizes the methylation of bladder cancer-specific genes. The methylation of bladder cancer-specific genes also occurred in tissue near tumor sites. Therefore, in the method for early diagnosis of bladder cancer, the methylation of bladder cancer-specific genes can be detected by examining all samples including liquid or solid tissue. The samples include, but are not limited to, tissue, cell, urine, serum or plasma.

Individual Genes and Panel

It is understood that the present invention may be practiced using each gene separately as a diagnostic or prognostic marker, or a few marker genes combined into a panel display format so that several marker genes may be detected to increase reliability and efficiency. Further, any of the genes identified in the present application may be used individually or as a set of genes in any combination with any of the other genes that are recited in the application. Also, genes may be ranked and weighted according to their importance together with the number of genes that are methylated, and a level of likelihood of development to cancer can be assigned. Such algorithms are within the scope of the present invention.

Methylation Detection Methods

Methylation Specific PCR

When genomic DNA is treated with bisulfite, the methylated cytosine in the 5'-CpG'-3 region remains without changes, and unmethylated cytosine is changed to uracil. Thus, for a base sequence modified by bisulfite treatment, PCR primers corresponding to regions in which a 5'-CpG-3' base sequence is present were constructed. Herein, two kinds of primers corresponding to the methylated case and the unmethylated case were constructed. When genomic DNA is modified with bisulfite and then subjected to PCR using the two kinds of primers, in the case in which the DNA is methylated, a PCR product is made from the DNA in which the primers corresponding to the methylated base sequence are used. In contrast, in the case in which the gene is unmethylated, a PCR product is made from the DNA in which the primers corresponding to the unmethylated base sequence are used. The methylation of DNA can be qualitatively analyzed using agarose gel electrophoresis.

Real-Time Methylation-Specific PCR

Real-time methylation-specific PCR is a real-time measurement method modified from methylation-specific PCR, and comprises treating genomic DNA with bisulfite, designing PCR primers corresponding to the methylated case and performing real-time PCR using the primers. Herein, methods of detecting methylation include two methods: a method of performing detection using a TanMan probe complementary to the amplified base sequence, and a method of performing detection using Sybergreen. Thus, real-time methylation-specific PCR selectively quantitatively analyze only DNA. Herein, a standard curve was prepared using an in vitro methylated DNA sample, and for standardization, a gene having no 5'-CpG-3' sequence in the base sequence was also amplified as a negative control group and was quantitatively analyzed for the methylation degree.

Pyrosequencing

Pyrosequencing is a real-time sequencing method modified from a bisulfite sequencing method. In the same manner as bisulfite sequencing, genomic DNA was modified by bisulfite treatment, and then primers corresponding to a region having no 5'-CpG-3' base sequence were constructed. After the genomic DNA had been treated with bisulfite, it was amplified with the PCR primers, and then subjected to real-time sequence analysis using sequencing primers. The amounts of cytosine and thymine in the 5'-CpG-3' region were quantitatively analyzed, and the methylation degree was expressed as a methylation index.

PCR or Quantitative PCR Using Methylated DNA-Specific Binding Protein and DNA Chip In a PCR or DNA chip method using a methylated DNA-specific binding protein, when a protein binding specifically only to methylated DNA is mixed with DNA, the protein binds specifically only to methylated DNA, and thus only methylated DNA can be isolated. In the present invention, genomic DNA was mixed with a methylated DNA-specific binding protein, and then only methylated DNA was selectively isolated. The isolated DNA was amplified using PCR primers corresponding to the promoter region thereof, and then the methylation of the DNA was measured by agarose gel electrophoresis.

In addition, the methylation of DNA can also be measured by a quantitative PCR method. Specifically, methylated DNA isolated using a methylated DNA-specific binding protein can be labeled with a fluorescent dye and hybridized to a DNA chip in which complementary probes are integrated, thus measuring the methylation of the DNA. Herein, the methylated DNA-specific binding protein is not limited to McrBt.

Detection of Differential Methylation-Methylation Sensitive Restriction Endonuclease Detection of differential methylation can be accomplished by contacting a nucleic acid sample with a methylation sensitive restriction endonuclease that cleaves only unmethylated CpG sites under conditions and for a time to allow cleavage of unmethylated nucleic acid.

In a separate reaction, the sample is further contacted with an isoschizomer of the methylation sensitive restriction endonuclease that cleaves both methylated and unmethylated CpG-sites under conditions and for a time to allow cleavage of methylated nucleic acid.

Specific primers are added to the nucleic acid sample under conditions and for a time to allow nucleic acid amplification to occur by conventional methods. The presence of amplified product in the sample digested with methylation sensitive restriction endonuclease but absence of an amplified product in sample digested with an isoschizomer of the methylation sensitive restriction enzyme endonuclease that cleaves both methylated and unmethylated CpG-sites indicates that methylation has occurred at the nucleic acid region being assayed. However, lack of amplified product in the sample digested with methylation sensitive restriction endonuclease together with lack of an amplified product in the sample digested with an isoschizomer of the methylation sensitive restriction enzyme endonuclease that cleaves both methylated and unmethylated CpG-sites indicates that methylation has not occurred at the nucleic acid region being assayed.

As used herein, a "methylation sensitive restriction endonuclease" is a restriction endonuclease that includes CG as part of its recognition site and has altered activity when the C is methylated as compared to when the C is not methylated (e.g., Sma I). Non-limiting examples of methylation sensitive restriction endonucleases include MspI, HpaII, BssHII, BstUI and NotI. Such enzymes can be used alone or in combination. Other methylation sensitive restriction endonucleases such as SacII and EagI may be applied to the present invention, but are not limited to these enzymes.

An "isoschizomer" of a methylation sensitive restriction endonuclease is a restriction endonuclease that recognizes the same recognition site as a methylation sensitive restriction endonuclease but cleaves both methylated CGs and unmethylated CGs, such as for example, MspI.

Primers of the invention are designed to be "substantially" complementary to each strand of the locus to be amplified and include the appropriate G or C nucleotides as discussed above. This means that the primers must be sufficiently complementary to hybridize with their respective strands under conditions that allow the agent for polymerization to perform. Primers of the invention are employed in the amplification process, which is an enzymatic chain reaction that produces exponentially increasing quantities of target locus relative to the number of reaction steps involved (e.g., polymerase chain reaction (PCR)). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

Preferably, the method of amplifying is by PCR, as described herein and as is commonly used by those of ordinary skill in the art. However, alternative methods of amplification have been described and can also be employed such as real time PCR or linear amplification using isothermal enzyme. Multiplex amplification reactions may also be used.

Detection of Differential Methylation-Bifulfite Sequencing Method

Another method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA. Such methods are described in U.S. Pat. No. 5,786,146, the contents of which are incorporated herein in their entirety especially as they relate to the bisulfite sequencing method for detection of methylated nucleic acid.

Substrates

Once the target nucleic acid region is amplified, the nucleic acid can be hybridized to a known gene probe immobilized on a solid support to detect the presence of the nucleic acid sequence.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics.

Several types of membranes are known to one of skill in the art for adhesion of nucleic acid sequences. Specific non-limiting examples of these membranes include nitrocellulose or other membranes used for detection of gene expression such as polyvinylchloride, diazotized paper and other commercially available membranes such as GENESCREEN™, ZETAPROBE™ (Biorad), and NYTRAN™. Beads, glass, wafer and metal substrates are included. Methods for attaching nucleic acids to these objects are well known to one of skill in the art. Alternatively, screening can be done in liquid phase.

Hybridization Conditions

In nucleic acid hybridization reactions, the conditions used to achieve a particular level of stringency will vary, depending on the nature of the nucleic acids being hybridized. For example, the length, degree of homology, nucleotide sequence composition (e.g., GC/AT content), and nucleic acid type (e.g., RNA, DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Kit

In accordance with the present invention, there is provided a kit useful for the detection of a cellular proliferative disorder in a subject. Kits according to the present invention include a carrier means compartmentalized to receive a sample therein, one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid. Primers contemplated for use in accordance with the invention include those set forth in SEQ ID NOS: 1-20, and any functional combination and fragments thereof.

In an embodiment of the present disclosure, primer(s) that could amplify a methylated CpG of PENK might be used, and such primer(s) comprises at least one or more CpG dinucleotide in a region which hybridizes to the methylated CpG of PENK Specifically, the primer(s) for amplifying a methylated CpG of PENK comprise sequence(s) having a homology of 50% or more with sequence(s) selected from the group consisting of SEQ ID NOs: 43-44, 46-185, 187-298, 300-341, 343-468, 470-579, 581-704, 706-841, 843-976, 978-1097, 1099-1210, 1212-1221. Preferably, the primer(s) for amplifying a methylated CpG of PENK comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 43-44, 46-185, 187-298, 300-341, 343-468, 470-579, 581-704, 706-841, 843-976, 978-1097, 1099-1210, 1212-1221.

If required, probe(s) capable of hybridizing with a methylated CpG of PENK might be used. The probe(s) capable of hybridizing with a methylated CpG of PENK comprise at least one or more CpG dinucleotide in a region which hybridizes to the methylated CpG of PENK. Specifically, probe(s) might comprise sequence(s) having a homology of 50% or more with sequence(s) selected from the group consisting of SEQ ID NOs: 45, 186, 299, 342, 469, 580, 705, 842, 977, 1098 and 1211. Preferably, the probe(s) capable of hybridizing with a methylated CpG of PENK comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 45, 186, 299, 342, 469, 580, 705, 842, 977, 1098 and 1211. Functional combination or fragment refers to its ability to be used as a primer to detect whether methylation has occurred on the region of the genome sought to be detected.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing methylation sensitive restriction endonuclease. One or more container means can also be included comprising a primer complementary to the nucleic acid locus of interest. In addition, one or more container means can also be included containing an isoschizomer of the methylation sensitive restriction enzyme.

EXAMPLES

Hereinafter, the present invention will be described in further detail with reference to examples. It is to be understood, however, that these examples are for illustrative purposes only and are not to be construed to limit the scope of the present invention.

Example 1: Discovery of Bladder Cancer-Specific Methylated Genes

In order to screen biomarkers which are methylated specifically in bladder cancer, about 20 ml of the urine of each of 10 bladder cancer patients and 10 normal persons was centrifuged in a centrifuge (Hanil Science Industrial Co., Ltd., Korea) at 4,200×g for 10 minutes to isolate urinary cells. The supernatant was discarded, and the cell precipitate was washed twice with 5 ml of PBS. Genomic DNA was isolated from the cell precipitate using the QIAamp DNA Mini kit (QIAGEN, USA). 500 ng of the isolated genomic DNA was sonicated (Vibra Cell, SONICS), thus constructing about 200-300-bp-genomic DNA fragments.

To obtain only methylated DNA from the genomic DNA, a methyl binding domain (MBD) known to bind to methylated DNA (Fraga et al., *Nucleic Acid Res.*, 31:1765-1774, 2003) was used. Specifically, 2 μg of 6× His-tagged MBD was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of the sonicated genomic DNA isolated from the urinary cells of the normal persons and the bladder cancer patients was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the methylated DNAs bound to the MBD were amplified using a genomic DNA amplification kit (Sigma, USA, Cat. No. WGA2), and 4 μg of the amplified DNAs were labeled with Cy3 for the normal person-originated DNA and with Cy5 for the bladder cancer patient-originated DNA using the BioPrime Total Genomic Labeling system I (Invitrogen Corp., USA). The DNA of the normal persons and the DNA of the bladder patients were mixed with each other, and then hybridized to 244K human CpG microarrays (Agilent, USA) (FIG. 1). After the hybridization, the DNA mixture was subjected to a series of washing processes, and then scanned using an Agilent scanner. The calculation of signal values from the microarray images was performed by calculating the relative difference in signal strength between the normal person sample and the bladder cancer patient sample using Feature Extraction program v. 9.5.3.1 (Agilent).

In order to select unmethylated spots from the normal sample, the whole Cy3 signal values were averaged, and then spots having a signal value of less than 10% of the averaged value were regarded as those unmethylated in the samples of the normal persons. As a result, 41,674 spots having a Cy3 signal value of less than 65 were selected.

In order to select the methylated spots in the samples of the bladder cancer patients from among the 41,674 spots, spots having a Cy5 signal value of more than 130 were regarded as the methylated spots in bladder cancer. As a result, 631 spots having a Cy5 signal value of more than 130 were selected. From these spots, 227 genes corresponding to the promoter region were secured as bladder cancer-specific methylated genes.

From the genes, 10 genes (CDX2, CYP1B1, VSX16, HOXA11, T, TBX5, PENK, PAQR9, LHX2, and SIM2) showing the greatest relative difference between methylation degree of the normal persons and that of the bladder cancer patients were selected, and the presence of CpG islands in the promoter region of the 10 genes was confirmed using MethPrimer (http://itsa.ucsf.edu/~urolab/methprimer/index1.html). The 10 genes were secured as methylation biomarkers for diagnosis of bladder cancer. The list of the 10 genes and the relative methylation degree thereof in the urinary cells of the bladder patients relative to those of the normal persons are shown in Table 1 below.

TABLE 1

10 methylation biomarkers for diagnosis of bladder cancer

| Biomarker for bladder cancer | GenBank No. | Description | Relative methylation[a] |
|---|---|---|---|
| CDX2 | NM_001265 | caudal type homeobox transcription factor 2 | 11.0 |
| CYP1B1 | NM_000104 | cytochrome P450, family 1, subfamily B, polypeptide 1 | 14.6 |
| VSX1 | NM_199425 | visual system homeobox 1 homolog, CHX10-like (zebrafish) | 33.4 |
| HOXA11 | NM_005523 | homeobox A11 | 14.2 |
| T | NM_003181 | T, brachyury homolog (mouse) | 51.4 |
| TBX5 | NM_080717 | T-box 5 | 18.7 |
| PENK | NM_006211 | Proenkephalin | 12.7 |
| PAQR9 | NM_198504 | progestin and adipoQ receptor family member IX | 4.1 |
| LHX2 | NM_004789 | LIM Homeobox 2 | 5.8 |
| SIM2 | U80456 | Single-minded homolog 2 (*Drosophila*) | 9.5 |

[a]Relative methylation degree between the normal sample and the bladder patient sample, calculated by dividing the average signal (Cy5) value in the bladder cancer patient sample in CpG microarrays by the average signal (Cy5) value in the normal person sample.

Example 2: Measurement of Methylation of Biomarker Genes in Cancer Cell Lines

In order to further determine the methylation status of the 10 genes, bisulfite sequencing for each promoter was performed.

In order to modify unmethylated cytosine to uracil using bisulfite, total genomic DNA was isolated from the bladder cancer cell lines RT-4 (Korean Cell Line Bank (KCLB 30002), J82 (KCLB 30001), HT1197 (KCLB 21473) and HT1376 (KCLB 21472), and 200 ng of the genomic DNA was treated with bisulfite using the EZ DNA methylation-gold kit (Zymo Research, USA). When DNA is treated with bisulfite, unmethylated cytosine is modified to uracil, and the methylated cytosine remains without changes. The DNA treated with bisulfite was eluted in 20 µl of sterile distilled water and subjected to pyrosequencing.

PCR and sequencing primers for performing pyrosequencing for the 10 genes were designed using the PSQ assay design program (Biotage, USA). The PCR and sequencing primers for measuring the methylation of each gene are shown in Tables 2 and 3 below.

TABLE 2

Primers and conditions

| Gene | Primer | Sequence (5'→3') | SEQ ID NO: | CpG position[a] | Amplicon size |
|---|---|---|---|---|---|
| CDX2 | forward | TGGTGTTTGTGTTATTATTAATAG | 1 | -138, -129, -121, -118 | 129 bp |
|  | reverse | Biotin-CACCTCCTTCCCACTAAACTA | 2 |  |  |
| CYP1B1 | forward | GTAAGGGTATGGGAATTGA | 3 | +73, +83, +105 | 90 bp |
|  | reverse | Biotin-CCCTTAAAAACCTAACAAAATC | 4 |  |  |
| VSX1 | forward | GGAGTGGGATTGAGGAGATTT | 5 | -1121, -1114, -1104, 1100 | 89 bp |
|  | reverse | Biotin-AAACCCAACCAACCCTCAT | 6 |  |  |
| HOXA11 | forward | AGTAAGTTTATGGGAGGGGGATT | 7 | -415, -405, -388 | 243 bp |
|  | reverse | Biotin-CCCCCATACAACATACTTATACTCA | 8 |  |  |
| T | forward | GGAGGAATGTTATTGTTTAAAGAGAT | 9 | -95, -89, -76, -71, -69 | 326 bp |
|  | reverse | Biotin-CAACCCCTTCTAAAAAATATCC | 10 |  |  |
| TBX5 | forward | GGGTTTGGAGTTAGGTTATG | 11 | -645, -643, -628, -621 | 95 bp |
|  | reverse | Biotin-AAATCTAAACTTACCCCCAACT | 12 |  |  |
| PENK | forward | ATATTTTATTGTATGGGTTTTTTAATAG | 13 | -150, -148, -139, -135, -133, | 322 bp 54 bp |
|  | reverse | Biotin-ACAACCTCAACAAAAAATC | 14 |  |  |
| PAQ?R9 | forward | Biotin-AGATAGGGGATAATTTTAT | 15 | -480, -475, -471, -469 | 54 bp |
|  | reverse | CCTCCCAAACTAAAATTT | 16 |  |  |
| LHX2 | forward | GTAGAAGGGAAATAAGGTTGAAA | 17 | +5093, +5102, +5113, +5125, +5127 | 233 bp |
|  | reverse | Biotin-ACTAAAACCCCAATACTCCCA | 18 |  |  |

TABLE 2-continued

Primers and conditions

| Gene | Primer | Sequence (5'→3') | SEQ ID NO: | CpG position[a] | Amplicon size |
|---|---|---|---|---|---|
| SIM2 | forward | Biotin-GTGGATTTAGATTAGGATTTTGT | 19 | −6776, −6774, | 205 bp |
|  | reverse | CACCCTCCCCAAATTCTT | 20 | −6747, −6744, −6743 |  |

[a] distances (nucleotides) from the transcription initiation site (+1): the positions of CpG regions on the genomic DNA used in the measurement of methylation

TABLE 3

Sequences of sequencing primers for methylation marker genes

| Gene | Sequence (5'→3') | SEQ ID NO: |
|---|---|---|
| CDX2 | ATT AAT AGA GTT TTG TAA ATA T | 21 |
| CYP1B1 | AAG GGT ATG GGA ATT G | 22 |
| VSX1 | TTT GGG ATT GGG AAG | 23 |
| HOXA11 | TAG TTT AGG GTA TTT TTT ATT TAT | 24 |
| T | GTG AAA GTA ATG ATA TAG TAG AAA | 25 |
| TBX5 | TTT GGG GGT TGG GGA | 26 |
| PENK | GGG TGT TTTAGG TAG TT | 27 |
| PAQ?R9 | CCT CCC AAA CTA AAA TTT C | 28 |
| LHX2 | TGG GGG TAG AGG AGA | 29 |
| SIM2 | CCT CCC CAA ATT CTT C | 30 |

TABLE 4

Promoter sequences of methylation marker genes

| Gene | SEQ ID NO: |
|---|---|
| CDX2 | 31 |
| CYP1B1 | 32 |
| VSX1 | 33 |
| HOXA11 | 34 |
| T | 35 |
| TBX5 | 36 |
| PENK | 37 |
| PAQR9 | 38 |
| LHX2 | 39 |
| SIM2 | 40 |

20 ng of the genomic DNA modified with bisulfite was amplified by PCR. In the PCR amplification, a PCR reaction solution (20 ng of the genomic DNA modified with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 2:
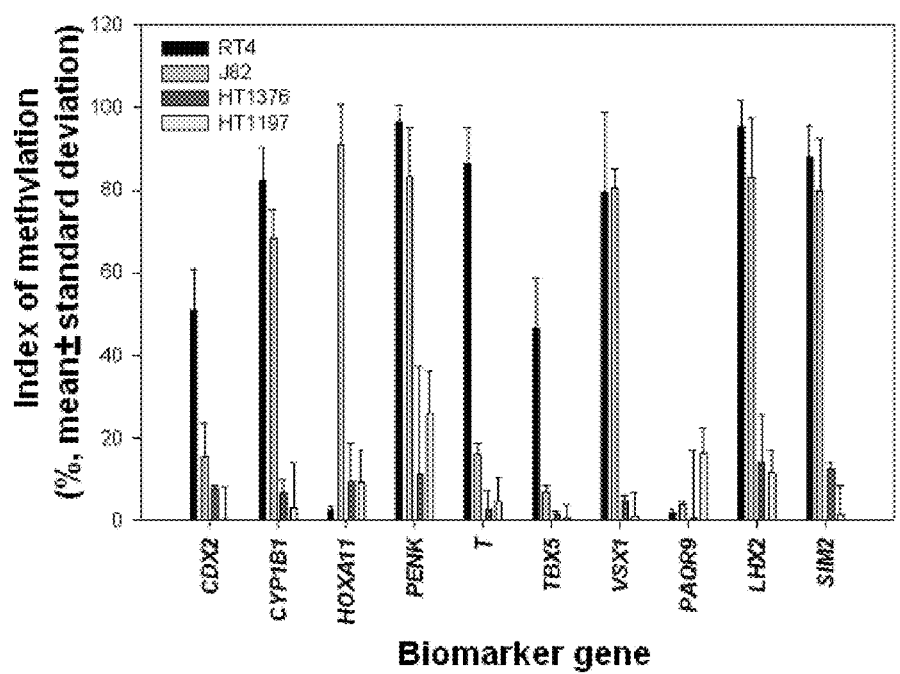
FIG. 2 quantitatively shows the methylation degree obtained through pyrosequencing of 10 methylation biomarkers in bladder cancer cell lines.
Figure 3A:
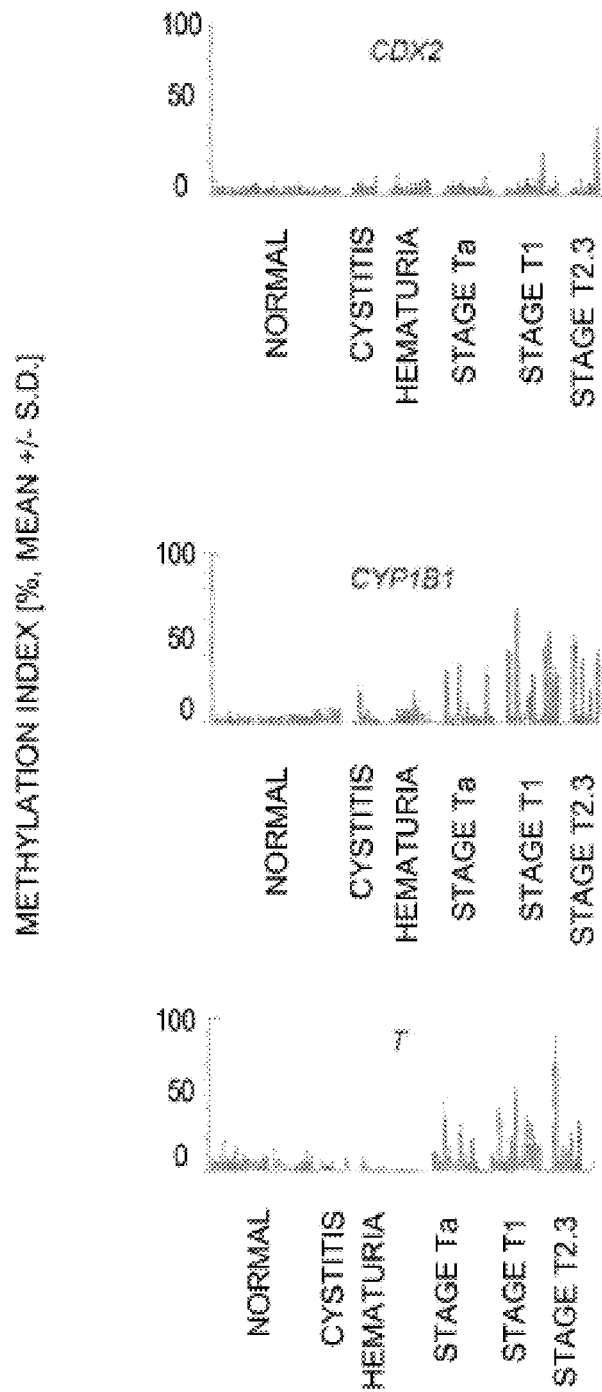
FIG. 3A shows measurement results for the methylation indexes of the CDX2, the CYP1B1 and the T biomarker genes in clinical samples.
Figure 3B:
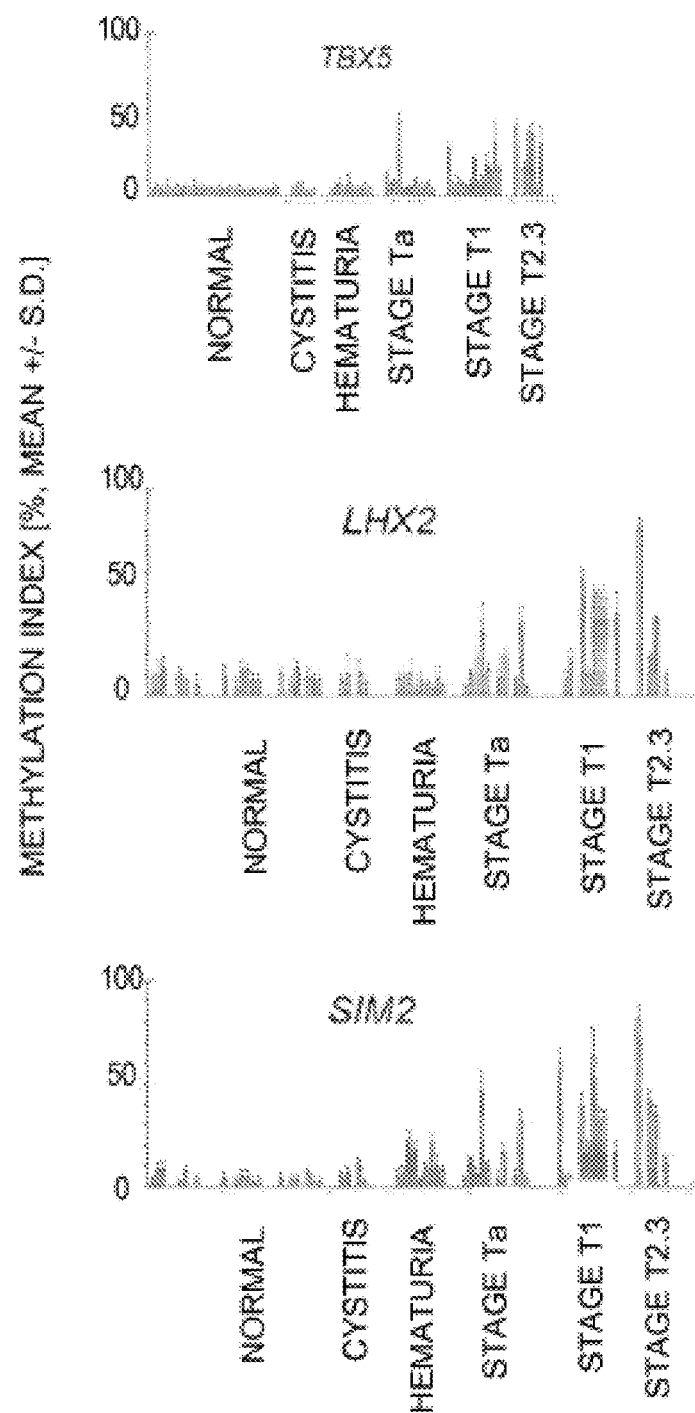
FIG. 3B shows measurement results for the methylation indexes of the TBX5, the LHX2 and the SIM2 biomarker genes in clinical samples.
Figure 3C:
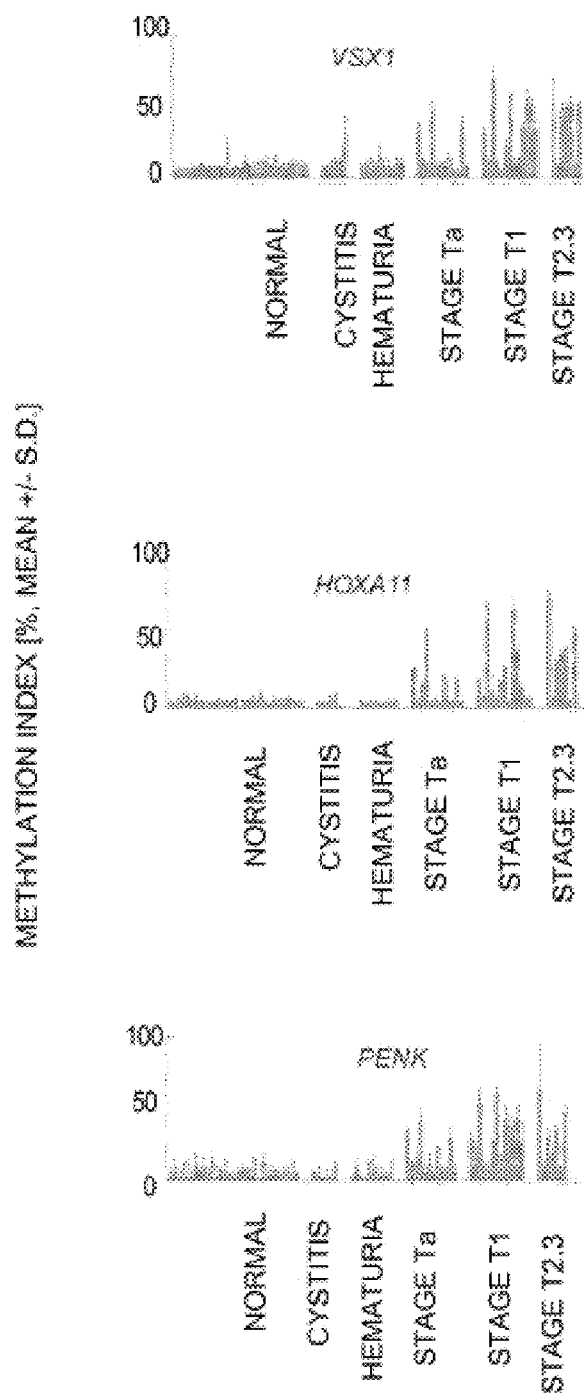
FIG. 3C shows measurement results for the methylation indexes of the VSX1, the HOXA11 and the PENK biomarker genes in clinical samples.
Figure 3D:
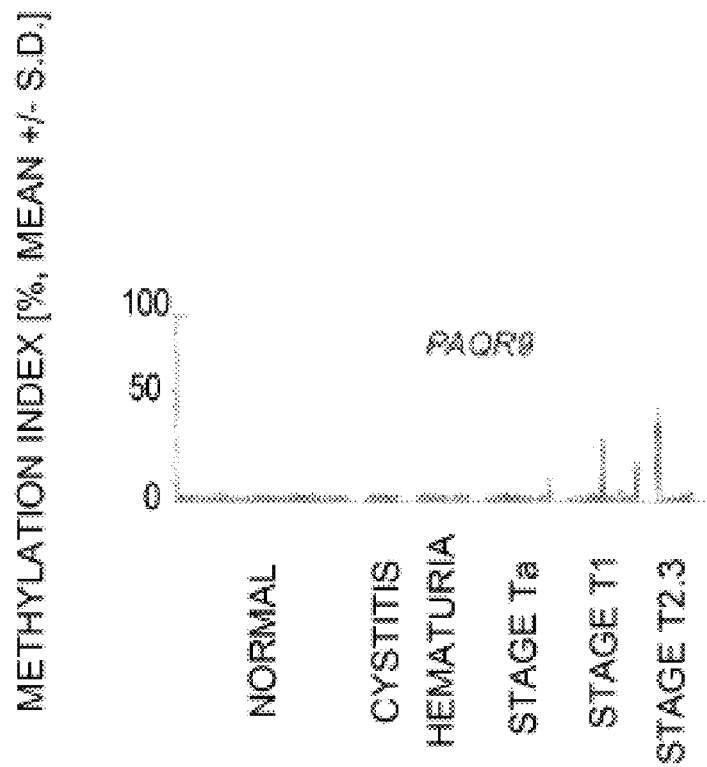
FIG. 3D shows measurement results for the methylation indexes of the PAQR9 biomarker genes in clinical samples.
Figure 4D:
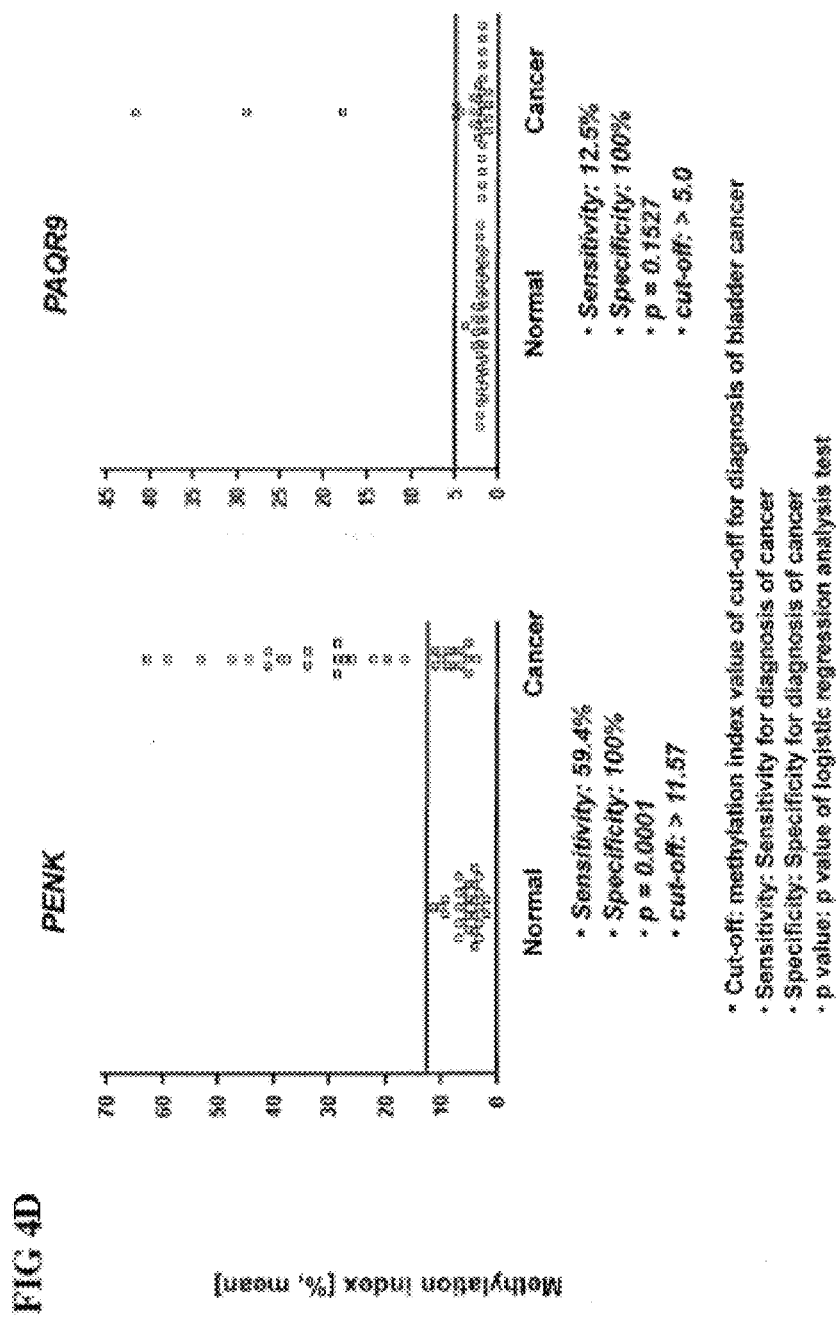
FIG. 4D shows the results of receiver operating characteristic (ROC) curve analysis conducted to measure the sensitivity and specificity of the PENK and the PAQR9 methylation biomarkers for diagnosis of bladder cancer.

FIG. 2 quantitatively shows the methylation degree of the 10 biomarkers in the bladder cancer cell lines, measured using the pyrosequencing method. As a result, it was shown that the 10 biomarkers were all methylated at high levels in at least one of the cell lines. Table 4 below shows the promoter sequences of the 10 genes.

Example 3: Measurement of Methylation of Biomarker Genes in Urinary Cells of Bladder Cancer Patients In order to verify whether the 10 genes can be used as biomarkers for diagnosis of bladder cancer, about 20 ml of the urine of each of 20 normal persons and 19 bladder cancer patients was centrifuged in a centrifuge (Hanil Science Industrial Co., Ltd., Korea) at 4,200×g for 10 minutes to isolate cells. The supernatant was discarded, and the cell precipitate was washed twice with 5 ml of PBS. Genomic DNA was isolated from the washed cells using the QIAamp DNA Mini kit (QIAGEN, USA), and 200 ng of the isolated genomic DNA was treated with bisulfite using the EZ DNA methylation-Gold kit (Zymo Research, USA). Then, the DNA was eluted in 20 µl of sterile distilled water and subjected to pyrosequencing.

20 ng of the genomic DNA converted with bisulfite was amplified by PCR. In the PCR amplification, a PCR reaction solution (20 ng of the genomic DNA modified with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region. After the methylation index of DNA in the urinary cells of the normal persons and the bladder cancer patients has been measured, a methylation index cut-off value for diagnosis of bladder cancer patients was determined through receiver operating characteristic (ROC) curve analysis.

FIGS. 3A-3D show measurement results for the methylation of the 10 biomarker genes in urinary cells. As can be seen, the methylation degree of the genes was higher in the sample of the bladder cancer patients than in the sample of the normal persons. Meanwhile, the methylation index in the cystitis patients and the hematuria patients was similar to that in the normal control group or was rarely higher than that in the normal control group. FIGS. 4A-4E show ROC analysis results for determining cut-off values for diagnosis of bladder cancer. Also, methylation index cut-off values for the 10 biomarkers, calculated based on the ROC curve analysis results, are shown in Table 5 below.

TABLE 5

Cut-off values for bladder cancer diagnosis of 10 biomarkers

| Gene | cut-off (%)[a] |
|---|---|
| CDX2 | 5.82< |
| CYP1B1 | 8.38< |
| VSX1 | 29.3< |
| HOXA11 | 8.81< |
| T | 11.3< |
| TBX5 | 6.93< |
| PENK | 11.57< |
| PAQR9 | 5.0< |
| LHX2 | 13.7< |
| SIM2 | 8.2< |

In the analysis of the methylation of the 10 biomarkers, the methylation index of each biomarker in the clinical sample was calculated. The case in which the calculated methylation index for diagnosis of bladder cancer was higher than the cut-off value obtained through receiver operating characteristic (ROC) analysis was judged to be methylation-positive, and the case in which the calculated methylation index was lower than the cut-off value was judged to be methylation-negative.

Figure 5:
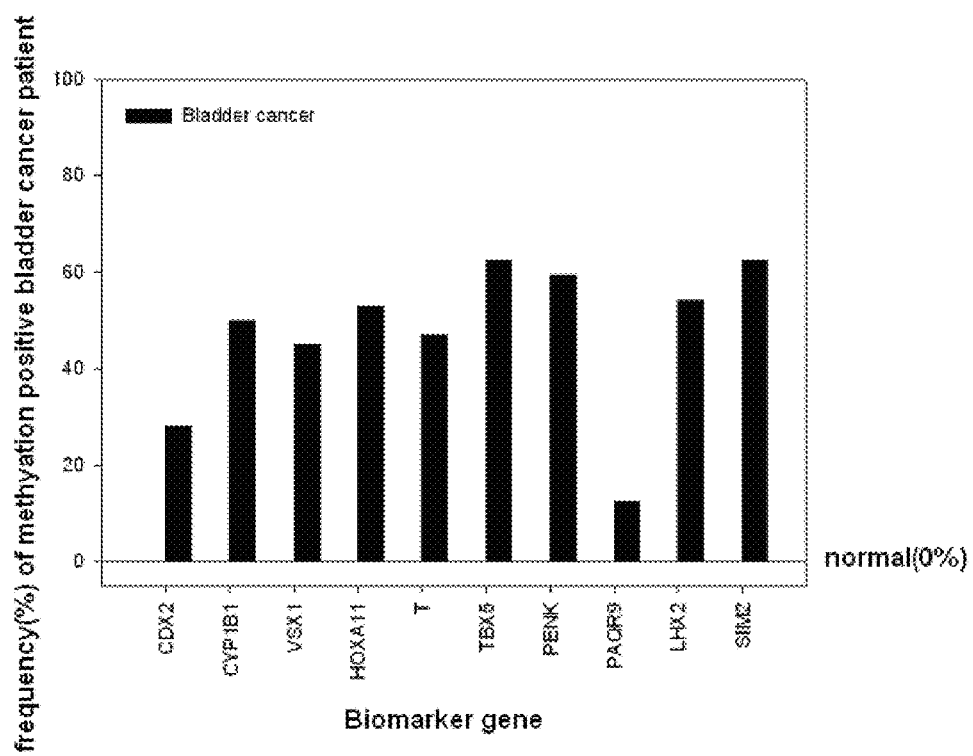
FIG. 5 shows the frequency of methylation in the urinary cells of normal persons and bladder cancer patients.

As shown in Table 6 below and FIG. 5, when judged on the basis of the cut-off value obtained by ROC curve analysis, the urinary cells of the normal persons were methylation-negative for all the 10 biomarkers, but 12.5-62.5% of the samples of the bladder cancer patients were methylation-positive for the 10 biomarkers. Also, statistical analysis was performed and, as a result, it could be seen that 9 of the samples of the bladder cancer samples were methylation-positive for 9 of the 10 biomarkers at a significant level (p<0.01) compared to the normal person group. This suggests that 9 of the 10 methylation markers are statistically significantly methylated specifically in bladder cancer and are highly useful for diagnosing bladder cancer.

TABLE 6

Frequency of methylation-positive samples for 10 biomarkers

| | No. of methylation-positive samples/ No. of total samples (%)[a] | | |
|---|---|---|---|
| Gene | Normal | bladder cancer patient | P value[b] |
| CDX2 | 0/31 (0) | 9/32 (28.1) | 0.002 |
| CYP1B1 | 0/31 (0) | 16/32 (50.0) | <0.001 |
| VSX1 | 0/31 (0) | 14/32 (45.2) | <0.001 |
| HOXA11 | 0/31 (0) | 17/32 (53.1) | <0.001 |
| T | 0/31 (0) | 15/32 (46.9) | <0.001 |

TABLE 6-continued

Frequency of methylation-positive samples for 10 biomarkers

| | No. of methylation-positive samples/ No. of total samples (%)[a] | | |
|---|---|---|---|
| Gene | Normal | bladder cancer patient | P value[b] |
| TBX5 | 0/31 (0) | 20/32 (62.5) | <0.001 |
| PENK | 0/31 (0) | 19/32 (59.4) | <0.001 |
| PAQR9 | 0/31 (0) | 4/32 (12.5) | 0.113 |
| LHX2 | 0/17 (0) | 13/24 (54.2) | <0.001 |
| SIM2 | 0/17 (0) | 15/24 (62.5)0 | <0.001 |

Figure 6A:
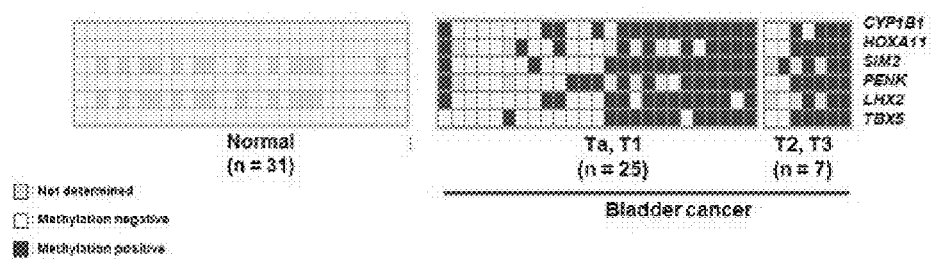
FIGS. 6A-6D show the methylation profile of an optimal panel of 6 biomarker genes for bladder cancer diagnosis (FIG. 6A), selected from among 10 biomarkers using logistic regression analysis, and shows the sensitivity and specificity of the gene panel for diagnosis of bladder cancer (FIG. 6B-D).
Figure 6B:
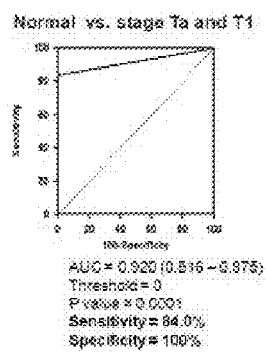
Figure 6C:
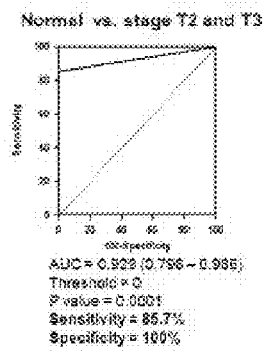
Figure 6D:
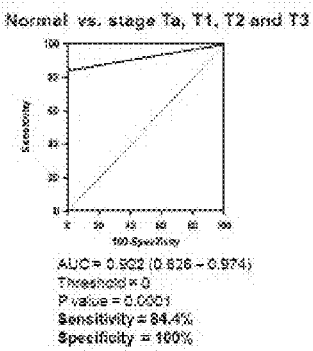

[a]frequency of methylation-positive samples; and
[b]p values obtained through the Chi-Square test Example 4: Evaluation of the Ability of 6 Biomarker Panel Genes to Diagnose Bladder Cancer Using the 10 methylation biomarkers, logistic regression analysis was performed. As a result, an optimal panel of 6 genes for diagnosing bladder cancer was established. FIG. 6A shows the methylation status of the 6 biomarkers (CYP1B1, HOXA11, SIM2, PENK, LHX2 and TBX5). Whether samples were methylation-positive or methylation-negative for the 6 genes was judged according to the method described in Example 3. As a result, it could be seen that all the normal samples were methylation-negative for the 6 genes, and only the bladder cancer samples were methylation-positive for the 6 genes. Particularly, early bladder cancer samples were also methylation-positive for the 6 genes at a high frequency, suggesting that the 6 genes are highly useful for early diagnosis of bladder cancer. When the methylation of at least one gene of the gene panel consisting of the six genes was diagnosed as bladder cancer, the sensitivity and specificity of the gene panel for early bladder cancer were as extremely high as 84.0% and 100%, respectively (FIG. 6D). Also, the sensitivity and specificity of the gene panel for advanced bladder cancer were measured to be 85.7% and 100%, respectively (FIG. 6C). In addition, the sensitivity and specificity of the gene panel for all early and advanced bladder cancers were measured to be 84.4% and 100%, respectively (FIG. 6B). This suggests that the methylation of the 6 genes is highly useful for early diagnosis of bladder cancer.

Example 5: Measurement of Methylation of Biomarker Genes Using Methylated DNA-Specific Binding Protein In order to measure the methylation of biomarkers which are methylated specifically in bladder cancer, 100 ng of the genomic DNA of each of the bladder cancer cell lines RT24 and HT1197 was sonicated (Vibra Cell, SONICS), thus obtaining about 200-400-bp genomic DNA fragments.

To obtain only methylated DNA from the genomic DNA, MBD known to bind to methylated DNA was used. Specifically, 2 μg of 6× His-tagged MBD was pre-incubated with 500 ng of the genomic DNA of E. coli JM110 (No. 2638, Biological Resource Center, Korea Research Institute of Bioscience & Biotechnology), and then bound to Ni-NTA magnetic beads (Qiagen, USA). 100 ng of the sonicated genomic DNA was allowed to react with the beads in the presence of binding buffer solution (10 mM Tris-HCl (pH 7.5), 50 mM NaCl, 1 mM EDTA, 1 mM DTT, 3 mM MgCl$_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the DNA methylated DNA bound to the MBD was amplified by PCR using primers of SEQ ID NOS: 41 and 42 corresponding to the promoter region (from −6842 to −6775 bp) of the SIM2 gene.

```
SEQ ID NO: 41:
5'-TTC TTA TTC TCA CCA GAC ATC TCA ACA CCC-3'

SEQ ID NO: 42:
5'-ATC TCC CAT CCT CCC TCC CAC TCT C-3'
```

The PCR reaction was performed in the following condition: predenaturation at 94° C. for 5 min, and then 40 cycles of denaturation at 94° C. for 30 sec, annealing at 62° C. for 30 sec and extension at 72° C. for 30 sec, followed by final extension at 72° C. for 5 min. The amplification of the PCR product was confirmed by electrophoresis on 2% agarose gel.

Figure 7:
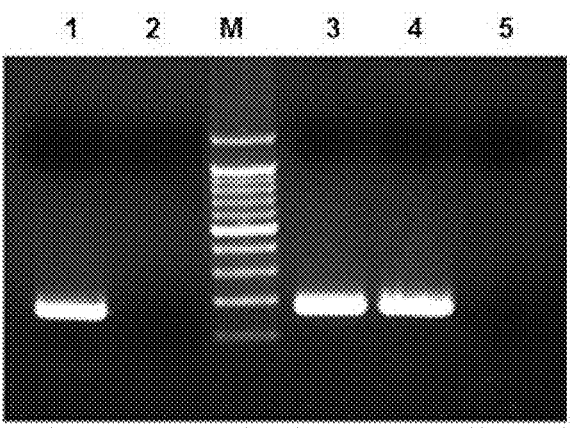
FIG. 7 shows the results of PCR performed using the methylated DNA-specific binding protein MBD in order to measure the methylation of the biomarker SIM2 gene for bladder cancer cell in bladder cancer cell lines.

As a result, it was seen that, for the SIM2 gene, a 168-bp amplified product was detected only in the genomic DNA of the RT24 cell line, suggesting that the gene was methylated, whereas no amplified product was detected in the HT1197 cell line, suggesting that the gene was not methylated in the HT1197 cell line (FIG. 7). Such results were consistent with the methylation measurement results obtained by the pyrosequencing method. Also, such results indicate that the use of MBD enables detection of methylated DNA.

Example 6: Evaluation of the Ability of PENK Gene to Diagnose Bladder Cancer by Using qMSP In order to analyze the ability of PENK gene to diagnose bladder cancer, 584 sets of primers and probes, which could amplify whole CpG island of PENK gene and detect methylation specific sites, were designed (Table 7) and methylation specific real time PCR (qMSP) was performed. First of all, genome DNA of urine cells were isolated from urines, which were obtained from normal control 20 people and 20 bladder cancer patients respectively. Treating bisulfite to the isolated genome DNA by using EZ DNA methylation-Gold kit (Zymo Research, USA) was followed by eluting with 10 μl distilled water, and then was subjected to methylation specific real time PCR (qMSP). qMSP was performed by using bisulfite treated genome DNA as a template and methylation specific primers and probes designed according to Table 1. qMSP was performed by using Rotor-Gene Q PCR equipment (Qiagen). Total 20 μl PCR reaction solution (template DNA, 2 μl; 5× AptaTaq DNA Master (Roche Diagnostics), 4 μl; PCR primers, 2 μl (2 pmole/μl), TaqMan probe, 2 μl (2 pmole/μl); D.W. 10 μl) was prepared. Total 40 times of PCR in which the condition is treated at 95° C. for 5 minutes, at 95° C. for 15 seconds and at annealing temperature (58° C.~61° C.) for 1 minute were performed. The amplification of the PCR product was confirmed by measuring the Ct (cycling threshold) value. Methylated and non-methylated control DNAs were tested with sample DNA by using EpiTect PCR control DNA set (Qiagen, cat. no. 59695). COL2A1 gene (Kristensen et al., 2008) was used as an internal control. The methylation level of each sample was measured by Ct (cycling threshold) value. Sensitivity and specificity for each set of primers and probes were calculated with ROC curve analysis (MedCalc Program, Belgium) (Table 8).

TABLE 7

Sequences of primer and probes for PENK gene qMSP

| Set | Primer | Sequences (5'→3') | Size of amplification product (bp) | SEQ ID NOs: |
|---|---|---|---|---|
| 1 | F1 | TTGTAATTATTAAT | 149 | 43 |
|   | R1 | CTCGCGAATCCCCG |   | 44 |
|   | Probe1 | GTTAATAAATGACGATATTTCGGAC |   | 45 |
| 2 | F2 | TGTAATTATTAATT | 148 | 46 |
|   | R1 | CTCGCGAATCCCCG |   | 47 |
|   | Probe1 | GTTAATAAATGACGATATTTCGGAC |   | 45 |
| 3 | F3 | GTAATTATTAATTG | 147 | 48 |
|   | R1 | CTCGCGAATCCCCG |   | 49 |
|   | Probe1 | GTTAATAAATGACGATATTTCGGAC |   | 45 |
| 4 | F4 | TAATTATTAATTGA | 146 | 50 |
|   | R1 | CTCGCGAATCCCCG |   | 51 |
|   | Probe1 | GTTAATAAATGACGATATTTCGGAC |   | 45 |
| 5 | F5 | AATTATTAATTGAG | 145 | 52 |
|   | R1 | CTCGCGAATCCCCG |   | 53 |
|   | Probe1 | GTTAATAAATGACGATATTTCGGAC |   | 45 |
| 6 | F6 | ATTATTAATTGAGC | 144 | 54 |
|   | R1 | CTCGCGAATCCCCG |   | 55 |
|   | Probe1 | GTTAATAAATGACGATATTTCGGAC |   | 45 |
| 7 | F7 | TTATTAATTGAGCG | 143 | 56 |
|   | R1 | CTCGCGAATCCCCG |   | 57 |
|   | Probe1 | GTTAATAAATGACGATATTTCGGAC |   | 45 |
| 8 | F8 | TATTAATTGAGCGT | 142 | 58 |
|   | R1 | CTCGCGAATCCCCG |   | 59 |
|   | Probe1 | GTTAATAAATGACGATATTTCGGAC |   | 45 |
| 9 | F9 | ATTAATTGAGCGTT | 141 | 60 |
|   | R1 | CTCGCGAATCCCCG |   | 61 |
|   | Probe1 | GTTAATAAATGACGATATTTCGGAC |   | 45 |
| 10 | F10 | TTAATTGAGCGTTT | 140 | 62 |
|   | R1 | CTCGCGAATCCCCG |   | 63 |
|   | Probe1 | GTTAATAAATGACGATATTTCGGAC |   | 45 |
| 11 | F11 | TAATTGAGCGTTTA | 139 | 64 |
|   | R1 | CTCGCGAATCCCCG |   | 65 |
|   | Probe1 | GTTAATAAATGACGATATTTCGGAC |   | 45 |
| 12 | F12 | AATTGAGCGTTTAA | 138 | 66 |
|   | R1 | CTCGCGAATCCCCG |   | 67 |
|   | Probe1 | GTTAATAAATGACGATATTTCGGAC |   | 45 |
| 13 | F13 | ATTGAGCGTTTAAA | 137 | 68 |
|   | R1 | CTCGCGAATCCCCG |   | 69 |
|   | Probe1 | GTTAATAAATGACGATATTTCGGAC |   | 45 |
| 14 | F14 | TTGAGCGTTTAAAT | 136 | 70 |
|   | R1 | CTCGCGAATCCCCG |   | 71 |
|   | Probe1 | GTTAATAAATGACGATATTTCGGAC |   | 45 |
| 15 | F15 | TGAGCGTTTAAATT | 135 | 72 |
|   | R1 | CTCGCGAATCCCCG |   | 73 |
|   | Probe1 | GTTAATAAATGACGATATTTCGGAC |   | 45 |
| 16 | F16 | GAGCGTTTAAATTG | 134 | 74 |
|   | R1 | CTCGCGAATCCCCG |   | 75 |
|   | Probe1 | GTTAATAAATGACGATATTTCGGAC |   | 45 |
| 17 | F17 | AGCGTTTAAATTGC | 133 | 76 |
|   | R1 | CTCGCGAATCCCCG |   | 77 |
|   | Probe1 | GTTAATAAATGACGATATTTCGGAC |   | 45 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 18 | F18 | GCGTTTAAATTGCG | 132 | 78 |
|  | R1 | CTCGCGAATCCCCG |  | 79 |
|  | Probe1 | GTTAATAAATGACGATATTTCGGAC |  | 45 |
| 19 | F19 | CGTTTAAATTGCGT | 131 | 80 |
|  | R1 | CTCGCGAATCCCCG |  | 81 |
|  | Probe1 | GTTAATAAATGACGATATTTCGGAC |  | 45 |
| 20 | F20 | GTTTAAATTGCGTA | 130 | 82 |
|  | R1 | CTCGCGAATCCCCG |  | 83 |
|  | Probe1 | GTTAATAAATGACGATATTTCGGAC |  | 45 |
| 21 | F21 | TTTAAATTGCGTAT | 129 | 84 |
|  | R1 | CTCGCGAATCCCCG |  | 85 |
|  | Probe1 | GTTAATAAATGACGATATTTCGGAC |  | 45 |
| 22 | F22 | TTAAATTGCGTATT | 128 | 86 |
|  | R1 | CTCGCGAATCCCCG |  | 87 |
|  | Probe1 | GTTAATAAATGACGATATTTCGGAC |  | 45 |
| 23 | F23 | TAAATTGCGTATTT | 127 | 88 |
|  | R1 | CTCGCGAATCCCCG |  | 89 |
|  | Probe1 | GTTAATAAATGACGATATTTCGGAC |  | 45 |
| 24 | F24 | AAATTGCGTATTTT | 126 | 90 |
|  | R1 | CTCGCGAATCCCCG |  | 91 |
|  | Probe1 | GTTAATAAATGACGATATTTCGGAC |  | 45 |
| 25 | F25 | AATTGCGTATTTTG | 125 | 92 |
|  | R1 | CTCGCGAATCCCCG |  | 93 |
|  | Probe1 | GTTAATAAATGACGATATTTCGGAC |  | 45 |
| 26 | F26 | ATTGCGTATTTTGA | 124 | 94 |
|  | R1 | CTCGCGAATCCCCG |  | 95 |
|  | Probe1 | GTTAATAAATGACGATATTTCGGAC |  | 45 |
| 27 | F27 | TTGCGTATTTTGAC | 123 | 96 |
|  | R1 | CTCGCGAATCCCCG |  | 97 |
|  | Probe1 | GTTAATAAATGACGATATTTCGGAC |  | 45 |
| 28 | F28 | TGCGTATTTTGACG | 122 | 98 |
|  | R1 | CTCGCGAATCCCCG |  | 99 |
|  | Probe1 | GTTAATAAATGACGATATTTCGGAC |  | 45 |
| 29 | F29 | GCGTATTTTGACGT | 121 | 100 |
|  | R1 | CTCGCGAATCCCCG |  | 101 |
|  | Probe1 | GTTAATAAATGACGATATTTCGGAC |  | 45 |
| 30 | F30 | CGTATTTTGACGTT | 120 | 102 |
|  | R1 | CTCGCGAATCCCCG |  | 103 |
|  | Probe1 | GTTAATAAATGACGATATTTCGGAC |  | 45 |
| 31 | F31 | GTATTTTGACGTTG | 119 | 104 |
|  | R1 | CTCGCGAATCCCCG |  | 105 |
|  | Probe1 | GTTAATAAATGACGATATTTCGGAC |  | 45 |
| 32 | F32 | TATTTTGACGTTGT | 118 | 106 |
|  | R1 | CTCGCGAATCCCCG |  | 107 |
|  | Probe1 | GTTAATAAATGACGATATTTCGGAC |  | 45 |
| 33 | F33 | ATTTTGACGTTGTT | 117 | 108 |
|  | R1 | CTCGCGAATCCCCG |  | 109 |
|  | Probe1 | GTTAATAAATGACGATATTTCGGAC |  | 45 |
| 34 | F34 | TTTTGACGTTGTTA | 116 | 110 |
|  | R1 | CTCGCGAATCCCCG |  | 111 |
|  | Probe1 | GTTAATAAATGACGATATTTCGGAC |  | 45 |
| 35 | F35 | TTTGACGTTGTTAG | 115 | 112 |
|  | R1 | CTCGCGAATCCCCG |  | 113 |
|  | Probe1 | GTTAATAAATGACGATATTTCGGAC |  | 45 |
| 36 | F36 | TTGACGTTGTTAGA | 114 | 114 |
|  | R1 | CTCGCGAATCCCCG |  | 115 |
|  | Probe1 | GTTAATAAATGACGATATTTCGGAC |  | 45 |
| 37 | F37 | TGACGTTGTTAGAT | 113 | 116 |
|  | R1 | CTCGCGAATCCCCG |  | 117 |
|  | Probe1 | GTTAATAAATGACGATATTTCGGAC |  | 45 |
| 38 | F38 | GACGTTGTTAGATG | 112 | 118 |
|  | R1 | CTCGCGAATCCCCG |  | 119 |
|  | Probe1 | GTTAATAAATGACGATATTTCGGAC |  | 45 |
| 39 | F39 | ACGTTGTTAGATGT | 111 | 120 |
|  | R1 | CTCGCGAATCCCCG |  | 121 |
|  | Probe1 | GTTAATAAATGACGATATTTCGGAC |  | 45 |
| 40 | F40 | CGTTGTTAGATGTT | 110 | 122 |
|  | R1 | CTCGCGAATCCCCG |  | 123 |
|  | Probe1 | GTTAATAAATGACGATATTTCGGAC |  | 45 |
| 41 | F41 | GTTGTTAGATGTTG | 109 | 124 |
|  | R1 | CTCGCGAATCCCCG |  | 125 |
|  | Probe1 | GTTAATAAATGACGATATTTCGGAC |  | 45 |
| 42 | F42 | TTGTTAGATGTTGT | 108 | 126 |
|  | R1 | CTCGCGAATCCCCG |  | 127 |
|  | Probe1 | GTTAATAAATGACGATATTTCGGAC |  | 45 |
| 43 | F43 | TGTTAGATGTTGTA | 107 | 128 |
|  | R1 | CTCGCGAATCCCCG |  | 129 |
|  | Probe1 | GTTAATAAATGACGATATTTCGGAC |  | 45 |
| 44 | F44 | GTTAGATGTTGTAG | 106 | 130 |
|  | R1 | CTCGCGAATCCCCG |  | 131 |
|  | Probe1 | GTTAATAAATGACGATATTTCGGAC |  | 45 |
| 45 | F45 | TTAGATGTTGTAGT | 105 | 132 |
|  | R1 | CTCGCGAATCCCCG |  | 133 |
|  | Probe1 | GTTAATAAATGACGATATTTCGGAC |  | 45 |
| 46 | F46 | TAGATGTTGTAGTA | 104 | 134 |
|  | R1 | CTCGCGAATCCCCG |  | 135 |
|  | Probe1 | GTTAATAAATGACGATATTTCGGAC |  | 45 |
| 47 | F47 | AGATGTTGTAGTAA | 103 | 136 |
|  | R1 | CTCGCGAATCCCCG |  | 137 |
|  | Probe1 | GTTAATAAATGACGATATTTCGGAC |  | 45 |
| 48 | F48 | GATGTTGTAGTAAG | 102 | 138 |
|  | R1 | CTCGCGAATCCCCG |  | 139 |
|  | Probe1 | GTTAATAAATGACGATATTTCGGAC |  | 45 |
| 49 | F49 | ATGTTGTAGTAAGG | 101 | 140 |
|  | R1 | CTCGCGAATCCCCG |  | 141 |
|  | Probe1 | GTTAATAAATGACGATATTTCGGAC |  | 45 |
| 50 | F50 | TGTTGTAGTAAGGA | 100 | 142 |
|  | R1 | CTCGCGAATCCCCG |  | 143 |
|  | Probe1 | GTTAATAAATGACGATATTTCGGAC |  | 45 |
| 51 | F51 | GTTGTAGTAAGGAA | 99 | 144 |
|  | R1 | CTCGCGAATCCCCG |  | 145 |
|  | Probe1 | GTTAATAAATGACGATATTTCGGAC |  | 45 |
| 52 | F52 | TTGTAGTAAGGAAT | 98 | 146 |
|  | R1 | CTCGCGAATCCCCG |  | 147 |
|  | Probe1 | GTTAATAAATGACGATATTTCGGAC |  | 45 |
| 53 | F53 | TGTAGTAAGGAATT | 97 | 148 |
|  | R1 | CTCGCGAATCCCCG |  | 149 |
|  | Probe1 | GTTAATAAATGACGATATTTCGGAC |  | 45 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 54 | F54 | GTAGTAAGGAATTC | 96 | 150 |
|  | R1 | CTCGCGAATCCCCG |  | 151 |
|  | Probe1 | GTTAATAAATGACGATATTTCGGAC |  | 45 |
| 55 | F55 | TAGTAAGGAATTCG | 95 | 152 |
|  | R1 | CTCGCGAATCCCCG |  | 153 |
|  | Probe1 | GTTAATAAATGACGATATTTCGGAC |  | 45 |
| 56 | F56 | AGTAAGGAATTCGG | 94 | 154 |
|  | R1 | CTCGCGAATCCCCG |  | 155 |
|  | Probe1 | GTTAATAAATGACGATATTTCGGAC |  | 45 |
| 57 | F57 | GTAAGGAATTCGGA | 93 | 156 |
|  | R1 | CTCGCGAATCCCCG |  | 157 |
|  | Probe1 | GTTAATAAATGACGATATTTCGGAC |  | 45 |
| 58 | F58 | TAAGGAATTCGGAG | 92 | 158 |
|  | R1 | CTCGCGAATCCCCG |  | 159 |
|  | Probe1 | GTTAATAAATGACGATATTTCGGAC |  | 45 |
| 59 | F59 | AAGGAATTCGGAGT | 91 | 160 |
|  | R1 | CTCGCGAATCCCCG |  | 161 |
|  | Probe1 | GTTAATAAATGACGATATTTCGGAC |  | 45 |
| 60 | F60 | AGGAATTCGGAGTT | 90 | 162 |
|  | R1 | CTCGCGAATCCCCG |  | 163 |
|  | Probe1 | GTTAATAAATGACGATATTTCGGAC |  | 45 |
| 61 | F61 | GGAATTCGGAGTTA | 89 | 164 |
|  | R1 | CTCGCGAATCCCCG |  | 165 |
|  | Probe1 | GTTAATAAATGACGATATTTCGGAC |  | 45 |
| 62 | F62 | GAATTCGGAGTTAA | 88 | 166 |
|  | R1 | CTCGCGAATCCCCG |  | 167 |
|  | Probe1 | GTTAATAAATGACGATATTTCGGAC |  | 45 |
| 63 | F63 | AATTCGGAGTTAAG | 87 | 168 |
|  | R1 | CTCGCGAATCCCCG |  | 169 |
|  | Probe1 | GTTAATAAATGACGATATTTCGGAC |  | 45 |
| 64 | F64 | ATTCGGAGTTAAGT | 86 | 170 |
|  | R1 | CTCGCGAATCCCCG |  | 171 |
|  | Probe1 | GTTAATAAATGACGATATTTCGGAC |  | 45 |
| 65 | F65 | TTCGGAGTTAAGTG | 85 | 172 |
|  | R1 | CTCGCGAATCCCCG |  | 173 |
|  | Probe1 | GTTAATAAATGACGATATTTCGGAC |  | 45 |
| 66 | F66 | TCGGAGTTAAGTGT | 84 | 174 |
|  | R1 | CTCGCGAATCCCCG |  | 175 |
|  | Probe1 | GTTAATAAATGACGATATTTCGGAC |  | 45 |
| 67 | F67 | CGGAGTTAAGTGTG | 83 | 176 |
|  | R1 | CTCGCGAATCCCCG |  | 177 |
|  | Probe1 | GTTAATAAATGACGATATTTCGGAC |  | 45 |
| 68 | F68 | GGAGTTAAGTGTGG | 82 | 178 |
|  | R1 | CTCGCGAATCCCCG |  | 179 |
|  | Probe1 | GTTAATAAATGACGATATTTCGGAC |  | 45 |
| 69 | F69 | GAGTTAAGTGTGGG | 81 | 180 |
|  | R1 | CTCGCGAATCCCCG |  | 181 |
|  | Probe1 | GTTAATAAATGACGATATTTCGGAC |  | 45 |
| 70 | F70 | AGTTAAGTGTGGGG | 80 | 182 |
|  | R1 | CTCGCGAATCCCCG |  | 183 |
|  | Probe1 | GTTAATAAATGACGATATTTCGGAC |  | 45 |
| 71 | F71 | GTTAAGTGTGGGGG | 135 | 184 |
|  | R2 | CTAAAAACCCAACG |  | 185 |
|  | Probe2 | ATTCGCGAGGGGGTTTAGGGAGGAG |  | 186 |
| 72 | F72 | TTAAGTGTGGGGGA | 134 | 187 |
|  | R2 | CTAAAAACCCAACG |  | 188 |
|  | Probe2 | ATTCGCGAGGGGGTTTAGGGAGGAG |  | 186 |
| 73 | F73 | TAAGTGTGGGGGAT | 133 | 189 |
|  | R2 | CTAAAAACCCAACG |  | 190 |
|  | Probe2 | ATTCGCGAGGGGGTTTAGGGAGGAG |  | 186 |
| 74 | F74 | AAGTGTGGGGGATA | 132 | 191 |
|  | R2 | CTAAAAACCCAACG |  | 192 |
|  | Probe2 | ATTCGCGAGGGGGTTTAGGGAGGAG |  | 186 |
| 75 | F75 | AGTGTGGGGGATAG | 131 | 193 |
|  | R2 | CTAAAAACCCAACG |  | 194 |
|  | Probe2 | ATTCGCGAGGGGGTTTAGGGAGGAG |  | 186 |
| 76 | F76 | GTGTGGGGGATAGG | 130 | 195 |
|  | R2 | CTAAAAACCCAACG |  | 196 |
|  | Probe2 | ATTCGCGAGGGGGTTTAGGGAGGAG |  | 186 |
| 77 | F77 | TGTGGGGGATAGGT | 129 | 197 |
|  | R2 | CTAAAAACCCAACG |  | 198 |
|  | Probe2 | ATTCGCGAGGGGGTTTAGGGAGGAG |  | 186 |
| 78 | F78 | GTGGGGGATAGGTT | 128 | 199 |
|  | R2 | CTAAAAACCCAACG |  | 200 |
|  | Probe2 | ATTCGCGAGGGGGTTTAGGGAGGAG |  | 186 |
| 79 | F79 | TGGGGGATAGGTTG | 127 | 201 |
|  | R2 | CTAAAAACCCAACG |  | 202 |
|  | Probe2 | ATTCGCGAGGGGGTTTAGGGAGGAG |  | 186 |
| 80 | F80 | GGGGGATAGGTTGG | 126 | 203 |
|  | R2 | CTAAAAACCCAACG |  | 204 |
|  | Probe2 | ATTCGCGAGGGGGTTTAGGGAGGAG |  | 186 |
| 81 | F81 | GGGGATAGGTTGGT | 125 | 205 |
|  | R2 | CTAAAAACCCAACG |  | 206 |
|  | Probe2 | ATTCGCGAGGGGGTTTAGGGAGGAG |  | 186 |
| 82 | F82 | GGGATAGGTTGGTT | 124 | 207 |
|  | R2 | CTAAAAACCCAACG |  | 208 |
|  | Probe2 | ATTCGCGAGGGGGTTTAGGGAGGAG |  | 186 |
| 83 | F83 | GGATAGGTTGGTTA | 123 | 209 |
|  | R2 | CTAAAAACCCAACG |  | 210 |
|  | Probe2 | ATTCGCGAGGGGGTTTAGGGAGGAG |  | 186 |
| 84 | F84 | GATAGGTTGGTTAA | 122 | 211 |
|  | R2 | CTAAAAACCCAACG |  | 212 |
|  | Probe2 | ATTCGCGAGGGGGTTTAGGGAGGAG |  | 186 |
| 85 | F85 | ATAGGTTGGTTAAT | 121 | 213 |
|  | R2 | CTAAAAACCCAACG |  | 214 |
|  | Probe2 | ATTCGCGAGGGGGTTTAGGGAGGAG |  | 186 |
| 86 | F86 | TAGGTTGGTTAATA | 120 | 215 |
|  | R2 | CTAAAAACCCAACG |  | 216 |
|  | Probe2 | ATTCGCGAGGGGGTTTAGGGAGGAG |  | 186 |
| 87 | F87 | AGGTTGGTTAATAA | 119 | 217 |
|  | R2 | CTAAAAACCCAACG |  | 218 |
|  | Probe2 | ATTCGCGAGGGGGTTTAGGGAGGAG |  | 186 |
| 88 | F88 | GGTTGGTTAATAAA | 118 | 219 |
|  | R2 | CTAAAAACCCAACG |  | 220 |
|  | Probe2 | ATTCGCGAGGGGGTTTAGGGAGGAG |  | 186 |
| 89 | F89 | GTTGGTTAATAAAT | 117 | 221 |
|  | R2 | CTAAAAACCCAACG |  | 222 |
|  | Probe2 | ATTCGCGAGGGGGTTTAGGGAGGAG |  | 186 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 90 | F90 | TTGGTTAATAAATG | 116 | 223 |
|  | R2 | CTAAAAACCCAACG |  | 224 |
|  | Probe2 | ATTCGCGAGGGGGTTTAGGGAGGAG |  | 186 |
| 91 | F91 | TGGTTAATAAATGA | 115 | 225 |
|  | R2 | CTAAAAACCCAACG |  | 226 |
|  | Probe2 | ATTCGCGAGGGGGTTTAGGGAGGAG |  | 186 |
| 92 | F92 | GGTTAATAAATGAC | 114 | 227 |
|  | R2 | CTAAAAACCCAACG |  | 228 |
|  | Probe2 | ATTCGCGAGGGGGTTTAGGGAGGAG |  | 186 |
| 93 | F93 | GTTAATAAATGACG | 113 | 229 |
|  | R2 | CTAAAAACCCAACG |  | 230 |
|  | Probe2 | ATTCGCGAGGGGGTTTAGGGAGGAG |  | 186 |
| 94 | F94 | TTAATAAATGACGA | 112 | 231 |
|  | R2 | CTAAAAACCCAACG |  | 232 |
|  | Probe2 | ATTCGCGAGGGGGTTTAGGGAGGAG |  | 186 |
| 95 | F95 | TAATAAATGACGAT | 111 | 233 |
|  | R2 | CTAAAAACCCAACG |  | 234 |
|  | Probe2 | ATTCGCGAGGGGGTTTAGGGAGGAG |  | 186 |
| 96 | F96 | AATAAATGACGATA | 110 | 235 |
|  | R2 | CTAAAAACCCAACG |  | 236 |
|  | Probe2 | ATTCGCGAGGGGGTTTAGGGAGGAG |  | 186 |
| 97 | F97 | ATAAATGACGATAT | 109 | 237 |
|  | R2 | CTAAAAACCCAACG |  | 238 |
|  | Probe2 | ATTCGCGAGGGGGTTTAGGGAGGAG |  | 186 |
| 98 | F98 | TAAATGACGATATT | 108 | 239 |
|  | R2 | CTAAAAACCCAACG |  | 240 |
|  | Probe2 | ATTCGCGAGGGGGTTTAGGGAGGAG |  | 186 |
| 99 | F99 | AAATGACGATATTT | 107 | 241 |
|  | R2 | CTAAAAACCCAACG |  | 242 |
|  | Probe2 | ATTCGCGAGGGGGTTTAGGGAGGAG |  | 186 |
| 100 | F100 | AATGACGATATTTC | 106 | 243 |
|  | R2 | CTAAAAACCCAACG |  | 244 |
|  | Probe2 | ATTCGCGAGGGGGTTTAGGGAGGAG |  | 186 |
| 101 | F101 | ATGACGATATTTCG | 105 | 245 |
|  | R2 | CTAAAAACCCAACG |  | 246 |
|  | Probe2 | ATTCGCGAGGGGGTTTAGGGAGGAG |  | 186 |
| 102 | F102 | TGACGATATTTCGG | 104 | 247 |
|  | R2 | CTAAAAACCCAACG |  | 248 |
|  | Probe2 | ATTCGCGAGGGGGTTTAGGGAGGAG |  | 186 |
| 103 | F103 | GACGATATTTCGGA | 103 | 249 |
|  | R2 | CTAAAAACCCAACG |  | 250 |
|  | Probe2 | ATTCGCGAGGGGGTTTAGGGAGGAG |  | 186 |
| 104 | F104 | ACGATATTTCGGAC | 102 | 251 |
|  | R2 | CTAAAAACCCAACG |  | 252 |
|  | Probe2 | ATTCGCGAGGGGGTTTAGGGAGGAG |  | 186 |
| 105 | F105 | CGATATTTCGGACG | 101 | 253 |
|  | R2 | CTAAAAACCCAACG |  | 254 |
|  | Probe2 | ATTCGCGAGGGGGTTTAGGGAGGAG |  | 186 |
| 106 | F106 | GATATTTCGGACGG | 100 | 255 |
|  | R2 | CTAAAAACCCAACG |  | 256 |
|  | Probe2 | ATTCGCGAGGGGGTTTAGGGAGGAG |  | 186 |
| 107 | F107 | ATATTTCGGACGGT | 99 | 257 |
|  | R2 | CTAAAAACCCAACG |  | 258 |
|  | Probe2 | ATTCGCGAGGGGGTTTAGGGAGGAG |  | 186 |
| 108 | F108 | TATTTCGGACGGTT | 98 | 259 |
|  | R2 | CTAAAAACCCAACG |  | 260 |
|  | Probe2 | ATTCGCGAGGGGGTTTAGGGAGGAG |  | 186 |
| 109 | F109 | ATTTCGGACGGTTG | 97 | 261 |
|  | R2 | CTAAAAACCCAACG |  | 262 |
|  | Probe2 | ATTCGCGAGGGGGTTTAGGGAGGAG |  | 186 |
| 110 | F110 | TTTCGGACGGTTGT | 96 | 263 |
|  | R2 | CTAAAAACCCAACG |  | 264 |
|  | Probe2 | ATTCGCGAGGGGGTTTAGGGAGGAG |  | 186 |
| 111 | F111 | TTCGGACGGTTGTG | 95 | 265 |
|  | R2 | CTAAAAACCCAACG |  | 266 |
|  | Probe2 | ATTCGCGAGGGGGTTTAGGGAGGAG |  | 186 |
| 112 | F112 | TCGGACGGTTGTGT | 94 | 267 |
|  | R2 | CTAAAAACCCAACG |  | 268 |
|  | Probe2 | ATTCGCGAGGGGGTTTAGGGAGGAG |  | 186 |
| 113 | F113 | CGGACGGTTGTGTT | 93 | 269 |
|  | R2 | CTAAAAACCCAACG |  | 270 |
|  | Probe2 | ATTCGCGAGGGGGTTTAGGGAGGAG |  | 186 |
| 114 | F114 | GGACGGTTGTGTTT | 92 | 271 |
|  | R2 | CTAAAAACCCAACG |  | 272 |
|  | Probe2 | ATTCGCGAGGGGGTTTAGGGAGGAG |  | 186 |
| 115 | F115 | GACGGTTGTGTTTG | 91 | 273 |
|  | R2 | CTAAAAACCCAACG |  | 274 |
|  | Probe2 | ATTCGCGAGGGGGTTTAGGGAGGAG |  | 186 |
| 116 | F116 | ACGGTTGTGTTTGG | 90 | 275 |
|  | R2 | CTAAAAACCCAACG |  | 276 |
|  | Probe2 | ATTCGCGAGGGGGTTTAGGGAGGAG |  | 186 |
| 117 | F117 | CGGTTGTGTTTGGT | 89 | 277 |
|  | R2 | CTAAAAACCCAACG |  | 278 |
|  | Probe2 | ATTCGCGAGGGGGTTTAGGGAGGAG |  | 186 |
| 118 | F118 | GGTTGTGTTTGGTG | 88 | 279 |
|  | R2 | CTAAAAACCCAACG |  | 280 |
|  | Probe2 | ATTCGCGAGGGGGTTTAGGGAGGAG |  | 186 |
| 119 | F119 | GTTGTGTTTGGTGT | 87 | 281 |
|  | R2 | CTAAAAACCCAACG |  | 282 |
|  | Probe2 | ATTCGCGAGGGGGTTTAGGGAGGAG |  | 186 |
| 120 | F120 | TTGTGTTTGGTGTT | 86 | 283 |
|  | R2 | CTAAAAACCCAACG |  | 284 |
|  | Probe2 | ATTCGCGAGGGGGTTTAGGGAGGAG |  | 186 |
| 121 | F121 | TGTGTTTGGTGTTT | 85 | 285 |
|  | R2 | CTAAAAACCCAACG |  | 286 |
|  | Probe2 | ATTCGCGAGGGGGTTTAGGGAGGAG |  | 186 |
| 122 | F122 | GTGTTTGGTGTTTA | 84 | 287 |
|  | R2 | CTAAAAACCCAACG |  | 288 |
|  | Probe2 | ATTCGCGAGGGGGTTTAGGGAGGAG |  | 186 |
| 123 | F123 | TGTTTGGTGTTTAC | 83 | 289 |
|  | R2 | CTAAAAACCCAACG |  | 290 |
|  | Probe2 | ATTCGCGAGGGGGTTTAGGGAGGAG |  | 186 |
| 124 | F124 | GTTTGGTGTTTACG | 82 | 291 |
|  | R2 | CTAAAAACCCAACG |  | 292 |
|  | Probe2 | ATTCGCGAGGGGGTTTAGGGAGGAG |  | 186 |
| 125 | F125 | TTTGGTGTTTACGG | 81 | 293 |
|  | R2 | CTAAAAACCCAACG |  | 294 |
|  | Probe2 | ATTCGCGAGGGGGTTTAGGGAGGAG |  | 186 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 126 | F126 | TTGGTGTTTACGGG | 80 | 295 |
|  | R2 | CTAAAAACCCAACG |  | 296 |
|  | Probe2 | ATTCGCGAGGGGGTTTAGGGAGGAG |  | 186 |
| 127 | F127 | TGGTGTTTACGGGG | 134 | 297 |
|  | R3 | ACGAAATAAAAACG |  | 298 |
|  | Probe3 | GGGAAAGGGGTAGGTTTATCGGTTC |  | 299 |
| 128 | F128 | GGTGTTTACGGGGA | 133 | 300 |
|  | R3 | ACGAAATAAAAACG |  | 301 |
|  | Probe3 | GGGAAAGGGGTAGGTTTATCGGTTC |  | 299 |
| 129 | F129 | GTGTTTACGGGGAT | 132 | 302 |
|  | R3 | ACGAAATAAAAACG |  | 303 |
|  | Probe3 | GGGAAAGGGGTAGGTTTATCGGTTC |  | 299 |
| 130 | F130 | TGTTTACGGGGATT | 131 | 304 |
|  | R3 | ACGAAATAAAAACG |  | 305 |
|  | Probe3 | GGGAAAGGGGTAGGTTTATCGGTTC |  | 299 |
| 131 | F131 | GTTTACGGGGATTC | 130 | 306 |
|  | R3 | ACGAAATAAAAACG |  | 307 |
|  | Probe3 | GGGAAAGGGGTAGGTTTATCGGTTC |  | 299 |
| 132 | F132 | TTTACGGGGATTCG | 129 | 308 |
|  | R3 | ACGAAATAAAAACG |  | 309 |
|  | Probe3 | GGGAAAGGGGTAGGTTTATCGGTTC |  | 299 |
| 133 | F133 | TTACGGGGATTCGC | 128 | 310 |
|  | R3 | ACGAAATAAAAACG |  | 311 |
|  | Probe3 | GGGAAAGGGGTAGGTTTATCGGTTC |  | 299 |
| 134 | F134 | TACGGGGATTCGCG | 127 | 312 |
|  | R3 | ACGAAATAAAAACG |  | 313 |
|  | Probe3 | GGGAAAGGGGTAGGTTTATCGGTTC |  | 299 |
| 135 | F135 | ACGGGGATTCGCGA | 126 | 314 |
|  | R3 | ACGAAATAAAAACG |  | 315 |
|  | Probe3 | GGGAAAGGGGTAGGTTTATCGGTTC |  | 299 |
| 136 | F136 | CGGGGATTCGCGAG | 125 | 316 |
|  | R3 | ACGAAATAAAAACG |  | 317 |
| 137 | F137 | GGGGATTCGCGAGG | 124 | 318 |
|  | R3 | ACGAAATAAAAACG |  | 319 |
| 138 | F138 | GGGATTCGCGAGGG | 123 | 320 |
|  | R3 | ACGAAATAAAAACG |  | 321 |
| 139 | F139 | GGATTCGCGAGGGG | 122 | 322 |
|  | R3 | ACGAAATAAAAACG |  | 323 |
|  | Probe3 | GGGAAAGGGGTAGGTTTATCGGTTC |  |  |
| 140 | F140 | GATTCGCGAGGGGG | 121 | 324 |
|  | R3 | ACGAAATAAAAACG |  | 325 |
|  | Probe3 | GGGAAAGGGGTAGGTTTATCGGTTC |  |  |
| 141 | F141 | ATTCGCGAGGGGGT | 120 | 326 |
|  | R3 | ACGAAATAAAAACG |  | 327 |
|  | Probe3 | GGGAAAGGGGTAGGTTTATCGGTTC |  |  |
| 142 | F142 | TTCGCGAGGGGGTT | 119 | 328 |
|  | R3 | ACGAAATAAAAACG |  | 329 |
|  | Probe3 | GGGAAAGGGGTAGGTTTATCGGTTC |  |  |
| 143 | F143 | TCGCGAGGGGGTTT | 118 | 330 |
|  | R3 | ACGAAATAAAAACG |  | 331 |
|  | Probe3 | GGGAAAGGGGTAGGTTTATCGGTTC |  |  |
| 144 | F144 | CGCGAGGGGGTTTA | 117 | 332 |
|  | R3 | ACGAAATAAAAACG |  | 333 |
|  | Probe3 | GGGAAAGGGGTAGGTTTATCGGTTC |  | 299 |
| 145 | F145 | GCGAGGGGGTTTAG | 116 | 334 |
|  | R3 | ACGAAATAAAAACG |  | 335 |
|  | Probe3 | GGGAAAGGGGTAGGTTTATCGGTTC |  | 299 |
| 146 | F146 | CGAGGGGGTTTAGG | 115 | 336 |
|  | R3 | ACGAAATAAAAACG |  | 337 |
|  | Probe3 | GGGAAAGGGGTAGGTTTATCGGTTC |  | 299 |
| 147 | F147 | GAGGGGGTTTAGGG | 114 | 338 |
|  | R3 | ACGAAATAAAAACG |  | 339 |
|  | Probe3 | GGGAAAGGGGTAGGTTTATCGGTTC |  | 299 |
| 148 | F148 | GTTTGTTATTTGGT | 142 | 340 |
|  | R4 | ACGCAAACCCTACG |  | 341 |
|  | Probe4 | ATTTTTTTCGCGAAGGCGTCGGCGC |  | 342 |
| 149 | F149 | TTTGTTATTTGGTC | 141 | 343 |
|  | R4 | ACGCAAACCCTACG |  | 344 |
|  | Probe4 | ATTTTTTTCGCGAAGGCGTCGGCGC |  | 342 |
| 150 | F150 | TTGTTATTTGGTCG | 140 | 345 |
|  | R4 | ACGCAAACCCTACG |  | 346 |
|  | Probe4 | ATTTTTTTCGCGAAGGCGTCGGCGC |  | 342 |
| 151 | F151 | TGTTATTTGGTCGT | 139 | 347 |
|  | R4 | ACGCAAACCCTACG |  | 348 |
|  | Probe4 | ATTTTTTTCGCGAAGGCGTCGGCGC |  | 342 |
| 152 | F152 | GTTATTTGGTCGTG | 138 | 349 |
|  | R4 | ACGCAAACCCTACG |  | 350 |
|  | Probe4 | ATTTTTTTCGCGAAGGCGTCGGCGC |  | 342 |
| 153 | F153 | TTATTTGGTCGTGT | 137 | 351 |
|  | R4 | ACGCAAACCCTACG |  | 352 |
|  | Probe4 | ATTTTTTTCGCGAAGGCGTCGGCGC |  | 342 |
| 154 | F154 | TATTTGGTCGTGTG | 136 | 353 |
|  | R4 | ACGCAAACCCTACG |  | 354 |
|  | Probe4 | ATTTTTTTCGCGAAGGCGTCGGCGC |  | 342 |
| 155 | F155 | ATTTGGTCGTGTGG | 135 | 355 |
|  | R4 | ACGCAAACCCTACG |  | 356 |
|  | Probe4 | ATTTTTTTCGCGAAGGCGTCGGCGC |  | 342 |
| 156 | F156 | TTTGGTCGTGTGGG | 134 | 357 |
|  | R4 | ACGCAAACCCTACG |  | 358 |
|  | Probe4 | ATTTTTTTCGCGAAGGCGTCGGCGC |  | 342 |
| 157 | F157 | TTGGTCGTGTGGGG | 133 | 359 |
|  | R4 | ACGCAAACCCTACG |  | 360 |
|  | Probe4 | ATTTTTTTCGCGAAGGCGTCGGCGC |  | 342 |
| 158 | F158 | TGGTCGTGTGGGGA | 132 | 361 |
|  | R4 | ACGCAAACCCTACG |  | 362 |
|  | Probe4 | ATTTTTTTCGCGAAGGCGTCGGCGC |  | 342 |
| 159 | F159 | GGTCGTGTGGGGAG | 131 | 363 |
|  | R4 | ACGCAAACCCTACG |  | 364 |
|  | Probe4 | ATTTTTTTCGCGAAGGCGTCGGCGC |  | 342 |
| 160 | F160 | GTCGTGTGGGGAGT | 130 | 365 |
|  | R4 | ACGCAAACCCTACG |  | 366 |
|  | Probe4 | ATTTTTTTCGCGAAGGCGTCGGCGC |  | 342 |
| 161 | F161 | TCGTGTGGGGAGTT | 129 | 367 |
|  | R4 | ACGCAAACCCTACG |  | 368 |
|  | Probe4 | ATTTTTTTCGCGAAGGCGTCGGCGC |  | 342 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 162 | F162 | CGTGTGGGGAGTTA | 128 | 369 |
|  | R4 | ACGCAAACCCTACG |  | 370 |
|  | Probe4 | ATTTTTTTCGCGAAGGCGTCGGCGC |  | 342 |
| 163 | F163 | GTGTGGGGAGTTAT | 127 | 371 |
|  | R4 | ACGCAAACCCTACG |  | 372 |
|  | Probe4 | ATTTTTTTCGCGAAGGCGTCGGCGC |  | 342 |
| 164 | F164 | TGTGGGGAGTTATC | 126 | 373 |
|  | R4 | ACGCAAACCCTACG |  | 374 |
|  | Probe4 | ATTTTTTTCGCGAAGGCGTCGGCGC |  | 342 |
| 165 | F165 | GTGGGGAGTTATCG | 125 | 375 |
|  | R4 | ACGCAAACCCTACG |  | 376 |
|  | Probe4 | ATTTTTTTCGCGAAGGCGTCGGCGC |  | 342 |
| 166 | F166 | TGGGGAGTTATCGA | 124 | 377 |
|  | R4 | ACGCAAACCCTACG |  | 378 |
|  | Probe4 | ATTTTTTTCGCGAAGGCGTCGGCGC |  | 342 |
| 167 | F167 | GGGGAGTTATCGAG | 123 | 379 |
|  | R4 | ACGCAAACCCTACG |  | 380 |
|  | Probe4 | ATTTTTTTCGCGAAGGCGTCGGCGC |  | 342 |
| 168 | F168 | GGGAGTTATCGAGC | 122 | 381 |
|  | R4 | ACGCAAACCCTACG |  | 382 |
|  | Probe4 | ATTTTTTTCGCGAAGGCGTCGGCGC |  | 342 |
| 169 | F169 | GGAGTTATCGAGCG | 121 | 383 |
|  | R4 | ACGCAAACCCTACG |  | 384 |
|  | Probe4 | ATTTTTTTCGCGAAGGCGTCGGCGC |  | 342 |
| 170 | F170 | GAGTTATCGAGCGT | 120 | 385 |
|  | R4 | ACGCAAACCCTACG |  | 386 |
|  | Probe4 | ATTTTTTTCGCGAAGGCGTCGGCGC |  | 342 |
| 171 | F171 | AGTTATCGAGCGTT | 119 | 387 |
|  | R4 | ACGCAAACCCTACG |  | 388 |
|  | Probe4 | ATTTTTTTCGCGAAGGCGTCGGCGC |  | 342 |
| 172 | F172 | GTTATCGAGCGTTT | 118 | 389 |
|  | R4 | ACGCAAACCCTACG |  | 390 |
|  | Probe4 | ATTTTTTTCGCGAAGGCGTCGGCGC |  | 342 |
| 173 | F173 | TTATCGAGCGTTTT | 117 | 391 |
|  | R4 | ACGCAAACCCTACG |  | 392 |
|  | Probe4 | ATTTTTTTCGCGAAGGCGTCGGCGC |  | 342 |
| 174 | F174 | TATCGAGCGTTTTT | 116 | 393 |
|  | R4 | ACGCAAACCCTACG |  | 394 |
|  | Probe4 | ATTTTTTTCGCGAAGGCGTCGGCGC |  | 342 |
| 175 | F175 | ATCGAGCGTTTTTT | 115 | 395 |
|  | R4 | ACGCAAACCCTACG |  | 396 |
|  | Probe4 | ATTTTTTTCGCGAAGGCGTCGGCGC |  | 342 |
| 176 | F176 | TCGAGCGTTTTTTG | 114 | 397 |
|  | R4 | ACGCAAACCCTACG |  | 398 |
|  | Probe4 | ATTTTTTTCGCGAAGGCGTCGGCGC |  | 342 |
| 177 | F177 | CGAGCGTTTTTTGT | 113 | 399 |
|  | R4 | ACGCAAACCCTACG |  | 400 |
|  | Probe4 | ATTTTTTTCGCGAAGGCGTCGGCGC |  | 342 |
| 178 | F178 | GAGCGTTTTTTGTG | 112 | 401 |
|  | R4 | ACGCAAACCCTACG |  | 402 |
|  | Probe4 | ATTTTTTTCGCGAAGGCGTCGGCGC |  | 342 |
| 179 | F179 | AGCGTTTTTTGTGG | 111 | 403 |
|  | R4 | ACGCAAACCCTACG |  | 404 |
|  | Probe4 | ATTTTTTTCGCGAAGGCGTCGGCGC |  | 342 |
| 180 | F180 | GCGTTTTTTGTGGT | 110 | 405 |
|  | R4 | ACGCAAACCCTACG |  | 406 |
|  | Probe4 | ATTTTTTTCGCGAAGGCGTCGGCGC |  | 342 |
| 181 | F181 | CGTTTTTTGTGGTT | 109 | 407 |
|  | R4 | ACGCAAACCCTACG |  | 408 |
|  | Probe4 | ATTTTTTTCGCGAAGGCGTCGGCGC |  | 342 |
| 182 | F182 | GTTTTTTGTGGTTT | 108 | 409 |
|  | R4 | ACGCAAACCCTACG |  | 410 |
|  | Probe4 | ATTTTTTTCGCGAAGGCGTCGGCGC |  | 342 |
| 183 | F183 | TTTTTTGTGGTTTT | 107 | 411 |
|  | R4 | ACGCAAACCCTACG |  | 412 |
|  | Probe4 | ATTTTTTTCGCGAAGGCGTCGGCGC |  | 342 |
| 184 | F184 | TTTTTGTGGTTTTT | 106 | 413 |
|  | R4 | ACGCAAACCCTACG |  | 414 |
|  | Probe4 | ATTTTTTTCGCGAAGGCGTCGGCGC |  | 342 |
| 185 | F185 | TTTTGTGGTTTTTA | 105 | 415 |
|  | R4 | ACGCAAACCCTACG |  | 416 |
|  | Probe4 | ATTTTTTTCGCGAAGGCGTCGGCGC |  | 342 |
| 186 | F186 | TTTGTGGTTTTTAT | 104 | 417 |
|  | R4 | ACGCAAACCCTACG |  | 418 |
|  | Probe4 | ATTTTTTTCGCGAAGGCGTCGGCGC |  | 342 |
| 187 | F187 | TTGTGGTTTTTATT | 103 | 419 |
|  | R4 | ACGCAAACCCTACG |  | 420 |
|  | Probe4 | ATTTTTTTCGCGAAGGCGTCGGCGC |  | 342 |
| 188 | F188 | TGTGGTTTTTATTC | 102 | 421 |
|  | R4 | ACGCAAACCCTACG |  | 422 |
|  | Probe4 | ATTTTTTTCGCGAAGGCGTCGGCGC |  | 342 |
| 189 | F189 | GTGGTTTTTATTCG | 101 | 423 |
|  | R4 | ACGCAAACCCTACG |  | 424 |
|  | Probe4 | ATTTTTTTCGCGAAGGCGTCGGCGC |  | 342 |
| 190 | F190 | TGGTTTTTATTCGA | 100 | 425 |
|  | R4 | ACGCAAACCCTACG |  | 426 |
|  | Probe4 | ATTTTTTTCGCGAAGGCGTCGGCGC |  | 342 |
| 191 | F191 | GGTTTTTATTCGAG | 99 | 427 |
|  | R4 | ACGCAAACCCTACG |  | 428 |
|  | Probe4 | ATTTTTTTCGCGAAGGCGTCGGCGC |  | 342 |
| 192 | F192 | GTTTTTATTCGAGT | 98 | 429 |
|  | R4 | ACGCAAACCCTACG |  | 430 |
|  | Probe4 | ATTTTTTTCGCGAAGGCGTCGGCGC |  | 342 |
| 193 | F193 | TTTTTATTCGAGTT | 97 | 431 |
|  | R4 | ACGCAAACCCTACG |  | 432 |
|  | Probe4 | ATTTTTTTCGCGAAGGCGTCGGCGC |  | 342 |
| 194 | F194 | TTTTATTCGAGTTC | 96 | 433 |
|  | R4 | ACGCAAACCCTACG |  | 434 |
|  | Probe4 | ATTTTTTTCGCGAAGGCGTCGGCGC |  | 342 |
| 195 | F195 | TTTATTCGAGTTCG | 95 | 435 |
|  | R4 | ACGCAAACCCTACG |  | 436 |
|  | Probe4 | ATTTTTTTCGCGAAGGCGTCGGCGC |  | 342 |
| 196 | F196 | TTATTCGAGTTCGG | 94 | 437 |
|  | R4 | ACGCAAACCCTACG |  | 438 |
|  | Probe4 | ATTTTTTTCGCGAAGGCGTCGGCGC |  | 342 |
| 197 | F197 | TATTCGAGTTCGGC | 93 | 439 |
|  | R4 | ACGCAAACCCTACG |  | 440 |
|  | Probe4 | ATTTTTTTCGCGAAGGCGTCGGCGC |  | 342 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 198 | F198 | ATTCGAGTTCGGCG | 92 | 441 |
|  | R4 | ACGCAAACCCTACG |  | 442 |
|  | Probe4 | ATTTTTTTCGCGAAGGCGTCGGCGC |  | 342 |
| 199 | F199 | TTCGAGTTCGGCGG | 91 | 443 |
|  | R4 | ACGCAAACCCTACG |  | 444 |
|  | Probe4 | ATTTTTTTCGCGAAGGCGTCGGCGC |  | 342 |
| 200 | F200 | TCGAGTTCGGCGGG | 90 | 445 |
|  | R4 | ACGCAAACCCTACG |  | 446 |
|  | Probe4 | ATTTTTTTCGCGAAGGCGTCGGCGC |  | 342 |
| 201 | F201 | CGAGTTCGGCGGGG | 89 | 447 |
|  | R4 | ACGCAAACCCTACG |  | 448 |
|  | Probe4 | ATTTTTTTCGCGAAGGCGTCGGCGC |  | 342 |
| 202 | F202 | GAGTTCGGCGGGGG | 88 | 449 |
|  | R4 | ACGCAAACCCTACG |  | 450 |
|  | Probe4 | ATTTTTTTCGCGAAGGCGTCGGCGC |  | 342 |
| 203 | F203 | AGTTCGGCGGGGGG | 87 | 451 |
|  | R4 | ACGCAAACCCTACG |  | 452 |
|  | Probe4 | ATTTTTTTCGCGAAGGCGTCGGCGC |  | 342 |
| 204 | F204 | GTTCGGCGGGGGGA | 86 | 453 |
|  | R4 | ACGCAAACCCTACG |  | 454 |
|  | Probe4 | ATTTTTTTCGCGAAGGCGTCGGCGC |  | 342 |
| 205 | F205 | TTCGGCGGGGGGAG | 85 | 455 |
|  | R4 | ACGCAAACCCTACG |  | 456 |
|  | Probe4 | ATTTTTTTCGCGAAGGCGTCGGCGC |  | 342 |
| 206 | F206 | TCGGCGGGGGGAGC | 84 | 457 |
|  | R4 | ACGCAAACCCTACG |  | 458 |
|  | Probe4 | ATTTTTTTCGCGAAGGCGTCGGCGC |  | 342 |
| 207 | F207 | CGGCGGGGGGAGCG | 83 | 459 |
|  | R4 | ACGCAAACCCTACG |  | 460 |
|  | Probe4 | ATTTTTTTCGCGAAGGCGTCGGCGC |  | 342 |
| 208 | F208 | GGCGGGGGGAGCGG | 82 | 461 |
|  | R4 | ACGCAAACCCTACG |  | 462 |
|  | Probe4 | ATTTTTTTCGCGAAGGCGTCGGCGC |  | 342 |
| 209 | F209 | GCGGGGGGAGCGGC | 81 | 463 |
|  | R4 | ACGCAAACCCTACG |  | 464 |
|  | Probe4 | ATTTTTTTCGCGAAGGCGTCGGCGC |  | 342 |
| 210 | F210 | CGGGGGGAGCGGCG | 80 | 465 |
|  | R4 | ACGCAAACCCTACG |  | 466 |
|  | Probe4 | ATTTTTTTCGCGAAGGCGTCGGCGC |  | 342 |
| 211 | F211 | GGGGGGAGCGGCGC | 134 | 467 |
|  | R5 | TTAACCCCAAACCG |  | 468 |
|  | Probe5 | AGTTCGTCGGCGATTGGGGCGCGCGC |  | 469 |
| 212 | F212 | GGGGGAGCGGCGCG | 133 | 470 |
|  | R5 | TTAACCCCAAACCG |  | 471 |
|  | Probe5 | AGTTCGTCGGCGATTGGGGCGCGCGC |  | 469 |
| 213 | F213 | GGGGAGCGGCGCGC | 132 | 472 |
|  | R5 | TTAACCCCAAACCG |  | 473 |
|  | Probe5 | AGTTCGTCGGCGATTGGGGCGCGCGC |  | 469 |
| 214 | F214 | GGGAGCGGCGCGCG | 131 | 474 |
|  | R5 | TTAACCCCAAACCG |  | 475 |
|  | Probe5 | AGTTCGTCGGCGATTGGGGCGCGCGC |  | 469 |
| 215 | F215 | GGAGCGGCGCGCGG | 130 | 476 |
|  | R5 | TTAACCCCAAACCG |  | 477 |
|  | Probe5 | AGTTCGTCGGCGATTGGGGCGCGCGC |  | 469 |
| 216 | F216 | GAGCGGCGCGCGGG | 129 | 478 |
|  | R5 | TTAACCCCAAACCG |  | 479 |
|  | Probe5 | AGTTCGTCGGCGATTGGGGCGCGCGC |  | 469 |
| 217 | F217 | AGCGGCGCGCGGGT | 128 | 480 |
|  | R5 | TTAACCCCAAACCG |  | 481 |
|  | Probe5 | AGTTCGTCGGCGATTGGGGCGCGCGC |  | 469 |
| 218 | F218 | GCGGCGCGCGGGTG | 127 | 482 |
|  | R5 | TTAACCCCAAACCG |  | 483 |
|  | Probe5 | AGTTCGTCGGCGATTGGGGCGCGCGC |  | 469 |
| 219 | F219 | CGGCGCGCGGGTGT | 126 | 484 |
|  | R5 | TTAACCCCAAACCG |  | 485 |
|  | Probe5 | AGTTCGTCGGCGATTGGGGCGCGCGC |  | 469 |
| 220 | F220 | GGCGCGCGGGTGTT | 125 | 486 |
|  | R5 | TTAACCCCAAACCG |  | 487 |
|  | Probe5 | AGTTCGTCGGCGATTGGGGCGCGCGC |  | 469 |
| 221 | F221 | GCGCGCGGGTGTTG | 124 | 488 |
|  | R5 | TTAACCCCAAACCG |  | 489 |
|  | Probe5 | AGTTCGTCGGCGATTGGGGCGCGCGC |  | 469 |
| 222 | F222 | CGCGCGGGTGTTGG | 123 | 490 |
|  | R5 | TTAACCCCAAACCG |  | 491 |
|  | Probe5 | AGTTCGTCGGCGATTGGGGCGCGCGC |  | 469 |
| 223 | F223 | GCGCGGGTGTTGGG | 122 | 492 |
|  | R5 | TTAACCCCAAACCG |  | 493 |
|  | Probe5 | AGTTCGTCGGCGATTGGGGCGCGCGC |  | 469 |
| 224 | F224 | CGCGGGTGTTGGGG | 121 | 494 |
|  | R5 | TTAACCCCAAACCG |  | 495 |
|  | Probe5 | AGTTCGTCGGCGATTGGGGCGCGCGC |  | 469 |
| 225 | F225 | GCGGGTGTTGGGGG | 120 | 496 |
|  | R5 | TTAACCCCAAACCG |  | 497 |
|  | Probe5 | AGTTCGTCGGCGATTGGGGCGCGCGC |  | 469 |
| 226 | F226 | CGGGTGTTGGGGGA | 119 | 498 |
|  | R5 | TTAACCCCAAACCG |  | 499 |
|  | Probe5 | AGTTCGTCGGCGATTGGGGCGCGCGC |  | 469 |
| 227 | F227 | GGGTGTTGGGGGAT | 118 | 500 |
|  | R5 | TTAACCCCAAACCG |  | 501 |
|  | Probe5 | AGTTCGTCGGCGATTGGGGCGCGCGC |  | 469 |
| 228 | F228 | GGTGTTGGGGGATC | 117 | 502 |
|  | R5 | TTAACCCCAAACCG |  | 503 |
|  | Probe5 | AGTTCGTCGGCGATTGGGGCGCGCGC |  | 469 |
| 229 | F229 | GTGTTGGGGGATCG | 116 | 504 |
|  | R5 | TTAACCCCAAACCG |  | 505 |
|  | Probe5 | AGTTCGTCGGCGATTGGGGCGCGCGC |  | 469 |
| 230 | F230 | TGTTGGGGGATCGA | 115 | 506 |
|  | R5 | TTAACCCCAAACCG |  | 507 |
|  | Probe5 | AGTTCGTCGGCGATTGGGGCGCGCGC |  | 469 |
| 231 | F231 | GTTGGGGGATCGAT | 114 | 508 |
|  | R5 | TTAACCCCAAACCG |  | 509 |
|  | Probe5 | AGTTCGTCGGCGATTGGGGCGCGCGC |  | 469 |
| 232 | F232 | TTGGGGGATCGATT | 113 | 510 |
|  | R5 | TTAACCCCAAACCG |  | 511 |
|  | Probe5 | AGTTCGTCGGCGATTGGGGCGCGCGC |  | 469 |
| 233 | F233 | TGGGGGATCGATTT | 112 | 512 |
|  | R5 | TTAACCCCAAACCG |  | 513 |
|  | Probe5 | AGTTCGTCGGCGATTGGGGCGCGCGC |  | 469 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 234 | F234 | GGGGGATCGATTTT | 111 | 514 |
|  | R5 | TTAACCCCAAACCG |  | 515 |
|  | Probe5 | AGTTCGTCGGCGATTGGGGCGCGCGC |  | 469 |
| 235 | F235 | GGGGATCGATTTTT | 110 | 516 |
|  | R5 | TTAACCCCAAACCG |  | 517 |
|  | Probe5 | AGTTCGTCGGCGATTGGGGCGCGCGC |  | 469 |
| 236 | F236 | GGGATCGATTTTTT | 109 | 518 |
|  | R5 | TTAACCCCAAACCG |  | 519 |
|  | Probe5 | AGTTCGTCGGCGATTGGGGCGCGCGC |  | 469 |
| 237 | F237 | GGATCGATTTTTTT | 108 | 520 |
|  | R5 | TTAACCCCAAACCG |  | 521 |
|  | Probe5 | AGTTCGTCGGCGATTGGGGCGCGCGC |  | 469 |
| 238 | F238 | GATCGATTTTTTTC | 107 | 522 |
|  | R5 | TTAACCCCAAACCG |  | 523 |
|  | Probe5 | AGTTCGTCGGCGATTGGGGCGCGCGC |  | 469 |
| 239 | F239 | ATCGATTTTTTTCG | 106 | 524 |
|  | R5 | TTAACCCCAAACCG |  | 525 |
|  | Probe5 | AGTTCGTCGGCGATTGGGGCGCGCGC |  | 469 |
| 240 | F240 | TCGATTTTTTTCGC | 105 | 526 |
|  | R5 | TTAACCCCAAACCG |  | 527 |
|  | Probe5 | AGTTCGTCGGCGATTGGGGCGCGCGC |  | 469 |
| 241 | F241 | CGATTTTTTTCGCG | 104 | 528 |
|  | R5 | TTAACCCCAAACCG |  | 529 |
|  | Probe5 | AGTTCGTCGGCGATTGGGGCGCGCGC |  | 469 |
| 242 | F242 | GATTTTTTTCGCGA | 103 | 530 |
|  | R5 | TTAACCCCAAACCG |  | 531 |
|  | Probe5 | AGTTCGTCGGCGATTGGGGCGCGCGC |  | 469 |
| 243 | F243 | ATTTTTTTCGCGAA | 102 | 532 |
|  | R5 | TTAACCCCAAACCG |  | 533 |
|  | Probe5 | AGTTCGTCGGCGATTGGGGCGCGCGC |  | 469 |
| 244 | F244 | TTTTTTTCGCGAAG | 101 | 534 |
|  | R5 | TTAACCCCAAACCG |  | 535 |
|  | Probe5 | AGTTCGTCGGCGATTGGGGCGCGCGC |  | 469 |
| 245 | F245 | TTTTTTCGCGAAGG | 100 | 536 |
|  | R5 | TTAACCCCAAACCG |  | 537 |
|  | Probe5 | AGTTCGTCGGCGATTGGGGCGCGCGC |  | 469 |
| 246 | F246 | TTTTTCGCGAAGGC | 99 | 538 |
|  | R5 | TTAACCCCAAACCG |  | 539 |
|  | Probe5 | AGTTCGTCGGCGATTGGGGCGCGCGC |  | 469 |
| 247 | F247 | TTTTCGCGAAGGCG | 98 | 540 |
|  | R5 | TTAACCCCAAACCG |  | 541 |
|  | Probe5 | AGTTCGTCGGCGATTGGGGCGCGCGC |  | 469 |
| 248 | F248 | TTTCGCGAAGGCGT | 97 | 542 |
|  | R5 | TTAACCCCAAACCG |  | 543 |
|  | Probe5 | AGTTCGTCGGCGATTGGGGCGCGCGC |  | 469 |
| 249 | F249 | TTCGCGAAGGCGTC | 96 | 544 |
|  | R5 | TTAACCCCAAACCG |  | 545 |
|  | Probe5 | AGTTCGTCGGCGATTGGGGCGCGCGC |  | 469 |
| 250 | F250 | TCGCGAAGGCGTCG | 95 | 546 |
|  | R5 | TTAACCCCAAACCG |  | 547 |
|  | Probe5 | AGTTCGTCGGCGATTGGGGCGCGCGC |  | 469 |
| 251 | F251 | CGCGAAGGCGTCGG | 94 | 548 |
|  | R5 | TTAACCCCAAACCG |  | 549 |
|  | Probe5 | AGTTCGTCGGCGATTGGGGCGCGCGC |  | 469 |
| 252 | F252 | GCGAAGGCGTCGGC | 93 | 550 |
|  | R5 | TTAACCCCAAACCG |  | 551 |
|  | Probe5 | AGTTCGTCGGCGATTGGGGCGCGCGC |  | 469 |
| 253 | F253 | CGAAGGCGTCGGCG | 92 | 552 |
|  | R5 | TTAACCCCAAACCG |  | 553 |
|  | Probe5 | AGTTCGTCGGCGATTGGGGCGCGCGC |  | 469 |
| 254 | F254 | GAAGGCGTCGGCGC | 91 | 554 |
|  | R5 | TTAACCCCAAACCG |  | 555 |
|  | Probe5 | AGTTCGTCGGCGATTGGGGCGCGCGC |  | 469 |
| 255 | F255 | AAGGCGTCGGCGCG | 90 | 556 |
|  | R5 | TTAACCCCAAACCG |  | 557 |
|  | Probe5 | AGTTCGTCGGCGATTGGGGCGCGCGC |  | 469 |
| 256 | F256 | AGGCGTCGGCGCGG | 89 | 558 |
|  | R5 | TTAACCCCAAACCG |  | 559 |
|  | Probe5 | AGTTCGTCGGCGATTGGGGCGCGCGC |  | 469 |
| 257 | F257 | GGCGTCGGCGCGGG | 88 | 560 |
|  | R5 | TTAACCCCAAACCG |  | 561 |
|  | Probe5 | AGTTCGTCGGCGATTGGGGCGCGCGC |  | 469 |
| 258 | F258 | GCGTCGGCGCGGGG | 87 | 562 |
|  | R5 | TTAACCCCAAACCG |  | 563 |
|  | Probe5 | AGTTCGTCGGCGATTGGGGCGCGCGC |  | 469 |
| 259 | F259 | CGTCGGCGCGGGGT | 86 | 564 |
|  | R5 | TTAACCCCAAACCG |  | 565 |
|  | Probe5 | AGTTCGTCGGCGATTGGGGCGCGCGC |  | 469 |
| 260 | F260 | GTCGGCGCGGGGTT | 85 | 566 |
|  | R5 | TTAACCCCAAACCG |  | 567 |
|  | Probe5 | AGTTCGTCGGCGATTGGGGCGCGCGC |  | 469 |
| 261 | F261 | TCGGCGCGGGGTTG | 84 | 568 |
|  | R5 | TTAACCCCAAACCG |  | 569 |
|  | Probe5 | AGTTCGTCGGCGATTGGGGCGCGCGC |  | 469 |
| 262 | F262 | CGGCGCGGGGTTGG | 83 | 570 |
|  | R5 | TTAACCCCAAACCG |  | 571 |
|  | Probe5 | AGTTCGTCGGCGATTGGGGCGCGCGC |  | 469 |
| 263 | F263 | GGCGCGGGGTTGGC | 82 | 572 |
|  | R5 | TTAACCCCAAACCG |  | 573 |
|  | Probe5 | AGTTCGTCGGCGATTGGGGCGCGCGC |  | 469 |
| 264 | F264 | GCGCGGGGTTGGCG | 81 | 574 |
|  | R5 | TTAACCCCAAACCG |  | 575 |
|  | Probe5 | AGTTCGTCGGCGATTGGGGCGCGCGC |  | 469 |
| 265 | F265 | CGCGGGGTTGGCGT | 80 | 576 |
|  | R5 | TTAACCCCAAACCG |  | 577 |
|  | Probe5 | AGTTCGTCGGCGATTGGGGCGCGCGC |  | 469 |
| 266 | F266 | GCGGGGTTGGCGTA | 141 | 578 |
|  | R6 | CGAAACTCTAAACG |  | 579 |
|  | Probe6 | AGTAGTCGTTAAGTTTCGGGACGGC |  | 580 |
| 267 | F267 | CGGGGTTGGCGTAG | 140 | 581 |
|  | R6 | CGAAACTCTAAACG |  | 582 |
|  | Probe6 | AGTAGTCGTTAAGTTTCGGGACGGC |  | 580 |
| 268 | F268 | GGGGTTGGCGTAGG | 139 | 583 |
|  | R6 | CGAAACTCTAAACG |  | 584 |
|  | Probe6 | AGTAGTCGTTAAGTTTCGGGACGGC |  | 580 |
| 269 | F269 | GGGTTGGCGTAGGG | 138 | 585 |
|  | R6 | CGAAACTCTAAACG |  | 586 |
|  | Probe6 | AGTAGTCGTTAAGTTTCGGGACGGC |  | 580 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 270 | F270 | GGTTGGCGTAGGGT | 137 | 587 |
| | R6 | CGAAACTCTAAACG | | 588 |
| | Probe6 | AGTAGTCGTTAAGTTTCGGGACGGC | | 580 |
| 271 | F271 | GTTGGCGTAGGGTT | 136 | 589 |
| | R6 | CGAAACTCTAAACG | | 590 |
| | Probe6 | AGTAGTCGTTAAGTTTCGGGACGGC | | 580 |
| 272 | F272 | TTGGCGTAGGGTTT | 135 | 591 |
| | R6 | CGAAACTCTAAACG | | 592 |
| | Probe6 | AGTAGTCGTTAAGTTTCGGGACGGC | | 580 |
| 273 | F273 | TGGCGTAGGGTTTG | 134 | 593 |
| | R6 | CGAAACTCTAAACG | | 594 |
| | Probe6 | AGTAGTCGTTAAGTTTCGGGACGGC | | 580 |
| 274 | F274 | GGCGTAGGGTTTGC | 133 | 595 |
| | R6 | CGAAACTCTAAACG | | 596 |
| | Probe6 | AGTAGTCGTTAAGTTTCGGGACGGC | | 580 |
| 275 | F275 | GCGTAGGGTTTGCG | 132 | 597 |
| | R6 | CGAAACTCTAAACG | | 598 |
| | Probe6 | AGTAGTCGTTAAGTTTCGGGACGGC | | 580 |
| 276 | F276 | CGTAGGGTTTGCGT | 131 | 599 |
| | R6 | CGAAACTCTAAACG | | 600 |
| | Probe6 | AGTAGTCGTTAAGTTTCGGGACGGC | | 580 |
| 277 | F277 | GTAGGGTTTGCGTT | 130 | 601 |
| | R6 | CGAAACTCTAAACG | | 602 |
| | Probe6 | AGTAGTCGTTAAGTTTCGGGACGGC | | 580 |
| 278 | F278 | TAGGGTTTGCGTTA | 129 | 603 |
| | R6 | CGAAACTCTAAACG | | 604 |
| | Probe6 | AGTAGTCGTTAAGTTTCGGGACGGC | | 580 |
| 279 | F279 | AGGGTTTGCGTTAG | 128 | 605 |
| | R6 | CGAAACTCTAAACG | | 606 |
| | Probe6 | AGTAGTCGTTAAGTTTCGGGACGGC | | 580 |
| 280 | F280 | GGGTTTGCGTTAGT | 127 | 607 |
| | R6 | CGAAACTCTAAACG | | 608 |
| | Probe6 | AGTAGTCGTTAAGTTTCGGGACGGC | | 580 |
| 281 | F281 | GGTTTGCGTTAGTT | 126 | 609 |
| | R6 | CGAAACTCTAAACG | | 610 |
| | Probe6 | AGTAGTCGTTAAGTTTCGGGACGGC | | 580 |
| 282 | F282 | GTTTGCGTTAGTTG | 125 | 611 |
| | R6 | CGAAACTCTAAACG | | 612 |
| | Probe6 | AGTAGTCGTTAAGTTTCGGGACGGC | | 580 |
| 283 | F283 | TTTGCGTTAGTTGT | 124 | 613 |
| | R6 | CGAAACTCTAAACG | | 614 |
| | Probe6 | AGTAGTCGTTAAGTTTCGGGACGGC | | 580 |
| 284 | F284 | TTGCGTTAGTTGTA | 123 | 615 |
| | R6 | CGAAACTCTAAACG | | 616 |
| | Probe6 | AGTAGTCGTTAAGTTTCGGGACGGC | | 580 |
| 285 | F285 | TGCGTTAGTTGTAG | 122 | 617 |
| | R6 | CGAAACTCTAAACG | | 618 |
| | Probe6 | AGTAGTCGTTAAGTTTCGGGACGGC | | 580 |
| 286 | F286 | GCGTTAGTTGTAGT | 121 | 619 |
| | R6 | CGAAACTCTAAACG | | 620 |
| | Probe6 | AGTAGTCGTTAAGTTTCGGGACGGC | | 580 |
| 287 | F287 | CGTTAGTTGTAGTT | 120 | 621 |
| | R6 | CGAAACTCTAAACG | | 622 |
| | Probe6 | AGTAGTCGTTAAGTTTCGGGACGGC | | 580 |
| 288 | F288 | GTTAGTTGTAGTTC | 119 | 623 |
| | R6 | CGAAACTCTAAACG | | 624 |
| | Probe6 | AGTAGTCGTTAAGTTTCGGGACGGC | | 580 |
| 289 | F289 | TTAGTTGTAGTTCG | 118 | 625 |
| | R6 | CGAAACTCTAAACG | | 626 |
| | Probe6 | AGTAGTCGTTAAGTTTCGGGACGGC | | 580 |
| 290 | F290 | TAGTTGTAGTTCGT | 117 | 627 |
| | R6 | CGAAACTCTAAACG | | 628 |
| | Probe6 | AGTAGTCGTTAAGTTTCGGGACGGC | | 580 |
| 291 | F291 | AGTTGTAGTTCGTC | 116 | 629 |
| | R6 | CGAAACTCTAAACG | | 630 |
| | Probe6 | AGTAGTCGTTAAGTTTCGGGACGGC | | 580 |
| 292 | F292 | GTTGTAGTTCGTCG | 115 | 631 |
| | R6 | CGAAACTCTAAACG | | 632 |
| | Probe6 | AGTAGTCGTTAAGTTTCGGGACGGC | | 580 |
| 293 | F293 | TTGTAGTTCGTCGG | 114 | 633 |
| | R6 | CGAAACTCTAAACG | | 634 |
| | Probe6 | AGTAGTCGTTAAGTTTCGGGACGGC | | 580 |
| 294 | F294 | TGTAGTTCGTCGGC | 113 | 635 |
| | R6 | CGAAACTCTAAACG | | 636 |
| | Probe6 | AGTAGTCGTTAAGTTTCGGGACGGC | | 580 |
| 295 | F295 | GTAGTTCGTCGGCG | 112 | 637 |
| | R6 | CGAAACTCTAAACG | | 638 |
| | Probe6 | AGTAGTCGTTAAGTTTCGGGACGGC | | 580 |
| 296 | F296 | TAGTTCGTCGGCGA | 111 | 639 |
| | R6 | CGAAACTCTAAACG | | 640 |
| | Probe6 | AGTAGTCGTTAAGTTTCGGGACGGC | | 580 |
| 297 | F297 | AGTTCGTCGGCGAT | 110 | 641 |
| | R6 | CGAAACTCTAAACG | | 642 |
| | Probe6 | AGTAGTCGTTAAGTTTCGGGACGGC | | 580 |
| 298 | F298 | GTTCGTCGGCGATT | 109 | 643 |
| | R6 | CGAAACTCTAAACG | | 644 |
| | Probe6 | AGTAGTCGTTAAGTTTCGGGACGGC | | 580 |
| 299 | F299 | TTCGTCGGCGATTG | 108 | 645 |
| | R6 | CGAAACTCTAAACG | | 646 |
| | Probe6 | AGTAGTCGTTAAGTTTCGGGACGGC | | 580 |
| 300 | F300 | TCGTCGGCGATTGG | 107 | 647 |
| | R6 | CGAAACTCTAAACG | | 648 |
| | Probe6 | AGTAGTCGTTAAGTTTCGGGACGGC | | 580 |
| 301 | F301 | CGTCGGCGATTGGG | 106 | 649 |
| | R6 | CGAAACTCTAAACG | | 650 |
| | Probe6 | AGTAGTCGTTAAGTTTCGGGACGGC | | 580 |
| 302 | F302 | GTCGGCGATTGGGG | 105 | 651 |
| | R6 | CGAAACTCTAAACG | | 652 |
| | Probe6 | AGTAGTCGTTAAGTTTCGGGACGGC | | 580 |
| 303 | F303 | TCGGCGATTGGGGC | 104 | 653 |
| | R6 | CGAAACTCTAAACG | | 654 |
| | Probe6 | AGTAGTCGTTAAGTTTCGGGACGGC | | 580 |
| 304 | F304 | CGGCGATTGGGGCG | 103 | 655 |
| | R6 | CGAAACTCTAAACG | | 656 |
| | Probe6 | AGTAGTCGTTAAGTTTCGGGACGGC | | 580 |
| 305 | F305 | GGCGATTGGGGCGC | 102 | 657 |
| | R6 | CGAAACTCTAAACG | | 658 |
| | Probe6 | AGTAGTCGTTAAGTTTCGGGACGGC | | 580 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 306 | F306 | GCGATTGGGGCGCG | 101 | 659 |
|  | R6 | CGAAACTCTAAACG |  | 660 |
|  | Probe6 | AGTAGTCGTTAAGTTTCGGGACGGC |  | 580 |
| 307 | F307 | CGATTGGGGCGCGC | 100 | 661 |
|  | R6 | CGAAACTCTAAACG |  | 662 |
|  | Probe6 | AGTAGTCGTTAAGTTTCGGGACGGC |  | 580 |
| 308 | F308 | GATTGGGGCGCGCG | 99 | 663 |
|  | R6 | CGAAACTCTAAACG |  | 664 |
|  | Probe6 | AGTAGTCGTTAAGTTTCGGGACGGC |  | 580 |
| 309 | F309 | ATTGGGGCGCGCGC | 98 | 665 |
|  | R6 | CGAAACTCTAAACG |  | 666 |
|  | Probe6 | AGTAGTCGTTAAGTTTCGGGACGGC |  | 580 |
| 310 | F310 | TTGGGGCGCGCGCG | 97 | 667 |
|  | R6 | CGAAACTCTAAACG |  | 668 |
|  | Probe6 | AGTAGTCGTTAAGTTTCGGGACGGC |  | 580 |
| 311 | F311 | TGGGGCGCGCGCGT | 96 | 669 |
|  | R6 | CGAAACTCTAAACG |  | 670 |
|  | Probe6 | AGTAGTCGTTAAGTTTCGGGACGGC |  | 580 |
| 312 | F312 | GGGGCGCGCGCGTT | 95 | 671 |
|  | R6 | CGAAACTCTAAACG |  | 672 |
|  | Probe6 | AGTAGTCGTTAAGTTTCGGGACGGC |  | 580 |
| 313 | F313 | GGGCGCGCGCGTTT | 94 | 673 |
|  | R6 | CGAAACTCTAAACG |  | 674 |
|  | Probe6 | AGTAGTCGTTAAGTTTCGGGACGGC |  | 580 |
| 314 | F314 | GGCGCGCGCGTTTT | 93 | 675 |
|  | R6 | CGAAACTCTAAACG |  | 676 |
|  | Probe6 | AGTAGTCGTTAAGTTTCGGGACGGC |  | 580 |
| 315 | F315 | GCGCGCGCGTTTTT | 92 | 677 |
|  | R6 | CGAAACTCTAAACG |  | 678 |
|  | Probe6 | AGTAGTCGTTAAGTTTCGGGACGGC |  | 580 |
| 316 | F316 | CGCGCGCGTTTTTT | 91 | 679 |
|  | R6 | CGAAACTCTAAACG |  | 680 |
|  | Probe6 | AGTAGTCGTTAAGTTTCGGGACGGC |  | 580 |
| 317 | F317 | GCGCGCGTTTTTTT | 90 | 681 |
|  | R6 | CGAAACTCTAAACG |  | 682 |
|  | Probe6 | AGTAGTCGTTAAGTTTCGGGACGGC |  | 580 |
| 318 | F318 | CGCGCGTTTTTTTC | 89 | 683 |
|  | R6 | CGAAACTCTAAACG |  | 684 |
|  | Probe6 | AGTAGTCGTTAAGTTTCGGGACGGC |  | 580 |
| 319 | F319 | GCGCGTTTTTTTCG | 88 | 685 |
|  | R6 | CGAAACTCTAAACG |  | 686 |
|  | Probe6 | AGTAGTCGTTAAGTTTCGGGACGGC |  | 580 |
| 320 | F320 | CGCGTTTTTTTCGG | 87 | 687 |
|  | R6 | CGAAACTCTAAACG |  | 688 |
|  | Probe6 | AGTAGTCGTTAAGTTTCGGGACGGC |  | 580 |
| 321 | F321 | GCGTTTTTTTCGGT | 86 | 689 |
|  | R6 | CGAAACTCTAAACG |  | 690 |
|  | Probe6 | AGTAGTCGTTAAGTTTCGGGACGGC |  | 580 |
| 322 | F322 | CGTTTTTTTCGGTT | 85 | 691 |
|  | R6 | CGAAACTCTAAACG |  | 692 |
|  | Probe6 | AGTAGTCGTTAAGTTTCGGGACGGC |  | 580 |
| 323 | F323 | GTTTTTTTCGGTTT | 84 | 693 |
|  | R6 | CGAAACTCTAAACG |  | 694 |
|  | Probe6 | AGTAGTCGTTAAGTTTCGGGACGGC |  | 580 |
| 324 | F324 | TTTTTTTCGGTTTG | 83 | 695 |
|  | R6 | CGAAACTCTAAACG |  | 696 |
|  | Probe6 | AGTAGTCGTTAAGTTTCGGGACGGC |  | 580 |
| 325 | F325 | TTTTTTCGGTTTGG | 82 | 697 |
|  | R6 | CGAAACTCTAAACG |  | 698 |
|  | Probe6 | AGTAGTCGTTAAGTTTCGGGACGGC |  | 580 |
| 326 | F326 | TTTTTCGGTTTGGG | 81 | 699 |
|  | R6 | CGAAACTCTAAACG |  | 700 |
|  | Probe6 | AGTAGTCGTTAAGTTTCGGGACGGC |  | 580 |
| 327 | F327 | TTTTCGGTTTGGGG | 80 | 701 |
|  | R6 | CGAAACTCTAAACG |  | 702 |
|  | Probe6 | AGTAGTCGTTAAGTTTCGGGACGGC |  | 580 |
| 328 | F328 | TTTCGGTTTGGGGT | 147 | 703 |
|  | R7 | TATACTAACGAACG |  | 704 |
|  | Probe7 | TCGTAGAGACGTTGAGGATCGCGAC |  | 705 |
| 329 | F329 | TTCGGTTTGGGGTT | 146 | 706 |
|  | R7 | TATACTAACGAACG |  | 707 |
|  | Probe7 | TCGTAGAGACGTTGAGGATCGCGAC |  | 705 |
| 330 | F330 | TCGGTTTGGGGTTA | 145 | 708 |
|  | R7 | TATACTAACGAACG |  | 709 |
|  | Probe7 | TCGTAGAGACGTTGAGGATCGCGAC |  | 705 |
| 331 | F331 | CGGTTTGGGGTTAA | 144 | 710 |
|  | R7 | TATACTAACGAACG |  | 711 |
|  | Probe7 | TCGTAGAGACGTTGAGGATCGCGAC |  | 705 |
| 332 | F332 | GGTTTGGGGTTAAT | 143 | 712 |
|  | R7 | TATACTAACGAACG |  | 713 |
|  | Probe7 | TCGTAGAGACGTTGAGGATCGCGAC |  | 705 |
| 333 | F333 | GTTTGGGGTTAATT | 142 | 714 |
|  | R7 | TATACTAACGAACG |  | 715 |
|  | Probe7 | TCGTAGAGACGTTGAGGATCGCGAC |  | 705 |
| 334 | F334 | TTTGGGGTTAATTA | 141 | 716 |
|  | R7 | TATACTAACGAACG |  | 717 |
|  | Probe7 | TCGTAGAGACGTTGAGGATCGCGAC |  | 705 |
| 335 | F335 | TTGGGGTTAATTAT | 140 | 718 |
|  | R7 | TATACTAACGAACG |  | 719 |
|  | Probe7 | TCGTAGAGACGTTGAGGATCGCGAC |  | 705 |
| 336 | F336 | TGGGGTTAATTATA | 139 | 720 |
|  | R7 | TATACTAACGAACG |  | 721 |
|  | Probe7 | TCGTAGAGACGTTGAGGATCGCGAC |  | 705 |
| 337 | F337 | GGGGTTAATTATAA | 138 | 722 |
|  | R7 | TATACTAACGAACG |  | 723 |
|  | Probe7 | TCGTAGAGACGTTGAGGATCGCGAC |  | 705 |
| 338 | F338 | GGGTTAATTATAAA | 137 | 724 |
|  | R7 | TATACTAACGAACG |  | 725 |
|  | Probe7 | TCGTAGAGACGTTGAGGATCGCGAC |  | 705 |
| 339 | F339 | GGTTAATTATAAAG | 136 | 726 |
|  | R7 | TATACTAACGAACG |  | 727 |
|  | Probe7 | TCGTAGAGACGTTGAGGATCGCGAC |  | 705 |
| 340 | F340 | GTTAATTATAAAGT | 135 | 728 |
|  | R7 | TATACTAACGAACG |  | 729 |
|  | Probe7 | TCGTAGAGACGTTGAGGATCGCGAC |  | 705 |
| 341 | F341 | TTAATTATAAAGTG | 134 | 730 |
|  | R7 | TATACTAACGAACG |  | 731 |
|  | Probe7 | TCGTAGAGACGTTGAGGATCGCGAC |  | 705 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 342 | F342 | TAATTATAAAGTGG | 133 | 732 |
| | R7 | TATACTAACGAACG | | 733 |
| | Probe7 | TCGTAGAGACGTTGAGGATCGCGAC | | 705 |
| 343 | F343 | AATTATAAAGTGGT | 132 | 734 |
| | R7 | TATACTAACGAACG | | 735 |
| | Probe7 | TCGTAGAGACGTTGAGGATCGCGAC | | 705 |
| 344 | F344 | ATTATAAAGTGGTT | 131 | 736 |
| | R7 | TATACTAACGAACG | | 737 |
| | Probe7 | TCGTAGAGACGTTGAGGATCGCGAC | | 705 |
| 345 | F345 | TTATAAAGTGGTTT | 130 | 738 |
| | R7 | TATACTAACGAACG | | 739 |
| | Probe7 | TCGTAGAGACGTTGAGGATCGCGAC | | 705 |
| 346 | F346 | TATAAAGTGGTTTT | 129 | 740 |
| | R7 | TATACTAACGAACG | | 741 |
| | Probe7 | TCGTAGAGACGTTGAGGATCGCGAC | | 705 |
| 347 | F347 | ATAAAGTGGTTTTA | 128 | 742 |
| | R7 | TATACTAACGAACG | | 743 |
| | Probe7 | TCGTAGAGACGTTGAGGATCGCGAC | | 705 |
| 348 | F348 | TAAAGTGGTTTTAG | 127 | 744 |
| | R7 | TATACTAACGAACG | | 745 |
| | Probe7 | TCGTAGAGACGTTGAGGATCGCGAC | | 705 |
| 349 | F349 | AAAGTGGTTTTAGT | 126 | 746 |
| | R7 | TATACTAACGAACG | | 747 |
| | Probe7 | TCGTAGAGACGTTGAGGATCGCGAC | | 705 |
| 350 | F350 | AAGTGGTTTTAGTA | 125 | 748 |
| | R7 | TATACTAACGAACG | | 749 |
| | Probe7 | TCGTAGAGACGTTGAGGATCGCGAC | | 705 |
| 351 | F351 | AGTGGTTTTAGTAG | 124 | 750 |
| | R7 | TATACTAACGAACG | | 751 |
| | Probe7 | TCGTAGAGACGTTGAGGATCGCGAC | | 705 |
| 352 | F352 | GTGGTTTTAGTAGT | 123 | 752 |
| | R7 | TATACTAACGAACG | | 753 |
| | Probe7 | TCGTAGAGACGTTGAGGATCGCGAC | | 705 |
| 353 | F353 | TGGTTTTAGTAGTC | 122 | 754 |
| | R7 | TATACTAACGAACG | | 755 |
| | Probe7 | TCGTAGAGACGTTGAGGATCGCGAC | | 705 |
| 354 | F354 | GGTTTTAGTAGTCG | 121 | 756 |
| | R7 | TATACTAACGAACG | | 757 |
| | Probe7 | TCGTAGAGACGTTGAGGATCGCGAC | | 705 |
| 355 | F355 | GTTTTAGTAGTCGT | 120 | 758 |
| | R7 | TATACTAACGAACG | | 759 |
| | Probe7 | TCGTAGAGACGTTGAGGATCGCGAC | | 705 |
| 356 | F356 | TTTTAGTAGTCGTT | 119 | 760 |
| | R7 | TATACTAACGAACG | | 761 |
| | Probe7 | TCGTAGAGACGTTGAGGATCGCGAC | | 705 |
| 357 | F357 | TTTAGTAGTCGTTA | 118 | 762 |
| | R7 | TATACTAACGAACG | | 763 |
| | Probe7 | TCGTAGAGACGTTGAGGATCGCGAC | | 705 |
| 358 | F358 | TTAGTAGTCGTTAA | 117 | 764 |
| | R7 | TATACTAACGAACG | | 765 |
| | Probe7 | TCGTAGAGACGTTGAGGATCGCGAC | | 705 |
| 359 | F359 | TAGTAGTCGTTAAG | 116 | 766 |
| | R7 | TATACTAACGAACG | | 767 |
| | Probe7 | TCGTAGAGACGTTGAGGATCGCGAC | | 705 |
| 360 | F360 | AGTAGTCGTTAAGT | 115 | 768 |
| | R7 | TATACTAACGAACG | | 769 |
| | Probe7 | TCGTAGAGACGTTGAGGATCGCGAC | | 705 |
| 361 | F361 | GTAGTCGTTAAGTT | 114 | 770 |
| | R7 | TATACTAACGAACG | | 771 |
| | Probe7 | TCGTAGAGACGTTGAGGATCGCGAC | | 705 |
| 362 | F362 | TAGTCGTTAAGTTT | 113 | 772 |
| | R7 | TATACTAACGAACG | | 773 |
| | Probe7 | TCGTAGAGACGTTGAGGATCGCGAC | | 705 |
| 363 | F363 | AGTCGTTAAGTTTC | 112 | 774 |
| | R7 | TATACTAACGAACG | | 775 |
| | Probe7 | TCGTAGAGACGTTGAGGATCGCGAC | | 705 |
| 364 | F364 | GTCGTTAAGTTTCG | 111 | 776 |
| | R7 | TATACTAACGAACG | | 777 |
| | Probe7 | TCGTAGAGACGTTGAGGATCGCGAC | | 705 |
| 365 | F365 | TCGTTAAGTTTCGG | 110 | 778 |
| | R7 | TATACTAACGAACG | | 779 |
| | Probe7 | TCGTAGAGACGTTGAGGATCGCGAC | | 705 |
| 366 | F366 | CGTTAAGTTTCGGG | 109 | 780 |
| | R7 | TATACTAACGAACG | | 781 |
| | Probe7 | TCGTAGAGACGTTGAGGATCGCGAC | | 705 |
| 367 | F367 | GTTAAGTTTCGGGA | 108 | 782 |
| | R7 | TATACTAACGAACG | | 783 |
| | Probe7 | TCGTAGAGACGTTGAGGATCGCGAC | | 705 |
| 368 | F368 | TTAAGTTTCGGGAC | 107 | 784 |
| | R7 | TATACTAACGAACG | | 785 |
| | Probe7 | TCGTAGAGACGTTGAGGATCGCGAC | | 705 |
| 369 | F369 | TAAGTTTCGGGACG | 106 | 786 |
| | R7 | TATACTAACGAACG | | 787 |
| | Probe7 | TCGTAGAGACGTTGAGGATCGCGAC | | 705 |
| 370 | F370 | AAGTTTCGGGACGG | 105 | 788 |
| | R7 | TATACTAACGAACG | | 789 |
| | Probe7 | TCGTAGAGACGTTGAGGATCGCGAC | | 705 |
| 371 | F371 | AGTTTCGGGACGGC | 104 | 790 |
| | R7 | TATACTAACGAACG | | 791 |
| | Probe7 | TCGTAGAGACGTTGAGGATCGCGAC | | 705 |
| 372 | F372 | GTTTCGGGACGGCG | 103 | 792 |
| | R7 | TATACTAACGAACG | | 793 |
| | Probe7 | TCGTAGAGACGTTGAGGATCGCGAC | | 705 |
| 373 | F373 | TTTCGGGACGGCGA | 102 | 794 |
| | R7 | TATACTAACGAACG | | 795 |
| | Probe7 | TCGTAGAGACGTTGAGGATCGCGAC | | 705 |
| 374 | F374 | TTCGGGACGGCGAG | 101 | 796 |
| | R7 | TATACTAACGAACG | | 797 |
| | Probe7 | TCGTAGAGACGTTGAGGATCGCGAC | | 705 |
| 375 | F375 | TCGGGACGGCGAGG | 100 | 798 |
| | R7 | TATACTAACGAACG | | 799 |
| | Probe7 | TCGTAGAGACGTTGAGGATCGCGAC | | 705 |
| 376 | F376 | CGGGACGGCGAGGT | 99 | 800 |
| | R7 | TATACTAACGAACG | | 801 |
| | Probe7 | TCGTAGAGACGTTGAGGATCGCGAC | | 705 |
| 377 | F377 | GGGACGGCGAGGTA | 98 | 802 |
| | R7 | TATACTAACGAACG | | 803 |
| | Probe7 | TCGTAGAGACGTTGAGGATCGCGAC | | 705 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 378 | F378 | GGACGGCGAGGTAG | 97 | 804 |
|  | R7 | TATACTAACGAACG |  | 805 |
|  | Probe7 | TCGTAGAGACGTTGAGGATCGCGAC |  | 705 |
| 379 | F379 | GACGGCGAGGTAGG | 96 | 806 |
|  | R7 | TATACTAACGAACG |  | 807 |
|  | Probe7 | TCGTAGAGACGTTGAGGATCGCGAC |  | 705 |
| 380 | F380 | ACGGCGAGGTAGGC | 95 | 808 |
|  | R7 | TATACTAACGAACG |  | 809 |
|  | Probe7 | TCGTAGAGACGTTGAGGATCGCGAC |  | 705 |
| 381 | F381 | CGGCGAGGTAGGCG | 94 | 810 |
|  | R7 | TATACTAACGAACG |  | 811 |
|  | Probe7 | TCGTAGAGACGTTGAGGATCGCGAC |  | 705 |
| 382 | F382 | GGCGAGGTAGGCGT | 93 | 812 |
|  | R7 | TATACTAACGAACG |  | 813 |
|  | Probe7 | TCGTAGAGACGTTGAGGATCGCGAC |  | 705 |
| 383 | F383 | GCGAGGTAGGCGTT | 92 | 814 |
|  | R7 | TATACTAACGAACG |  | 815 |
|  | Probe7 | TCGTAGAGACGTTGAGGATCGCGAC |  | 705 |
| 384 | F384 | CGAGGTAGGCGTTT | 91 | 816 |
|  | R7 | TATACTAACGAACG |  | 817 |
|  | Probe7 | TCGTAGAGACGTTGAGGATCGCGAC |  | 705 |
| 385 | F385 | GAGGTAGGCGTTTA | 90 | 818 |
|  | R7 | TATACTAACGAACG |  | 819 |
|  | Probe7 | TCGTAGAGACGTTGAGGATCGCGAC |  | 705 |
| 386 | F386 | AGGTAGGCGTTTAG | 89 | 820 |
|  | R7 | TATACTAACGAACG |  | 821 |
|  | Probe7 | TCGTAGAGACGTTGAGGATCGCGAC |  | 705 |
| 387 | F387 | GGTAGGCGTTTAGA | 88 | 822 |
|  | R7 | TATACTAACGAACG |  | 823 |
|  | Probe7 | TCGTAGAGACGTTGAGGATCGCGAC |  | 705 |
| 388 | F388 | GTAGGCGTTTAGAG | 87 | 824 |
|  | R7 | TATACTAACGAACG |  | 825 |
|  | Probe7 | TCGTAGAGACGTTGAGGATCGCGAC |  | 705 |
| 389 | F389 | TAGGCGTTTAGAGT | 86 | 826 |
|  | R7 | TATACTAACGAACG |  | 827 |
|  | Probe7 | TCGTAGAGACGTTGAGGATCGCGAC |  | 705 |
| 390 | F390 | AGGCGTTTAGAGTT | 85 | 828 |
|  | R7 | TATACTAACGAACG |  | 829 |
|  | Probe7 | TCGTAGAGACGTTGAGGATCGCGAC |  | 705 |
| 391 | F391 | GGCGTTTAGAGTTT | 84 | 830 |
|  | R7 | TATACTAACGAACG |  | 831 |
|  | Probe7 | TCGTAGAGACGTTGAGGATCGCGAC |  | 705 |
| 392 | F392 | GCGTTTAGAGTTTC | 83 | 832 |
|  | R7 | TATACTAACGAACG |  | 833 |
|  | Probe7 | TCGTAGAGACGTTGAGGATCGCGAC |  | 705 |
| 393 | F393 | CGTTTAGAGTTTCG | 82 | 834 |
|  | R7 | TATACTAACGAACG |  | 835 |
|  | Probe7 | TCGTAGAGACGTTGAGGATCGCGAC |  | 705 |
| 394 | F394 | GTTTAGAGTTTCGT | 81 | 836 |
|  | R7 | TATACTAACGAACG |  | 837 |
|  | Probe7 | TCGTAGAGACGTTGAGGATCGCGAC |  | 705 |
| 395 | F395 | TTTAGAGTTTCGTA | 80 | 838 |
|  | R7 | TATACTAACGAACG |  | 839 |
|  | Probe7 | TCGTAGAGACGTTGAGGATCGCGAC |  | 705 |
| 396 | F396 | TTAGAGTTTCGTAG | 146 | 840 |
|  | R8 | CGACTCTAAAAAAA |  | 841 |
|  | Probe8 | TCGGGTTCGTTTTTTTTCGACGTTC |  | 842 |
| 397 | F397 | TAGAGTTTCGTAGT | 145 | 843 |
|  | R8 | CGACTCTAAAAAAA |  | 844 |
|  | Probe8 | TCGGGTTCGTTTTTTTTCGACGTTC |  | 842 |
| 398 | F398 | AGAGTTTCGTAGTT | 144 | 845 |
|  | R8 | CGACTCTAAAAAAA |  | 846 |
|  | Probe8 | TCGGGTTCGTTTTTTTTCGACGTTC |  | 842 |
| 399 | F399 | GAGTTTCGTAGTTT | 143 | 847 |
|  | R8 | CGACTCTAAAAAAA |  | 848 |
|  | Probe8 | TCGGGTTCGTTTTTTTTCGACGTTC |  | 842 |
| 400 | F400 | AGTTTCGTAGTTTG | 142 | 849 |
|  | R8 | CGACTCTAAAAAAA |  | 850 |
|  | Probe8 | TCGGGTTCGTTTTTTTTCGACGTTC |  | 842 |
| 401 | F401 | GTTTCGTAGTTTGG | 141 | 851 |
|  | R8 | CGACTCTAAAAAAA |  | 852 |
|  | Probe8 | TCGGGTTCGTTTTTTTTCGACGTTC |  | 842 |
| 402 | F402 | TTTCGTAGTTTGGT | 140 | 853 |
|  | R8 | CGACTCTAAAAAAA |  | 854 |
|  | Probe8 | TCGGGTTCGTTTTTTTTCGACGTTC |  | 842 |
| 403 | F403 | TTCGTAGTTTGGTT | 139 | 855 |
|  | R8 | CGACTCTAAAAAAA |  | 856 |
|  | Probe8 | TCGGGTTCGTTTTTTTTCGACGTTC |  | 842 |
| 404 | F404 | TCGTAGTTTGGTTC | 138 | 857 |
|  | R8 | CGACTCTAAAAAAA |  | 858 |
|  | Probe8 | TCGGGTTCGTTTTTTTTCGACGTTC |  | 842 |
| 405 | F405 | CGTAGTTTGGTTCG | 137 | 859 |
|  | R8 | CGACTCTAAAAAAA |  | 860 |
|  | Probe8 | TCGGGTTCGTTTTTTTTCGACGTTC |  | 842 |
| 406 | F406 | GTAGTTTGGTTCGT | 136 | 861 |
|  | R8 | CGACTCTAAAAAAA |  | 862 |
|  | Probe8 | TCGGGTTCGTTTTTTTTCGACGTTC |  | 842 |
| 407 | F407 | TAGTTTGGTTCGTG | 135 | 863 |
|  | R8 | CGACTCTAAAAAAA |  | 864 |
|  | Probe8 | TCGGGTTCGTTTTTTTTCGACGTTC |  | 842 |
| 408 | F408 | AGTTTGGTTCGTGA | 134 | 865 |
|  | R8 | CGACTCTAAAAAAA |  | 866 |
|  | Probe8 | TCGGGTTCGTTTTTTTTCGACGTTC |  | 842 |
| 409 | F409 | GTTTGGTTCGTGAT | 133 | 867 |
|  | R8 | CGACTCTAAAAAAA |  | 868 |
|  | Probe8 | TCGGGTTCGTTTTTTTTCGACGTTC |  | 842 |
| 410 | F410 | TTTGGTTCGTGATT | 132 | 869 |
|  | R8 | CGACTCTAAAAAAA |  | 870 |
|  | Probe8 | TCGGGTTCGTTTTTTTTCGACGTTC |  | 842 |
| 411 | F411 | TTGGTTCGTGATTT | 131 | 871 |
|  | R8 | CGACTCTAAAAAAA |  | 872 |
|  | Probe8 | TCGGGTTCGTTTTTTTTCGACGTTC |  | 842 |
| 412 | F412 | TGGTTCGTGATTTC | 130 | 873 |
|  | R8 | CGACTCTAAAAAAA |  | 874 |
|  | Probe8 | TCGGGTTCGTTTTTTTTCGACGTTC |  | 842 |
| 413 | F413 | GGTTCGTGATTTCG | 129 | 875 |
|  | R8 | CGACTCTAAAAAAA |  | 876 |
|  | Probe8 | TCGGGTTCGTTTTTTTTCGACGTTC |  | 842 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 414 | F414 | GTTCGTGATTTCGT | 128 | 877 |
|  | R8 | CGACTCTAAAAAAA |  | 878 |
|  | Probe8 | TCGGGTTCGTTTTTTTTCGACGTTC |  | 842 |
| 415 | F415 | TTCGTGATTTCGTA | 127 | 879 |
|  | R8 | CGACTCTAAAAAAA |  | 880 |
|  | Probe8 | TCGGGTTCGTTTTTTTTCGACGTTC |  | 842 |
| 416 | F416 | TCGTGATTTCGTAG | 126 | 881 |
|  | R8 | CGACTCTAAAAAAA |  | 882 |
|  | Probe8 | TCGGGTTCGTTTTTTTTCGACGTTC |  | 842 |
| 417 | F417 | CGTGATTTCGTAGA | 125 | 883 |
|  | R8 | CGACTCTAAAAAAA |  | 884 |
|  | Probe8 | TCGGGTTCGTTTTTTTTCGACGTTC |  | 842 |
| 418 | F418 | GTGATTTCGTAGAG | 124 | 885 |
|  | R8 | CGACTCTAAAAAAA |  | 886 |
|  | Probe8 | TCGGGTTCGTTTTTTTTCGACGTTC |  | 842 |
| 419 | F419 | TGATTTCGTAGAGA | 123 | 887 |
|  | R8 | CGACTCTAAAAAAA |  | 888 |
|  | Probe8 | TCGGGTTCGTTTTTTTTCGACGTTC |  | 842 |
| 420 | F420 | GATTTCGTAGAGAC | 122 | 889 |
|  | R8 | CGACTCTAAAAAAA |  | 890 |
|  | Probe8 | TCGGGTTCGTTTTTTTTCGACGTTC |  | 842 |
| 421 | F421 | ATTTCGTAGAGACG | 121 | 891 |
|  | R8 | CGACTCTAAAAAAA |  | 892 |
|  | Probe8 | TCGGGTTCGTTTTTTTTCGACGTTC |  | 842 |
| 422 | F422 | TTTCGTAGAGACGT | 120 | 893 |
|  | R8 | CGACTCTAAAAAAA |  | 894 |
|  | Probe8 | TCGGGTTCGTTTTTTTTCGACGTTC |  | 842 |
| 423 | F423 | TTCGTAGAGACGTT | 119 | 895 |
|  | R8 | CGACTCTAAAAAAA |  | 896 |
|  | Probe8 | TCGGGTTCGTTTTTTTTCGACGTTC |  | 842 |
| 424 | F424 | TCGTAGAGACGTTG | 118 | 897 |
|  | R8 | CGACTCTAAAAAAA |  | 898 |
|  | Probe8 | TCGGGTTCGTTTTTTTTCGACGTTC |  | 842 |
| 425 | F425 | CGTAGAGACGTTGA | 117 | 899 |
|  | R8 | CGACTCTAAAAAAA |  | 900 |
|  | Probe8 | TCGGGTTCGTTTTTTTTCGACGTTC |  | 842 |
| 426 | F426 | GTAGAGACGTTGAG | 116 | 901 |
|  | R8 | CGACTCTAAAAAAA |  | 902 |
|  | Probe8 | TCGGGTTCGTTTTTTTTCGACGTTC |  | 842 |
| 427 | F427 | TAGAGACGTTGAGG | 115 | 903 |
|  | R8 | CGACTCTAAAAAAA |  | 904 |
|  | Probe8 | TCGGGTTCGTTTTTTTTCGACGTTC |  | 842 |
| 428 | F428 | AGAGACGTTGAGGA | 114 | 905 |
|  | R8 | CGACTCTAAAAAAA |  | 906 |
|  | Probe8 | TCGGGTTCGTTTTTTTTCGACGTTC |  | 842 |
| 429 | F429 | GAGACGTTGAGGAT | 113 | 907 |
|  | R8 | CGACTCTAAAAAAA |  | 908 |
|  | Probe8 | TCGGGTTCGTTTTTTTTCGACGTTC |  | 842 |
| 430 | F430 | AGACGTTGAGGATC | 112 | 909 |
|  | R8 | CGACTCTAAAAAAA |  | 910 |
|  | Probe8 | TCGGGTTCGTTTTTTTTCGACGTTC |  | 842 |
| 431 | F431 | GACGTTGAGGATCG | 111 | 911 |
|  | R8 | CGACTCTAAAAAAA |  | 912 |
|  | Probe8 | TCGGGTTCGTTTTTTTTCGACGTTC |  | 842 |
| 432 | F432 | ACGTTGAGGATCGC | 110 | 913 |
|  | R8 | CGACTCTAAAAAAA |  | 914 |
|  | Probe8 | TCGGGTTCGTTTTTTTTCGACGTTC |  | 842 |
| 433 | F433 | CGTTGAGGATCGCG | 109 | 915 |
|  | R8 | CGACTCTAAAAAAA |  | 916 |
|  | Probe8 | TCGGGTTCGTTTTTTTTCGACGTTC |  | 842 |
| 434 | F434 | GTTGAGGATCGCGA | 108 | 917 |
|  | R8 | CGACTCTAAAAAAA |  | 918 |
|  | Probe8 | TCGGGTTCGTTTTTTTTCGACGTTC |  | 842 |
| 435 | F435 | TTGAGGATCGCGAC | 107 | 919 |
|  | R8 | CGACTCTAAAAAAA |  | 920 |
|  | Probe8 | TCGGGTTCGTTTTTTTTCGACGTTC |  | 842 |
| 436 | F436 | TGAGGATCGCGACG | 106 | 921 |
|  | R8 | CGACTCTAAAAAAA |  | 922 |
|  | Probe8 | TCGGGTTCGTTTTTTTTCGACGTTC |  | 842 |
| 437 | F437 | GAGGATCGCGACGG | 105 | 923 |
|  | R8 | CGACTCTAAAAAAA |  | 924 |
|  | Probe8 | TCGGGTTCGTTTTTTTTCGACGTTC |  | 842 |
| 438 | F438 | AGGATCGCGACGGT | 104 | 925 |
|  | R8 | CGACTCTAAAAAAA |  | 926 |
|  | Probe8 | TCGGGTTCGTTTTTTTTCGACGTTC |  | 842 |
| 439 | F439 | GGATCGCGACGGTG | 103 | 927 |
|  | R8 | CGACTCTAAAAAAA |  | 928 |
|  | Probe8 | TCGGGTTCGTTTTTTTTCGACGTTC |  | 842 |
| 440 | F440 | GATCGCGACGGTGA | 102 | 929 |
|  | R8 | CGACTCTAAAAAAA |  | 930 |
|  | Probe8 | TCGGGTTCGTTTTTTTTCGACGTTC |  | 842 |
| 441 | F441 | ATCGCGACGGTGAG | 101 | 931 |
|  | R8 | CGACTCTAAAAAAA |  | 932 |
|  | Probe8 | TCGGGTTCGTTTTTTTTCGACGTTC |  | 842 |
| 442 | F442 | TCGCGACGGTGAGG | 100 | 933 |
|  | R8 | CGACTCTAAAAAAA |  | 934 |
|  | Probe8 | TCGGGTTCGTTTTTTTTCGACGTTC |  | 842 |
| 443 | F443 | CGCGACGGTGAGGT | 99 | 935 |
|  | R8 | CGACTCTAAAAAAA |  | 936 |
|  | Probe8 | TCGGGTTCGTTTTTTTTCGACGTTC |  | 842 |
| 444 | F444 | GCGACGGTGAGGTT | 98 | 937 |
|  | R8 | CGACTCTAAAAAAA |  | 938 |
|  | Probe8 | TCGGGTTCGTTTTTTTTCGACGTTC |  | 842 |
| 445 | F445 | CGACGGTGAGGTTT | 97 | 939 |
|  | R8 | CGACTCTAAAAAAA |  | 940 |
|  | Probe8 | TCGGGTTCGTTTTTTTTCGACGTTC |  | 842 |
| 446 | F446 | GACGGTGAGGTTTT | 96 | 941 |
|  | R8 | CGACTCTAAAAAAA |  | 942 |
|  | Probe8 | TCGGGTTCGTTTTTTTTCGACGTTC |  | 842 |
| 447 | F447 | ACGGTGAGGTTTTA | 95 | 943 |
|  | R8 | CGACTCTAAAAAAA |  | 944 |
|  | Probe8 | TCGGGTTCGTTTTTTTTCGACGTTC |  | 842 |
| 448 | F448 | CGGTGAGGTTTTAC | 94 | 945 |
|  | R8 | CGACTCTAAAAAAA |  | 946 |
|  | Probe8 | TCGGGTTCGTTTTTTTTCGACGTTC |  | 842 |
| 449 | F449 | GGTGAGGTTTTACG | 93 | 947 |
|  | R8 | CGACTCTAAAAAAA |  | 948 |
|  | Probe8 | TCGGGTTCGTTTTTTTTCGACGTTC |  | 842 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 450 | F450 | GTGAGGTTTTACGT | 92 | 949 |
| | R8 | CGACTCTAAAAAAA | | 950 |
| | Probe8 | TCGGGTTCGTTTTTTTTCGACGTTC | | 842 |
| 451 | F451 | TGAGGTTTTACGTT | 91 | 951 |
| | R8 | CGACTCTAAAAAAA | | 952 |
| | Probe8 | TCGGGTTCGTTTTTTTTCGACGTTC | | 842 |
| 452 | F452 | GAGGTTTTACGTTC | 90 | 953 |
| | R8 | CGACTCTAAAAAAA | | 954 |
| | Probe8 | TCGGGTTCGTTTTTTTTCGACGTTC | | 842 |
| 453 | F453 | AGGTTTTACGTTCG | 89 | 955 |
| | R8 | CGACTCTAAAAAAA | | 956 |
| | Probe8 | TCGGGTTCGTTTTTTTTCGACGTTC | | 842 |
| 454 | F454 | GGTTTTACGTTCGT | 88 | 957 |
| | R8 | CGACTCTAAAAAAA | | 958 |
| | Probe8 | TCGGGTTCGTTTTTTTTCGACGTTC | | 842 |
| 455 | F455 | GTTTTACGTTCGTT | 87 | 959 |
| | R8 | CGACTCTAAAAAAA | | 960 |
| | Probe8 | TCGGGTTCGTTTTTTTTCGACGTTC | | 842 |
| 456 | F456 | TTTTACGTTCGTTA | 86 | 961 |
| | R8 | CGACTCTAAAAAAA | | 962 |
| | Probe8 | TCGGGTTCGTTTTTTTTCGACGTTC | | 842 |
| 457 | F457 | TTTACGTTCGTTAG | 85 | 963 |
| | R8 | CGACTCTAAAAAAA | | 964 |
| | Probe8 | TCGGGTTCGTTTTTTTTCGACGTTC | | 842 |
| 458 | F458 | TTACGTTCGTTAGT | 84 | 965 |
| | R8 | CGACTCTAAAAAAA | | 966 |
| | Probe8 | TCGGGTTCGTTTTTTTTCGACGTTC | | 842 |
| 459 | F459 | TACGTTCGTTAGTA | 83 | 967 |
| | R8 | CGACTCTAAAAAAA | | 968 |
| | Probe8 | TCGGGTTCGTTTTTTTTCGACGTTC | | 842 |
| 460 | F460 | ACGTTCGTTAGTAT | 82 | 969 |
| | R8 | CGACTCTAAAAAAA | | 970 |
| | Probe8 | TCGGGTTCGTTTTTTTTCGACGTTC | | 842 |
| 461 | F461 | CGTTCGTTAGTATA | 81 | 971 |
| | R8 | CGACTCTAAAAAAA | | 972 |
| | Probe8 | TCGGGTTCGTTTTTTTTCGACGTTC | | 842 |
| 462 | F462 | GTTCGTTAGTATAT | 80 | 973 |
| | R8 | CGACTCTAAAAAAA | | 974 |
| | Probe8 | TCGGGTTCGTTTTTTTTCGACGTTC | | 842 |
| 463 | F463 | TTCGTTAGTATATT | 143 | 975 |
| | R9 | CAAATTCACTCACG | | 976 |
| | Probe9 | AATTGGTTTGTTTTATTCGAATAGC | | 977 |
| 464 | F464 | TCGTTAGTATATTC | 142 | 978 |
| | R9 | CAAATTCACTCACG | | 979 |
| | Probe9 | AATTGGTTTGTTTTATTCGAATAGC | | 977 |
| 465 | F465 | CGTTAGTATATTCG | 141 | 980 |
| | R9 | CAAATTCACTCACG | | 981 |
| | Probe9 | AATTGGTTTGTTTTATTCGAATAGC | | 977 |
| 466 | F466 | GTTAGTATATTCGG | 140 | 982 |
| | R9 | CAAATTCACTCACG | | 983 |
| | Probe9 | AATTGGTTTGTTTTATTCGAATAGC | | 977 |
| 467 | F467 | TTAGTATATTCGGG | 139 | 984 |
| | R9 | CAAATTCACTCACG | | 985 |
| | Probe9 | AATTGGTTTGTTTTATTCGAATAGC | | 977 |
| 468 | F468 | TAGTATATTCGGGT | 138 | 986 |
| | R9 | CAAATTCACTCACG | | 987 |
| | Probe9 | AATTGGTTTGTTTTATTCGAATAGC | | 977 |
| 469 | F469 | AGTATATTCGGGTT | 137 | 988 |
| | R9 | CAAATTCACTCACG | | 989 |
| | Probe9 | AATTGGTTTGTTTTATTCGAATAGC | | 977 |
| 470 | F470 | GTATATTCGGGTTC | 136 | 990 |
| | R9 | CAAATTCACTCACG | | 991 |
| | Probe9 | AATTGGTTTGTTTTATTCGAATAGC | | 977 |
| 471 | F471 | TATATTCGGGTTCG | 135 | 992 |
| | R9 | CAAATTCACTCACG | | 993 |
| | Probe9 | AATTGGTTTGTTTTATTCGAATAGC | | 977 |
| 472 | F472 | ATATTCGGGTTCGT | 134 | 994 |
| | R9 | CAAATTCACTCACG | | 995 |
| | Probe9 | AATTGGTTTGTTTTATTCGAATAGC | | 977 |
| 473 | F473 | TATTCGGGTTCGTT | 133 | 996 |
| | R9 | CAAATTCACTCACG | | 997 |
| | Probe9 | AATTGGTTTGTTTTATTCGAATAGC | | 977 |
| 474 | F474 | ATTCGGGTTCGTTT | 132 | 998 |
| | R9 | CAAATTCACTCACG | | 999 |
| | Probe9 | AATTGGTTTGTTTTATTCGAATAGC | | 977 |
| 475 | F475 | TTCGGGTTCGTTTT | 131 | 1000 |
| | R9 | CAAATTCACTCACG | | 1001 |
| | Probe9 | AATTGGTTTGTTTTATTCGAATAGC | | 977 |
| 476 | F476 | TCGGGTTCGTTTTT | 130 | 1002 |
| | R9 | CAAATTCACTCACG | | 1003 |
| | Probe9 | AATTGGTTTGTTTTATTCGAATAGC | | 977 |
| 477 | F477 | CGGGTTCGTTTTTT | 129 | 1004 |
| | R9 | CAAATTCACTCACG | | 1005 |
| | Probe9 | AATTGGTTTGTTTTATTCGAATAGC | | 977 |
| 478 | F478 | GGGTTCGTTTTTTT | 128 | 1006 |
| | R9 | CAAATTCACTCACG | | 1007 |
| | Probe9 | AATTGGTTTGTTTTATTCGAATAGC | | 977 |
| 479 | F479 | GGTTCGTTTTTTTT | 127 | 1008 |
| | R9 | CAAATTCACTCACG | | 1009 |
| | Probe9 | AATTGGTTTGTTTTATTCGAATAGC | | 977 |
| 480 | F480 | GTTCGTTTTTTTTC | 126 | 1010 |
| | R9 | CAAATTCACTCACG | | 1011 |
| | Probe9 | AATTGGTTTGTTTTATTCGAATAGC | | 977 |
| 481 | F481 | TTCGTTTTTTTTCG | 125 | 1012 |
| | R9 | CAAATTCACTCACG | | 1013 |
| | Probe9 | AATTGGTTTGTTTTATTCGAATAGC | | 977 |
| 482 | F482 | TCGTTTTTTTTCGA | 124 | 1014 |
| | R9 | CAAATTCACTCACG | | 1015 |
| | Probe9 | AATTGGTTTGTTTTATTCGAATAGC | | 977 |
| 483 | F483 | CGTTTTTTTTCGAC | 123 | 1016 |
| | R9 | CAAATTCACTCACG | | 1017 |
| | Probe9 | AATTGGTTTGTTTTATTCGAATAGC | | 977 |
| 484 | F484 | GTTTTTTTTCGACG | 122 | 1018 |
| | R9 | CAAATTCACTCACG | | 1019 |
| | Probe9 | AATTGGTTTGTTTTATTCGAATAGC | | 977 |
| 485 | F485 | TTTTTTTTCGACGT | 121 | 1020 |
| | R9 | CAAATTCACTCACG | | 1021 |
| | Probe9 | AATTGGTTTGTTTTATTCGAATAGC | | 977 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 486 | F486 | TTTTTTCGACGTT | 120 | 1022 |
|  | R9 | CAAATTCACTCACG |  | 1023 |
|  | Probe9 | AATTGGTTTGTTTTATTCGAATAGC |  | 977 |
| 487 | F487 | TTTTTTCGACGTTC | 119 | 1024 |
|  | R9 | CAAATTCACTCACG |  | 1025 |
|  | Probe9 | AATTGGTTTGTTTTATTCGAATAGC |  | 977 |
| 488 | F488 | TTTTTCGACGTTCG | 118 | 1026 |
|  | R9 | CAAATTCACTCACG |  | 1027 |
|  | Probe9 | AATTGGTTTGTTTTATTCGAATAGC |  | 977 |
| 489 | F489 | TTTTCGACGTTCGT | 117 | 1028 |
|  | R9 | CAAATTCACTCACG |  | 1029 |
|  | Probe9 | AATTGGTTTGTTTTATTCGAATAGC |  | 977 |
| 490 | F490 | TTTCGACGTTCGTT | 116 | 1030 |
|  | R9 | CAAATTCACTCACG |  | 1031 |
|  | Probe9 | AATTGGTTTGTTTTATTCGAATAGC |  | 977 |
| 491 | F491 | TTCGACGTTCGTTT | 115 | 1032 |
|  | R9 | CAAATTCACTCACG |  | 1033 |
|  | Probe9 | AATTGGTTTGTTTTATTCGAATAGC |  | 977 |
| 492 | F492 | TCGACGTTCGTTTT | 114 | 1034 |
|  | R9 | CAAATTCACTCACG |  | 1035 |
|  | Probe9 | AATTGGTTTGTTTTATTCGAATAGC |  | 977 |
| 493 | F493 | CGACGTTCGTTTTT | 113 | 1036 |
|  | R9 | CAAATTCACTCACG |  | 1037 |
|  | Probe9 | AATTGGTTTGTTTTATTCGAATAGC |  | 977 |
| 494 | F494 | GACGTTCGTTTTTT | 112 | 1038 |
|  | R9 | CAAATTCACTCACG |  | 1039 |
|  | Probe9 | AATTGGTTTGTTTTATTCGAATAGC |  | 977 |
| 495 | F495 | ACGTTCGTTTTTTT | 111 | 1040 |
|  | R9 | CAAATTCACTCACG |  | 1041 |
|  | Probe9 | AATTGGTTTGTTTTATTCGAATAGC |  | 977 |
| 496 | F496 | CGTTCGTTTTTTTT | 110 | 1042 |
|  | R9 | CAAATTCACTCACG |  | 1043 |
|  | Probe9 | AATTGGTTTGTTTTATTCGAATAGC |  | 977 |
| 497 | F497 | GTTCGTTTTTTTTA | 109 | 1044 |
|  | R9 | CAAATTCACTCACG |  | 1045 |
|  | Probe9 | AATTGGTTTGTTTTATTCGAATAGC |  | 977 |
| 498 | F498 | TTCGTTTTTTTTAT | 108 | 1046 |
|  | R9 | CAAATTCACTCACG |  | 1047 |
|  | Probe9 | AATTGGTTTGTTTTATTCGAATAGC |  | 977 |
| 499 | F499 | TCGTTTTTTTTATA | 107 | 1048 |
|  | R9 | CAAATTCACTCACG |  | 1049 |
|  | Probe9 | AATTGGTTTGTTTTATTCGAATAGC |  | 977 |
| 500 | F500 | CGTTTTTTTTATAT | 106 | 1050 |
|  | R9 | CAAATTCACTCACG |  | 1051 |
|  | Probe9 | AATTGGTTTGTTTTATTCGAATAGC |  | 977 |
| 501 | F501 | GTTTTTTTTATATT | 105 | 1052 |
|  | R9 | CAAATTCACTCACG |  | 1053 |
|  | Probe9 | AATTGGTTTGTTTTATTCGAATAGC |  | 977 |
| 502 | F502 | TTTTTTTTATATTT | 104 | 1054 |
|  | R9 | CAAATTCACTCACG |  | 1055 |
|  | Probe9 | AATTGGTTTGTTTTATTCGAATAGC |  | 977 |
| 503 | F503 | TTTTTTTATATTTG | 103 | 1056 |
|  | R9 | CAAATTCACTCACG |  | 1057 |
|  | Probe9 | AATTGGTTTGTTTTATTCGAATAGC |  | 977 |
| 504 | F504 | TTTTTTATATTTGT | 102 | 1058 |
|  | R9 | CAAATTCACTCACG |  | 1059 |
|  | Probe9 | AATTGGTTTGTTTTATTCGAATAGC |  | 977 |
| 505 | F505 | TTTTTATATTTGTT | 101 | 1060 |
|  | R9 | CAAATTCACTCACG |  | 1061 |
|  | Probe9 | AATTGGTTTGTTTTATTCGAATAGC |  | 977 |
| 506 | F506 | TTTTATATTTGTTT | 100 | 1062 |
|  | R9 | CAAATTCACTCACG |  | 1063 |
|  | Probe9 | AATTGGTTTGTTTTATTCGAATAGC |  | 977 |
| 507 | F507 | TTTATATTTGTTTT | 99 | 1064 |
|  | R9 | CAAATTCACTCACG |  | 1065 |
|  | Probe9 | AATTGGTTTGTTTTATTCGAATAGC |  | 977 |
| 508 | F508 | TTATATTTGTTTTT | 98 | 1066 |
|  | R9 | CAAATTCACTCACG |  | 1067 |
|  | Probe9 | AATTGGTTTGTTTTATTCGAATAGC |  | 977 |
| 509 | F509 | TATATTTGTTTTTT | 97 | 1068 |
|  | R9 | CAAATTCACTCACG |  | 1069 |
|  | Probe9 | AATTGGTTTGTTTTATTCGAATAGC |  | 977 |
| 510 | F510 | ATATTTGTTTTTTT | 96 | 1070 |
|  | R9 | CAAATTCACTCACG |  | 1071 |
|  | Probe9 | AATTGGTTTGTTTTATTCGAATAGC |  | 977 |
| 511 | F511 | TATTTGTTTTTTTT | 95 | 1072 |
|  | R9 | CAAATTCACTCACG |  | 1073 |
|  | Probe9 | AATTGGTTTGTTTTATTCGAATAGC |  | 977 |
| 512 | F512 | ATTTGTTTTTTTTT | 94 | 1074 |
|  | R9 | CAAATTCACTCACG |  | 1075 |
|  | Probe9 | AATTGGTTTGTTTTATTCGAATAGC |  | 977 |
| 513 | F513 | TTTGTTTTTTTTTT | 93 | 1076 |
|  | R9 | CAAATTCACTCACG |  | 1077 |
|  | Probe9 | AATTGGTTTGTTTTATTCGAATAGC |  | 977 |
| 514 | F514 | TTGTTTTTTTTTTT | 92 | 1078 |
|  | R9 | CAAATTCACTCACG |  | 1079 |
|  | Probe9 | AATTGGTTTGTTTTATTCGAATAGC |  | 977 |
| 515 | F515 | TGTTTTTTTTTTTT | 91 | 1080 |
|  | R9 | CAAATTCACTCACG |  | 1081 |
|  | Probe9 | AATTGGTTTGTTTTATTCGAATAGC |  | 977 |
| 516 | F516 | GTTTTTTTTTTTTT | 90 | 1082 |
|  | R9 | CAAATTCACTCACG |  | 1083 |
|  | Probe9 | AATTGGTTTGTTTTATTCGAATAGC |  | 977 |
| 517 | F517 | TTTTTTTTTTTTTT | 85-89 | 1084 |
|  | R9 | CAAATTCACTCACG |  | 1085 |
|  | Probe9 | AATTGGTTTGTTTTATTCGAATAGC |  | 977 |
| 518 | F518 | TTTTTTTTTTTTTA | 84 | 1086 |
|  | R9 | CAAATTCACTCACG |  | 1087 |
|  | Probe9 | AATTGGTTTGTTTTATTCGAATAGC |  | 977 |
| 519 | F519 | TTTTTTTTTTTTAG | 83 | 1088 |
|  | R9 | CAAATTCACTCACG |  | 1089 |
|  | Probe9 | AATTGGTTTGTTTTATTCGAATAGC |  | 977 |
| 520 | F520 | TTTTTTTTTTTAGA | 82 | 1090 |
|  | R9 | CAAATTCACTCACG |  | 1091 |
|  | Probe9 | AATTGGTTTGTTTTATTCGAATAGC |  | 977 |
| 521 | F521 | TTTTTTTTTTAGAG | 81 | 1092 |
|  | R9 | CAAATTCACTCACG |  | 1093 |
|  | Probe9 | AATTGGTTTGTTTTATTCGAATAGC |  | 977 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 522 | F522 | TTTTTTTTTAGAGT | 80 | 1094 |
|  | R9 | CAAATTCACTCACG |  | 1095 |
|  | Probe9 | AATTGGTTTGTTTTATTCGAATAGC |  | 977 |
| 523 | F523 | TTTTTTTAGAGTC | 135 | 1096 |
|  | R10 | AAAAAAAAAAAACG |  | 1097 |
|  | Probe10 | TGTTCGAAGTTTGTTTTGTTGAGC |  | 1098 |
| 524 | F524 | TTTTTTAGAGTCG | 134 | 1099 |
|  | R10 | AAAAAAAAAAAACG |  | 1100 |
|  | Probe10 | TGTTCGAAGTTTGTTTTGTTGAGC |  | 1098 |
| 525 | F525 | TTTTTAGAGTCGT | 133 | 1101 |
|  | R10 | AAAAAAAAAAAACG |  | 1102 |
|  | Probe10 | TGTTCGAAGTTTGTTTTGTTGAGC |  | 1098 |
| 526 | F526 | TTTTAGAGTCGTG | 132 | 1103 |
|  | R10 | AAAAAAAAAAAACG |  | 1104 |
|  | Probe10 | TGTTCGAAGTTTGTTTTGTTGAGC |  | 1098 |
| 527 | F527 | TTTTAGAGTCGTGT | 131 | 1105 |
|  | R10 | AAAAAAAAAAAACG |  | 1106 |
|  | Probe10 | TGTTCGAAGTTTGTTTTGTTGAGC |  | 1098 |
| 528 | F528 | TTTAGAGTCGTGTT | 130 | 1107 |
|  | R10 | AAAAAAAAAAAACG |  | 1108 |
|  | Probe10 | TGTTCGAAGTTTGTTTTGTTGAGC |  | 1098 |
| 529 | F529 | TTAGAGTCGTGTTT | 129 | 1109 |
|  | R10 | AAAAAAAAAAAACG |  | 1110 |
|  | Probe10 | TGTTCGAAGTTTGTTTTGTTGAGC |  | 1098 |
| 530 | F530 | TAGAGTCGTGTTTG | 128 | 1111 |
|  | R10 | AAAAAAAAAAAACG |  | 1112 |
|  | Probe10 | TGTTCGAAGTTTGTTTTGTTGAGC |  | 1098 |
| 531 | F531 | AGAGTCGTGTTTGA | 127 | 1113 |
|  | R10 | AAAAAAAAAAAACG |  | 1114 |
|  | Probe10 | TGTTCGAAGTTTGTTTTGTTGAGC |  | 1098 |
| 532 | F532 | GAGTCGTGTTTGAA | 126 | 1115 |
|  | R10 | AAAAAAAAAAAACG |  | 1116 |
|  | Probe10 | TGTTCGAAGTTTGTTTTGTTGAGC |  | 1098 |
| 533 | F533 | AGTCGTGTTTGAAT | 125 | 1117 |
|  | R10 | AAAAAAAAAAAACG |  | 1118 |
|  | Probe10 | TGTTCGAAGTTTGTTTTGTTGAGC |  | 1098 |
| 534 | F534 | GTCGTGTTTGAATT | 124 | 1119 |
|  | R10 | AAAAAAAAAAAACG |  | 1120 |
|  | Probe10 | TGTTCGAAGTTTGTTTTGTTGAGC |  | 1098 |
| 535 | F535 | TCGTGTTTGAATTC | 123 | 1121 |
|  | R10 | AAAAAAAAAAAACG |  | 1122 |
|  | Probe10 | TGTTCGAAGTTTGTTTTGTTGAGC |  | 1098 |
| 536 | F536 | CGTGTTTGAATTCG | 122 | 1123 |
|  | R10 | AAAAAAAAAAAACG |  | 1124 |
|  | Probe10 | TGTTCGAAGTTTGTTTTGTTGAGC |  | 1098 |
| 537 | F537 | GTGTTTGAATTCGG | 121 | 1125 |
|  | R10 | AAAAAAAAAAAACG |  | 1126 |
|  | Probe10 | TGTTCGAAGTTTGTTTTGTTGAGC |  | 1098 |
| 538 | F538 | TGTTTGAATTCGGT | 120 | 1127 |
|  | R10 | AAAAAAAAAAAACG |  | 1128 |
|  | Probe10 | TGTTCGAAGTTTGTTTTGTTGAGC |  | 1098 |
| 539 | F539 | GTTTGAATTCGGTT | 119 | 1129 |
|  | R10 | AAAAAAAAAAAACG |  | 1130 |
|  | Probe10 | TGTTCGAAGTTTGTTTTGTTGAGC |  | 1098 |
| 540 | F540 | TTTGAATTCGGTTT | 118 | 1131 |
|  | R10 | AAAAAAAAAAAACG |  | 1132 |
|  | Probe10 | TGTTCGAAGTTTGTTTTGTTGAGC |  | 1098 |
| 541 | F541 | TTGAATTCGGTTTT | 117 | 1133 |
|  | R10 | AAAAAAAAAAAACG |  | 1134 |
|  | Probe10 | TGTTCGAAGTTTGTTTTGTTGAGC |  | 1098 |
| 542 | F542 | TGAATTCGGTTTTT | 116 | 1135 |
|  | R10 | AAAAAAAAAAAACG |  | 1136 |
|  | Probe10 | TGTTCGAAGTTTGTTTTGTTGAGC |  | 1098 |
| 543 | F543 | GAATTCGGTTTTTT | 115 | 1137 |
|  | R10 | AAAAAAAAAAAACG |  | 1138 |
|  | Probe10 | TGTTCGAAGTTTGTTTTGTTGAGC |  | 1098 |
| 544 | F544 | AATTCGGTTTTTTT | 114 | 1139 |
|  | R10 | AAAAAAAAAAAACG |  | 1140 |
|  | Probe10 | TGTTCGAAGTTTGTTTTGTTGAGC |  | 1098 |
| 545 | F545 | ATTCGGTTTTTTTA | 113 | 1141 |
|  | R10 | AAAAAAAAAAAACG |  | 1142 |
|  | Probe10 | TGTTCGAAGTTTGTTTTGTTGAGC |  | 1098 |
| 546 | F546 | TTCGGTTTTTTTAA | 112 | 1143 |
|  | R10 | AAAAAAAAAAAACG |  | 1144 |
|  | Probe10 | TGTTCGAAGTTTGTTTTGTTGAGC |  | 1098 |
| 547 | F547 | TCGGTTTTTTTAAT | 111 | 1145 |
|  | R10 | AAAAAAAAAAAACG |  | 1146 |
|  | Probe10 | TGTTCGAAGTTTGTTTTGTTGAGC |  | 1098 |
| 548 | F548 | CGGTTTTTTTAATT | 110 | 1147 |
|  | R10 | AAAAAAAAAAAACG |  | 1148 |
|  | Probe10 | TGTTCGAAGTTTGTTTTGTTGAGC |  | 1098 |
| 549 | F549 | GGTTTTTTTAATTG | 109 | 1149 |
|  | R10 | AAAAAAAAAAAACG |  | 1150 |
|  | Probe10 | TGTTCGAAGTTTGTTTTGTTGAGC |  | 1098 |
| 550 | F550 | GTTTTTTTAATTGG | 108 | 1151 |
|  | R10 | AAAAAAAAAAAACG |  | 1152 |
|  | Probe10 | TGTTCGAAGTTTGTTTTGTTGAGC |  | 1098 |
| 551 | F551 | TTTTTTTAATTGGT | 107 | 1153 |
|  | R10 | AAAAAAAAAAAACG |  | 1154 |
|  | Probe10 | TGTTCGAAGTTTGTTTTGTTGAGC |  | 1098 |
| 552 | F552 | TTTTTTAATTGGTT | 106 | 1155 |
|  | R10 | AAAAAAAAAAAACG |  | 1156 |
|  | Probe10 | TGTTCGAAGTTTGTTTTGTTGAGC |  | 1098 |
| 553 | F553 | TTTTTAATTGGTTT | 105 | 1157 |
|  | R10 | AAAAAAAAAAAACG |  | 1158 |
|  | Probe10 | TGTTCGAAGTTTGTTTTGTTGAGC |  | 1098 |
| 554 | F554 | TTTTAATTGGTTTG | 104 | 1159 |
|  | R10 | AAAAAAAAAAAACG |  | 1160 |
|  | Probe10 | TGTTCGAAGTTTGTTTTGTTGAGC |  | 1098 |
| 555 | F555 | TTTAATTGGTTTGT | 103 | 1161 |
|  | R10 | AAAAAAAAAAAACG |  | 1162 |
|  | Probe10 | TGTTCGAAGTTTGTTTTGTTGAGC |  | 1098 |
| 556 | F556 | TTAATTGGTTTGTT | 102 | 1163 |
|  | R10 | AAAAAAAAAAAACG |  | 1164 |
|  | Probe10 | TGTTCGAAGTTTGTTTTGTTGAGC |  | 1098 |
| 557 | F557 | TAATTGGTTTGTTT | 101 | 1165 |
|  | R10 | AAAAAAAAAAAACG |  | 1166 |
|  | Probe10 | TGTTCGAAGTTTGTTTTGTTGAGC |  | 1098 |

TABLE 7-continued

Sequences of primer and probes for PENK gene qMSP

| Set | Primer | Sequences (5'→3') | Size of amplification product (bp) | SEQ ID NOs: |
|---|---|---|---|---|
| 558 | F558 | AATTGGTTTGTTTT | 100 | 1167 |
|  | R10 | AAAAAAAAAAAACG |  | 1168 |
|  | Probe10 | TGTTCGAAGTTTGTTTTTGTTGAGC |  | 1098 |
| 559 | F559 | ATTGGTTTGTTTTA | 99 | 1169 |
|  | R10 | AAAAAAAAAAAACG |  | 1170 |
|  | Probe10 | TGTTCGAAGTTTGTTTTTGTTGAGC |  | 1098 |
| 560 | F560 | TTGGTTTGTTTTAT | 98 | 1171 |
|  | R10 | AAAAAAAAAAAACG |  | 1172 |
|  | Probe10 | TGTTCGAAGTTTGTTTTTGTTGAGC |  | 1098 |
| 561 | F561 | TGGTTTGTTTTATT | 97 | 1173 |
|  | R10 | AAAAAAAAAAAACG |  | 1174 |
|  | Probe10 | TGTTCGAAGTTTGTTTTTGTTGAGC |  | 1098 |
| 562 | F562 | GGTTTGTTTTATTC | 96 | 1175 |
|  | R10 | AAAAAAAAAAAACG |  | 1176 |
|  | Probe10 | TGTTCGAAGTTTGTTTTTGTTGAGC |  | 1098 |
| 563 | F563 | GTTTGTTTTATTCG | 95 | 1177 |
|  | R10 | AAAAAAAAAAAACG |  | 1178 |
|  | Probe10 | TGTTCGAAGTTTGTTTTTGTTGAGC |  | 1098 |
| 564 | F564 | TTTGTTTTATTCGA | 94 | 1179 |
|  | R10 | AAAAAAAAAAAACG |  | 1180 |
|  | Probe10 | TGTTCGAAGTTTGTTTTTGTTGAGC |  | 1098 |
| 565 | F565 | TTGTTTTATTCGAA | 93 | 1181 |
|  | R10 | AAAAAAAAAAAACG |  | 1182 |
|  | Probe10 | TGTTCGAAGTTTGTTTTTGTTGAGC |  | 1098 |
| 566 | F566 | TGTTTTATTCGAAT | 92 | 1183 |
|  | R10 | AAAAAAAAAAAACG |  | 1184 |
|  | Probe10 | TGTTCGAAGTTTGTTTTTGTTGAGC |  | 1098 |
| 567 | F567 | GTTTTATTCGAATA | 91 | 1185 |
|  | R10 | AAAAAAAAAAAACG |  | 1186 |
|  | Probe10 | TGTTCGAAGTTTGTTTTTGTTGAGC |  | 1098 |
| 568 | F568 | TTTTATTCGAATAG | 90 | 1187 |
|  | R10 | AAAAAAAAAAAACG |  | 1188 |
|  | Probe10 | TGTTCGAAGTTTGTTTTTGTTGAGC |  | 1098 |
| 569 | F569 | TTTATTCGAATAGC | 89 | 1189 |
|  | R10 | AAAAAAAAAAAACG |  | 1190 |
|  | Probe10 | TGTTCGAAGTTTGTTTTTGTTGAGC |  | 1098 |
| 570 | F570 | TTATTCGAATAGCG | 88 | 1191 |
|  | R10 | AAAAAAAAAAAACG |  | 1192 |
|  | Probe10 | TGTTCGAAGTTTGTTTTTGTTGAGC |  | 1098 |
| 571 | F571 | TATTCGAATAGCGT | 87 | 1193 |
|  | R10 | AAAAAAAAAAAACG |  | 1194 |
|  | Probe10 | TGTTCGAAGTTTGTTTTTGTTGAGC |  | 1098 |
| 572 | F572 | ATTCGAATAGCGTT | 86 | 1195 |
|  | R10 | AAAAAAAAAAAACG |  | 1196 |
|  | Probe10 | TGTTCGAAGTTTGTTTTTGTTGAGC |  | 1098 |
| 573 | F573 | TTCGAATAGCGTTA | 85 | 1197 |
|  | R10 | AAAAAAAAAAAACG |  | 1198 |
|  | Probe10 | TGTTCGAAGTTTGTTTTTGTTGAGC |  | 1098 |
| 574 | F574 | TCGAATAGCGTTAA | 84 | 1199 |
|  | R10 | AAAAAAAAAAAACG |  | 1200 |
|  | Probe10 | TGTTCGAAGTTTGTTTTTGTTGAGC |  | 1098 |
| 575 | F575 | CGAATAGCGTTAAC | 83 | 1201 |
|  | R10 | AAAAAAAAAAAACG |  | 1202 |
|  | Probe10 | TGTTCGAAGTTTGTTTTTGTTGAGC |  | 1098 |
| 576 | F576 | GAATAGCGTTAACG | 82 | 1203 |
|  | R10 | AAAAAAAAAAAACG |  | 1204 |
|  | Probe10 | TGTTCGAAGTTTGTTTTTGTTGAGC |  | 1098 |
| 577 | F577 | AATAGCGTTAACGT | 81 | 1205 |
|  | R10 | AAAAAAAAAAAACG |  | 1206 |
|  | Probe10 | TGTTCGAAGTTTGTTTTTGTTGAGC |  | 1098 |
| 578 | F578 | ATAGCGTTAACGTG | 80 | 1207 |
|  | R10 | AAAAAAAAAAAACG |  | 1208 |
|  | Probe10 | TGTTCGAAGTTTGTTTTTGTTGAGC |  | 1098 |
| 579 | F579 | TAGCGTTAACGTGA | 123 | 1209 |
|  | R11 | AAAACCAAAAAACG |  | 1210 |
|  | Probe11 | CGTTTGTTCGTTTTTTTTTTTTTA |  | 1211 |
| 580 | F580 | AGCGTTAACGTGAG | 122 | 1212 |
|  | R11 | AAAACCAAAAAACG |  | 1213 |
|  | Probe11 | CGTTTGTTCGTTTTTTTTTTTTTA |  | 1211 |
| 581 | F581 | GCGTTAACGTGAGT | 121 | 1214 |
|  | R11 | AAAACCAAAAAACG |  | 1215 |
|  | Probe11 | CGTTTGTTCGTTTTTTTTTTTTTA |  | 1211 |
| 582 | F582 | CGTTAACGTGAGTG | 120 | 1216 |
|  | R11 | AAAACCAAAAAACG |  | 1217 |
|  | Probe11 | CGTTTGTTCGTTTTTTTTTTTTTA |  | 1211 |
| 583 | F583 | GTTAACGTGAGTGA | 119 | 1218 |
|  | R11 | AAAACCAAAAAACG |  | 1219 |
|  | Probe11 | CGTTTGTTCGTTTTTTTTTTTTTA |  | 1211 |
| 584 | F584 | TTAACGTGAGTGAA | 118 | 1220 |
|  | R11 | AAAACCAAAAAACG |  | 1221 |
|  | Probe11 | CGTTTGTTCGTTTTTTTTTTTTTA |  | 1211 |

As a result of evaluating methylation of PENK gene using urine cell DNA from normal and bladder cancer patients, it was found that the sensitivity of PENK gene for bladder cancer diagnosis was 75% (15/20)~90.0% (18/20) and the specificity of the PENK gene was 85% (3/20)~95% (1/20). Such results suggest that the PENK methylation biomarker gene is useful for diagnosis of bladder cancer.

TABLE 8

Evaluation of ability to diagnose bladder cancer using PENK gene

| Set of primers and probes | Cut-off (Ct) | Sensitivity (%), n = 20 | Specificity (%), n = 20 |
|---|---|---|---|
| 1 | <32.0 | 90 | 85 |
| 2 | <32.0 | 80 | 95 |
| 3 | <32.3 | 85 | 90 |
| 4 | <32.2 | 85 | 85 |
| 5 | <32.3 | 85 | 90 |
| 6 | <32.2 | 85 | 90 |
| 7 | <32.3 | 85 | 90 |
| 8 | <32.1 | 80 | 90 |
| 9 | <32.0 | 80 | 90 |
| 10 | <32.2 | 90 | 85 |
| 11 | <32.5 | 80 | 90 |
| 12 | <32.2 | 80 | 90 |
| 13 | <32.2 | 85 | 90 |
| 14 | <32.3 | 75 | 90 |
| 15 | <32.1 | 85 | 85 |
| 16 | <32.3 | 85 | 85 |
| 17 | <32.4 | 80 | 90 |
| 18 | <32.3 | 85 | 85 |

TABLE 8-continued

Evaluation of ability to diagnose bladder cancer using PENK gene

| Set of primers and probes | Cut-off (Ct) | Sensitivity (%), n = 20 | Specificity (%), n = 20 |
| --- | --- | --- | --- |
| 19 | <32.3 | 75 | 90 |
| 20 | <32.5 | 80 | 90 |
| 21 | <32.3 | 85 | 90 |
| 22 | <32.1 | 75 | 95 |
| 23 | <32.5 | 75 | 90 |
| 24 | <32.3 | 85 | 90 |
| 25 | <32.3 | 85 | 90 |
| 26 | <32.5 | 80 | 90 |
| 27 | <32.1 | 80 | 85 |
| 28 | <32.5 | 90 | 80 |
| 29 | <32.3 | 75 | 90 |
| 30 | <32.5 | 80 | 95 |
| 31 | <32.5 | 80 | 85 |
| 32 | <32.0 | 85 | 85 |
| 33 | <32.3 | 85 | 90 |
| 34 | <32.0 | 80 | 90 |
| 35 | <32.5 | 80 | 90 |
| 36 | <32.0 | 80 | 95 |
| 37 | <32.1 | 80 | 90 |
| 38 | <32.4 | 80 | 90 |
| 39 | <32.0 | 90 | 85 |
| 40 | <32.5 | 75 | 95 |
| 41 | <32.2 | 80 | 90 |
| 42 | <32.5 | 80 | 90 |
| 43 | <32.5 | 75 | 95 |
| 44 | <32.0 | 75 | 95 |
| 45 | <32.2 | 85 | 90 |
| 46 | <32.3 | 75 | 85 |
| 47 | <32.0 | 80 | 90 |
| 48 | <32.5 | 85 | 90 |
| 49 | <32.5 | 75 | 90 |
| 50 | <32.2 | 85 | 90 |
| 51 | <32.3 | 85 | 85 |
| 52 | <32.5 | 80 | 90 |
| 53 | <32.0 | 75 | 90 |
| 54 | <32.0 | 80 | 95 |
| 55 | <32.5 | 85 | 90 |
| 56 | <32.3 | 85 | 90 |
| 57 | <32.5 | 80 | 90 |
| 58 | <32.1 | 85 | 90 |
| 59 | <32.0 | 90 | 85 |
| 60 | <32.5 | 75 | 90 |
| 61 | <32.1 | 85 | 90 |
| 62 | <32.3 | 75 | 90 |
| 63 | <32.0 | 90 | 85 |
| 64 | <32.1 | 85 | 90 |
| 65 | <32.5 | 75 | 95 |
| 66 | <32.5 | 75 | 90 |
| 67 | <32.0 | 85 | 85 |
| 68 | <32.1 | 90 | 85 |
| 69 | <32.5 | 85 | 90 |
| 70 | <32.0 | 90 | 80 |
| 71 | <32.3 | 75 | 90 |
| 72 | <32.2 | 90 | 85 |
| 73 | <32.0 | 90 | 85 |
| 74 | <32.0 | 75 | 95 |
| 75 | <32.3 | 75 | 90 |
| 76 | <32.5 | 80 | 95 |
| 77 | <32.5 | 85 | 90 |
| 78 | <32.2 | 75 | 85 |
| 79 | <32.0 | 80 | 90 |
| 80 | <32.0 | 75 | 90 |
| 81 | <32.3 | 85 | 90 |
| 82 | <32.1 | 85 | 90 |
| 83 | <32.3 | 85 | 90 |
| 84 | <32.0 | 80 | 85 |
| 85 | <32.2 | 80 | 90 |
| 86 | <32.1 | 90 | 85 |
| 87 | <32.5 | 90 | 85 |
| 88 | <32.3 | 75 | 90 |
| 89 | <32.3 | 85 | 90 |
| 90 | <32.5 | 90 | 80 |
| 91 | <32.2 | 85 | 90 |
| 92 | <32.5 | 80 | 90 |
| 93 | <32.5 | 85 | 90 |
| 94 | <32.3 | 75 | 90 |
| 95 | <32.5 | 80 | 90 |
| 96 | <32.0 | 75 | 90 |
| 97 | <32.3 | 85 | 90 |
| 98 | <32.3 | 75 | 85 |
| 99 | <32.0 | 80 | 90 |
| 100 | <32.0 | 80 | 90 |
| 101 | <32.3 | 75 | 90 |
| 102 | <32.1 | 80 | 85 |
| 103 | <32.3 | 85 | 90 |
| 104 | <32.3 | 85 | 85 |
| 105 | <32.3 | 85 | 85 |
| 106 | <32.3 | 85 | 90 |
| 107 | <32.1 | 85 | 90 |
| 108 | <32.2 | 80 | 90 |
| 109 | <32.3 | 85 | 90 |
| 110 | <32.5 | 80 | 90 |
| 111 | <32.0 | 85 | 85 |
| 112 | <32.0 | 90 | 80 |
| 113 | <32.0 | 85 | 90 |
| 114 | <32.3 | 85 | 90 |
| 115 | <32.5 | 75 | 95 |
| 116 | <32.5 | 80 | 90 |
| 117 | <32.3 | 85 | 90 |
| 118 | <32.1 | 80 | 85 |
| 119 | <32.2 | 85 | 90 |
| 120 | <32.2 | 85 | 90 |
| 121 | <32.5 | 85 | 90 |
| 122 | <32.2 | 85 | 90 |
| 123 | <32.0 | 75 | 90 |
| 124 | <32.3 | 85 | 85 |
| 125 | <32.3 | 85 | 85 |
| 126 | <32.3 | 85 | 90 |
| 127 | <32.5 | 75 | 95 |
| 128 | <32.5 | 75 | 95 |
| 129 | <32.3 | 75 | 90 |
| 130 | <32.1 | 85 | 85 |
| 131 | <32.5 | 80 | 90 |
| 132 | <32.3 | 75 | 90 |
| 133 | <32.3 | 85 | 85 |
| 134 | <32.5 | 80 | 85 |
| 135 | <32.3 | 75 | 90 |
| 136 | <32.0 | 85 | 85 |
| 137 | <32.3 | 85 | 95 |
| 138 | <32.1 | 80 | 95 |
| 139 | <32.1 | 80 | 85 |
| 140 | <32.0 | 75 | 90 |
| 141 | <32.5 | 75 | 95 |
| 142 | <32.5 | 75 | 90 |
| 143 | <32.2 | 85 | 85 |
| 144 | <32.3 | 85 | 90 |
| 145 | <32.4 | 80 | 95 |
| 146 | <32.3 | 85 | 90 |
| 147 | <32.5 | 80 | 90 |
| 148 | <32.5 | 90 | 85 |
| 149 | <32.2 | 75 | 90 |
| 150 | <32.4 | 80 | 95 |
| 151 | <32.2 | 75 | 90 |
| 152 | <32.0 | 90 | 85 |
| 153 | <32.5 | 75 | 95 |
| 154 | <32.0 | 90 | 85 |
| 155 | <32.5 | 80 | 85 |
| 156 | <32.3 | 85 | 90 |
| 157 | <32.3 | 85 | 85 |
| 158 | <32.3 | 85 | 85 |
| 159 | <32.0 | 80 | 90 |
| 160 | <32.0 | 90 | 85 |
| 161 | <32.0 | 90 | 85 |
| 162 | <32.5 | 90 | 80 |
| 163 | <32.3 | 85 | 90 |
| 164 | <32.0 | 80 | 90 |
| 165 | <32.3 | 85 | 90 |

TABLE 8-continued

Evaluation of ability to diagnose bladder cancer using PENK gene

| Set of primers and probes | Cut-off (Ct) | Sensitivity (%), n = 20 | Specificity (%), n = 20 |
|---|---|---|---|
| 166 | <32.1 | 85 | 85 |
| 167 | <32.1 | 80 | 85 |
| 168 | <32.1 | 85 | 90 |
| 169 | <32.0 | 80 | 90 |
| 170 | <32.5 | 80 | 90 |
| 171 | <32.1 | 75 | 85 |
| 172 | <32.5 | 80 | 90 |
| 173 | <32.3 | 85 | 90 |
| 174 | <32.5 | 80 | 85 |
| 175 | <32.1 | 80 | 90 |
| 176 | <32.0 | 85 | 85 |
| 177 | <32.5 | 80 | 90 |
| 178 | <32.2 | 85 | 90 |
| 179 | <32.3 | 85 | 85 |
| 180 | <32.1 | 80 | 85 |
| 181 | <32.5 | 90 | 80 |
| 182 | <32.5 | 90 | 80 |
| 183 | <32.3 | 85 | 90 |
| 184 | <32.0 | 80 | 90 |
| 185 | <32.0 | 90 | 85 |
| 186 | <32.1 | 90 | 85 |
| 187 | <32.5 | 75 | 90 |
| 188 | <32.0 | 75 | 95 |
| 189 | <32.0 | 80 | 95 |
| 190 | <32.2 | 75 | 90 |
| 191 | <32.1 | 80 | 90 |
| 192 | <32.0 | 85 | 95 |
| 193 | <32.3 | 85 | 90 |
| 194 | <32.5 | 85 | 90 |
| 195 | <32.5 | 80 | 90 |
| 196 | <32.5 | 90 | 85 |
| 197 | <32.0 | 90 | 80 |
| 198 | <32.1 | 75 | 95 |
| 199 | <32.5 | 85 | 85 |
| 200 | <32.0 | 75 | 90 |
| 201 | <32.2 | 85 | 90 |
| 202 | <32.0 | 75 | 90 |
| 203 | <32.5 | 90 | 85 |
| 204 | <32.0 | 80 | 90 |
| 205 | <32.0 | 85 | 85 |
| 206 | <32.3 | 85 | 90 |
| 207 | <32.0 | 75 | 90 |
| 208 | <32.3 | 75 | 90 |
| 209 | <32.5 | 85 | 90 |
| 210 | <32.0 | 90 | 85 |
| 211 | <32.0 | 85 | 85 |
| 212 | <32.0 | 80 | 90 |
| 213 | <32.2 | 85 | 90 |
| 214 | <32.2 | 85 | 90 |
| 215 | <32.0 | 80 | 90 |
| 216 | <32.0 | 90 | 85 |
| 217 | <32.3 | 85 | 85 |
| 218 | <32.5 | 75 | 95 |
| 219 | <32.0 | 80 | 90 |
| 220 | <32.3 | 85 | 85 |
| 221 | <32.2 | 80 | 90 |
| 222 | <32.5 | 80 | 90 |
| 223 | <32.5 | 80 | 90 |
| 224 | <32.5 | 75 | 95 |
| 225 | <32.4 | 80 | 90 |
| 226 | <32.5 | 90 | 80 |
| 227 | <32.4 | 80 | 90 |
| 228 | <32.2 | 85 | 90 |
| 229 | <32.0 | 75 | 90 |
| 230 | <32.1 | 90 | 85 |
| 231 | <32.1 | 85 | 85 |
| 232 | <32.1 | 75 | 95 |
| 233 | <32.1 | 85 | 90 |
| 234 | <32.5 | 80 | 90 |
| 235 | <32.0 | 85 | 90 |
| 236 | <32.0 | 80 | 90 |
| 237 | <32.2 | 85 | 90 |
| 238 | <32.2 | 80 | 90 |
| 239 | <32.5 | 75 | 95 |
| 240 | <32.1 | 90 | 85 |
| 241 | <32.3 | 85 | 90 |
| 242 | <32.5 | 85 | 90 |
| 243 | <32.2 | 80 | 95 |
| 244 | <32.3 | 85 | 85 |
| 245 | <32.3 | 85 | 85 |
| 246 | <32.0 | 80 | 90 |
| 247 | <32.1 | 85 | 90 |
| 248 | <32.5 | 80 | 90 |
| 249 | <32.5 | 80 | 90 |
| 250 | <32.0 | 80 | 90 |
| 251 | <32.3 | 75 | 90 |
| 252 | <32.4 | 80 | 90 |
| 253 | <32.0 | 80 | 90 |
| 254 | <32.3 | 85 | 85 |
| 255 | <32.1 | 75 | 95 |
| 256 | <32.3 | 75 | 90 |
| 257 | <32.5 | 75 | 90 |
| 258 | <32.3 | 85 | 90 |
| 259 | <32.2 | 80 | 90 |
| 260 | <32.0 | 85 | 85 |
| 261 | <32.2 | 85 | 90 |
| 262 | <32.4 | 80 | 90 |
| 263 | <32.0 | 85 | 85 |
| 264 | <32.2 | 85 | 90 |
| 265 | <32.5 | 80 | 90 |
| 266 | <32.5 | 75 | 95 |
| 267 | <32.1 | 85 | 85 |
| 268 | <32.0 | 75 | 95 |
| 269 | <32.2 | 85 | 90 |
| 270 | <32.2 | 75 | 90 |
| 271 | <32.1 | 90 | 85 |
| 272 | <32.5 | 75 | 95 |
| 273 | <32.0 | 75 | 95 |
| 274 | <32.5 | 75 | 90 |
| 275 | <32.0 | 80 | 90 |
| 276 | <32.0 | 80 | 95 |
| 277 | <32.5 | 75 | 90 |
| 278 | <32.0 | 90 | 85 |
| 279 | <32.1 | 80 | 95 |
| 280 | <32.2 | 90 | 85 |
| 281 | <32.2 | 80 | 90 |
| 282 | <32.0 | 75 | 90 |
| 283 | <32.2 | 80 | 95 |
| 284 | <32.5 | 85 | 85 |
| 285 | <32.1 | 85 | 90 |
| 286 | <32.5 | 90 | 85 |
| 287 | <32.3 | 85 | 90 |
| 288 | <32.0 | 75 | 95 |
| 289 | <32.0 | 75 | 95 |
| 290 | <32.1 | 85 | 90 |
| 291 | <32.3 | 85 | 90 |
| 292 | <32.2 | 75 | 90 |
| 293 | <32.0 | 75 | 95 |
| 294 | <32.2 | 80 | 90 |
| 295 | <32.0 | 90 | 85 |
| 296 | <32.0 | 90 | 85 |
| 297 | <32.0 | 85 | 85 |
| 298 | <32.5 | 75 | 95 |
| 299 | <32.5 | 80 | 90 |
| 300 | <32.5 | 90 | 80 |
| 301 | <32.5 | 80 | 90 |
| 302 | <32.5 | 80 | 90 |
| 303 | <32.5 | 80 | 90 |
| 304 | <32.2 | 85 | 90 |
| 305 | <32.4 | 80 | 90 |
| 306 | <32.3 | 85 | 85 |
| 307 | <32.3 | 85 | 85 |
| 308 | <32.1 | 80 | 85 |
| 309 | <32.5 | 75 | 95 |
| 310 | <32.5 | 80 | 90 |
| 311 | <32.2 | 85 | 90 |
| 312 | <32.1 | 90 | 85 |
| 313 | <32.4 | 80 | 95 |
| 314 | <32.3 | 85 | 90 |
| 315 | <32.5 | 90 | 80 |

TABLE 8-continued

Evaluation of ability to diagnose bladder cancer using PENK gene

| Set of primers and probes | Cut-off (Ct) | Sensitivity (%), n = 20 | Specificity (%), n = 20 |
|---|---|---|---|
| 316 | <32.5 | 80 | 90 |
| 317 | <32.5 | 75 | 90 |
| 318 | <32.0 | 85 | 90 |
| 319 | <32.3 | 85 | 90 |
| 320 | <32.0 | 85 | 85 |
| 321 | <32.3 | 85 | 90 |
| 322 | <32.3 | 85 | 90 |
| 323 | <32.3 | 85 | 90 |
| 324 | <32.0 | 75 | 85 |
| 325 | <32.0 | 75 | 95 |
| 326 | <32.1 | 90 | 85 |
| 327 | <32.1 | 85 | 90 |
| 328 | <32.0 | 85 | 90 |
| 329 | <32.1 | 90 | 85 |
| 330 | <32.2 | 85 | 90 |
| 331 | <32.5 | 75 | 95 |
| 332 | <32.3 | 75 | 90 |
| 333 | <32.2 | 80 | 95 |
| 334 | <32.5 | 80 | 90 |
| 335 | <32.1 | 85 | 90 |
| 336 | <32.5 | 80 | 90 |
| 337 | <32.5 | 85 | 85 |
| 338 | <32.3 | 85 | 90 |
| 339 | <32.5 | 80 | 90 |
| 340 | <32.5 | 90 | 80 |
| 341 | <32.5 | 75 | 95 |
| 342 | <32.0 | 80 | 90 |
| 343 | <32.5 | 75 | 90 |
| 344 | <32.3 | 85 | 90 |
| 345 | <32.5 | 90 | 80 |
| 346 | <32.0 | 90 | 85 |
| 347 | <32.3 | 75 | 90 |
| 348 | <32.5 | 75 | 90 |
| 349 | <32.5 | 80 | 90 |
| 350 | <32.5 | 80 | 90 |
| 351 | <32.0 | 75 | 95 |
| 352 | <32.1 | 75 | 95 |
| 353 | <32.0 | 75 | 95 |
| 354 | <32.3 | 85 | 90 |
| 355 | <32.3 | 85 | 90 |
| 356 | <32.5 | 80 | 90 |
| 357 | <32.3 | 85 | 90 |
| 358 | <32.1 | 80 | 90 |
| 359 | <32.1 | 80 | 85 |
| 360 | <32.3 | 85 | 90 |
| 361 | <32.3 | 85 | 90 |
| 362 | <32.0 | 90 | 80 |
| 363 | <32.5 | 90 | 80 |
| 364 | <32.3 | 85 | 90 |
| 365 | <32.5 | 75 | 95 |
| 366 | <32.5 | 85 | 90 |
| 367 | <32.0 | 80 | 90 |
| 368 | <32.1 | 85 | 90 |
| 369 | <32.3 | 75 | 90 |
| 370 | <32.5 | 90 | 80 |
| 371 | <32.3 | 75 | 90 |
| 372 | <32.0 | 75 | 90 |
| 373 | <32.3 | 85 | 90 |
| 374 | <32.5 | 80 | 95 |
| 375 | <32.3 | 85 | 85 |
| 376 | <32.0 | 90 | 85 |
| 377 | <32.5 | 90 | 80 |
| 378 | <32.1 | 85 | 90 |
| 379 | <32.0 | 75 | 90 |
| 380 | <32.3 | 75 | 90 |
| 381 | <32.5 | 90 | 80 |
| 382 | <32.0 | 85 | 90 |
| 383 | <32.0 | 75 | 95 |
| 384 | <32.0 | 80 | 95 |
| 385 | <32.5 | 85 | 85 |
| 386 | <32.0 | 80 | 90 |
| 387 | <32.0 | 80 | 90 |
| 388 | <32.0 | 85 | 95 |
| 389 | <32.0 | 90 | 85 |
| 390 | <32.5 | 90 | 85 |
| 391 | <32.2 | 85 | 90 |
| 392 | <32.2 | 85 | 90 |
| 393 | <32.1 | 85 | 85 |
| 394 | <32.2 | 85 | 90 |
| 395 | <32.0 | 75 | 90 |
| 396 | <32.0 | 75 | 95 |
| 397 | <32.0 | 80 | 90 |
| 398 | <32.5 | 80 | 90 |
| 399 | <32.3 | 85 | 90 |
| 400 | <32.0 | 75 | 95 |
| 401 | <32.2 | 80 | 90 |
| 402 | <32.1 | 75 | 95 |
| 403 | <32.2 | 85 | 90 |
| 404 | <32.5 | 85 | 90 |
| 405 | <32.5 | 80 | 90 |
| 406 | <32.0 | 90 | 85 |
| 407 | <32.0 | 80 | 90 |
| 408 | <32.5 | 80 | 90 |
| 409 | <32.1 | 85 | 90 |
| 410 | <32.3 | 85 | 90 |
| 411 | <32.3 | 85 | 90 |
| 412 | <32.5 | 75 | 90 |
| 413 | <32.5 | 90 | 80 |
| 414 | <32.0 | 80 | 95 |
| 415 | <32.1 | 85 | 90 |
| 416 | <32.0 | 80 | 90 |
| 417 | <32.5 | 75 | 90 |
| 418 | <32.3 | 85 | 90 |
| 419 | <32.0 | 90 | 85 |
| 420 | <32.1 | 80 | 90 |
| 421 | <32.0 | 80 | 90 |
| 422 | <32.5 | 80 | 90 |
| 423 | <32.5 | 80 | 90 |
| 424 | <32.0 | 80 | 90 |
| 425 | <32.3 | 85 | 90 |
| 426 | <32.5 | 80 | 90 |
| 427 | <32.2 | 80 | 90 |
| 428 | <32.4 | 80 | 90 |
| 429 | <32.1 | 85 | 90 |
| 430 | <32.0 | 80 | 95 |
| 431 | <32.1 | 75 | 95 |
| 432 | <32.0 | 85 | 85 |
| 433 | <32.5 | 75 | 95 |
| 434 | <32.3 | 85 | 85 |
| 435 | <32.3 | 85 | 90 |
| 436 | <32.5 | 90 | 80 |
| 437 | <32.3 | 85 | 95 |
| 438 | <32.5 | 75 | 95 |
| 439 | <32.2 | 85 | 90 |
| 440 | <32.3 | 85 | 95 |
| 441 | <32.2 | 85 | 90 |
| 442 | <32.0 | 90 | 85 |
| 443 | <32.1 | 80 | 85 |
| 444 | <32.1 | 85 | 85 |
| 445 | <32.2 | 75 | 90 |
| 446 | <32.1 | 85 | 85 |
| 447 | <32.1 | 85 | 90 |
| 448 | <32.0 | 75 | 95 |
| 449 | <32.5 | 75 | 95 |
| 450 | <32.5 | 80 | 90 |
| 451 | <32.0 | 80 | 90 |
| 452 | <32.4 | 80 | 95 |
| 453 | <32.4 | 80 | 90 |
| 454 | <32.5 | 80 | 90 |
| 455 | <32.2 | 85 | 90 |
| 456 | <32.2 | 75 | 90 |
| 457 | <32.3 | 75 | 90 |
| 458 | <32.5 | 75 | 90 |
| 459 | <32.5 | 80 | 90 |
| 460 | <32.3 | 85 | 95 |
| 461 | <32.0 | 90 | 85 |
| 462 | <32.0 | 85 | 85 |
| 463 | <32.3 | 85 | 90 |
| 464 | <32.3 | 75 | 90 |
| 465 | <32.2 | 90 | 85 |

TABLE 8-continued

Evaluation of ability to diagnose bladder cancer using PENK gene

| Set of primers and probes | Cut-off (Ct) | Sensitivity (%), n = 20 | Specificity (%), n = 20 |
|---|---|---|---|
| 466 | <32.2 | 75 | 90 |
| 467 | <32.3 | 85 | 90 |
| 468 | <32.1 | 85 | 90 |
| 469 | <32.0 | 90 | 85 |
| 470 | <32.1 | 85 | 90 |
| 471 | <32.5 | 75 | 95 |
| 472 | <32.5 | 80 | 95 |
| 473 | <32.0 | 75 | 90 |
| 474 | <32.2 | 90 | 90 |
| 475 | <32.3 | 75 | 90 |
| 476 | <32.1 | 85 | 85 |
| 477 | <32.0 | 80 | 95 |
| 478 | <32.3 | 75 | 85 |
| 479 | <32.0 | 85 | 95 |
| 480 | <32.3 | 85 | 90 |
| 481 | <32.3 | 85 | 85 |
| 482 | <32.1 | 90 | 85 |
| 483 | <32.1 | 85 | 90 |
| 484 | <32.3 | 75 | 90 |
| 485 | <32.0 | 75 | 95 |
| 486 | <32.1 | 75 | 85 |
| 487 | <32.0 | 90 | 80 |
| 488 | <32.2 | 80 | 90 |
| 489 | <32.0 | 90 | 85 |
| 490 | <32.0 | 80 | 95 |
| 491 | <32.5 | 80 | 90 |
| 492 | <32.5 | 80 | 90 |
| 493 | <32.5 | 80 | 90 |
| 494 | <32.5 | 80 | 85 |
| 495 | <32.4 | 80 | 90 |
| 496 | <32.0 | 90 | 85 |
| 497 | <32.1 | 85 | 85 |
| 498 | <32.1 | 85 | 90 |
| 499 | <32.3 | 85 | 90 |
| 500 | <32.0 | 75 | 90 |
| 501 | <32.0 | 75 | 95 |
| 502 | <32.2 | 90 | 85 |
| 503 | <32.0 | 80 | 85 |
| 504 | <32.3 | 85 | 85 |
| 505 | <32.2 | 90 | 85 |
| 506 | <32.1 | 80 | 95 |
| 507 | <32.2 | 80 | 90 |
| 508 | <32.1 | 90 | 85 |
| 509 | <32.5 | 75 | 95 |
| 510 | <32.5 | 75 | 95 |
| 511 | <32.5 | 80 | 90 |
| 512 | <32.0 | 85 | 90 |
| 513 | <32.3 | 75 | 90 |
| 514 | <32.0 | 75 | 85 |
| 515 | <32.0 | 80 | 95 |
| 516 | <32.5 | 80 | 95 |
| 517 | <32.3 | 85 | 85 |
| 518 | <32.2 | 90 | 90 |
| 519 | <32.0 | 85 | 85 |
| 520 | <32.1 | 90 | 85 |
| 521 | <32.5 | 80 | 85 |
| 522 | <32.0 | 90 | 85 |
| 523 | <32.0 | 75 | 95 |
| 524 | <32.2 | 85 | 85 |
| 525 | <32.3 | 75 | 90 |
| 526 | <32.0 | 80 | 90 |
| 527 | <32.1 | 85 | 85 |
| 528 | <32.3 | 85 | 90 |
| 529 | <32.0 | 80 | 90 |
| 530 | <32.3 | 85 | 90 |
| 531 | <32.2 | 90 | 85 |
| 532 | <32.3 | 75 | 90 |
| 533 | <32.3 | 85 | 85 |
| 534 | <32.2 | 85 | 90 |
| 535 | <32.0 | 75 | 90 |
| 536 | <32.0 | 80 | 85 |
| 537 | <32.5 | 85 | 90 |
| 538 | <32.1 | 80 | 95 |
| 539 | <32.0 | 80 | 90 |
| 540 | <32.2 | 80 | 90 |
| 541 | <32.3 | 85 | 85 |
| 542 | <32.3 | 75 | 90 |
| 543 | <32.0 | 80 | 90 |
| 544 | <32.3 | 85 | 85 |
| 545 | <32.5 | 75 | 95 |
| 546 | <32.5 | 75 | 90 |
| 547 | <32.0 | 80 | 90 |
| 548 | <32.0 | 85 | 85 |
| 549 | <32.2 | 85 | 90 |
| 550 | <32.1 | 80 | 85 |
| 551 | <32.0 | 80 | 90 |
| 552 | <32.0 | 75 | 95 |
| 553 | <32.5 | 80 | 90 |
| 554 | <32.0 | 80 | 90 |
| 555 | <32.5 | 80 | 90 |
| 556 | <32.1 | 80 | 85 |
| 557 | <32.0 | 90 | 85 |
| 558 | <32.1 | 80 | 85 |
| 559 | <32.0 | 80 | 90 |
| 560 | <32.0 | 75 | 95 |
| 561 | <32.1 | 85 | 85 |
| 562 | <32.5 | 85 | 90 |
| 563 | <32.2 | 85 | 90 |
| 564 | <32.0 | 80 | 90 |
| 565 | <32.1 | 80 | 90 |
| 566 | <32.2 | 75 | 85 |
| 567 | <32.0 | 90 | 85 |
| 568 | <32.5 | 80 | 90 |
| 569 | <32.3 | 85 | 90 |
| 570 | <32.0 | 85 | 85 |
| 571 | <32.2 | 85 | 90 |
| 572 | <32.5 | 85 | 90 |
| 573 | <32.5 | 75 | 95 |
| 574 | <32.2 | 75 | 90 |
| 575 | <32.3 | 85 | 90 |
| 576 | <32.1 | 80 | 85 |
| 577 | <32.2 | 85 | 90 |
| 578 | <32.1 | 90 | 85 |
| 579 | <32.3 | 85 | 85 |
| 580 | <32.3 | 85 | 95 |
| 581 | <32.3 | 75 | 90 |
| 582 | <32.2 | 75 | 90 |
| 583 | <32.0 | 80 | 90 |
| 584 | <32.1 | 85 | 85 |

INDUSTRIAL APPLICABILITY

As described above in detail, the present invention provides a kit and nucleic acid chip for diagnosing bladder cancer, which can detect the methylation of CpG islands of bladder cancer-specific marker genes. It is possible to diagnose bladder cancer at an early stage of transformation using the diagnostic kit or nucleic acid chip of the present invention, thus enabling early diagnosis of bladder cancer, and the diagnostic kit or nucleic acid chip can diagnose bladder cancer in a more accurate and rapid manner compared to a conventional method.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed:

1. A method for detecting CpG methylation of PENK (proenkephalin gene), the method comprising the steps of:
   (a) isolating a genomic DNA from a clinical sample;
   (b) treating the genomic DNA from step (a) with bisulfite; and
   (c) determining hypermethylation of the CpG of the PENK gene in the bisulfite-treated genomic DNA from step (b) by using primer(s) to amplify a methylated CpG of the bisulfite-treated PENK gene, wherein the primer(s) for amplifying a methylated CpG of PENK comprises sequence(s) selected from the group consisting of SEQ ID NOs: 43-44, 46-185, 187-298, 300-341, 343-468, 470-579, 581-704, 706-841, 843-976, 978-1097, 1099-1210, 1212-1221.

2. The method according to claim 1, wherein step (c) is performed by one selected from the group consisting of PCR, methylation specific PCR, real-time methylation specific PCR, PCR using a methylated DNA-specific binding protein, quantitative PCR, pyrosequencing, and bisulfite sequencing.

3. The method according to claim 1, wherein step (c) comprises examining a CpG methylation of a promoter or exon region of PENK in the clinical sample.

4. The method according to claim 3, wherein the promoter comprises a DNA sequence represented in SEQ ID NO: 37.

5. The method according to claim 1, wherein the method further comprises the step of examining CpG methylation of a gene selected from the group consisting of TBX5—T-box 5; CDX2—caudal type homeobox transcription factor 2; CYP1B1—cytochrome P450, family 1, subfamily B, polypeptide 1; VSX1—visual system homeobox 1 homolog, CHX10-like (zebrafish); HOXA11—homeobox A11; T—T, brachyury homolog (mouse); PAQR9—progestin and adipoQ receptor family member IV; and LHX2—LIM Homeobox 2.

6. The method according to claim 5, wherein the step of examining comprises examining CpG methylation of a promoter or exon region of the gene selected from the group consisting of TBX5; CDX2; CYP1B1; VSX1; HOXA11; T; PAQR9; and LHX2.

7. The method according to claim 1, wherein the method further comprises the step of contacting at least one nucleic acid isolated from the clinical sample with an agent capable of determining a CpG methylation status of PENK gene.

8. The method according to claim 1, wherein the primer(s) for amplifying a methylated CpG of PENK comprises at least one or more CpG dinucleotide in a region which hybridizes to the methylated CpG of PENK.

9. The method according to claim 8, further comprising probe(s) capable of hybridizing with a methylated CpG of PENK comprising at least one or more CpG dinucleotide in a region which hybridizes to the methylated CpG of PENK.

10. The method according to claim 8, further comprising probe(s) capable of hybridizing with a methylated CpG of PENK comprising sequence(s) selected from the group consisting of SEQ ID NOs: 45, 186, 299, 342, 469, 580, 705, 842, 977, 1098 and 1211.

11. A method for detecting CpG methylation of PENK—proenkephalin gene for bladder carcinoma or bladder cell proliferative disorder diagnosis, the method comprising the steps of:
(a) isolating a genomic DNA from a clinical sample;
(b) treating the genomic DNA from step (a) with bisulfite; and
(c) determining hypermethylation of the CpG of the PENK gene in the bisulfite-treated genomic DNA from step (b) by using primer(s) to amplify a methylated CpG of the bisulfite-treated PENK gene, wherein a bladder carcinoma or bladder cell proliferative disorder is detected in the human subject based on increased CpG methylation of the PENK gene relative to that of a control, wherein the primer(s) for amplifying a methylated CpG of PENK comprises sequence(s) selected from the group consisting of SEQ ID NOs: 43-44, 46-185, 187-298, 300-341, 343-468, 470-579, 581-704, 706-841, 843-976, 978-1097, 1099-1210, 1212-1221.

12. The method according to claim 11, wherein step (c) is performed by one selected from the group consisting of PCR, methylation specific PCR, real-time methylation specific PCR, PCR using a methylated DNA-specific binding protein, quantitative PCR, pyrosequencing, and bisulfite sequencing.

13. The method according to claim 12, wherein the clinical sample is tissue, cell, blood, urine, serum or plasma from a patient suspected of cancer or a subject to be diagnosed.

14. The method according to claim 11, wherein step (c) comprises examining a CpG methylation of a promoter or exon region of PENK in the clinical sample.

15. The method according to claim 12, wherein the promoter comprises a DNA sequence represented in SEQ ID NO: 37.

16. The method according to claim 11, wherein the method further comprises the step of examining CpG methylation of a gene selected from the group consisting of TBX5—T-box 5; CDX2—caudal type homeobox transcription factor 2; CYP1B1—cytochrome P450, family 1, subfamily B, polypeptide 1; VSX1—visual system homeobox 1 homolog, CHX10-like (zebrafish); HOXA11—homeobox A11; T—T, brachyury homolog (mouse); PAQR9—progestin and adipoQ receptor family member IV; and LHX2—LIM Homeobox 2.

17. The method according to claim 16, wherein the step of examining comprises examining CpG methylation of a promoter or exon region of the gene selected from the group consisting of TBX5; CDX2; CYP1B1; VSX1; HOXA11; T; PAQR9; and LHX2.

18. The method according to claim 11, wherein the method further comprises the step of contacting at least one nucleic acid isolated from the clinical sample with an agent capable of determining a CpG methylation status of PENK gene.

19. The method according to claim 11, wherein the primer(s) for amplifying a methylated CpG of PENK comprises at least one or more CpG dinucleotide in a region which hybridizes to the methylated CpG of PENK.

20. The method according to claim 19, further comprising probe(s) capable of hybridizing with a methylated CpG of PENK comprising at least one or more CpG dinucleotide in a region which hybridizes to the methylated CpG of PENK.

21. The method according to claim 19, further comprising probe(s) capable of hybridizing with a methylated CpG of PENK comprising sequence(s) selected from the group consisting of SEQ ID NOs: 45, 186, 299, 342, 469, 580, 705, 842, 977, 1098 and 1211.

* * * * *

UNITED STATES PATENT AND TRADEMARK OFFICE
CERTIFICATE OF CORRECTION

PATENT NO. : 10,113,203 B2  
APPLICATION NO. : 15/709348  
DATED : October 30, 2018  
INVENTOR(S) : Sung Whan An et al.

Page 1 of 1

It is certified that error appears in the above-identified patent and that said Letters Patent is hereby corrected as shown below:

In the Specification

Column 18, Table 2, 8th entry in column under heading "Gene": "PAQ?R9" should be -- PAQR9 --.

Column 19, Line 34, Table 3, 8th entry in column under heading "Gene": "PAQ?R9" should be -- PAQR9 --.

Signed and Sealed this  
Fourth Day of December, 2018

Andrei Iancu  
*Director of the United States Patent and Trademark Office*